US012582634B2

(12) United States Patent
Becker et al.

(10) Patent No.: US 12,582,634 B2
(45) Date of Patent: Mar. 24, 2026

(54) SYNTHETIC METHODS FOR PREPARATION OF 4-(2-CHLORO-4-METHOXY-5-METHYLPHENYL)-N-[(1S)-2-CYCLOPROPYL-1-(3-FLUORO-4-METHYLPHENYL)ETHYL]-5-METHYL-N-PROP-2-YNYL-1,3-THIAZOL-2-AMINE

(71) Applicants: Neurocrine Biosciences, Inc., San Diego, CA (US); Sanofi, Paris (FR)

(72) Inventors: Andrew Becker, San Diego, CA (US); Scott Stirn, San Diego, CA (US); Joel Radisson, Paris (FR); Christina Marie Costa, San Diego, CA (US)

(73) Assignees: Neurocrine Biosciences, Inc., San Diego, CA (US); Sanofi, Paris (FR)

(*) Notice: Subject to any disclaimer, the term of this patent is extended or adjusted under 35 U.S.C. 154(b) by 946 days.

(21) Appl. No.: 17/782,617

(22) PCT Filed: Jun. 10, 2020

(86) PCT No.: PCT/IB2020/000575
§ 371 (c)(1),
(2) Date: Jun. 3, 2022

(87) PCT Pub. No.: WO2021/111179
PCT Pub. Date: Jun. 10, 2021

(65) Prior Publication Data

US 2023/0018740 A1 Jan. 19, 2023
US 2023/0286932 A1 Sep. 14, 2023

(30) Foreign Application Priority Data

Dec. 6, 2019 (WO) .................. PCT/IB2019/001325

(51) Int. Cl.
*A61K 31/426* (2006.01)
*A61K 9/00* (2006.01)
(Continued)

(52) U.S. Cl.
CPC .......... *A61K 31/426* (2013.01); *A61K 9/0095* (2013.01); *A61K 9/107* (2013.01);
(Continued)

(58) Field of Classification Search
CPC .... A61K 31/426; A61K 9/0095; A61K 9/107; A61K 9/28; A61K 9/4833; A61K 45/06;
(Continued)

(56) References Cited

U.S. PATENT DOCUMENTS

| | | | |
|---|---|---|---|
| 5,464,847 | A | 11/1995 | Courtemanche et al. |
| 6,344,470 | B1 | 2/2002 | Fontaine et al. |

(Continued)

FOREIGN PATENT DOCUMENTS

| | | |
|---|---|---|
| CN | 1370154 | 9/2002 |
| CN | 101381314 | 3/2009 |

(Continued)

OTHER PUBLICATIONS

Nahm et al., N-methoxy-n-methylamides as effective acylating agents, Tet. Lett., 22, pp. 3815-3818 (Year: 1981).*

(Continued)

*Primary Examiner* — Jeffrey S Lundgren
*Assistant Examiner* — Alexander K. Showalter
(74) *Attorney, Agent, or Firm* — Fish & Richardson P.C.

(57) ABSTRACT

The present disclosure relates to the fields of chemistry and medicine, more particularly to processes for making 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), pharmaceutically acceptable salts, and crystalline forms thereof, for the treatment of congenital adrenal hyperplasia (CAH).

101 Claims, 25 Drawing Sheets

The General Synthetic Scheme for the Preparation of Compound 1

(51) Int. Cl.

| | |
|---|---|
| ***A61K 9/107*** | (2006.01) |
| ***A61K 9/28*** | (2006.01) |
| ***A61K 9/48*** | (2006.01) |
| ***A61K 45/06*** | (2006.01) |
| ***A61K 47/10*** | (2017.01) |
| ***A61K 47/14*** | (2017.01) |
| ***A61K 47/22*** | (2006.01) |
| ***A61K 47/26*** | (2006.01) |
| ***A61K 47/32*** | (2006.01) |
| ***C07D 277/42*** | (2006.01) |

(52) U.S. Cl.

CPC .............. *A61K 9/28* (2013.01); *A61K 9/4833* (2013.01); *A61K 45/06* (2013.01); *A61K 47/10* (2013.01); *A61K 47/14* (2013.01); *A61K 47/22* (2013.01); *A61K 47/26* (2013.01); *A61K 47/32* (2013.01); *C07D 277/42* (2013.01); *C07B 2200/13* (2013.01)

(58) Field of Classification Search

CPC ........ A61K 47/10; A61K 47/14; A61K 47/22; A61K 47/26; A61K 47/32; A61K 31/573; A61K 2300/00; A61K 9/0053; A61K 9/1635; A61K 9/1652; C07D 277/42; C07B 2200/13; A61P 5/00; C07C 209/52; C07C 249/02; C07C 259/06; C07C 211/29; C07C 251/24; G01N 33/74

See application file for complete search history.

(56) References Cited

U.S. PATENT DOCUMENTS

| | | | | |
|---|---|---|---|---|
| 6,365,180 | B1 | 4/2002 | Meyer et al. | |
| 6,531,475 | B1 | 3/2003 | Haddach et al. | |
| 6,586,456 | B1 | 7/2003 | Fontaine et al. | |
| 6,610,678 | B2 | 8/2003 | Huang et al. | |
| 6,664,261 | B2 | 12/2003 | Chen et al. | |
| 6,806,282 | B2 | 10/2004 | Geslin et al. | |
| 7,276,526 | B2 | 10/2007 | Termin et al. | |
| 7,297,708 | B2 | 11/2007 | Termin et al. | |
| 7,951,803 | B2 | 5/2011 | Cole et al. | |
| 8,030,304 | B2 | 10/2011 | Chen et al. | |
| 8,153,127 | B2 | 4/2012 | Paez-Pereda et al. | |
| 8,314,249 | B2 * | 11/2012 | Fazekas ................ | C07C 331/04 548/190 |
| 8,420,679 | B2 * | 4/2013 | Fontaine ................. | A61P 27/02 514/366 |
| 9,351,517 | B2 | 5/2016 | Bromley | |
| 10,849,908 | B2 | 12/2020 | Howerton et al. | |
| 10,905,690 | B2 * | 2/2021 | Grigoriadis ........ | A61K 31/4985 |
| 11,007,201 | B2 | 5/2021 | Howerton et al. | |
| 11,304,950 | B2 | 4/2022 | Howerton et al. | |
| 11,311,544 | B2 * | 4/2022 | Grigoriadis .......... | A61K 31/519 |
| 11,730,739 | B2 * | 8/2023 | Grigoriadis ............... | A61P 5/38 514/250 |
| 11,858,932 | B2 | 1/2024 | Barnes et al. | |
| 12,128,033 | B2 * | 10/2024 | Becker ................. | C07D 277/42 |
| 12,383,536 | B2 | 8/2025 | Smith et al. | |
| 2005/0209250 | A1 | 9/2005 | Romano | |
| 2006/0078623 | A1 | 4/2006 | Dhoot et al. | |
| 2007/0281919 | A1 | 12/2007 | Fontaine et al. | |
| 2009/0203755 | A1 | 8/2009 | Richard | |
| 2010/0216751 | A1 | 8/2010 | Jacob et al. | |
| 2010/0222339 | A1 | 9/2010 | Chen et al. | |
| 2013/0183383 | A1 | 7/2013 | Phang et al. | |
| 2015/0094310 | A1 | 4/2015 | Holsboer | |
| 2015/0284362 | A1 | 10/2015 | Bersot et al. | |
| 2017/0020877 | A1 | 1/2017 | Grigoriadis | |
| 2019/0231781 | A1 | 8/2019 | Grigoriadis | |
| 2020/0255436 | A1 | 8/2020 | Howerton et al. | |
| 2021/0137926 | A1 | 5/2021 | Grigoriadis | |
| 2021/0361659 | A1 | 11/2021 | Grigoriadis | |
| 2022/0023266 | A1 | 1/2022 | Farber et al. | |
| 2022/0133742 | A1 | 5/2022 | Ghosh et al. | |
| 2022/0211711 | A1 | 7/2022 | Howerton et al. | |
| 2022/0409592 | A1 | 12/2022 | Smith et al. | |
| 2023/0065034 | A1 | 3/2023 | Ashweek et al. | |
| 2023/0233534 | A1 | 7/2023 | Palmer et al. | |
| 2023/0255942 | A1 * | 8/2023 | Farber .................. | A61K 9/2018 |
| 2023/0295161 | A1 | 9/2023 | Barnes et al. | |
| 2024/0024330 | A1 | 1/2024 | Loewen et al. | |
| 2024/0058342 | A1 * | 2/2024 | Grigoriadis .......... | A61K 31/519 |
| 2024/0238257 | A1 | 7/2024 | Becker et al. | |

FOREIGN PATENT DOCUMENTS

| | | |
|---|---|---|
| CN | 102414185 | 4/2012 |
| CN | 106102740 | 11/2016 |
| CN | 107438606 | 12/2017 |
| JP | 2002-030048 | 1/2002 |
| JP | 4949582 | 3/2012 |
| JP | 2012-525368 | 10/2012 |
| JP | 2013-231063 | 11/2013 |
| JP | 2015-516979 | 6/2015 |
| JP | 2018-516231 | 6/2018 |
| RU | 2523793 | 7/2014 |
| RU | 2667977 | 9/2018 |
| WO | WO 1987/005297 | 9/1987 |
| WO | WO 1998/008846 | 3/1998 |
| WO | WO 1998/011075 | 3/1998 |
| WO | WO 1999/010350 | 3/1999 |
| WO | WO 2000/059888 | 10/2000 |
| WO | WO 2001/005776 | 1/2001 |
| WO | WO 2003/006015 | 1/2003 |
| WO | WO 2003/022820 | 3/2003 |
| WO | WO 2006/044821 | 4/2006 |
| WO | WO 2006/044958 | 4/2006 |
| WO | WO 2006/102194 | 9/2006 |
| WO | WO 2006/107784 | 10/2006 |
| WO | WO 2006/116412 | 11/2006 |
| WO | WO 2006/126718 | 11/2006 |
| WO | WO 2007/069565 | 6/2007 |
| WO | WO 2007/069671 | 6/2007 |
| WO | WO 2007/090631 | 8/2007 |
| WO | WO 2007/104053 | 9/2007 |
| WO | WO 2007/105113 | 9/2007 |
| WO | WO 2007/137227 | 11/2007 |
| WO | WO 2008/036541 | 3/2008 |
| WO | WO 2008/036579 | 3/2008 |
| WO | WO 2008/051533 | 5/2008 |
| WO | WO 2008/082003 | 7/2008 |
| WO | WO 2008/083070 | 7/2008 |
| WO | WO 2008/136377 | 11/2008 |
| WO | WO 2009/008552 | 1/2009 |
| WO | WO 2009/144632 | 12/2009 |
| WO | WO 2010/014280 | 2/2010 |
| WO | WO 2010/014687 | 2/2010 |
| WO | WO 2010/015628 | 2/2010 |
| WO | WO 2010/015655 | 2/2010 |
| WO | WO 2010/062718 | 6/2010 |
| WO | WO 2010/096426 | 8/2010 |
| WO | WO 2010/125414 | 11/2010 |
| WO | WO 2011/043381 | 4/2011 |
| WO | WO 2011/043387 | 4/2011 |
| WO | WO 2011/092290 | 8/2011 |
| WO | WO 2011/092293 | 8/2011 |
| WO | WO 2011/095450 | 8/2011 |
| WO | WO 2011/128783 | 10/2011 |
| WO | WO 2013/155464 | 10/2013 |
| WO | WO 2013/160315 | 10/2013 |
| WO | WO 2013/160317 | 10/2013 |
| WO | WO 2014/151109 | 9/2014 |
| WO | WO 2015/112642 | 7/2015 |
| WO | WO 2015/159170 | 10/2015 |
| WO | WO 2016/065177 | 4/2016 |
| WO | WO 2016/127133 | 8/2016 |
| WO | WO 2016/156576 | 10/2016 |
| WO | WO 2016156575 A2 | 10/2016 |
| WO | WO 2017/031325 | 2/2017 |
| WO | WO 2017218379 A1 | 12/2017 |
| WO | WO 2018/102552 | 6/2018 |
| WO | WO 2018213634 A1 | 11/2018 |

(56) References Cited

FOREIGN PATENT DOCUMENTS

| | | |
|---|---|---|
| WO | WO 2018/219804 | 12/2018 |
| WO | WO 2019/036472 | 2/2019 |
| WO | WO 2019/036503 | 2/2019 |
| WO | WO 2019/210266 | 10/2019 |
| WO | WO 2020/115555 | 6/2020 |
| WO | WO 2021/016208 | 1/2021 |
| WO | WO 2021/062246 | 4/2021 |
| WO | WO 2021/111179 | 6/2021 |
| WO | WO 2021/113263 | 6/2021 |
| WO | WO 2021/250468 | 12/2021 |
| WO | WO 2021/252669 | 12/2021 |
| WO | WO 2022/036123 | 2/2022 |
| WO | WO 2022/046905 | 3/2022 |
| WO | WO 2022/153062 | 7/2022 |
| WO | WO 2022/184549 | 9/2022 |

OTHER PUBLICATIONS

[No Author], "Guidance for Industry: Q3A Impurities in New Drug Substances," U.S. Department of Health and Human Services, Jun. 2008, 17 pages.

Auchus et al., "Crinecerfont Lowers Elevated Biomarkers of Disease Control in Adults with Congenital Adrenal Hyperplasia Due to 21-Hydroxylase Deficiency," submitted to Lancet Apr. 30, 2021, 33 pages.

Auchus et al., "Phase 3 Trial of Crinecerfont in Adult Congenital Adrenal Hyperplasia," The New England Journal of Medicine, Jun. 1, 2024, 11 pages.

Bastin et al., "Salt Selection and Optimisation Procedures for Pharmaceutical New Chemical Entities," Organic Process Research & Development, 2000, 4:427-435.

Boston University, "InterQuartile Range (IQR)," available on or before Oct. 31, 2013, via Internet Archive: Wayback Machine URL<https://web.archive.org/web/20131031075431/https://sphweb.bumc.bu.edu/otlt/mph-modules/bs/bs704_summarizingdata/bs704_summarizingdata7.html>, retrieved on Feb. 17, 2024, retrieved from URL<https://sphweb.bumc.bu.edu/otlt/mph-modules/bs/bs704_summarizingdata/bs704_summarizingdata7.html>, 3 pages.

Byrn et al., "Pharmaceutical Solids: A Strategic Approach to Regulatory Considerations," Pharmaceutical Research, 1995, 12(7):945-954.

Croce et al., "A Simple Procedure for N-Propenylation and N-Propynylation of Secondary Amines," Gazetta Chimica Italiana, 1996, 126(2):107-109.

De Villiers, "Pharmaceutical solvents and solubilizing agents," Pharmaceutical Excipients, Part 4, 2009, 15 pages.

De Villiers, "Vehicles for Liquid Preparations," A Practical Guide to Contemporary Pharmacy Practice, 3rd Editions, Jan. 2009, 22:267-276 pages.

Gupta al., "Formulation strategies to improve the bioavailability of poorly absorbed drugs with special emphasis on self-emulsifying systems," ISRN Pharmaceutics, 2013, pp. 1-16.

Habibzadeh, "Statistical Data Editing in Scientific Articles," Journal of Korean Medical Science, Jul. 2017, 32(7):1072-1076.

Hirayama, "[Handbook for manufacturing crystal of organic compound—principle and know-how]," Maruzen, Jul. 2008, 57-84 (with English translation).

Kojima, "[Effective solid form selection for the pharmaceutical development," Journal of Pharmaceutical Science and Technology, Sep. 1, 2008, 68(5):344-349 (with English translation).

Kumbhar et al., "D-α-tocopheryl polyethylene glycol succinate: A review of multifarious applications in nanomedicines," OpenNano, Mar. 2022, 6:100036, 13 pages.

Lee et al., "Standard deviation and standard error of the mean," Korean Journal of Anesthesiology, Jun. 2015, 68(3):220-223.

Li et al., "Use of Spray-Dried Dispersions in Early Pharmaceutical Development: Theoretical and Practical Challenges," AAPS J, Mar. 2017, 19:321-333.

Mercado-Asis et al., "Acute Effects of Bromocriptine, Cyproheptadine, and Valproic Acid on Plasma Adrenocorticotropin Secretion in Nelson's Syndrome," Journal of Clinical Endocrinology & Metabolism, 1997, 82(2):514-517.

*Neurocrine Biosciences, Inc.*, Petitioner, v. *Spruce Biosciences, Inc.*, Patent Owner, Case No. PGR2021-00088, U.S. Pat. No. 10,849,908, Decision Denying Institution of Post-Grant Review 35 U.S.C. § 324, filed Dec. 10, 2021, 36 pages.

*Neurocrine Biosciences, Inc.*, Petitioner, v. *Spruce Biosciences, Inc.*, Patent Owner, Case No. PGR2021-00088, U.S. Pat. No. 10,849,908, Decision Granting Institution of Post-Grant Review 35 U.S.C. § 324, filed Dec. 1, 2023, 57 pages.

*Neurocrine Biosciences, Inc.*, Petitioner, v. *Spruce Biosciences, Inc.*, Patent Owner, Patent Owner, Case No. PGR2021-00088, U.S. Pat. No. 10,849,908, Decision Vacating the Decision Denying Institution and Remanding to the Patent Trial and Appeal Board Panel for Further Proceedings, filed Aug. 4, 2023, 16 pages.

*Neurocrine Biosciences, Inc.*, Petitioner, v. *Spruce Biosciences, Inc.*, Patent Owner, Case No. PGR2021-00088, U.S. Pat. No. 10,849,908, Declaration of Adrian Dobs, M.D., M.H.S., filed Mar. 12, 2024, 68 pages.

*Neurocrine Biosciences, Inc.*, Petitioner, v. *Spruce Biosciences, Inc.*, Patent Owner, Case No. PGR2021-00088, U.S. Pat. No. 10,849,908, Declaration of Gordon B. Cutler, Jr., M.D. in Support of Petition for Post Grant Review of U.S. Pat. No. 10,849,908, filed Jan. 5, 2024, 228 pages.

*Neurocrine Biosciences, Inc.*, Petitioner, v. *Spruce Biosciences, Inc.*, Patent Owner, Case No. PGR2021-00088, U.S. Pat. No. 10,849,908, Deposition of Dr. Gordon B. Cutler, Jr., Washington, D.C., Thursday, Jul. 25, 2024, 207 pages.

*Neurocrine Biosciences, Inc.*, Petitioner, v. *Spruce Biosciences, Inc.*, Patent Owner, Case No. PGR2021-00088, U.S. Pat. No. 10,849,908, filed Mar. 12, 2024, 91 pages.

*Neurocrine Biosciences, Inc.*, Petitioner, v. *Spruce Biosciences, Inc.*, Patent Owner, Case No. PGR2021-00088, U.S. Pat. No. 10,849,908, filed on Jun. 20, 2024, 38 pages.

*Neurocrine Biosciences, Inc.*, Petitioner, v. *Spruce Biosciences, Inc.*, Patent Owner, Case No. PGR2021-00088, U.S. Pat. No. 10,849,908, filed on Jun. 27, 2024, 9 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner Spruce Biosciences' Motion To Exclude 37 C.F.R. §42.64(c), filed Aug. 14, 2024, 10 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner's Opposition To Petitioner's Motion to Exclude Evidence 37 C.F.R. §42.64, filed Aug. 20, 2024, 15 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner's Opposition to Petitioner's Motion to Strike, filed Aug. 28, 2024, 8 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner's Preliminary Response, filed Sep. 15, 2021, 57 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner's Reply in Support of its Motion to Exclude, filed Aug. 23, 2024, 8 pages.

*Neurocrine Biosciences, Inc.*, Petitioner, v. *Spruce Biosciences, Inc.*, Patent Owner, Case No. PGR2021-00088, U.S. Pat. No. 10,849,908, Patent Owner's Sur-Reply, filed Aug. 12, 2024, 36 pages.

*Neurocrine Biosciences, Inc.*, Petitioner, v. *Spruce Biosciences, Inc.*, Patent Owner, Case No. PGR2021-00088, U.S. Pat. No. 10,849,908, Petition for Post Grant Review of U.S. Pat. No. 10,849,908, filed May 28, 2021, 90 pages.

*Neurocrine Biosciences, Inc.*, Petitioner, v. *Spruce Biosciences, Inc.*, Patent Owner, Case No. PGR2021-00088, U.S. Pat. No. 10,849,908, Petitioner's Motion to Exclude Evidence, filed Aug. 14, 2024, 16 pages.

*Neurocrine Biosciences, Inc.*, Petitioner, v. *Spruce Biosciences, Inc.*, Patent Owner, Case No. PGR2021-00088, U.S. Pat. No. 10,849,908, Petitioner's Motion to Strike, filed Aug. 22, 2024, 13 pages.

(56) References Cited

OTHER PUBLICATIONS

*Neurocrine Biosciences, Inc.*, Petitioner, v. *Spruce Biosciences, Inc.*, Patent Owner, Case No. PGR2021-00088, U.S. Pat. No. 10,849,908, Petitioner's Opposition to Patent Owner's Motion to Exclude Evidence, filed Aug. 20, 2024, 19 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Reply in Support of Its Motion to Exclude Evidence, filed Aug. 23, 2024, 9 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Request for Rehearing, filed Jan. 10, 2022, 18 pages.
*Neurocrine Biosciences, Inc.*, Petitioner, v. *Spruce Biosciences, Inc.*, Patent Owner, Case No. PGR2021-00088, U.S. Pat. No. 10,849,908, Reply Declaration of Gordon B. Cutler, Jr., M.D., filed Jun. 20, 2024, 64 pages.
*Neurocrine Biosciences, Inc.*, Petitioner, v. *Spruce Biosciences, Inc.*, Patent Owner, Case No. PGR2022-00025, U.S. Pat. No. 11,007,201, Decision Denying Institution of Post-Grant Review 35 U.S.C. § 324(a), filed Sep. 15, 2022, 35 pages.
*Neurocrine Biosciences, Inc.*, Petitioner, v. *Spruce Biosciences, Inc.*, Patent Owner, Case No. PGR2022-00025, U.S. Pat. No. 11,007,201, Decision Granting Institution of Post-Grant Review 35 U.S.C. § 324(a), filed Dec. 1, 2023, 38 pages.
*Neurocrine Biosciences, Inc.*, Petitioner, v. *Spruce Biosciences, Inc.*, Patent Owner, Case No. PGR2022-00025, U.S. Pat. No. 11,007,201, Declaration of Adrian Dobs, M.D., M.H.S., filed Mar. 12, 2024, 63 pages.
*Neurocrine Biosciences, Inc.*, Petitioner, v. *Spruce Biosciences, Inc.*, Patent Owner, Case No. PGR2022-00025, U.S. Pat. No. 11,007,201, Declaration of Gordon B. Cutler, Jr., M.D. in Support of Petition for Post Grant Review of U.S. Pat. No. 11,007,201, filed Jan. 5, 2024, 224 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner Spruce Biosciences' Motion to Exclude 37 C.F.R. §42.64(c), filed Aug. 14, 2024, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Objections to Evidence, filed Jun. 27, 2024, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Objections to Evidence, filed on Dec. 15, 2023, 7 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Opposition to Petitioner's Motion to Exclude Evidence 37 C.F.R. §42.64, filed Aug. 20, 2024, 15 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Opposition to Petitioner's Motion to Strike, filed Aug. 28, 2024, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Pre-Institution Sur-Reply, filed Jul. 28, 2022, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Preliminary Response, filed Jun. 17, 2022, 72 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Reply in Support of Its Motion to Exclude, filed Aug. 23, 2024, 7 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Response, filed Mar. 12, 2024, 93 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Sur-Reply, filed Aug. 12, 2024, 33 pages.
*Neurocrine Biosciences, Inc.*, Petitioner, v. *Spruce Biosciences, Inc.*, Patent Owner, Case No. PGR2022-00025, U.S. Pat. No. 11,007,201, Petition for Post Grant Review of U.S. Pat. No. 11,007,201, filed Feb. 18, 2022, 92 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion to Exclude Evidence, filed Aug. 14, 2024, 16 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion to Strike, filed Aug. 22, 2024, 14 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections to Evidence, filed Aug. 19, 2024, 4 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections to Evidence, filed Mar. 19, 2024, 6 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Opposition to Patent Owner's Motion to Exclude Evidence, filed Aug. 20, 2024, 15 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply in Support of its Motion to Exclude Evidence, filed Aug. 23, 2024, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply to Patent Owner's Preliminary Response, filed Jul. 14, 2022, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply to Patent Owner's Response, filed Jun. 20, 2024, 36 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Request for Rehearing, filed Oct. 13, 2022, 17 pages.
*Neurocrine Biosciences, Inc.*, Petitioner, v. *Spruce Biosciences, Inc.*, Patent Owner, Patent Owner, Case No. PGR2022-00025, U.S. Pat. No. 11,007,201, Reply Declaration of Gordon B. Cutler, Jr., M.D., filed Jun. 20, 2024, 60 pages.
*Neurocrine Biosciences, Inc.*, Petitioner, v. *Spruce Biosciences, Inc.*, Patent Owner, Case Nos. PGR2021-00088 and PGR2022-00025, U.S. Pat. No. 10,849,908 and U.S. Pat. No. 11,007,201, "Transcript of Feb. 29, 2024 Deposition of Gordon B. Cutler, Jr., M.D.," filed on Mar. 12, 2024, 147 pages.
*Neurocrine Biosciences, Inc.*, Petitioner, v. *Spruce Biosciences, Inc.*, Patent Owner, Case Nos. PGR2021-00088 and PGR2022-00025, U.S. Pat. No. 10,849,908 and U.S. Pat. No. 11,007,201, "Transcript of Jun. 5, 2024 Deposition of Dr. Adrian Dobs," filed on Jun. 20, 2024, 169 pages.
Newfield et al., "ACTH receptor blockade: A novel approach to treat congenital adrenal hyperplasia, or Cushing's disease," Medical Hypotheses, Apr. 2010, 74(4):705-706.
Recto II et al., "Comparison of the Efficacy and Tolerability of Simvastatin and Atorvastatin in the Treatment of Hypercholesterolemia," Clinical Cardiology, 2000, 23(9):682-688.
Saal et al., "Pharmaceutical salts: A summary on doses of salt formers from the Orange Book," European Journal of Pharmaceutical Sciences, Jul. 16, 2013, 49(4):614-623.
Souron, "New Introduction of Pharmacology," Nanzando Co., 3rd edition, 1987, p. 414-416 (with English translation).
Yanovski et al., "Etiology of the Differences in Corticotropin-Releasing Hormone-Induced Adrenocorticotropin Secretion of Black and White Women," Journal of Clinical Endocrinology & Metabolism, 1996, 81(9):3307-3311.
[No Author Listed], "Assessing the Effects of Food on Drugs in INDs and NDAs—Clinical Pharmacology Considerations Guidance for Industry," U.S. Department of Health and Human Services, Food and Drug Administration, Center for Drug Evaluation and Research (CDER), Feb. 2019, Clinical Pharmacology, 17 pages.
[No Author Listed], "Form 8-K: Current Report," Securities and Exchange Commission, Washington, D.C., Apr. 5, 2000, 4 pages.

(56) References Cited

OTHER PUBLICATIONS

[No Author Listed], "IUPAC-IUB, Commission on Biochemical Nomenclature—Abbreviated Nomenclature of Synthetic Polypeptides (Polymerized Amino Acids)*—Revised Recommendations (1971)," Biochemistry, 1972, 11(5):942-944.
[No Author Listed], "Neurocrine announces top-line results of corticotropin releasing factor antagonist GSK561679 for treatment of major depressive disorder," Neurocrine Biosciences, Inc., Sep. 14, 2010, 1 page.
[No Author Listed], "Sanofi-Aventis: strong performance of growth platforms in Q1 2011," Sanofi Press Release, Apr. 28, 2011, 13 pages.
[No Author Listed], "Neurocrine Biosciences Reports Positive Phase II Data for Crinecerfont in Adults with Congenital Adrenal Hyperplasia at ENDO Online 2020," Neurocrine Biosciences Inc., Jun. 8, 2020, 3 pages.
[No Author Listed], "Neurocrine Biosciences to Present New Data Analyses for Crinecerfont in Adults with Classical Congenital Adrenal Hyperplasia at ENDO 2021," Neurocrine Biosciences Inc., Mar. 20, 2021, 5 pages.
[No Author Listed], "Spruce Biosciences Presents Phase 1 and 2 Data for Tildacerfont in Adults with Congenital Adrenal Hyperplasia from Endocrine Society's 2021 Annual Meeting," Spruce Biosciences, Mar. 17, 2021, 2 pages.
Abdellatif, "Microparticles Formulation as a Targeting Drug Delivery System," J Nanomed Res., 2017, 6(2):00151.
Alejandro et al., "Behavioral, Adrenal, and Sympathetic Responses to Long-Term Administration of an Oral Corticotropin-Releasing Hormone Receptor Antagonist in a Primate Stress Paradigm," The Journal of Clinical Endocrinology & Metabolism, Nov. 1, 2004, 89(11):5729-5737.
Allen et al., "Psychometric evaluation and tests of validity of the Medical Outcomes Study 12-item Sleep Scale (MOS sleep)," Sleep Medicine, May 1, 2009;10(5):531-9.
Ambroziak et al., "Congenital adrenal hyperplasia due to 21-hydroxylase deficiency—management in adults," Polish Journal of Endocrinology, 2010, 61:142-155.
Anthenelli et al., "Sex Differences in the ACTH and Cortisol Response to Pharmacological Probes are Stressor-Specific and Occur Regardless of Alcohol Dependence History," Psychoneuroendocrinology, Aug. 2018, 94:72-82.
Arlt et al., "Health status of adults with congenital adrenal hyperplasia: a cohort study of 203 patients," J Clin Endocrinol Metab., Nov. 2010, 95(11):5110-21.
Arvanitis, AG., et al., "Non-Peptide Corticotropin-Releasing Hormone Antagonists: Syntheses and Structure—Activity Relationships of 2-Anilinopyrimidines and -triazines," J. Med. Chem., 1999, 42(5): 805-818.
Auchus et al., "A pharmacokinetic and biomarker study of the corticotropin-releasing factor receptor antagonist NBI-77860 in adult females with classic, 21-hydroxylase deficiency, congenital adrenal hyperplasia (CAH)," OR06 HPA Axis and Adrenal: Receptors To Clinical Impact, Platform presentation at the 97th annual meeting of the Endocrine Society (ENDO 2015), Mar. 2015, 1 page.
Auchus et al., "Approach to the patient: the adult with congenital adrenal hyperplasia," J Clin Endocrinol Metab., Jul. 2013, 98(7):2645-55.
Auchus et al., "Crinecerfont (NBI-74788), a novel CRF1 receptor antagonist, reduces adrenal androgens and precursors in patients with classic congenital adrenal hyperplasia: Results from a phase 2, multiple-dose study," Poster Presentation, Presented Virtually at The 22nd European Congress of Endocrinology, Sep. 5-9, 2020, 1 page.
Auchus et al., "Crinecerfont lowers elevated hormone markers in adults with 21-hydroxylase deficiency congenital adrenal hyperplasia," The Journal of Clinical Endocrinology & Metabolism, 2022, 107(3):801-812.
Auchus et al., "OR18-4 Crinecerfont (NBI-74788), a Novel CRF1 Receptor Antagonist, Lowers Adrenal Androgens and Precursors in Adolescents with Classic Congenital Adrenal Hyperplasia," Journal of the Endocrine Society, 2022, 6(Supplement_1):A618.
Auchus et al., "Response to Crinecerfont Treatment in Adults with Classic Congenital Adrenal Hyperplasia Is Correlated with Elevated Baseline Hormone Levels But Not Glucocorticoid Dose," Abstract submitted to ECE for consideration at 2023 annual meeting, prepared on Mar. 2023, 2 pages.
Auchus et al., "The Effects of Crinecerfont (NBI-74788), a Novel CRF1 Receptor Antagonist, on Adrenal Androgens and Precursors in Patients with Classic Congenital Adrenal Hyperplasia: Results from A Multiple-Dose Phase 2 Study," J Endocrin Soc., 2020, 4(Supplement 1):OR25-03.
Auchus et al., "The effects of crinecerfont (NBI-74788), a novel CRF1 receptor antagonist, on adrenal androgens and precursors in patients with classic congenital adrenal hyperplasia: Results from a multiple-dose phase 2 study," Journal of the Endocrine Society, 2020, 4(Abstract Supplement):A111.
Auchus RJ, et al., "Management of the adult with congenital adrenal hyperplasia," Int J Ped Endocrinol., 2010, Article ID 614107: 1-9.
Bachelot A, et al., "Bone health should be an important concern in the care of patients affected by 21 hydroxylase deficiency," Int J Ped Endocrinol., 2010, Article ID 326275: 1-7.
Bakshi VP, et al., "Reduction of Stress-Induced Behavior by Antagonism of Corticotropin-Releasing Hormone 2 (CRH2) Receptors in Lateral Septum or CRH1 Receptors in Amygdala", J. Neurosci., 2002, 22(7): 2926-2935.
Bale et al., "Overview on Therapeutic Applications of Microparticulate Drug Delivery Systems," Crit Rev Ther Drug Carrier Syst., 2016, 33(4):309-361.
Barreau F. et al., "Pathways involved in gut mucosal barrier dysfunction induced in adult rats by maternal deprivation: corticotrophin-releasing factor and nerve growth factor interplay," Journal of Physiology—London, 2007, 580(1):347-356.
Behan DP et al., "Neurobiology of corticotropin releasing factor (CRF) receptors and CRF-binding protein: implications for the treatment of CNS disorders," Molecular Psychiatry, 1996, 1(4):265-277.
Belza et al., "A systematic review of studies using the multidimensional assessment of fatigue scale," Journal of Nursing Measurement, May 1, 2018;26(1):36-74.
Belza, "Comparison of self-reported fatigue in rheumatoid arthritis and controls," J Rheumatol., Apr. 1995, 22(4):639-643.
Benedetti et al., "The Biochemical and Neuroendocrine Bases of the Hyperalgesic Nocebo Effect," J Neurosci., Nov. 15, 2006, 26(46):12014-12022.
Berge et al., "Pharmaceutical salts," Journal of Pharmaceutical Sciences, 1977, 66(1):1-9.
Bleicken B, et al., "Improvement of health-related quality of life in adult women with 21-hydroxylase deficiency over a seven-year period," Endocr J., 2012, 59(10):931-939.
Blume et al., "Oral medicine acceptance in infants and toddlers: measurement properties of the caregiver-administered Children's acceptance tool (CareCAT)," BMC pediatrics, 2018, 18:117.
Bonfig et al., "Reduced final height outcome in congenital adrenal hyperplasia under prednisone treatment: deceleration of growth velocity during puberty," J Clin Endocrinol Metab., May 2007, 92(5):1635-1639.
Bonfig W. et al., "Hydrocortisone Dosing During Puberty in Patients With Classical Congenital Adrenal Hyperplasia: An Evidence-Based Recommendation," J Clin Endocrinol Metab., 2009, 94(10):3882-3888.
Bornstein et al., "Chronic effects of a nonpeptide corticotropin-releasing hormone type I receptor antagonist on pituitary-adrenal function, body weight, and metabolic regulation," Endocrinology, 1998, 139(4):1546-1555.
Brazier et al., "Validating the SF-36 health survey questionnaire: new outcome measure for primary care," BMJ, Jul. 18, 1992, 305(6846):160-164.
Brunson KL, et al., "Corticotropin-Releasing Hormone (CRH) Downregulates the Function of Its Receptor (CRF1) and Induces CRF1 Expression in Hippocampal and Cortical Regions of the Immature Rat Brain," Experimental Neurology, 2002, 176(1):75-86.

(56) References Cited

OTHER PUBLICATIONS

Buxton et al., "Pharmacokinetics: The Dynamics of Drug Absorption, Distribution, Metabolism, and Elimination," Goodman & Gilman's The Pharmacological Basis of Therapeutics., Brunton L.L. ed., 12th ed. 2011, Chapter 2, 29 pages.
Caira, "Crystalline polymorphism of organic compounds," Design of Organic Solids, 1998, pp. 163-208.
Caresfoundation.org [Online], "Emergency Instructions—Treatment for Congenital Adrenal Hyperplasia in times of stress," 2014, [retrieved on Mar. 6, 2023], retrieved from: URL<https://caresfoundation.org/wp-content/uploads/2014/08/EmergencyBrochure2014.pdf>, 2 pages.
CAS Registry No. 321839-75-2, Feb. 15, 2001, 1 page.
Chakhtoura Z. et al., "Impact of total cumulative glucocorticoid dose on bone mineral density in patients with 21-hydroxylase deficiency," Eur J Endocrinol., 2008, 158(6):879-887.
Charmandari et al., "Bioavailability of oral hydrocortisone in patients with congenital adrenal hyperplasia due to 21-hydroxylase deficiency," J Endocrinol, Apr. 2001, 169(1):65-70.
Chatzaki, E, et al., "CRF receptor type 1 and 2 expression and anatomical distribution in the rat colon," Journal of Neurochemistry, 2004, 90: 309-316.
Chen C, et al., "NBI 30775 (R121919), an Orally Active Antagonist of the Corticotropin-releasing Factor (CRF) Type-1 Receptor for the Treatment of Anxiety and Depression," Drug Development Research, 2005, 65(4):216-226.
Chen C, et al., "1-Alkyl-3-amino-5-aryl-1H-[1,2,4]triazoles: novel synthesis via cyclization of N-Acyl-S-methylisothioureas with alkylhydrazines and their potent corticotropin-Releasing factor-1 (CRF1) receptor antagonist activities," Bioorganic & Medicinal Chemistry Letters, 2001, 11(24): 3165-3168.
Chen C, et al., "Design and Synthesis of a Series of Non-Peptide High-Affinity Human Corticotropin-Releasing Factor1 Receptor Antagonists," J. Med. Chem., 1996, 39(22): 4358-4360.
Chen C, et al., "Optimization of 3-phenylpyrazolo[1,5-a]pyrimidines as potent corticotropin-releasing factor-1 antagonists with adequate lipophilicity and water solubility" Bioorganic & Medicinal Chemistry Letters, 2004, 14(14): 3669-3673.
Chen et al., "Design of 2,5-dimethyl-3-(6-dimethyl-4-methylpyridin-3-yl)-7-dipropylaminopyrazolo[1,5-a] pyrimidine (NBI 30775/R121919) and structure-activity relationships of a series of potent and orally active corticotropin-releasing factor receptor antagonists," Journal of Medicinal Chemistry, 2004, 47(19):4787-4798.
Chen Y, et al., "Cellular and molecular mechanisms of hippocampal activation by acute stress are age-dependent," Molecular Psychiatry, 2006, 11: 992-1002.
Chen Y, et al., "Modulation of dendritic differentiation by corticotropin-releasing factor in the developing hippocampus," Proceedings of the National Academy of Sciences, 2004, 101(44): 15782-15787.
Cheng and Speiser, "Treatment outcomes in congenital adrenal hyperplasia," Adv Pediatr., 2012, 59(1):269-281.
Claahsen-van der Grinten et al., "Prevalence of testicular adrenal rest tumours in male children with congenital adrenal hyperplasia due to 21-hydroxylase deficiency," Eur J Endocrinol., Sep. 2007, 157(3):339-344.
Claustre et al., "Effects of the Vasopressin ($V_{1b}$) Receptor Antagonist, SSR149415, and the Corticotropin-Releasing Factor 1 Receptor Antagonist, SSR125543, on FG 7142-induced Increase in Acetylcholine and Norepinephrine Release in the Rat," Neuroscience, 2006, 141:1481-1488.
Clinicaltrials.gov [Online], "Safety, Tolerability, Pharmacokinetics, and Pharmacodynamics of NBI-74788 in Pediatric Subjects With Congenital Adrenal Hyperplasia," First Posted Aug. 5, 2019, [Retrieved on Nov. 30, 2022], retrieved from: URL<https://clinicaltrials.gov/ct2/show/NCT04045145>, 7 pages.
Clinicaltrials.gov, "A study in patients with irritable bowel syndrome to measure hormone response after dosing with GW876008 and Gsk561679," U.S. National Library of Medicine, Aug. 6, 2007, retrieved on Jun. 11, 2020, retrieved from URL: https://clinicaltrials.gov/ct2/show/NCT00511563?term=NCT00511563&draw=1&rank=1, 5 pages.
Clinicaltrials.gov, "A study of the effects of a new antidepressant treatment (GSK561679) in females with major depressive disorder," U.S. National Library of Medicine, Aug. 13, 2008, retrieved on Jun. 11, 2020, retrieved from URL: https://clinicaltrials.gov/ct2/show/NCT00733980?term=NCT00733980&draw=2&rank=1, 14 pages.
Clinicaltrials.gov, "A study to compare the putative anxiolytic effect of 2 new drugs in subjects with social anxiety disorder," U.S. National Library of Medicine, Nov. 7, 2007, retrieved on Jun. 11, 2020, retrieved from URL: https://clinicaltrials.gov/ct2/show/NCT00555139?term=NCT00555139&draw=2&rank=1, 10 pages.
Clinicaltrials.gov, "CRF1 antagonist GSK561679 in alcoholism," U.S. National Library of Medicine, Aug. 24, 2010, retrieved on Sep. 25, 2020, retrieved from URL: https://clinicaltrials.gov/ct2/show/NCT01187511?term=NCT01187511&draw=2&rank=1, 20 pages.
Clinicaltrials.gov, "Evaluation of GSK561679 in women with post-traumatic stress disorder," U.S. National Library of Medicine, Nov. 25, 2009, retrieved on Jun. 11, 2020, retrieved from URL: https://clinicaltrials.gov/ct2/show/NCT01018992?term=NCT01018992&draw=2&rank=1, 9 pages.
Collier et al., "Radiosynthesis and In-Vivo Evaluation of the Pseudopeptide δ-Opioid Antagonist [$^{125}$]-ITIPP(Ψ)," XIIIth International Symposium on Radiopharmaceutical Chemistry, J. Labelled Cpd. Radiopharm., 1999, 42(Suppl. 1):S264-S266.
Cottone P, et al., "CRF system recruitment mediates dark side of compulsive eating," Proceedings of the National Academy of Sciences, 2009, 106(47): 20016-20020.
Cui et al., "Modification of sample size in group sequential clinical trials," Biometrics, 1999, 55(3):853-857.
Curtis AL, et al., "Pharmacological comparison of two corticotropin-releasing factor antagonists: in vivo and in vitro studies," Journal of Pharmacology and Experimental Therapeutics, 1994, 268(1): 359-365.
Dai et al., "A Generic Headspace GC Method for Residual Solvents in Pharmaceuticals: Benefits, Rationale, and Adaptations for New Chemical Entities," LCGC North America, 2010, 28(1):54-66.
Dauber et al., "Nocturnal dexamethasone versus Hydrocortisone for the treatment of children with congenital adrenal hyperplasia," Int. J. of Pediatric Endocrinology, 2010, 2010(1):347636.
De Vries et al., "Mental health of a large group of adults with disorders of sex development in six European countries," Psychosomatic Medicine, 2019, 81(7):629-640.
Deak et al., "The impact of the nonpeptide corticotropin-releasing hormone antagonist antalarmin on behavioral and endocrine responses to stress," Endocrinology, 1999, 140(1):79-86.
Derendorf et al., "Pharmacokinetics and oral bioavailability of hydrocortisone," J Clin Pharmacol. May 1991, 31(5):473-476.
Douma et al., "CRF1 receptor antagonists do not reverse pharmacological disruption of prepulse inhibition in rodents," Psychopharmacology, 2014, 231:1289-1303.
Dournes et al., "Deep brain stimulation in treatment-resistant depression in mice: comparison with the $CRF_1$ antagonist, SSR125543," Progress in Neuro-Psychopharmacology & Biological Psychiatry, 2013, 40:213-220.
Doyon et al., "Effects of the $CRF_1$ receptor antagonist SSR125543 on energy balance and food deprivation-induced in neuronal activation in obese Zucker rats," J. of Endocrinology, 2007, 193:11-19.
Dudzinska B, et al., "Sexual Well-Being in Adult Male Patients with Congenital Adrenal Hyperplasia," Int J Endocrinol., 2014, ID 469289: 1-9.
Dunn et al., "Physiological and behavioral responses to corticotropin-releasing factor administration: is CRF a mediator of anxiety or stress responses?" Brain Res Brain Res Rev., May-Aug. 1990, 15(2):71-100.
Dyck B, et al., "Potent, Orally Active Corticotropin-Releasing Factor Receptor-1 Antagonists Containing a Tricyclic Pyrrolopyridine or Pyrazolopyridine Core," J. Med. Chem., 2005, 48(12): 4100-4110.
Elder et al., "The utility of sulfonate salts in drug development," Journal of Pharmaceutical Sciences, Jan. 1, 2010, 99(7):2948-2961.

(56) References Cited

OTHER PUBLICATIONS

El-Maouche et al., "Adrenal morphology and associated comorbidities in congenital adrenal hyperplasia," Clinical Endocrinology, 2019, 91(2):247-255.
El-Maouche et al., "Longitudinal assessment of illnesses, stress dosing, and illness sequelae in patients with congenital adrenal hyperplasia," The Journal of Clinical Endocrinology & Metabolism, 2018, 103(6):2336-2345.
El-Maouche et al., "Congenital Adrenal Hyperplasia," Lancet., Nov. 11, 2017, 390:2194-2210.
Elnecave et al., "Bone mineral density in girls with classical congenital adrenal hyperplasia due to CYP21 deficiency," J Pediatr Endocrinol Metab., Dec. 2008, 21(12):1155-62.
Esteban et al., "Daily cortisol production rate in man determined by stable isotope dilution/mass spectrometry," J Clin Endocrinol Metab., Jan. 1991, 72(1):39-45.
EU Clinical Trials Register, "Abbreviated Style Clinical Study Report," Sanofi-Aventis Group, Sep. 5, 2011, 4 pages.
Fahmy et al., "Structure and Function of Small Non-Peptide CRF Antagonists and their Potential Clinical Use," Curr Mol Pharmacol., 2017, 10(4):270-281.
Falhammar et al., "Fertility, sexuality and testicular adrenal rest tumors in adult males with congenital adrenal hyperplasia," Eur J Endocrinol., Mar. 2012, 166(3):441-449.
Falhammar et al., "Fractures and bone mineral density in adult women with 21-hydroxylase deficiency," J Clin Endocrinol Metab. Dec. 2007; 92(12):4643-4649.
Falhammar et al., "Increased mortality in patients with congenital adrenal hyperplasia due to 21-hydroxylase deficiency," J Clin Endocrinol Metab., Dec. 2014, 99(12):E2715-21.
Falhammar et al., "Quality of life, social situation, and sexual satisfaction, in adult males with congenital adrenal hyperplasia," Endocrine, 2014, 47:299-307.
Finkielstain et al., "Clinical Characteristics of a Cohort of 244 Patients with Congenital Adrenal Hyperplasia," J Clin Endocrinol Metab, 2012, 97(12):4429-4438.
Fleck et al., "Binding Kinetics Redefine the Antagonist Pharmacology of the Corticotropin-Releasing Factor Type 1 Receptor," The Journal of Pharmacology and Experimental Therapeutics, 2012, 341(2):518-531.
Forest, "Recent advances in the diagnosis and management of congenital adrenal hyperplasia due to 21-hydroxylase deficiency," Human Reproduction Update, 2004, 10(6): 469-485.
Frederic et al., "Radiosynthesis of [C-11]SSR126374, a new selective CRF1 antagonist," Journal of Labelled Compounds & Radiopharmaceuticals, 2011, 54(1):273.
Fuqua et al., "Duration of suppression of adrenal steroids after glucocorticoid administration," International Journal of Pediatric Endocrinology, 2010, 2010:1-8.
Gilban D, et al., "Health related quality of life of children and adolescents with congenital hyperplasia in Brazil," Health Qual Life Outcomes, 2014, 12:107 (9 pages).
Gilligan et al., "Corticotropin-releasing factor antagonists: recent advances and exciting prospects for the treatment of human diseases," Curr. Opin. In Drug Discov. & Develop., 2004, 7(4)487-497.
Grammatopoulos et al., Functional characteristics of CRH receptors and potential clinical applications of CRH-receptor antagonists, Trends in Endocrinology & Metabolism, 2002, 13(10):436-444.
Griebel et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine Hydrochloride (SSR125543A), a Potent and Selective Corticotrophin-Releasing factor(1) Receptor Antagonist. II. Characterization in Rodent Models of Stress-Related Disorders," J. Pharmacol. Exp. Ther., 2002, 301(1):333-345.
Grigoriadis DE, "Corticotropin-Releasing Factor Receptor Antagonists: Potential Novel Therapies for Human Disease," Celltransmissions, 2003, 19(4): 3-10.
Grigoriadis DE, "The corticotropin-releasing factor receptor: a novel target for the treatment of depression and anxiety-related disorders," Expert Opin. Ther. Targets, 2005, 9(4): 651-684.
Grigoriadis DE, et al., "$^{125}$I-Tyr$^0$-Sauvagine: A Novel High Affinity Radioligand for the Pharmacological and Biochemical Study of Human Corticotropin-Releasing Factor $_{2\alpha}$ Receptors," Molecular Pharmacology, 1996, 50:679-686.
Grigoriadis DE, et al., "Drugability of Extracellular Targets: Discovery of Small Molecule Drugs Targeting Allosteric, Functional, and Subunit-Selective Sites on GPCRs and Ion Channels," Neuropsychopharmacology, 2009, 34: 106-125.
Grigoriadis, DE, et al., "The CRF Receptor Structure, Function and Potential for Therapeutic Intervention," Current Medicinal Chemistry—Central Nervous System Agents, 2001, 1(1): 63-97.
Gross RS, et al., "Design and Synthesis of Tricyclic Corticotropin-Releasing Factor-1 Antagonists," J. Med. Chem., 2005, 48(18): 5780-5793.
Grossi et al., "Development and validation of the short version of the Psychological General Well-Being Index (PGWB-S)," Health and Quality of Life Outcomes, 2006, 4(1):1-8.
Gully et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine hydrochloride (SSR125543A): A potent and selective corticotrophin-releasing factor$_1$ receptor antagonist. I. Biochemical and Pharmacological Characterization," Journal of Pharmacology and Experimental Therapeutics, 2002, 301(1):322-332.
Guo Z, et al., "Design and Synthesis of Tricyclic Imidazo[4,5-b]pyridin-2-ones as Corticotropin-Releasing Factor-1 Antagonists," J. Med. Chem., 2005 , 48(16): 5104-5107.
Habib et al., "Oral administration of a corticotropin-releasing hormone receptor antagonist significantly attenuates behavioral, neuroendocrine, and autonomic responses to stress in primates," Proceedings of the National Academy of Sciences, 2000, 97(11):6079-6084.
Halper et al., "Health-related quality of life in children with congenital adrenal hyperplasia," Health Qual. Life Outcomes, 2017, 15(1):194.
Hamilton, "Needle Phobia: A Neglected Diagnosis," J Fam Pract., Aug. 1995, 41(2):169-175.
Han et al., "Quality of life in adults with congenital adrenal hyperplasia relates to glucocorticoid treatment, adiposity and insulin resistance: United Kingdom Congenital Adrenal Hyperplasia Adult Study Executive (CaHASE)" Eur J Endocrinol., May 3, 2013, 168(6):887-893.
Han TS, et al., "Glucocorticoid treatment regimen and health outcomes in adults with congenital adrenal hyperplasia," Clin Endocrinol, 2013, 8:197-203.
Han TS, et al., "Relationship Between Final Height and Health Outcomes in Adults with Congenital Adrenal Hyperplasia: United Kingdom Congenital Adrenal Hyperplasia Adult Study Executive (CaHASE)," J Clin Endocrinol Metab., 2014, 99(8):E1547-E1555.
Han TS, et al., "Treatment and health outcomes in adults with congenital adrenal hyperplasia," Nat Rev Endocrinol., 2014, 10:115-124.
Hannah-Shmouni et al., "Genetics of Congenital Adrenal Hyperplasia," Best Pract Res Clin Endocrinol Metab., Apr. 2009, 23(2):181-192.
Hauger RL, et al., "International Union of Pharmacology. XXXVI. Current Status of the Nomenclature for Receptors for Corticotropin-Releasing Factor and Their Ligands," Pharmacological Reviews, 2003, 55(1): 21-26.
He et al., "Changes in adrenal and gonadal androgens after 14-day treatment with a CRF1 receptor antagonist, crinecerfont (NBI-74788), in men with classic 21-hydroxylase deficiency," Journal of the Endocrine Society, 2021, 5(Supplement_1):A78.
Heike et al., "Treatment of depression with the CRH-1-receptor antagonist R121919: endocrine changes and side effects", J Psych Res., Nov. 1, 2003, 37(8):525-533.
Heinrichs SC, et al., "Brain Penetrance, Receptor Occupancy and Antistress In Vivo Efficacy of a Small Molecule Corticotropin Releasing Factor Type I Receptor Selective Antagonist," Neuropsychopharmacology, 2002, 27:194-202.
Herdman et al., "Development and preliminary testing of the new five-level version of EQ-5D (EQ-5D-5L)," Qual Life Res., Dec. 2011, 20(10):1727-1736.

(56) References Cited

OTHER PUBLICATIONS

Hertzberg et al., "Birth prevalence rates of newborn screening disorders in relation to screening practices in the United States," J Pediatr., Oct. 2011, 159(4):555-560.
Hines et al., "Spatial abilities following prenatal androgen abnormality: targeting and mental rotations performance in individuals with congenital adrenal hyperplasia," Psychoneuroendocrinology, Nov. 2003, 28(8):1010-1026.
Hoare et al., "Mechanism of Corticotropin-Releasing Factor Type I Receptor Regulation by Nonpeptide Antagonists," Molecular Pharmacology, 2003, 63(3):751-756.
Hoare SRJ, et al., "Allosteric Ligands for the Corticotropin Releasing Factor Type 1 Receptor Modulate Conformational States Involved in Receptor Activation," Molecular Pharmacology, 2008, 73(5): 1371-1380.
Hoare SRJ, et al., "Conformational states of the corticotropin releasing factor 1 (CRF1) receptor: detection, and pharmacological evaluation by peptide ligands," Peptides, 2003, 24(12): 1881-1897.
Hoare SRJ, et al., "Ligand Affinity for Amino-Terminal and Juxtamembrane Domains of the Corticotropin Releasing Factor Type I Receptor: Regulation by G-Protein and Nonpeptide Antagonists," Biochemistry, 2004, 43(13): 3996-4011.
Hoare SRJ, et al., "Single amino acid residue determinants of non-peptide antagonist binding to the corticotropin-releasing factor1 (CRF1) receptor," Biochemical Pharmacology, 2006, 72(2): 244-255.
Holm, "A simple sequentially rejective multiple test procedure," Scandinavian Journal of Statistics, 1979, 65-70.
Huang CQ, et al., "Design and synthesis of 3-(2-pyridyl)pyrazolo[1,5-a]pyrimidines as potent CRF1 receptor antagonists," Bioorganic & Medicinal Chemistry Letters, 2004, 14(15): 3943-3947.
Huang CQ, et al., "Design, synthesis, and SAR of 2-dialkylamino-4-arylpyrimidines as potent and selective corticotropin-releasing factor1 (CRF1) receptor antagonists," Bioorganic & Medicinal Chemistry Letters, 2004, 14(9): 2083-2086.
Huang CQ, et al., "Synthesis and SAR of 8-Arylquinolines as potent corticotropin-Releasing factor1 (CRF1) receptor antagonists," Bioorganic & Medicinal Chemistry Letters, 2003, 13(19): 3375-3379.
Huang CQ, et al., "Synthesis of 1-methyl-3-phenylpyrazolo[4,3-b]pyridines via a methylation of 4-phthalimino-3-phenylpyrazoles and optimization toward highly potent corticotropin-releasing factor type-1 antagonists," Bioorganic & Medicinal Chemistry Letters, 2003, 13(19): 3371-3374.
Iranmanesh et al., "Glucose Ingestion Selectively Amplifies ACTH and Cortisol Secretory-Burst Mass and Enhances Their Joint Synchrony in Healthy Men," J Endocrinol and Metab., Sep. 2011, 96(9):2882-2888.
Ising M, et al., "High-Affinity CRF1 Receptor Antagonist NBI-34041: Preclinical and Clinical Data Suggest Safety and Efficacy in Attenuating Elevated Stress Response," Neuropsychopharmacology, 2007, 32:1941-1949.
Ivy AS, et al., "Hippocampal Dysfunction and Cognitive Impairments Provoked by Chronic Early-Life Stress Involve Excessive Activation of CRH Receptors," J. Neurosci., 2010, 30(39):13005-13015.
Jain et al., "Spray Drying in Pharmaceutical Industry: A review," Research Journal of Pharmaceutical Dosage Forms and Technology, Apr. 10, 2012, 4(2):74-79.
Jenkins-Jones et al., "Poor compliance and increased mortality, depression and healthcare costs in patients with congenital adrenal hyperplasia," European Journal of Endocrinology, 2018, 178(4):309-320.
Jha et al., "SUN-371 Successful Induction of Fertility with Low-Dose Dexamethasone in a Patient with Congenital Adrenal Hyperplasia and Testicular Adrenal Rest Tumor," Journal of the Endocrine Society, 2019, 3(Supplement_1):SUN-371.
Johannsen et al., "Impaired cognitive function in women with congenital adrenal hyperplasia," J Clin Endocrinol Metab., Apr. 2006, 91(4):1376-1381.
Katkade et al., "Real world data: an opportunity to supplement existing evidence for the use of long-established medicines in health care decision making," J Multidiscip Healthc., 2018, 11:295-304.
Kehne et al., "Therapeutic Utility of Non-Peptidic $CRF_1$ Receptor Antagonists in Anxiety, Depression, and Stress-Related Disorders: Evidence from Animal Models," Pharmacol Ther., Dec. 2010; 128(3):460-487.
Kiddoo DA, et al., "Impact of state of arousal and stress neuropeptides on urodynamic function in freely moving rats," Am J Physiol Regul Integr Comp Physiol, 2006, 290:R1697-R1706.
Kim et al., "Cardiovascular Disease Risk in Adult Women with Congenital Adrenal Hyperplasia Due to 21-hydroxylase Deficiency," Semin Reprod Med, 2009, 27(4):316-321.
King et al., "Long-Term Corticosteroid Replacement and Bone Mineral Density in Adult Women with Classical Congenital Adrenal Hyperplasia," The Journal of Clinical Endocrinology & Metabolism, 2006, 91(3):865-869.
Kitagawa et al., "Basic Pharmaceutical Science Textbook Series 20," Pharmaceutical Science, 2nd print, Kagaku-Dojin Publishing Co., Inc., 2012, p. 16-19.
Koelsch et al., "The Impact of Acute Stress on Hormones and Cytokines, and How Their Recovery is Affected by Music-Evoked Positive Mood," Sci Reps., Mar. 2016, 6:1-11.
Koob et al., "Update on Corticotropin-Releasing Factor Pharmacotherapy for Psychiatric Disorders: A Revisionist View," Neuropsychopharmacology Reviews, 2012, 37:308-309.
Kosoyan HP, et al., "The CRF1 receptor antagonist, NBI-35965, abolished the activation of locus coeruleus neurons induced by colorectal distension and intracisternal CRF in rats," Brain Research, 2005, 1056(1):85-96.
Kulshreshtha B, et al., "Pubertal development among girls with classical congenital adrenal hyperplasia initiated on treatment at different ages," Indian J Endocrinol Metab., 2012, 16(4):599-603.
Le Bas et al., "Radioiodinated analogs of EP 00652218 for the exploration of the tachykinin NK1 receptor by spect," Journal of Labelled Compounds and Radiopharmaceuticals, 2001, 44(S1):S280-S282.
Lehmacher et al., "Adaptive sample size calculations in group sequential trials," Biometrics, 1999, 55(4):1286-1290.
Lekarev et al., "Adrenal disease in pregnancy," Best Practice & Research, Clinical Endocrinology & Metabolism, Dec. 2011, 25(6):959-973.
Li et al., "The pharmacology of DMP696 and DMP904, non-peptidergic $CRF_1$ receptor antagonists," CNS Drug Reviews, 2005, 11(1):21-52.
Liapakis G, et al., "Members of CRF Family and their Receptors: From Past to Future," Current Medicinal Chemistry, 2011, 18(17):2583-2600.
Linder et al., "Cortisol production rate in childhood and adolescence," J Pediatr, Dec. 1990, 117(6):892-896.
Liu J, et al., "Corticotropin-Releasing Factor and Urocortin I Modulate Excitatory Glutamatergic Synaptic Transmission," Journal of Neuroscience, 2004, 24(16): 4020-4029.
Loechner et al., "Alternative Strategies for the Treatment of Classical Congenital Adrenal Hyperplasia: Pitfalls and Promises," International Journal of Pediatric Endocrinology, vol. 2010, No. 1, Jun. 8, 2010, Article ID 670960, 10 pages.
Logachev et al., "Congenital Adrenal Hyperplasia: Modern Problems of Terminology and Treatment," Pediatrics, Apr. 19, 2012, 91(3):130-135 pages (with English Translation).
Louis et al., "Antidepressant-like Effects of the Corticotropin-Releasing Factor 1 Receptor Antagonist, SSR125543, and the Vasopressin 1b Receptor Antagonist, SSR149415, in a DRL-72 S Schedule in the Rat," Neuropsychopharmacology, 2006, 31:2180-2187.
Lovenberg TW, et al., "Cloning and characterization of a functionally distinct corticotropin-releasing factor receptor subtype from rat brain," Proceedings of the National Academy of Sciences, 1995, 92(3): 836-840.
Lowe RF, et al., "Rational Design, Synthesis, and Structure—Activity Relationships of Aryltriazoles as Novel Corticotropin-Releasing Factor-1 Receptor Antagonists," J. Med. Chem., 2005, 48(5):1540-1549.

(56) References Cited

OTHER PUBLICATIONS

Maciejewski-Lenoir D, et al., "Selective Impairment of Corticotropin-Releasing Factor1 (CRF1) Receptor-Mediated Function Using CRF Coupled to Saporin," Endocrinology, 2000, 141(2):498-504.
Mackay, KB, et al., "Neuroprotective Effects of the CRF1 Antagonist R121920 after Permanent Focal Ischemia in the Rat," Journal of Cerebral Blood Flow & Metabolism, 2001, 21(10): 1208-1214.
Malouf et al., "Cognitive outcome in adult women affected by congenital adrenal hyperplasia due to 21-hydroxylase deficiency," Horm Res., 2006, 65(3):142-150.
Martínez V, et al., "Central CRF, urocortins and stress increase colonic transit via CRF1 receptors while activation of CRF2 receptors delays gastric transit in mice," J Physiol., 2004, 556.1: 221-234.
Martínez-Aguayo et al., "Testicular adrenal rest tumors and Leydig and Sertoli cell function in boys with classical congenital adrenal hyperplasia," J Clin Endocrinol Metab., Dec. 2007, 92(12):4583-9.
McCarthy JR, et al., "Chapter 2. Recent Progress in Corticotropin-Releasing Factor Receptor Agents," Annual Reports in Medicinal Chemistry, 1999, 34: 11-20.
McCarthy JR, et al., "Recent advances with the CRF1 receptor: design of small molecule inhibitors, receptor subtypes and clinical indications," Curr Pharm Des., 1999, 5(5):289-315.
Medlineplus.gov, "21-Hydroxylase Deficiency," NIH US National Library of Medicine, Updated Aug. 18, 2020 [retrieved Dec. 13, 2021], retrieved from URL<https://medlineplus.gov/genetics/condition/21-hydroxylase-deficiency/>, 6 pages.
Mehta et al., "Adaptive increase in sample size when interim results are promising: a practical guide with examples," Statistics in Medicine, 2011, 30(28):3267-3284.
Merke et al., "Congenital adrenal hyperplasia," Lancet, 2005, 365:2125-2136.
Merke et al., "Congenital adrenal hyperplasia: epidemiology, management and practical drug treatment," Paediatr Drugs., 2001, 3(8):599-611.
Merke et al., "Flutamide, testolactone, and reduced hydrocortisone dose maintain normal growth velocity and bone maturation despite elevated androgen levels in children with congenital adrenal hyperplasia," J Clin Endocrinol Metab., Mar. 2000, 85(3):1114-1120.
Merke et al., "Management of adolescents with congenital adrenal hyperplasia," Lancet Diabetes Endocrinol., Dec. 2013, 1(4):341-352.
Merke et al., "New ideas for medical treatment of congenital adrenal hyperplasia," Endocrinol. Metab. Clin. North. Am., 2001, 30(1):121-135.
Merke et al., "NIH conference: Future directions in the study and management of congenital adrenal hyperplasia due to 21-hydroxylase deficiency," Ann. Intern. Med., 2002, 136:320-334.
Merke et al., "Congenital Adrenal Hyperplasia Due to 21-Hydroxylase Deficiency," N Engl J Med., Sep. 24, 2020, 383(13):1248-1261.
Meslamani et al., "Computational profiling of bioactive compounds using a target-dependent composite workflow," J. Chem. Inf. Model., 2013, 2322-2333.
Migeon et al., "Congenital Adrenal Hyperplasia Owing to 21-Hydroxylase Deficiency," Endocrinology and Metabolism Clinics of North America, 2001, 30(1):193-206.
Miller et al., "Emergency management of adrenal insufficiency in children: advocating for treatment options in outpatient and field settings," Journal of Investigative Medicine, 2020, 68(1):16-25.
Million et al., "The newly developed CRF1-receptor antagonists, NGD 98-2 and NGD 9002, suppress acute stress-induced stimulation of colonic motor function and visceral hypersensitivity in rats," PLOS One, 2013, 8(9):e73749.
Million M, et al., "A novel water-soluble selective CRF1 receptor antagonist, NBI 35965, blunts stress-induced visceral hyperalgesia and colonic motor function in rats," Brain Research, 2003, 985(1): 32-42.
Mims et al., "Plasma ACTH in Rats Following Medical Adrenalectomy," Journal of the National Medical Association 69(3):145-147, 1977.
Morikawa S, et al., "Results from 28 years of Newborn Screening for Congenital Adrenal Hyperplasia in Sapporo," Clin Pediatr Endocrinol., 2014, 23(2):35-43.
Mullins et al., "Brief psychiatric rating scale for children: quantitative scoring of medical records," Psychiatry Research, 1986, 19(1):43-49.
Muthusamy et al., "Clinical review: Adult height in patients with congenital adrenal hyperplasia: a systematic review and metaanalysis," J Clin Endocrinol Metab., Sep. 2010, 95(9):4161-4172.
Nebesio TD, et al., "Growth and Reproductive Outcomes in Congenital Adrenal Hyperplasia," Int J Pediatr Endocrinol., 2010, Article ID 298937, 1-10.
Nermoen et al., "Subjective health status in men and women with congenital adrenal hyperplasia: a population-based survey in Norway," Eur J Endocrinol., Sep. 2010, 163(3):453-459.
*Neurocrine Biosciences, Inc.*, Petitioner, v. *Spruce Biosciences, Inc.*, Patent Owner, Case No. PGR2021-00088, U.S. Pat. No. 10,849,908, Declaration of Robert M. Carey, M.D., dated May 28, 2021, 154 pages.
Newfield et al., "Crinecerfont (NBI-74788), a Novel CRF1 Receptor Antagonist, Lowers Adrenal Androgens and Precursors in Adolescents with Classic Congenital Adrenal Hyperplasia," Abstract submitted to ECE for consideration at 2023 annual meeting, 2 pages.
Newfield et al., "Crinecerfont (NBI-74788), a novel CRF1 receptor antagonist, lowers adrenal androgens and precursors in adolescents with classic congenital adrenal hyperplasia," Presentation Slides presented at the 104th annual meeting and expo of the Endocrine Society (ENDO 2022), Atlanta, GA, Jun. 2022, 13 pages.
Newfield R.S., "ACTH receptor blockade: A novel approach to treat congenital adrenal hyperplasia, or Cushing's disease," Medical Hypotheses, 2010, 74:705-706.
Nieves-Remacha et al., "Scale-up of N-alkylation reaction using phase-transfer catalysis with integrated separation in flow," Reaction Chemistry & Engineering, 2019, 4(2):334-345.
Nokoff et al., "Sex differences in effects of obesity on reproductive hormones and glucose metabolism in early puberty," The Journal of Clinical Endocrinology & Metabolism, 2019, 104(10):4390-4397.
Okuyama et al., "Receptor Binding, Behavioral, and Electrophysiological Profiles of Nonpeptide Corticotropin-Releasing Factor Subtype 1 Receptor Antagonists CRA1000 and CRA1001," Journal of Pharmacology and Experimental Therapeutics, 1999, 289(2):926-935.
Oray et al., "Long-term effect of glucocorticoids," Expert Opinion on Drug Safety, 2016, 15(4):457-465.
Oster et al., "The functional and clinical significance of the 24-hour rhythm of circulating glucocorticoids," Endocrine Reviews, 2017, 38(1):3-45.
Overall et al., "The Brief Psychiatric Rating Scale (BPRS): recent developments in ascertainment and scaling," Psychopharmacology Bulletin, 1988, 24(1):97-99.
Overall et al., "The brief psychiatric rating scale," Psychological Reports, 1962, 10(3):799-812.
Overstreet et al., "Antidepressant-like effects of $CRF_1$ receptor antagonist SSR125543 in an animal model of depression," European Journal of Pharmacology, 2004, 497:49-53.
Owens et al., "Physiology and pharmacology of corticotropin-releasing factor," Pharmacol Rev., Dec. 1991, 43(4):425-473.
Pang et al., "Worldwide Experience in Newborn Screening for Classical Congenital Adrenal Hyperplasia due to 21-Hydroxylase Deficiency," Pediatrics, 1988, 81(6):866-874.
Pang S, et al., "Congenital adrenal hyperplasia due to 21-hydroxylase deficiency: newborn screening and its relationship to the diagnosis and treatment of the disorder," Screening, 1993, 2:105-139.
Pelleymounter MA, et al., "Role of Corticotropin-Releasing Factor (CRF) Receptors in the Anorexic Syndrome Induced by CRF," Journal of Pharmacology and Experimental Therapeutics, 2000, 293(3): 799-806.
Peplow et al., "Blood draws up to 3% of blood volume in clinical trials are safe in children," Acta Paediatrica, 2019, 108(5):940-944.

(56) References Cited

OTHER PUBLICATIONS

Perry SJ, et al., "Distinct Conformations of the Corticotropin Releasing Factor Type 1 Receptor Adopted following Agonist and Antagonist Binding Are Differentially Regulated," J. Biol. Chem., 2005, 280(12): 11560-11568.
Philbert et al., "The $CRF_1$ Receptor Antagonist SSR125543 Attenuates Long-Term Cognitive Deficit Induced by Acute Inescapable Stress in Mice, Independently From the Hypothalamic Pituitary Adrenal Axis," Pharmacology, Biochemistry, and Behavior, 2012, 10:415-422.
Philbert et al., "The $CRF_1$ Receptor Antagonist SSR125543 Prevents Stress-Induced Cognitive Deficit Associated With Hippocampal Dysfunction: Comparison With Paroxetine and D-cycloserine," Psychopharmacology, 2013, 228:97-107.
Purnell et al., "Association of 24-hour cortisol production rates, cortisol-binding globulin, and plasma-free cortisol levels with body composition, leptin levels, and aging in adult men and women," The Journal of Clinical Endocrinology & Metabolism, 2004, 89(1):281-287.
Ramos et al., "Drug-induced suppression of ACTH secretion does not promote anti-depressive or anxiolytic effects," Behavioral Brain Research, 2014, 265:69-75.
Ravens-Sieberer et al., "Feasibility, reliability, and validity of the EQ-5D-Y: results from a multinational study," Quality of Life Research, 2010, 19(6):887-897.
Reisch, "Substitution therapy in adult patients with congenital adrenal hyperplasia," Best Practice & Research Clinical Endocrinology & Metabolism, 2015, 29(1):33-45.
Rief et al., "Mechanisms involved in placebo and nocebo responses and implications for drug trials," Clinical Pharmacology & Therapeutics, 2011, 90(5):722-726.
Rivier CL, et al., "Role of Corticotropin-Releasing Factor Receptors Type 1 and 2 in Modulating the Rat Adrenocorticotropin Response to Stressors," Endocrinology, 2003, 144(6): 2396-2403.
Rivier JE, et al., "Constrained Corticotropin Releasing Factor Antagonists (Astressin Analogues) with Long Duration of Action in the Rat," J. Med. Chem. 1999, 42(16):3175-3182.
Rose & Hurst, "Plasma Cortisol and Growth Hormone Responses to Intravenous Catheterization," J Hum Stress., Mar. 1975, 1(1):22-36.
Ross et al., "Improved biochemical control with dose reduction in chronic glucocorticoid therapy: A phase III extension study of Chronocort (Efmody) in the treatment of Congenital Adrenal Hyperplasia (CAH)," Abstract submitted to ENDO 2023 for consideration, prepared on Dec. 2022, 2 pages.
Ross et al., "Switching patients with Congenital Adrenal Hyperplasia to Modified release hydrocortisone capsules: relative bioavailability and disease control," Abstract submitted to European Congress of Endocrinology 2023 for consideration, prepared on Jan. 2023, 2 pages.
Sarafoglou et al., "Tildacerfont in adults with classic congenital adrenal hyperplasia: results from two phase 2 studies," Manuscript, The Journal of Clinical Endocrinology & Metabolism, 2021, 106(11):e4666-79.
Sarafoglou K, et al., "Impact of Hydrocortisone on Adult Height in Congenital Adrenal Hyperplasia—The Minnesota Cohort," J Pediatr., 2014, 164(5):1141-1146.
Science.nichd.nih.gov [Online], "Pediatric Endocrinology Training Program," 2020, [Retrieved on Mar. 6, 2023], retrieved from: URL<https://science.nichd.nih.gov/confluence/display/pe/Patient+Handouts+and+Support+Groups#PatientHandoutsandSupportGroups-CAHandAdrenalInsufficiency>, 3 pages.
Scott et al., "The use of the EQ-5D-Y health related quality of life outcome measure in children in the Western Cape, South Africa: psychometric properties, feasibility and usefulness—a longitudinal, analytical study," Health and Quality of Life Outcomes, 2017, 15:12.
Seymour et al., "The pharmacology of CP-154,526, a non-peptide antagonist of the CRH1 receptor: a review," CNS Drug Reviews, 2003, 9(1):57-96.
Shargel et al., "Multiple-Dosage Regiments," Applied Biopharmaceutics & Pharmacokinetics, 2012, 6th Edition, 31 pages.
Shargel et al., "Multiple-Dosage Regiments," Applied Biopharmaceutics & Pharmacokinetics, 2016, 7th Edition, 33 pages.
Silva IN, et al., "Randomised controlled trial of growth effect of hydrocortisone in congenital adrenal hyperplasia," Archives of Disease in Childhood, 1997, 77:214-218.
Smith et al., "Measures of sleep: the insomnia severity index, medical outcomes study (MOS) sleep scale, Pittsburgh sleep diary (PSD), and Pittsburgh sleep quality index (PSQI)," Arthritis Care & Research: Official Journal of the American College of Rheumatology, 2003, 49(S5):S184-S196.
Smith et al., "The role of the hypothalamic-pituitary-adrenal axis in neuroendocrine responses to stress," Dialogues Clin Neurosci., 2006, 8:383-395.
Soliman et al., "Congenital adrenal hyperplasia complicated by central precocious puberty: linear growth during infancy and treatment with gonadotropin-releasing hormone analog," Metabolism., May 1997, 46(5):513-517.
Somajni et al., "Neuropsychological assessment in prepubertal patients with congenital adrenal hyperplasia: preliminary study," Minerva Pediatr., Feb. 2011, 63(1):1-9.
Speiser et al., "Congenital adrenal hyperplasia due to steroid 21-hydroxylase deficiency: an Endocrine Society clinical practice guideline," J Clin Endocrinol Metab., Sep. 2010, 95(9):4133-60.
Speiser et al., "A Summary of the Endocrine Society Clinical Practice Guidelines on Congenital Adrenal Hyperplasia due to Steroid 21-Hydroxylase Deficiency," International Journal of Pediatric Endocrinology 2010, 2010:494173.
Speiser et al., "Congenital Adrenal Hyperplasia Due to Steroid 21-Hydroxylase Deficiency: An Endocrine Society Clinical Practice Guideline," J Clin Endocrinol Metab., 2018, 103(11):4043-4088.
Spierling et al., "Don't stress about CRF: assessing the translational failures of $CRF_1$ antagonists," Psychopharmacology, 2017, 234(9-10):1467-1481.
Steckler, "Developing small molecule nonpeptidergic drugs for the treatment of anxiety disorders: is the challenge still ahead?" Curr. Topics in Behav. Neurosciences, 2009, 415-428.
Stewart et al., "Development of a Biorelevant, Material-Sparing Membrane Flux Test for Rapid Screening of Bioavailability-Enhancing Drug Product Formulations," Mol Pharm., 2017, 14(6):2032-2046.
Stewart et al., "Exploring inpatient hospitalizations and morbidity in patients with adrenal insufficiency," The Journal of Clinical Endocrinology & Metabolism, 2016, 101(12):4843-4850.
Stikkelbroeck et al., "High prevalence of testicular adrenal rest tumors, impaired spermatogenesis, and Leydig cell failure in adolescent and adult males with congenital adrenal hyperplasia," J Clin Endocrinol Metab., Dec. 2001, 86(12):5721-5728.
Surget et al., "Corticolimbic transcriptome changes are state-dependent and region-specific in a rodent model of depression and of antidepressant reversal," Neuropsychopharmacology, 2009, 34:1363-1380.
Surget et al., "Drug-dependent requirement of hippocampal neurogenesis in a model of depression and of antidepressant reversal," Biol. Psychiatry, 2008, 64:293-301.
Teitelbaum, "Chronic peripheral administration of corticotropin-releasing factor causes colonic barrier dysfunction similar to psychological stress," Am J Physiol Gastrointest Liver Physiol, 2008, 295: G452-G459.
Tellew et al., "Discovery ofNBI-77860/GSK561679, a potent corticotropin-releasing factor ($CRF_1$) receptor antagonist with improved pharmacokinetic properties," Bioorganic & Medicinal Chemistry Letters, 2010, 20(24):7259-7264.
Thefreedictionary.com, "Baseline," available on or before Nov. 7, 2016, via Internet Archive: Wayback Machine URL <https://web.archive.org/web/20161107132345/http:/medical-dictionary.thefreedictionary.com/baseline>, 3 pages.
Therrell BL, et al., "Newborn Screening for Congenital Adrenal Hyperplasia," Endocrinol Metab Clin North Am., 2001, 30(1):15-30.
Trakakis et al., "An update to 21-hydroxylase deficient congenital adrenal hyperplasia," Gynecol Endocrinol., Jan. 2010, 26(1):63-71.

(56) References Cited

OTHER PUBLICATIONS

Trapp CM, et al. "Recommendations for Treatment of Nonclassic Congenital Adrenal Hyperplasia (NCCAH): an Update," Steroids, 2012, 77(4):342-346.
Trapp et al., "Congenital adrenal hyperplasia: an update in children," Curr Opin Endocrinol Diabetes Obes., 2011, 18(3):166-170.
Turcu et al., "Novel treatment strategies in congenital adrenal hyperplasia," Curr Opin Endocrinol Diabetes Obes., 2016, 23(3):225-232.
Turcu et al., "Single-Dose Study of a Corticotropin-Releasing Factor Receptor-1 Antagonist in Women With 21-Hydroxylase Deficiency," J Clin Endocrinol Metab., Mar. 2016, 101(3):1174-1180.
Turcu et al., "The Next 150 Years of Congenital Adrenal Hyperplasia," J Steroid Biochem Mol Biol., Sep. 2015, 153:63-71.
Urani et al., "The Corticotropin-Releasing Factor 1 Receptor Antagonist, SSR125543, and the Vasopressin 1b Receptor Antagonist, SSR149415, Prevent Stress-Induced Cognitive Impairment in Mice," Pharmacology, Biochemistry, and Behavior, 2011, 98:425-431.
U.S. Appl. No. 62/545,406, Howerton et al., "Corticotropin Releasing Factor Receptor Antagonists," filed Aug. 14, 2017, 65 pages.
Vale et al., "Chemical and biological characterization of corticotropin releasing factor," Recent Prog Horm Res., 1983, 39:245-270.
Vale et al., "Characterization of a 41-Residue Ovine Hypothalamic Peptide That Stimulates Secretion of Corticotropin and β-Endorphin," Science, 1981, 213:1394-1397.
Varni et al., "PedsQL™ 4.0: Reliability and validity of the Pediatric Quality of Life Inventory™ Version 4.0 Generic Core Scales in healthy and patient populations," Medical Care, 2001, 39(8):800-812.
Varni et al., "The PedsQL™ 4.0 as a school population health measure: feasibility, reliability, and validity," Quality of Life Research, 2006, 15:203-215.
Varni et al., "The PedsQL™ family impact module: preliminary reliability and validity," Health and Quality of Life Outcomes, 2004, 2:55.
Vickers et al., "Why Use Placebos in Clinical Trials? A Narrative Review of the Methodological Literature," Journal of Clinical Epidemiology, 2000, 53(2):157-161.
Vijayan et al., "Metabolic profile, cardiovascular risk factors and health-related quality of life in children, adolescents and young adults with congenital adrenal hyperplasia," 2019, 32(8):871-877.
Vokl TMK, et al., "Adrenarche and Puberty in Children with Classic Congenital Adrenal Hyperplasia due to 21-Hydroxylase Deficiency," Horm Res Paediatr., 2011, 76(6):400-410.
Vokl TMK, et al., "Obesity Among Children and Adolescents with Classic Congenital Adrenal Hyperplasia due to 21-Hydroxylase Deficiency," Pediatrics, 2006, 117(1):e98-e105.
Webb et al., "Current and Novel Approaches to Children and Young People with Congenital Adrenal Hyperplasia and Adrenal Insufficiency," Best Pract Res Clin Endocrinol Metab., 2015, 29:449-468.
Webb TR, et al., "Synthesis of benzoylpyrimidines as antagonists of the corticotropin-releasing factor-1 receptor," Bioorganic & Medicinal Chemistry Letters, 2004, 14(15): 3869-3873.
Webster et al., "In Vivo and In Vitro Characterization of Antalarmin, a Nonpeptide Corticotropin-Releasing Hormone (CRH) Receptor Antagonist: Suppression of Pituitary ACTH Release and Peripheral Inflammation," Endocrinology, Jan. 1, 1996, 137(12):5747-5750.
White PC, et al., "Congenital Adrenal Hyperplasia due to 21-Hydroxylase Deficiency," Endocr Rev., 2000, 21(3):245-291.
White PC, et al., "Optimizing Newborn Screening for Congenital Adrenal Hyperplasia," J. Pediatr., 2013, 163:10-12.
Whitten JP, et al., "Rapid Microscale Synthesis, a New Method for Lead Optimization Using Robotics and Solution Phase Chemistry: Application to the Synthesis and Optimization of Corticotropin-Releasing Factor1 Receptor Antagonists," J. Med. Chem., 1996, 39(22): 4354-4357.
Wiens, "A fixed sequence Bonferroni procedure for testing multiple endpoints," Pharmaceutical Statistics: The Journal of Applied Statistics in the Pharmaceutical Industry, 2003, 2(3):211-215.
Wilcoxen K, et al., "Synthesis of 3-phenylpyrazolo[4,3-b]pyridines via a convenient synthesis of 4-amino-3-arylpyrazoles and SAR of corticotropin-Releasing factor receptor type-1 antagonists," Bioorganic & Medicinal Chemistry Letters, 2003, 13(19): 3367-3370.
Williams, "Corticotropin-releasing factor I receptor antagonists: a patent review," Expert Opin. Ther. Patents, 2013, 23(8):1057-1068.
Witchel et al., "Congenital Adrenal Hyperplasia," J. Pediatr. Adolesc. Gynecol., 2011, 24:116-126.
Witchel et al., "Congenital Adrenal Hyperplasia," J. Pediatr. Adolesc. Gynecol., 2017, 30(5):520-534.
Wong et al., "Increased hepatobiliary clearance of unconjugated thyroxine determines DMP 904-induced alterations in thyroid hormone homeostasis in rats," Toxicological Sciences, 2005, 84(2):232-242.
Wood S, et al., "Depressive and cardiovascular disease comorbidity in a rat model of social stress: a putative role for corticotropin-releasing factor," Psychopharmacology, 2012, 222(2): 325-336.
Wustrow DJ, et al., "Pyrazolo[1,5-a]pyrimidine CRF-1 receptor antagonists," Bioorganic & Medicinal Chemistry Letters, 1998, 8(16): 2067-2070.
Yuan J, et al., "3-Aryl pyrazolo[4,3-d]pyrimidine derivatives: nonpeptide CRF-1 antagonists," Bioorganic & Medicinal Chemistry Letters, 2002, 12(16): 2133-2136.
Zhu et al., "Synthesis and mode of action of $^{125}I$- and $^{3}H$-labeled thieno [2,3-c]pyridine antagonists of cell adhesion molecule expression," The Journal of Organic Chemistry, 2002, 67(3):943-948.
Zorrilla et al., "Behavioral, biological, and chemical perspectives on targeting CRF(1) receptor antagonists to treat alcoholism," Drug and Alcohol Dependence, (2013), 128(3):175-186.
Zorrilla et al., "The therapeutic potential of CRFI antagonists for anxiety," Expert Opin. Investig. Drugs, 2004, 13(7):799-828.
Zorrilla, "Progress in corticotropin-releasing factor-1 antagonist development," Drug Discov Today, 2010, 15:371-383.
Zoumakis et al., "Corticotropin-releasing hormone receptor antagonists," European Journal of Endocrinology, 2006, 155(1):S85-S91.
Zoumakis et al., "Corticotropin-releasing hormone receptor antagonists: an update," Pediatric Neuroendocrinology Endocr Dev., 2010, 17:36-43.
[No Author Listed], "Search Results for CAS No. 121548-04-7," American Chemical Society CAS SciFinder, search performed on Apr. 7, 2025 at www.cas.org, 2 pages.
Accessdata.fda.gov [online], "FDA, Center for Drug Evaluation and Research, 218808Orig1s000, 218820Orig1s000, Product Quality Review(s)," Oct. 7, 2024, retrieved on Apr. 10, 2025, retrieved from URL <https://www.accessdata.fda.gov/drugsatfda_docs/nda/2025/218808Orig1s000,218820Orig1s000ChemR.pdf>, 90 pages.
Ceramella et al., "A Look at the Importance of Chirality in Drug Activity: Some Significative Examples," Applied Sciences, Oct. 27, 2022, 12:10909, 22 pages.
Claahsen-van der Grinten et al., "Challenges in Adolescent and Adult Males With Classic Congenital Adrenal Hyperplasia Due to 21-Hydroxylase Deficiency," J Clinical Endocrinology & Metabolism, Feb. 2025, 110 (Supplement_1):S25-36.
Do Thi et al., "Formulate-ability of ten compounds with different physicochemical profiles in SMEDDS," European journal of pharmaceutical sciences, Dec. 8, 2009, 38(5):479-88.
Dwivedi et al., "Evergreening: a deceptive device in patent rights," Technology in Society, Nov. 1, 2010, 32(4):324-30.
Eitel et al., "Barriers to the Management of Classic Congenital Adrenal Hyperplasia Due to 21-Hydroxylase Deficiency," J Clinical Endocrinology & Metabolism, Feb. 2025, 110 (Supplement_1):S67-73.
Engberg et al., "Clinical Manifestations and Challenges in Adolescent and Adult Females With Classic Congenital Adrenal Hyperplasia Due to 21-Hydroxylase Deficiency," J Clinical Endocrinology & Metabolism, Feb. 2025, 110 (Supplement_1):S37-45.
Feldman, "Understanding 'Evergreening': Making Minor Modifications of Existing Medications To Extend Protections," Health Affairs, Jun. 1, 2022, 41(6):801-4.
Foster, "Deuterium isotope effects in the metabolism of drugs and xenobiotics: implications for drug design," Advances in Drug Research, 1985, 14:1-40.

(56) References Cited

OTHER PUBLICATIONS

Gattefosse.com [online], "Gelucire® 44/14," available on or before Nov. 30, 2023 via Internet Archive: Wayback Machine URL<https://web.archive.org/web/20231130013520/https://www.gattefosse.com/pharmaceuticals/product-finder/gelucire-4414>, retrieved on Apr. 10, 2025, retrieved from URL <https://www.gattefosse.com/pharmaceuticals/product-finder/gelucire-4414>, 6 pages.

Gattefosse.com [online], "LabrafacT™ Lipophile WL 1349," available on or before Nov. 30, 2023 via Internet Archive: Wayback Machine URL<https://web.archive.org/web/20231130120205/https://www.gattefosse.com/pharmaceuticals/product-finder/labrafac-lipophile-wl-1349>, retrieved on Apr. 10, 2025, retrieved from URL <https://www.gattefosse.com/pharmaceuticals/product-finder/labrafac-lipophile-wl-1349>, 6 pages.

Gattefosse.com [online], "Labrafac™ PG," available on or before Nov. 30, 2023 via Internet Archive: Wayback Machine URL<https://web.archive.org/web/20231130184227/https://www.gattefosse.com/pharmaceuticals/product-finder/labrafac-pg>, retrieved on Apr. 10, 2025, retrieved from URL <https://www.gattefosse.com/pharmaceuticals/product-finder/labrafac-pg>, 5 pages.

Gupta et al., "Salts of therapeutic agents: chemical, physicochemical, and biological considerations," Molecules, Jul. 14, 2018, 23(7):1719.

Kamrath et al., "CRH receptor antagonist crinecerfont—a promising new treatment option for patients with congenital adrenal hyperplasia due to 21-hydroxylase deficiency," Journal of Pediatric Endocrinology and Metabolism, Nov. 25, 2024, 38(1):16-21.

Kushner et al., "Pharmacological uses and perspectives of heavy water and deuterated compounds," Canadian journal of physiology and pharmacology, Feb. 1, 1999, 77(2):79-88.

Nokoff et al., "Clinical Manifestations and Treatment Challenges in Infants and Children With Classic Congenital Adrenal Hyperplasia Due to 21-Hydroxylase Deficiency," J Clinical Endocrinology & Metabolism, Feb. 2025, 110 (Supplement_1):S13-24.

Online.Uspnf.com [online], "Medium-Chain Triglycerides," Nov. 1, 2020, retrieved on Mar. 26, 2025, retrieved from URL <https://online.uspnf.com/uspnf/document/1_GUID-995A5AEA-A8B8-473A-BE2C-94DA0912145B_5_en-US?source=Activity>, 4 pages.

Online.Uspnf.com [online], "Propylene Glycol Dicaprylate/Dicaprate," May 1, 2020, retrieved on Mar. 27, 2025, retrieved from URL <https://online.uspnf.com/uspnf/document/1_GUID-8CD288A0-4573-4B12-9F29-87144943C326_2_en-US?source=Search Results &highlight=Pro . . . >, 2 pages.

Peter, "Congenital adrenal hyperplasia: 11β-hydroxylase deficiency," Seminars in reproductive medicine, Aug. 2002, 20(3):249-254, abstract.

Pouton, "Lipid formulations for oral administration of drugs: non-emulsifying, self-emulsifying and 'self-microemulsifying' drug delivery systems," European journal of pharmaceutical sciences, Oct. 1, 2000, 11:S93-8.

Sandberg et al., "Mental Health Issues Associated With Classic Congenital Adrenal Hyperplasia Due to 21-Hydroxylase Deficiency," J Clinical Endocrinology & Metabolism, Feb. 2025, 110(Supplement_1):S46-55.

Sarafoglou et al., "Future Directions in the Management of Classic Congenital Adrenal Hyperplasia Due to 21-Hydroxylase Deficiency," J Clinical Endocrinology & Metabolism, Feb. 2025, 110 (Supplement_1):S74-87.

Sarafoglou et al., "Phase 3 Trial of Crinecerfont in Pediatric Congenital Adrenal Hyperplasia," New England Journal of Medicine, Jun. 2, 2024, 1-11.

Spernath et al., "Microemulsions as carriers for drugs and nutraceuticals," Advances in colloid and interface science, Dec. 21, 2006, 128:47-64.

Wikipedia.org [online], "Medium-chain triglyceride," last updated on Dec. 28, 2024, retrieved on Apr. 10, 2025, retrieved from URL<https://en.wikipedia.org/w/index.php?title=Medium-chain_triglyceride&oldid=1265809727>, 4 pages.

Wikipedia.org [online], "Molecular mass," last updated on Nov. 2, 2024, retrieved on Apr. 10, 2025, retrieved from URL<https://en.wikipedia.org/w/index.php?title=Molecular_mass&oldid=1254996685>, 4 pages.

Witchel et al., "Life With Classic Congenital Adrenal Hyperplasia Due to 21-Hydroxylase Deficiency: Challenges and Burdens," J Clinical Endocrinology & Metabolism, Feb. 2025, 110 (Supplement 1):S56-66.

Yang et al., "Genetics and Pathophysiology of Classic Congenital Adrenal Hyperplasia Due to 21-Hydroxylase Deficiency," J Clinical Endocrinology & Metabolism, Feb. 2025, 110 (Supplement_1):S1-2.

* cited by examiner

Differential Scanning Calorimetry (DSC) and Thermogravimetric Analysis (TGA) Thermograms for Compound 1 (Form I)

Gravimetric Vapor Sorption (GVS) for Compound 1 (Form I)

The General Synthetic Schemes for the Preparation of Intermediates

General Synthetic Scheme for the Preparation of Compound 8A 7A 8A

General Synthetic Scheme for the Preparation of Compounds 7A' and 8A'

7A' 8A'

The General Synthetic Scheme for the Preparation of Compound 1

The General Synthetic Scheme for the Preparation of Compound 3

1A 2A 3A (Ic) (Ie) (Ig) 6A 9A' Compound 3

Overlay of X-Ray Powder Diffractions for Compound 1 (Form I)

X-Ray Powder Diffraction (XRPD) for Compound 9A

Differential Scanning Calorimetry (DSC) and Thermogravimetric Analysis (TGA) Thermograms for Compound 9A (Crystal Form)

X-Ray Powder Diffraction (XRPD) for Compound 8A

Differential Scanning Calorimetry (DSC) and Thermogravimetric Analysis (TGA) Thermograms for Compound 8A (Crystal Form)

X-Ray Powder Diffraction (XRPD) for Compound 6A HCl Salt (Crystal Form)

Differential Scanning Calorimetry (DSC) and Thermogravimetric Analysis (TGA) Thermograms for Compound 6A HCl Salt (Crystal Form)

X-Ray Powder Diffraction (XRPD) for Compound 3A (Crystal Form)

Differential Scanning Calorimetry (DSC) and Thermogravimetric Analysis (TGA) Thermograms for Compound 3A (Crystal Form)

X-Ray Powder Diffraction (XRPD) for Compound 5A HCl Salt (Crystal Form)

Differential Scanning Calorimetry (DSC) and Thermogravimetric Analysis (TGA) Thermograms for Compound 5A HCl Salt (Crystal Form)

Dissolution Performance of Several SDD formulations in SIF

Vertical Membrane Flux Cell

Non-sink Dissolution Data for Several SDD Formulations

Flow Diagram of the Spray Drying Manufacturing Process

X-Ray Powder Diffraction (XRPD) for Compound 1 Tosylate Salt (Crystal Form)

Differential Scanning Calorimetry (DSC) and Thermogravimetric Analysis (TGA) Thermograms for Compound 1 Tosylate Salt (Crystal Form)

SYNTHETIC METHODS FOR PREPARATION OF 4-(2-CHLORO-4-METHOXY-5-METHYLPHENYL)-N-[(1S)-2-CYCLOPROPYL-1-(3-FLUORO-4-METHYLPHENYL)ETHYL]-5-METHYL-N-PROP-2-YNYL-1,3-THIAZOL-2-AMINE

CROSS-REFERENCE TO RELATED APPLICATIONS

This application is a National Stage Application under 35 U.S.C. § 371 and claims the benefit of International Application No. PCT/IB2020/000575, filed Jun. 10, 2020, which claims priority to International Application No. PCT/IB2019/001325, filed Dec. 6, 2019. The disclosures of the foregoing applications are hereby incorporated by reference in their entireties.

FIELD OF THE INVENTION

The present disclosure relates to the fields of chemistry and medicine, more particularly to processes for making 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), pharmaceutically acceptable salts, and crystalline forms thereof, for the treatment of congenital adrenal hyperplasia (CAH).

BACKGROUND OF THE INVENTION

Classic congenital adrenal hyperplasia (CAH) is a disease that includes a group of autosomal recessive disorders that result in an enzyme deficiency that alters the production of adrenal steroids due to 21-hydroxylase deficiency, a condition that results in little or no cortisol biosynthesis. One clinical manifestation of the absence of cortisol is the lack of feedback inhibition of pituitary adrenocorticotropic hormone (ACTH) secretion. Increased ACTH levels cause adrenal hyperplasia and the enzyme mutation causes a shunting of cortisol precursor steroids to alternate pathways. Most notably, the shunting of androgens leads to virilization and other developmental complications in females and the over-accumulation of ACTH is associated with the formation of testicular adrenal rest tumors in males. In addition, since the same enzyme (21-hydroxylase) is used in the pathway for the biosynthesis of the mineralocorticoids, a number of these patients suffer from aldosterone deficiency which can result in dehydration and death due to salt-wasting. The prevalence of classic 21-hydroxylase deficiency CAH in the US general population, based on newborn screening, has been documented as 1:10,000 to 1:20,800 (Trakakis et al., "An update to 21-hydroxylase deficient congenital adrenal hyperplasia," *Gynecol. Endocrinol.* (2010) 26(1):63-71; Hertzberg et al., "Birth prevalence rates of newborn screening disorders in relation to screening practices in the United States," *J. Pediatr.* (2011) 159(4): 555-560).

Pediatric patients from birth through adolescence, and females in particular, appear to be the most vulnerable population of CAH sufferers and represent the subgroup of patients with the greatest unmet medical need (Cheng and Speiser, "Treatment outcomes in congenital adrenal hyperplasia," *Adv. Pediatr.* (2012) 59(1):269-281; Merke and Poppas, "Management of adolescents with congenital adrenal hyperplasia," *Lancet Diabetes Endocrinol.* (2013) 1(4): 341-352). Excessive androgen production in these younger patients results in early onset puberty and adrenarche, changes in skeletal maturation patterns, short stature caused by premature growth plate fusion, as well as significant hirsutism and acne problems. While survival is properly ensured through steroid replacement strategies based on physiologic dosing of glucocorticoids (e.g., hydrocortisone) and mineralocorticoids (e.g., fludrocortisone), these doses are often inadequate to suppress the accumulating ACTH and overproduction of progestogens and androgens (e.g., 17-hydroxyprogesterone [17-OHP], androstenedione, and testosterone). The uncontrolled symptoms of androgen excess, indeed, have a substantial impact on the day-to-day functioning and development of these patients.

Currently, exogenous corticosteroids are the standard of care for treating patients with classic CAH. This treatment is used to correct the cortisol deficiency and reduce the excessive ACTH levels and androgen excess. However, the dose and duration of steroid use required to suppress ACTH are typically well above the normal physiological level used for cortisol replacement alone (as in patients with Addison's disease). This increased exposure to glucocorticoids can lead to iatrogenic Cushing's syndrome, increased cardiovascular risk factors, glucose intolerance, reduced growth velocity, and decreased bone mineral density in CAH patients (Elnecave et al., "Bone mineral density in girls with classical congenital adrenal hyperplasia due to CYP21 deficiency," *J. Pediatr. Endocrinol. Metab.* (2008) 21(12):1155-1162; King et al., "Long-term corticosteroid replacement and bone mineral density in adult women with classical congenital adrenal hyperplasia," *J. Clin. Endocrinol. Metab.* (2006) 91(3):865-869; and Migeon and Wisniewski, "Congenital adrenal hyperplasia owing to 21-hydroxylase deficiency. Growth, development, and therapeutic considerations," *Endocrinol. Metab. Clin. North Am.* (2001) 30(1): 193-206).

It has been demonstrated in clinical trials that orally active compounds that block $CRF_1$, such as 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), provide a reduction from baseline in 17-hydroxyprogesterone (17-OHP) and androstenedione levels in amounts believed to allow use of lower, more physiologic doses of glucocorticoid (e.g. hydrocortisone) in patients with CAH. The structure of Compound 1 is shown below:

Compound 1

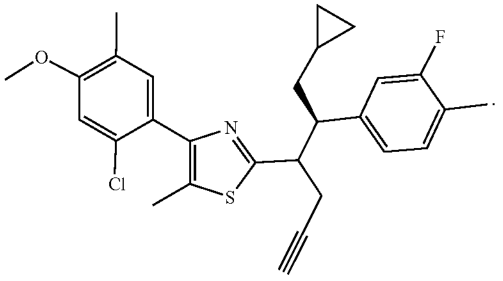

Accordingly, a significant need exists for efficient methods for the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) to support further clinical trials and commercial efforts.

SUMMARY OF THE INVENTION

The present invention provides, inter alia, processes for the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) and intermediates related thereto.

The processes and intermediates of the present invention are useful in preparing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), pharmaceutical salts, crystalline forms, and pharmaceutical compositions that are useful in the treatment of corticotropin releasing factor 1 ($CRF_1$) receptor-mediated disorders.

One aspect of the present invention pertains to processes for preparing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof:

Compound 1

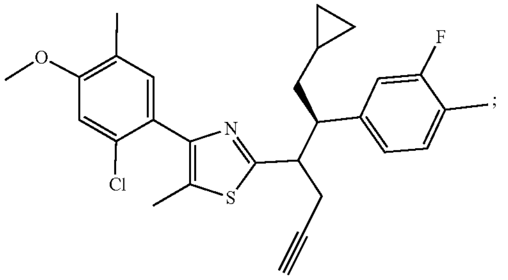

comprising:

alkylating (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

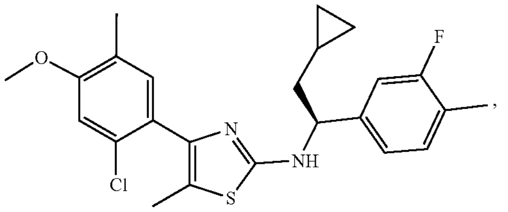

with a Compound of Formula (Ii):

(Ii)

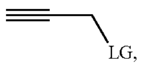

wherein: LG is a leaving group;

in the presence of an alkylating-step solvent, a phase-transfer catalyst, an alkylating-step base, and water to form 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof.

One aspect of the present invention pertains to processes for preparing (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

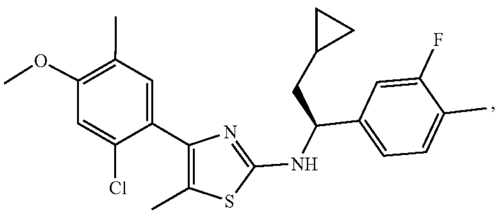

comprising:

cyclizing (S)-2-cyclopropyl-1-(3-fluoro-4-methylphenyl)ethan-1-amine (Compound 6A) or a salt thereof:

6A

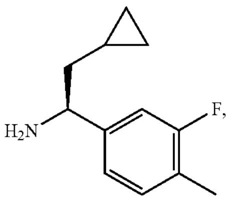

with 1-(2-chloro-4-methoxy-5-methylphenyl)-2-thiocyanatopropan-1-one (Compound 8A) or a tautomeric form thereof:

8A

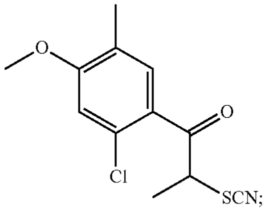

in the presence of a cyclizing-step solvent to form (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof.

One aspect of the present invention pertains to processes for preparing (S)-2-cyclopropyl-1-(3-fluoro-4-methylphenyl)ethan-1-amine (Compound 6A) or a salt thereof:

6A

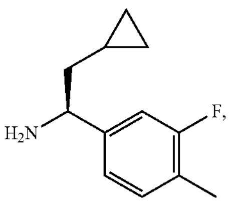

comprising:

deprotecting a Compound of Formula (Ig), or a salt thereof, (Ig)

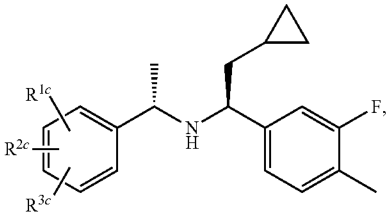

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a deprotecting-catalyst, hydrogen, and a deprotecting-step solvent to form (S)-2-cyclopropyl-1-(3-fluoro-4-methylphenyl)ethan-1-amine (Compound 6A) or a salt thereof.

One aspect of the present invention pertains to processes for preparing a Compound of Formula (Ig), or a salt thereof, (Ig)

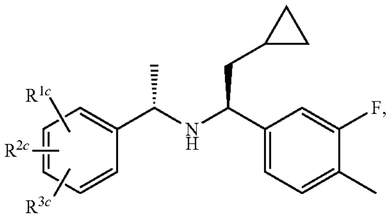

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

reducing a Compound of Formula (Ie):

(Ie)

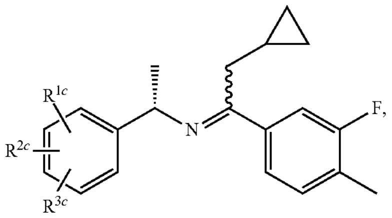

in the presence of a reducing-catalyst, hydrogen, and a reducing-step solvent to form a Compound of Formula (Ig), or a salt thereof.

One aspect of the present invention pertains to processes for preparing a Compound of Formula (Ie):

(Ie)

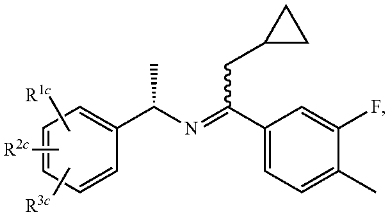

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

condensing 2-cyclopropyl-1-(3-fluoro-4-methylphenyl) ethan-1-one (Compound 3A):

3A

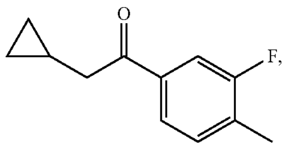

with a Compound of Formula (Ic), or a salt thereof:

(Ic)

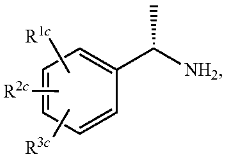

in the presence of a condensing-step acid and a condensing-step solvent to a Compound of Formula (Ie).

One aspect of the present invention pertains to processes for preparing 2-cyclopropyl-1-(3-fluoro-4-methylphenyl) ethan-1-one (Compound 3A):

3A

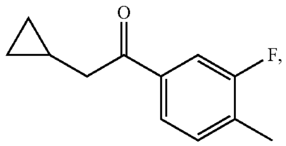

comprising:

reacting 2-cyclopropyl-N-methoxy-N-methylacetamide (Compound 2A):

2A

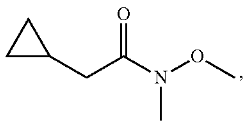

with an organomagnesium reagent of 4-bromo-2-fluoro-1-methylbenzene in the presence of a reacting-step solvent to form 2-cyclopropyl-1-(3-fluoro-4-methylphenyl)ethan-1-one (Compound 3A).

One aspect of the present invention pertains an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base).

One aspect of the present invention pertains to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt).

One aspect of the present invention pertains to pharmaceutical compositions comprising a crystalline form (Compound 1, free base) as described herein, and a pharmaceutically acceptable carrier.

One aspect of the present invention pertains to pharmaceutical products selected from: a pharmaceutical composition, a formulation, a unit dosage form, and a kit; each comprising a crystalline form (Compound 1, free base) as described herein.

One aspect of the present invention pertains to pharmaceutical compositions comprising a crystalline form (Compound 1, tosylate salt) as described herein, and a pharmaceutically acceptable carrier.

One aspect of the present invention pertains to pharmaceutical products selected from: a pharmaceutical composition, a formulation, a unit dosage form, and a kit; each comprising a crystalline form (Compound 1, tosylate salt) as described herein.

One aspect of the present invention pertains to compositions comprising:

a. 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof; and b. at least one compound selected from:

(S)-4-(2-Chloro-4-methoxy-5-methylphenyl)-N-(2-cyclopropyl-1-(3-fluoro-4-methylphenyl)ethyl)-5-methylthiazol-2-amine (Compound 9A);

(S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa);

(S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb);

4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc);

ethanol; and propargyl bromide.

One aspect of the present invention pertains to methods of treating a disorder in a subject in need thereof, comprising administering to the subject a therapeutically effective amount of a crystalline form (Compound 1, free base) as described herein; a crystalline form (Compound 1, tosylate base) as described herein; a pharmaceutical composition as described herein; a pharmaceutical product as described herein; or a composition as described herein; wherein the subject has abnormal levels of $CRF_1$.

One aspect of the present invention pertains to methods of treating a Corticotropin Releasing Factor 1 ($CRF_1$) disorder in a subject in need thereof, comprising administering to the subject a therapeutically effective amount of a crystalline form (Compound 1, free base) as described herein; a crystalline form (Compound 1, tosylate base) as described herein; a pharmaceutical composition as described herein; a pharmaceutical product as described herein; or a composition as described herein.

One aspect of the present invention pertains to methods of treating congenital adrenal hyperplasia (CAH), in a subject in need thereof, comprising administering to the subject a therapeutically effective amount of a crystalline form (Compound 1, free base) as described herein; a crystalline form (Compound 1, tosylate base) as described herein; a pharmaceutical composition as described herein; a pharmaceutical product as described herein; or a composition as described herein.

One aspect of the present invention pertains to uses of an anhydrous crystalline form (Compound 1, free base) as described herein; or the crystalline form (Compound 1, tosylate base) as described herein; for the manufacture of a medicament for the treatment of a subject wherein the subject has abnormal levels of $CRF_1$.

One aspect of the present invention pertains to uses of an anhydrous crystalline form (Compound 1, free base) as described herein; or the crystalline form (Compound 1, tosylate base) as described herein; for the manufacture of a medicament for the treatment of a Corticotropin Releasing Factor 1 ($CRF_1$) disorder.

One aspect of the present invention pertains to uses of an anhydrous crystalline form (Compound 1, free base) as described herein; or the crystalline form (Compound 1, tosylate base) as described herein; for the manufacture of a medicament for the treatment of congenital adrenal hyperplasia (CAH).

One aspect of the present invention pertains to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treatment of the human or animal body by therapy.

One aspect of the present invention pertains to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treatment of a disorder in a subject wherein the subject has abnormal levels of $CRF_1$.

One aspect of the present invention pertains to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treatment of a Corticotropin Releasing Factor 1 ($CRF_1$) disorder.

One aspect of the present invention pertains to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treating congenital adrenal hyperplasia (CAH).

One aspect of the present invention pertains to Compounds of Formula (Ie):

(Ie)

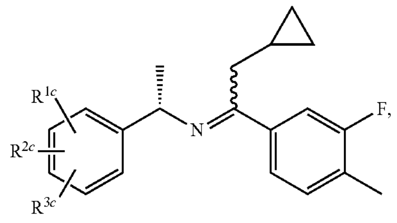

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

One aspect of the present invention pertains to Compounds of Formula (Ig) or a salt thereof:

(Ig)

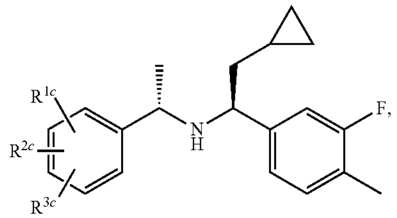

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

One aspect of the present invention pertains to processes for preparing a pharmaceutical composition comprising admixing a crystalline form (Compound 1, free base) as described herein; a crystalline form (Compound 1, tosylate base) as described herein; or a composition according as described herein; and a pharmaceutically acceptable carrier.

These and other aspects of the invention disclosed herein will be set forth in greater detail as the patent disclosure proceeds.

DETAILED DESCRIPTION OF THE INVENTION

Definitions

Figure 1:
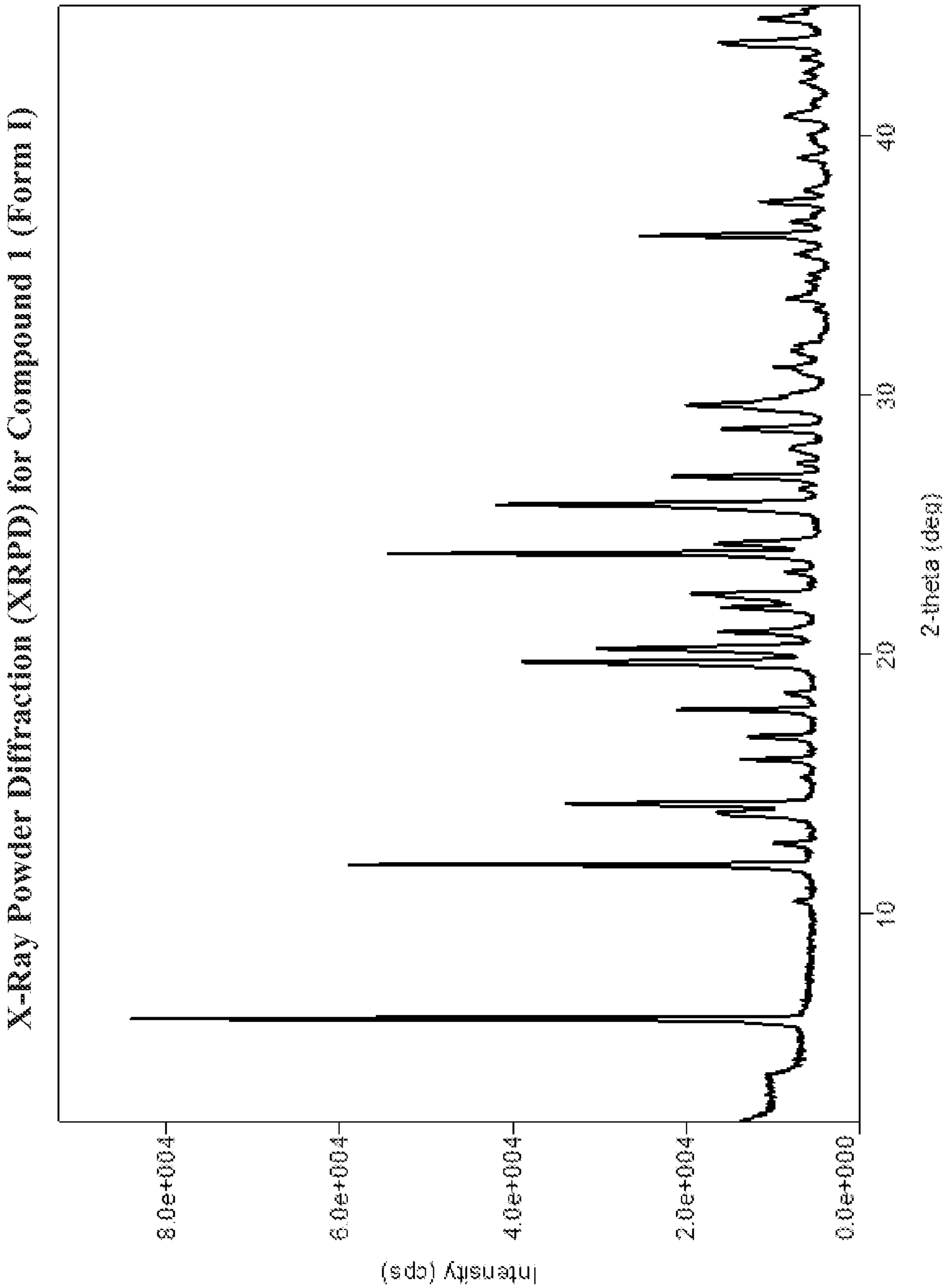
FIG. 1 shows an exemplary X-ray powder diffraction (XRPD) pattern for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) prepared according to Example 3.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The term "about" preceding a temperature have an allowable variability of ±5° C. In all other instances, unless otherwise specified, the term "about" preceding a stated value includes the stated value and also includes ±20% of the stated value, and includes more specifically values of ±10%, ±5%, ±2%, and ±1% of the stated value.

To provide a more concise description, some of the quantitative expressions herein are recited as a range from about amount X to about amount Y. It is understood that when a range is recited, the range is not limited to the recited upper and lower bounds, but rather includes the full range from about amount X through about amount Y, or any range therein.

As used herein, "room temperature", or "RT", refers to the ambient temperature of a typical laboratory, which is generally around 25° C.

As used herein, "administration", or "administering", refers to a method of giving a dosage of a compound or pharmaceutical formulation to a vertebrate or invertebrate, including a mammal, a bird, a fish, or an amphibian. The preferred method of administration can vary depending on various factors, e.g., the components of the pharmaceutical formulation, the site of the disease, and the severity of the disease.

The term "$C_6$-$C_{10}$ aryl" refers to a saturated ring system containing 6 to 10 carbon atoms that can contain a single ring or two fused rings and is aromatic, such as phenyl and naphthalenyl. When one or more substituents are present on the "aryl" ring, the substituent(s) can be bonded at any available ring carbon.

The term "$C_1$-$C_6$ alkyl" and "$C_1$-$C_4$ alkyl" refers to a saturated straight or branched carbon radical containing 1 to 6 carbons (i.e., "$C_1$-$C_6$ alkyl") or 1 to 4 carbons (i.e., "$C_1$-$C_4$ alkyl"). Some embodiments are 1 to 5 carbons (i.e., $C_1$-$C_5$ alkyl), some embodiments are 1 to 3 carbons (i.e., $C_1$-$C_3$ alkyl), and some embodiments are 1 or 2 carbons. Examples of an alkyl group include: methyl, ethyl, n-propyl, isopropyl, n-butyl, sec-butyl, isobutyl, tert-butyl, pentyl, isopentyl, tert-pentyl, neo-pentyl, 1-methylbutyl [i.e., —$CH(CH_3)CH_2CH_2CH_3$], 2-methylbutyl [i.e., —$CH_2CH(CH_3)CH_2CH_3$], n-hexyl and the like.

The term "$C_1$-$C_4$ alkylsulphonyloxy" refers to a radical consisting of a $C_1$-$C_4$ alkyl group attached directly to the sulfur of an $SO_3$ group. The "$C_1$-$C_4$ alkylsulphonyloxy" group can be represented by the formula: $C_1$-$C_4$ alkylS(=O)$_2$O— or the following:

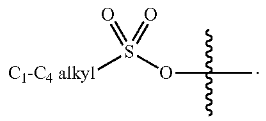

The term $C_1$-$C_4$ alkyl has the same definition as found herein. Examples include: methanesulfonate [$CH_3S(=O)_2O$—, or (methylsulfonyl)oxy], ethanesulfonate, propanesulfonate, isopropylsulfonate, butanesulfonate, and the like.

The term "$C_1$-$C_6$ alkoxy" refers to a radical consisting of a $C_1$-$C_6$ alkyl group attached directly to an oxygen atom, wherein $C_1$-$C_6$ alkyl has the same definition as found herein. Some embodiments contain 1 to 5 carbons (i.e., $C_1$-$C_5$ alkoxy). Some embodiments contain 1 to 4 carbons (i.e., $C_1$-$C_4$ alkoxy). Some embodiments contain 1 to 3 carbons (i.e., $C_1$-$C_3$ alkoxy). Some embodiments contain 1 or 2 carbons. Examples include: methoxy, ethoxy, n-propoxy, isopropoxy, n-butoxy, t-butoxy, isobutoxy, sec-butoxy, and the like.

The term "amorphous" means a solid that is in a non-crystalline state. Amorphous solids are disordered arrangements of molecules and therefore possess no distinguishable crystal lattice or unit cell and consequently have no definable long-range ordering. The solid-state form of a solid can be determined by polarized light microscopy, X-ray powder diffraction (XRPD), differential scanning calorimetry (DSC), or other standard techniques known to those of skill in the art.

The term "$C_6$-$C_{10}$ arylsulfonyloxy" refers to a radical consisting of an aryl group attached directly to the sulfur atom of an $SO_3$ group and can be represented by the formula aryl-S(=O)$_2$O— or the following:

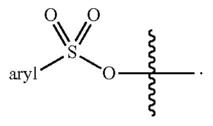

The term aryl has the same definition as found herein. Examples include: benzenesulfonate [PhS(=O)$_2$O—, or (phenylsulfonyl)oxy, besylate], (naphthalen-1-ylsulfonyl)oxy, and (naphthalen-2-ylsulfonyl)oxy.

The term "composition" refers to a compound or crystalline form thereof, including but not limited to, salts, solvates, and hydrates of a compound of the present invention, in combination with at least one additional component, such as, a composition obtained/prepared during synthesis, preformulation, in-process testing/control (e.g., TLC, HPLC, NMR samples), and the like.

The term "% crystallinity" or "crystalline purity" refers to the percentage of a crystalline form in a preparation or sample. It is understood that the preparation or sample may contain other forms, such as, an amorphous form of the same compound, or different crystalline form(s) of the same compound, or mixtures thereof. In some embodiments, the crystalline form can be isolated as the desired form (i.e., the crystalline form as described herein) with a crystalline purity of at least about 75% by weight, about 80% by weight, about 85% by weight, about 90% by weight, about 95% by weight, about 96% by weight, about 97% by weight, about 98% by weight, or about 99% by weight. In some embodiments, the crystalline form can be isolated with a purity of about 90% or greater by weight. In some embodiments, the crystalline form can be isolated with a purity of about 95% or greater by weight. In some embodiments, the crystalline form can be isolated with a purity of about 99% or greater by weight.

When describing particle size for a sample, "D10", "D50", "D90" are used and have the following definitions: the term "D10" as used herein means that 10% of the particles (based on volume) are smaller than or equal to the indicated size; the term "D50" as used herein means that 50% of the particles (based on volume) are smaller than or equal to the indicated size; and the term "D90" as used herein means that 90% of the particles (based on volume) are smaller than or equal to the indicated size. As an example, when a sample as a D10 of 21 μM, then 10% of the particles in that sample are smaller than or equal to 21 μM based on volume.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit, or ameliorate the disease, condition, or disorder.

The term "halo" or "halogen" refers to fluoro, chloro, bromo, or iodo. In some embodiments, halogen is chloro, bromo, or iodo. In some embodiments, halogen is fluoro, chloro, or bromo. In some embodiments, halogen is fluoro. In some embodiments, halogen is chloro. In some embodiments, halogen is bromo. In some embodiments, halogen is iodo.

The term "$C_1$-$C_6$ haloalkyl" refers to a radical consisting of a $C_1$-$C_6$ alkyl group substituted with one or more halogens, wherein $C_1$-$C_6$ alkyl has the same definition as found herein. The $C_1$-$C_6$ haloalkyl may be fully substituted in which case it can be represented by the formula $C_nL_{2n+1}$, wherein L is a halogen and "n" is 1, 2, 3, 4, 5, or 6. When more than one halogen is present then they may be the same or different and selected from: fluorine, chlorine, bromine, and iodine. In some embodiments, haloalkyl contains 1 to 5 carbons (i.e., $C_1$-$C_5$ haloalkyl). In some embodiments, haloalkyl contains 1 to 4 carbons (i.e., $C_1$-$C_4$ haloalkyl). In some embodiments, haloalkyl contains 1 to 3 carbons (i.e., $C_1$-$C_3$ haloalkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "hydroxyl" refers to the group —OH.

The term "individual" or "subject" refers to any animal, including mammals, such as, mice, rats, other rodents, rabbits, dogs, cats, swine, cattle, sheep, horses, primates, and humans. In some embodiment "individual" refers to humans. In the context of a clinical trial or screening or activity experiment the subject may be a healthy volunteer or healthy participant without an underlying CFR-mediated disorder or condition or a volunteer or participant that has received a diagnosis for a disorder or condition in need of medical treatment as determined by a health care professional. In the context outside of a clinical trial a subject under the care of a health care professional who has received a diagnosis for a disorder or condition is typically described as a patient.

The term "inorganic base" refers to a base that does not include at least one C—H bond and includes at least one alkali metal or alkaline earth metal. Examples of an inorganic base include, but are not limited to, barium carbonate, calcium carbonate, cesium carbonate, lithium carbonate, magnesium carbonate, potassium carbonate, sodium carbonate, cesium hydrogen carbonate, potassium hydrogen carbonate, sodium hydrogen carbonate, barium hydroxide, calcium hydroxide, cesium hydroxide, lithium hydroxide, magnesium hydroxide, potassium hydroxide, sodium hydroxide, and the like.

As used herein, "leaving group" refers to an atom or a group of atoms that is displaced in a chemical reaction as a stable species. Suitable leaving groups are well known in the art, e.g., see, March's Advanced Organic Chemistry, 5th Ed., Ed.: Smith, M. B. and March, J., John Wiley & Sons, New York: 2001 and T. W. Greene, Protective Groups in Organic Synthesis, 3rd Ed., John Wiley & Sons, New York, 1999. Such leaving groups include, but are not limited to, halogen, optionally substituted alkylsulphonyloxy, and optionally substituted arylsulfonyloxy. Examples of some leaving groups include chloro, bromo, iodo, mesylate, tosylate, triflate, nosylate, and brosylate.

The term "nitro" refers to the group —$NO_2$.

The term "pediatric subject" refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)) see e.g., Berhman et al., *Textbook of Pediatrics,* 15th Ed. Philadelphia: W.B. Saunders Company, 1996; Rudolph et al., *Rudolph's Pediatrics,* 21st Ed. New York: McGraw-Hill, 2002; and Avery et al., *Pediatric Medicine,* 2nd Ed. Baltimore: Williams & Wilkins; 1994.

In some embodiments, a "pediatric subject" is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

The phrase "pharmaceutically acceptable" refers to compounds (and salts thereof), compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" or "pharmaceutically acceptable excipient" includes any and all solvents, co-solvents, complexing agents, dispersion media, coatings, antibacterial and antifungal agents, isotonic and absorption delaying agents, and the like, which are not biologically or otherwise undesirable. The use of such media and agents for pharmaceutically active substances is well known in the art. Except insofar as any conventional media or agent is incompatible with the active ingredient, its use in the therapeutic formulations is contemplated. Supplementary active ingredients can also be incorporated into the formulations. In addition, various excipients, such as are commonly used in the art, can be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (2010); Goodman and Gilman's: The Pharmacological Basis of Therapeutics, 12th Ed., The McGraw-Hill Companies.

The term "pharmaceutical composition" refers to a specific composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "phase-transfer catalyst" is any ionic catalyst, such as quaternary ammonium salts, that can enable the migration of a reactant from one phase into another phase where the reaction occurs. Suitable leaving groups are well known in the art. Examples include, acetylcholine chloride, (2-aminoethyl)trimethylammonium chloride hydrochloride, benzalkonium chloride, benzyldimethyldecylammonium chloride, benzyldimethyldodecylammonium chloride, benzyldimethylhexadecylammonium chloride, benzyldimethylhexylammonium chloride, benzyldimethyloctylammonium chloride, benzyldimethyltetradecylammonium chloride, benzyldodecyldimethylammonium bromide, benzyltributylammonium bromide, benzyltributylammonium chloride, benzyltributylammonium iodide, benzyltriethylammonium bromide, benzyltriethylammonium chloride, benzyltrimethylammonium bromide, benzyltrimethylammonium chloride, (3-carboxypropyl)trimethylammonium chloride, cetyltrimethylammonium chloride, cetyltrimethylammonium hydrogensulfate, choline chloride, decyltrimethylammonium bromide, diallyldimethylammonium chloride, didecyldimethylammonium bromide, didodecyldimethylammonium bromide, dihexadecyldimethylammonium bromide, dimethyldioctadecylammonium bromide, dimethylditetradecylammonium bromide, dimethyloctadecyl[3-(trimethoxysilyl)propyl]ammonium chloride, dodecylethyldimethylammonium bromide, dodecyltrimethylammonium chloride, domiphen bromide, heptadecafluorooctanesulfonic acid tetraethylammonium salt, hexadecyltrimethylammonium bromide, hexadecyltrimethylammonium chloride, hexyltrimethylammonium bromide, malondialdehyde tetrabutylammonium salt, methyltrioctylammonium bromide, methyltrioctylammonium chloride, methyltrioctylammonium hydrogen sulfate, methyltrioctylammonium thiosalicylate, myristyltrimethylammonium bromide, tetrabutylammonium acetate, tetrabutylammonium benzoate, tetrabutylammonium bisulfate, tetrabutylammonium bromide, tetrabutylammonium chloride, tetrabutylammonium cyanide, tetrabutylammonium hexafluorophosphate, tetrabutylammonium hydrogensulfate, tetrabutylammonium iodide, tetrabutylammonium methanesulfonate, tetrabutylammonium methoxide, tetrabutylammonium nonafluorobutanesulfonate, tetrabutylammonium perchlorate, tetrabutylammonium phosphate monobasic, tetrabutylammonium succinimide, tetrabutylammonium sulfate, tetrabutylammonium tetrabutylborate, tetrabutylammonium tetrafluoroborate, tetrabutylammonium tetraphenylborate, tetrabutylammonium thiocyanate, tetrabutylammonium p-toluenesulfonate, tetrabutylammonium trifluoromethanesulfonate, tetradodecylammonium bromide, tetradodecylammonium chloride, tetraethylammonium acetate tetrahydrate, tetraethylammonium benzoate, tetraethylammonium bicarbonate, tetraethylammonium bromide, tetraethylammonium chloride, tetraethylammonium cyanide, tetraethylammonium hexafluorophosphate, tetraethylammonium iodide, tetraethylammonium tetrafluoroborate, tetraethylammonium p-toluenesulfonate, tetraethylammonium trifluoromethanesulfonate, tetraheptylammonium bromide, tetrahexadecylammonium bromide, tetrahexylammonium bromide, tetrahexylammonium chloride, tetrahexylammonium hexafluorophosphate, tetrahexylammonium hydrogensulfate, tetrahexylammonium iodide, tetrahexylammonium tetrafluoroborate, tetrakis(decyl)ammonium bromide, tetramethylammonium acetate, tetramethylammonium bis(trifluoromethanesulfonyl)imide, tetramethylammoniumbisulfate, tetramethylammonium bromide, tetramethylammonium chloride, tetramethylammonium chloride, tetramethylammonium hexafluorophosphate, tetramethylammonium hydrogen sulfate, tetramethylammonium hydrogensulfate, tetramethylammonium iodide, tetramethylammonium silicate, tetramethylammonium sulfate, tetramethylammonium tetrafluoroborate, tetraoctadecylammonium bromide, tetraoctylammonium bromide, tetraoctylammonium chloride, tetrapentylammonium bromide, tetrapentylammonium chloride, tetrapropylammonium bromide, tetrapropylammonium chloride, tetrapropylammonium iodide, tetrapropylammonium tetrafluoroborate, tributylammonium pyrophosphate, tributylmethylammonium bromide, tributylmethylammonium chloride, tridodecylmethylammonium chloride, tridodecylmethylammonium iodide, triethylhexylammonium bromide, triethylmethylammonium chloride, trihexyltetradecylammonium bromide, trimethyloctadecylammonium bromide, trimethyloctylammonium bromide, trimethyloctylammonium chloride, trimethylphenylammonium bromide, trimethylphenylammonium chloride, trimethyl-tetradecylammonium chloride, and the like.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual. The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein. A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "prevent", "preventing", and "prevention" refer to the elimination or reduction of the occurrence or onset of one or more symptoms associated with a specific disorder. For example, the terms "prevent", "preventing", and "prevention" can refer to the administration of therapy on a prophylactic or preventative basis to an individual who may ultimately manifest at least one symptom of a disorder but who has not yet done so. Such individuals can be identified on the basis of risk factors that are known to correlate with the subsequent occurrence of the disease, such as the presence of a biomarker. Alternatively, prevention therapy can be administered as a prophylactic measure without prior identification of a risk factor. Delaying the onset of the at least one episode and/or symptom of a disorder can also be considered prevention or prophylaxis.

As used herein, the term "reacting", "contacting", or "treating" when describing a certain chemical reaction or process is used as known in the art and generally refers to the bringing together chemical reagents and/or intermediates in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product. Additional terms are also used herein solely to provide descriptive clarity between the different process steps and each of these terms have the same definition as described above. These additional terms include, "alkylating", "cyclizing", "deprotecting", "reducing", and "condensing".

The term "solvate" as used herein refers to a solid-state form of a compound of the present invention or a pharmaceutically acceptable salt thereof which includes a stoichiometric or non-stoichiometric amount of a solvent bound by non-covalent intermolecular forces. When the solvent is water, the solvate is a hydrate.

The term "subject", as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate. In some embodiments, the subject is a human.

In some embodiments, the subject has experienced and/or exhibited at least one symptom of the disease or disorder to be treated and/or prevented. In some embodiments, the subject has been identified or diagnosed as having congenital adrenal hyperplasia (CAH). In some embodiments, the subject is suspected of having CAH. In some embodiments, the subject has a clinical record indicating that the subject has CAH (and optionally the clinical record indicates that the subject should be treated with any of the compositions provided herein). In some embodiments, the subject is a pediatric subject.

As used herein, the term "substituted" refers to the replacement of at least one of hydrogen atom of a chemical group with a non-hydrogen substituent or group, the non-hydrogen substituent can be monovalent or divalent. When the chemical group or substituent is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group substituted with one substituent up to the total number of substituents physically allowed by the group. It is understood that "optionally substituted" as used herein refers to the group being either "unsubstituted" or "substituted" with a group. Accordingly, when a group is "optionally substituted with one or more substituents", it is understood that the group is either "unsubstituted" or "substituted" and when substituted, the group is substituted with one substituent up to the total number of substituents physically allowed by the group as described above. In some embodiments, a group can be "optionally substituted with one, two, three, or four substituents". In some embodiments, a group can be "optionally substituted with one, two, or three substituents". In some embodiments, a group can be "optionally substituted with one or two substituents". In some embodiments, a group can be "optionally substituted with one substituent". Further, when a group is substituted with more than one substituent, then the substituents can be identical, or they can be different. Examples of substituents include, without limitation, halogen, alkoxy, alkyl, haloalkyl, hydroxy, nitro.

As used herein, "treat", or "treatment", refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

The term "therapeutically effective amount" refers to the amount of the compound of the present invention or a pharmaceutically acceptable salt thereof, or an amount of a pharmaceutical composition comprising the compound of the invention or a pharmaceutically acceptable salt thereof, that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

Crystalline Forms

The crystalline forms of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) and intermediates related thereto can be identified by their unique solid state signatures with respect to, for example, Differential Scanning Calorimetry (DSC), X-ray Powder Diffraction (XRPD), and other solid state methods. Further characterization with respect to water or solvent content of the crystalline forms can be gauged by any of the following methods for example, Thermogravimetric Analysis (TGA), DSC and the like.

For DSC, it is known that the temperatures observed for thermal events will depend upon sample purity and may also depend on the rate of temperature change, as well as sample preparation technique, and the instrument employed. Thus, the values reported herein relating to DSC thermograms can vary by plus or minus about 5° C. (i.e., ±about 5° C.). The values reported herein relating to DSC thermograms can also vary by plus or minus about 20 joules per gram (i.e., ±about 20 joules per gram).

For XRPD, the relative intensities of the peaks can vary, depending upon the sample preparation technique, the sample mounting procedure and the instrument employed. Moreover, instrument variation and other factors can often affect the 2θ values. Therefore, the peak assignments of diffraction patterns can vary by plus or minus about 0.2° (i.e., ±about 0.2°). For TGA, the temperature features reported herein can vary by plus or minus about 5° C. (i.e., ±about 5° C.). The TGA % weight changes reported herein over a specified temperature range can vary by plus or minus about 2% weight change (i.e., ±about 2% weight change) due to, for example, variations in sample quality and sample size. All X-ray powder diffraction patterns (diffractograms) were obtained using Cu-Kα radiation.

Further characterization with respect to hygroscopicity of the crystalline form can be gauged by, for example, Gravimetric Vapor Sorption (GVS). The GVS features reported herein can vary by plus or minus about 5% relative humidity (i.e., ±about 5% relative humidity). The GVS features reported herein can also vary by plus or minus about 2% weight change (i.e., ±about 2% weight change).

A. 4-(2-Chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, Anhydrous Crystalline Form I)

One aspect of the present invention relates to a novel anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) and processes related thereto.

A summary of representative physical properties for the anhydrous crystalline form are provided in Table 1 and Table 2.

TABLE 1

| | Compound 1 (Free Base, Anhydrous Form, Form I) |
|---|---|
| PXRD | FIG. 1: Peaks at 25.7, 19.7, 14.3, 20.2, 26.8, 29.6, 22.3, and 43.5°2θ |
| TGA | FIG. 2: Decrease in weight of about 0.2% out to about 125° C. |
| DSC | FIG. 2: Endotherm extrapolated onset temperature: about 83.7° C. |
| GVS | FIG. 3: The adsorption/desorption isotherm shows about 0.1% or less weight change from about 10% relative humidity (RH) to about 90% RH; and about 0.015% or less weight change after an adsorption/desorption cycle from 10% RH to 90% RH and back to 10% RH. |

Certain other XRPD peaks for the anhydrous form of 4-(2-chloro-4-methoxy-5-methylphenyl)-N-[(1S)-2-cyclopropyl-11-(3-fluoro-4-methylphenyl)ethyl]-5-methyl-N-prop-2-ynyl-1,3-thiazol-2-amine (Compound 1, free base) are shown in Table 2 below.

TABLE 2

Selected X-Ray Powder Diffraction (XRPD) Peaks for Form I of Compound 1 (Free Base)

| 2-Theta | Height (cps) |
|---|---|
| 3.7 | 1367 |
| 6.0 | 54956 |
| 10.5 | 1411 |
| 11.9 | 38857 |
| 12.7 | 2962 |
| 13.9 | 7511 |
| 14.3 | 19162 |
| 15.3 | 633 |
| 15.9 | 5554 |
| 16.8 | 5276 |
| 17.9 | 12355 |
| 18.5 | 2151 |

TABLE 2-continued

| Selected X-Ray Powder Diffraction (XRPD) Peaks for Form I of Compound 1 (Free Base) | |
|---|---|
| 2-Theta | Height (cps) |
| 19.7 | 23327 |
| 20.2 | 16234 |
| 20.9 | 8301 |
| 21.8 | 7076 |
| 22.3 | 9288 |
| 23.2 | 2553 |
| 23.9 | 40096 |
| 24.2 | 8183 |
| 25.7 | 28318 |
| 26.4 | 1402 |
| 26.8 | 12745 |
| 27.4 | 1756 |
| 27.9 | 2135 |
| 28.7 | 8128 |
| 29.6 | 9678 |
| 30.8 | 1608 |
| 31.1 | 3504 |
| 31.7 | 2234 |
| 31.9 | 2063 |
| 33.3 | 1006 |
| 33.7 | 3078 |
| 34.3 | 981 |
| 34.6 | 1161 |
| 35.4 | 1906 |
| 36.0 | 2386 |
| 36.1 | 19374 |
| 36.7 | 2685 |
| 36.9 | 1007 |
| 37.4 | 5567 |
| 37.9 | 1583 |
| 39.1 | 2220 |
| 39.8 | 898 |
| 40.0 | 1084 |
| 40.7 | 2910 |
| 41.2 | 894 |
| 42.0 | 1390 |
| 42.4 | 1279 |
| 42.9 | 1844 |
| 43.5 | 8967 |
| 43.6 | 5252 |
| 44.2 | 535 |
| 44.5 | 4977 |

Figure 3:
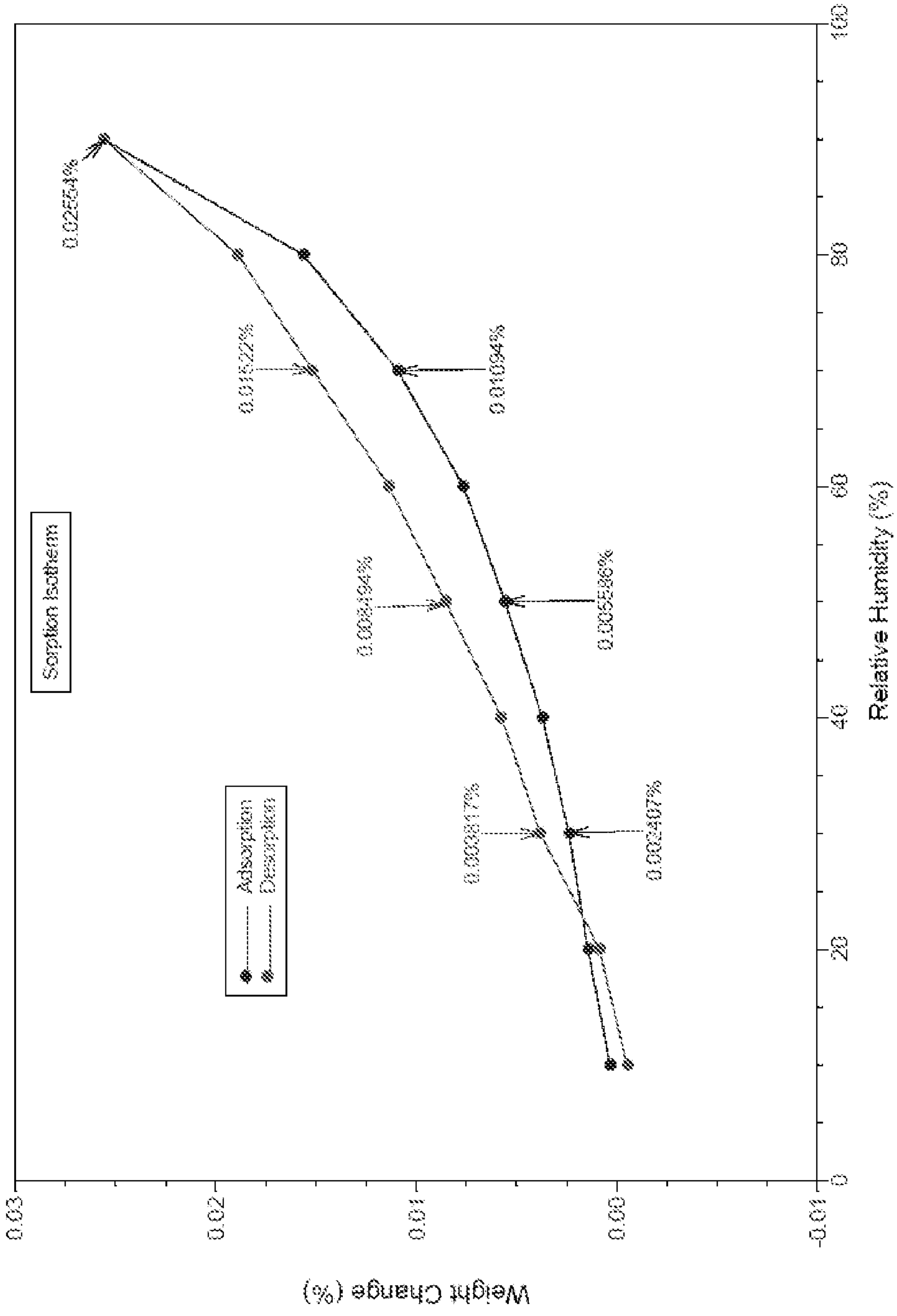
FIG. 3 shows an exemplary Gravimetric Vapor Sorption (GVS) for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) as described in Example 4.

The GVS profile (adsorption/desorption isotherm) for the anhydrous crystalline Form I of Compound 1 (free base) is shown in FIG. 3. The corresponding data in tabular form is provided in Table 3, where there was substantially no weight change after a cycle from 10% RH to 90% RH and back to 10% RH.

TABLE 3

| Relative Humidity (%) | Phase | Weight Change (%) |
|---|---|---|
| 30 | Adsorption | 0.002407 |
| 50 | Adsorption | 0.005586 |
| 70 | Adsorption | 0.01094 |
| 90 | Adsorption | 0.02554 |
| 90 | Desorption | 0.02554 |
| 70 | Desorption | 0.01522 |
| 50 | Desorption | 0.008494 |
| 30 | Desorption | 0.003817 |

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base). Anhydrous crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) refers to anhydrous crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has an X-ray powder diffraction pattern comprising at least three peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least four peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least five peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least six peaks, in terms of 2θ, selected from the group consisting of: 6.0°±0.2°, 11.9°±0.2°, 13.9°±0.2°, 14.3° 0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.70°±0.2°, 29.6°±0.2°, 36.1°±0.2°, and 43.5°±0.2°. In some embodiments, the anhydrous crystalline form (Compound 1, free base) has an X-ray powder diffraction pattern comprising at least seven peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least eight peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least nine peaks, in terms of 2θ, selected from the group consisting of: 6.0°±0.2°, 11.9°±±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°. In some embodiments, the anhydrous crystalline form (Compound 1, free base) has an X-ray powder diffraction pattern comprising at least ten peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has an X-ray powder diffraction pattern comprising a peak, in terms of 2θ, at 14.3°±0.2°. In some embodiments, the anhydrous crystalline form (Compound 1, free base) an X-ray powder diffraction pattern comprising a peak, in terms of 2θ, at 19.7°±0.2°. In some embodiments, the anhydrous crystalline form (Compound 1, free base) has an X-ray powder diffraction pattern comprising a peak, in terms of 2θ, at 25.7°±0.2°. In some embodiments, the anhydrous crystalline form (Compound 1, free base) has an X-ray powder diffraction pattern comprising peaks, in terms of 2θ, at 14.3°±0.2°, and 25.7°±0.2°. In some embodiments, the anhydrous crystalline form (Compound 1, free base) has an X-ray powder diffraction pattern comprising peaks, in terms of 2θ, at 14.3°±0.2°, and 19.7°±0.2°. In some embodiments, the anhydrous crystalline form (Compound 1, free base) has an X-ray powder diffraction pattern comprising peaks, in terms of 2θ, at 19.7°±0.2°, and 25.7°±0.2°. In some embodiments, the anhydrous crystalline form (Compound 1, free base) has an X-ray powder diffraction pattern comprising peaks, in terms of 2θ, at 14.3°±0.2°, 19.7°±0.2°, and 25.7°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, and 25.7°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, 25.7°±0.2°, 26.8°±0.2°, and 29.6°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, 22.3°±0.2°, 25.7°±0.2°, 26.8°±0.2°, and 29.6°±0.2°. In some embodiments, the anhydrous crystalline form (Compound 1, free base) an X-ray powder diffraction pattern comprising peaks, in terms of 2θ, at 14.3°±0.2°, 19.7°±0.2°, 20.2°±0.2°, 22.3°±0.2°, 25.7°±0.2°, 26.8°±0.2°, 29.6°±0.2°, and 43.5°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, 20.9°±0.2°, 22.3°±0.2°, 25.7°±0.2°, 24.2°±0.2°, 26.8°±0.2°, 29.6°±0.2°, and 43.5°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, 20.9°±0.2°, 22.3°±0.2°, 25.7°±0.2°, 24.2°±0.2°, 26.8°±0.2°, 28.7°±0.2°, 29.6°±0.2°, and 43.5°±0.2°. In some embodiments, the anhydrous crystalline form (Compound 1, free base) has an X-ray powder diffraction pattern comprising peaks, in terms of 2θ, at 14.3°±0.2°, 19.7°±0.2°, 20.2°±0.2°, 20.9°±0.2°, 21.8°±0.2°, 22.3°±0.2°, 25.7°±0.2°, 24.2°±0.2°, 26.8°±0.2°, 28.7°±0.2°, 29.6°±0.2°, and 43.5°±0.2°. In some embodiments, the anhydrous crystalline form (Compound 1, free base) has an X-ray powder diffraction pattern substantially as shown in FIG. 1, wherein by "substantially" is meant that the reported peaks can vary by about ±0.2° 2θ.

Figure 7:
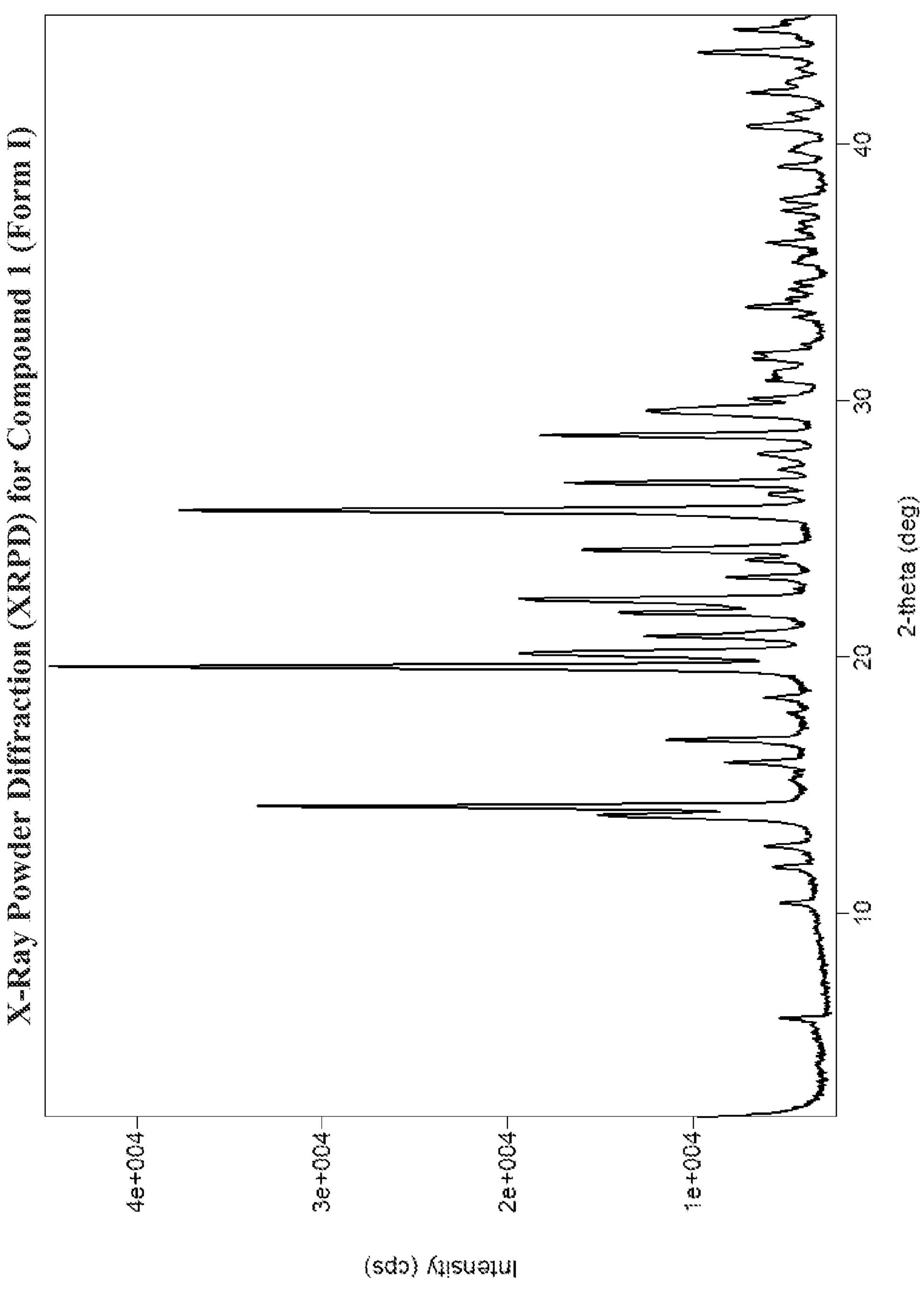
FIG. 7 shows an exemplary X-ray powder diffraction (XRPD) pattern for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).
Figure 8:
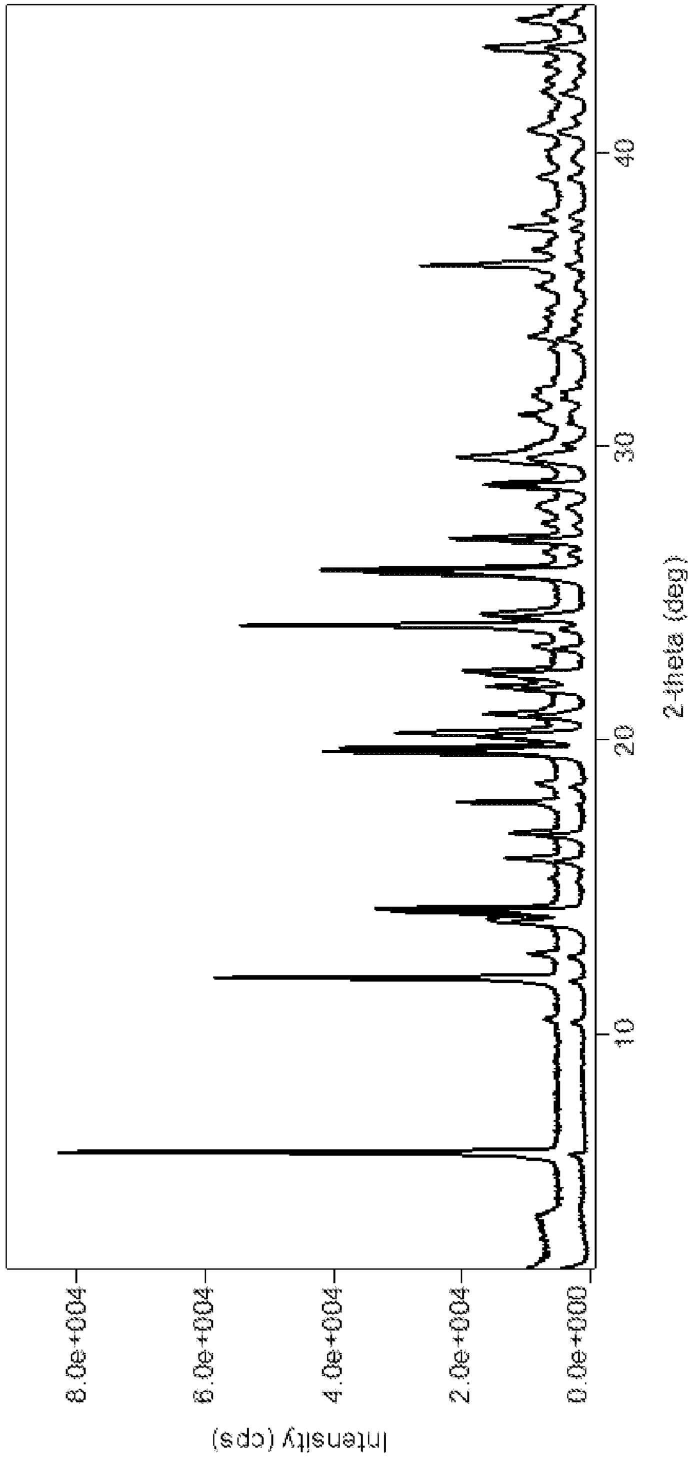
FIG. 8 shows an overlay of the exemplary X-ray powder diffraction (XRPD) patterns from FIG. 1 and FIG. 7 for crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), and although the intensities for certain peaks are rather dramatic, the overlay clearly shows substantially the same peak positioning.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One example is the XRPD for Form I shown in FIG. 7 showing substantially the same peak positions but dramatic peak intensity differences. One skilled in the art would understand that FIG. 1 and FIG. 7 are the XRPD's for Form I, despite the differences in the peak intensities. Similarly, those skilled in the art would readily be capable of comparing the diffractograms provided herein with a diffractogram generated for an unknown crystal form and confirm whether the diffractogram is characterizing the same crystal form as provided herein or a different form.

Figure 2:
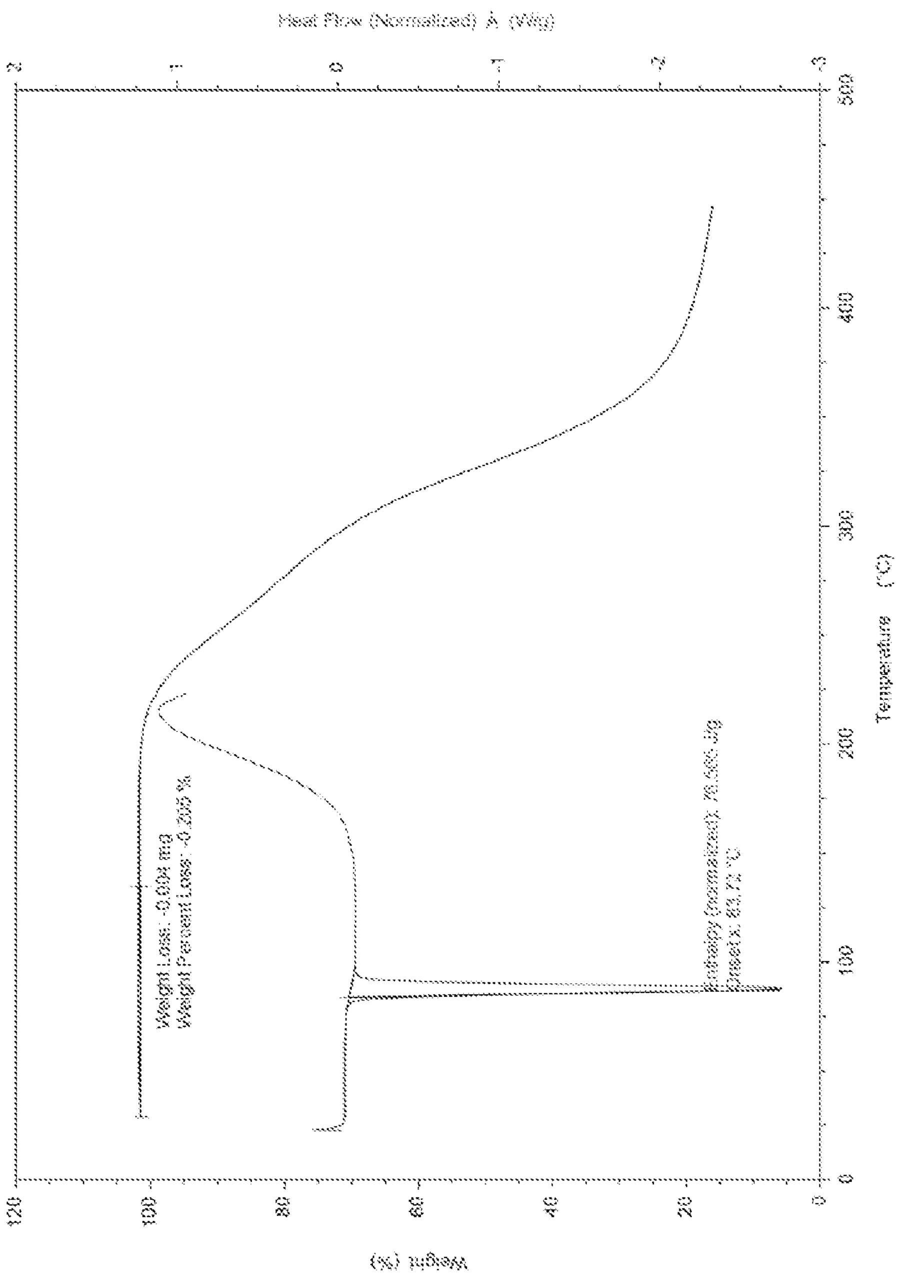
FIG. 2 shows an exemplary Differential Scanning Calorimetry (DSC) and Thermogravimetric Analysis (TGA) thermograms for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) prepared according to Example 3.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has a differential scanning calorimetry (DSC) thermogram comprising an endotherm with an extrapolated onset temperature of about 81° C. to about 89.5° C. In some embodiments, the anhydrous crystalline form (Compound 1, free base) has a differential scanning calorimetry thermogram comprising an endotherm with an extrapolated onset temperature of about 82° C. to about 88° C. In some embodiments, the anhydrous crystalline form (Compound 1, free base) has a differential scanning calorimetry thermogram comprising an endotherm with an extrapolated onset temperature of about 82.5° C. to about 88.5° C. In some embodiments, the anhydrous crystalline form (Compound 1, free base) has a differential scanning calorimetry thermogram comprising an endotherm with an extrapolated onset temperature of about 83° C. to about 88° C. In some embodiments, the anhydrous crystalline form (Compound 1, free base) has a differential scanning calorimetry thermogram comprising an endotherm with an extrapolated onset temperature of about 83.5° C. to about 87.5° C. In some embodiments, the anhydrous crystalline form (Compound 1, free base) has a differential scanning calorimetry thermogram substantially as shown in FIG. 2, wherein by "substantially" is meant that the reported DSC features can vary by about ±5° C. and the reported DSC features can vary by about ±20 joules per gram.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has a thermogravimetric analysis (TGA) profile showing about 1.0% or less weight loss out to about 125° C. In some embodiments, the anhydrous crystalline form (Compound 1, free base) has a thermogravimetric analysis profile showing about 0.9% or less weight loss out to about 125° C. In some embodiments, the anhydrous crystalline form (Compound 1, free base) has a thermogravimetric analysis profile showing about 0.7% or less weight loss out to about 125° C. In some embodiments, the anhydrous crystalline form (Compound 1, free base) has a thermogravimetric analysis profile showing about 0.6% or less weight loss out to about 125° C. In some embodiments, the anhydrous crystalline form (Compound 1, free base) has a thermogravimetric analysis profile showing about 0.5% or less weight loss out to about 125° C.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has a thermogravimetric analysis (TGA) profile showing about 0.05% to about 1.0% weight loss out to about 125° C. In some embodiments, the anhydrous crystalline form (Compound 1, free base) has a thermogravimetric analysis profile showing about 0.1% to about 0.9% weight loss out to about 125° C. In some embodiments, the anhydrous crystalline form (Compound 1, free base) has a thermogravimetric analysis profile showing about 0.1% to about 0.7% weight loss out to about 125° C. In some embodiments, the anhydrous crystalline form (Compound 1, free base) has a thermogravimetric analysis profile showing about 0.10% to about 0.6% weight loss out to about 125° C. In some embodiments, the anhydrous crystalline form (Compound 1, free base) has a thermogravimetric analysis profile showing about 0.1% to about 0.4% weight loss out to about 125° C. In some embodiments, the anhydrous crystalline form (Compound 1, free base) has a thermogravimetric analysis profile substantially as shown in FIG. 2, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has a gravimetric vapor sorption profile showing about 0.015% or less weight change after an adsorption/desorption cycle from 10% relative humidity (RH) to 90% RH and back to 10% RH. In some embodiments, the anhydrous crystalline form (Compound 1, free base) has a gravimetric vapor sorption profile showing about 0.01% or less weight change after an adsorption/desorption cycle from 10% RH to 90% RH and back to 10% RH. In some embodiments, the anhydrous crystalline form (Compound 1, free base) has a gravimetric vapor sorption profile showing about 0.008% or less weight change after an adsorption/desorption cycle from 10% RH to 90% RH and back to 10% RH. In some embodiments, the anhydrous crystalline form (Compound 1, free base) has a gravimetric vapor sorption profile showing about 0.005% or less weight change after an adsorption/desorption cycle from 10% RH to 90% RH and back to 10% RH. In some embodiments, the anhydrous crystalline form (Compound 1, free base) has a gravimetric vapor sorption profile showing about 0.003% or less weight change after an adsorption/desorption cycle from 10% RH to 90% RH and back to 10% RH. In some embodiments, the anhydrous crystalline form (Compound 1, free base) has a gravimetric vapor sorption profile showing substantially no weight change after an adsorption/desorption cycle from 10% RH to 90% RH and back to 10% RH.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has a gravimetric vapor sorption profile showing about 0.1% or less weight change from about 10% relative humidity (RH) to about 90% RH; and about 0.015% or less weight change after an adsorption/desorption cycle from 10% RH to 90% RH and back to 10% RH. In some embodiments, the anhydrous crystalline form (Compound 1, free base) has a gravimetric vapor sorption profile showing about 0.08% or less weight change from about 10% relative humidity (RH) to about 90% RH; and about 0.01% or less weight change after an adsorption/desorption cycle from 10% RH to 90% RH and back to 10% RH. In some embodiments, the anhydrous crystalline form (Compound 1, free base) has a gravimetric vapor sorption profile showing about 0.05% or less weight change from about 10% relative humidity (RH) to about 90% RH; and about 0.008% or less weight change after an adsorption/desorption cycle from 10% RH to 90% RH and back to 10% RH. In some embodiments, the anhydrous crystalline form (Compound 1, free base) has a gravimetric vapor sorption profile showing about 0.04% or less weight change from about 10% RH to about 90% RH; and about 0.005% or less weight change after an adsorption/desorption cycle from 10% RH to 90% RH and back to 10% RH. In some embodiments, the anhydrous crystalline form (Compound 1, free base) has a gravimetric vapor sorption profile showing about 0.03% or less weight change from about 10% RH to about 90% RH; and about 0.003% or less weight change after an adsorption/desorption cycle from 10% RH to 90% RH and back to 10% RH. In some embodiments, the anhydrous crystalline form (Compound 1, free base) has a gravimetric vapor sorption profile showing about 0.2% or less weight change from about 10% RH to about 90% RH; and substantially no weight change after an adsorption/desorption cycle from 10% RH to 90% RH and back to 10% RH. In some embodiments, the anhydrous crystalline form (Compound 1, free base) has a gravimetric vapor sorption profile substantially as shown in FIG. 3, wherein "substantially" is meant that the reported GVS features can vary by plus or minus about 5% relative humidity (i.e., ±about 5% relative humidity) and also vary by plus or minus about 2% weight change (i.e., ±about 2% weight change).

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has:

an X-ray powder diffraction pattern comprising at least three peaks, in terms of 2θ, selected from the group consisting of: 6.0°±0.2°, 11.9°±0.2°, 13.9°±0.2°, 14.3°±0.2°, 16.8°±0.2°, 17.9° 0.2°, 19.7°±0.2°, 20.2°±0.2°, 20.9°±0.2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°;

a differential scanning calorimetry thermogram comprising an endotherm with an extrapolated onset temperature of about 81° C. to about 89.5° C.;

a thermogravimetric analysis profile showing about 0.05% to about 1.0% weight loss out to about 125° C.; and/or a gravimetric vapor sorption profile showing about 0.015% or less weight change after an adsorption/desorption cycle from 10% RH to 90% RH and back to 10% RH.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has:

an X-ray powder diffraction pattern comprising peaks, in terms of 2θ, at 14.3°±0.2°, 19.7°±0.2°, and 25.7°±0.2°;

a differential scanning calorimetry thermogram comprising an endotherm with an extrapolated onset temperature of about 82.5° C. to about 88.5° C.;

a thermogravimetric analysis profile showing about 0.7% or less weight loss out to about 125° C.; and/or a gravimetric vapor sorption profile showing about 0.005% or less weight change after an adsorption/desorption cycle from 10% RH to 90% RH and back to 10% RH.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has:

an X-ray powder diffraction pattern comprising peaks, in terms of 2θ, at 14.3°±0.2°, 19.7°±0.2°, 20.2°±0.2°, 22.3°±0.2°, 25.7°±0.2°, 26.8°±0.2°, 29.6°±0.2°, and 43.5°±0.2°;

a differential scanning calorimetry thermogram comprising an endotherm with an extrapolated onset temperature of about 83° C. to about 88° C.;

a thermogravimetric analysis profile showing about 0.5% or less weight loss out to about 125° C.; and/or a gravimetric vapor sorption profile showing about 0.003% or less weight change after an adsorption/desorption cycle from 10% RH to 90% RH and back to 10% RH.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has:

an X-ray powder diffraction pattern substantially as shown in FIG. 1;

a differential scanning calorimetry thermogram substantially as shown in FIG. 2;

a thermogravimetric analysis profile substantially as shown in FIG. 2; and/or a gravimetric vapor sorption profile substantially as shown in FIG. 3.

In some embodiments, the anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

The manufacturing batches of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) have been prepared with the following particle size distribution characterization, as shown in Table 4.

TABLE 4

| Particle size distribution | Batch 1 | Batch 2 | Batch 3 | Batch 4 |
|---|---|---|---|---|
| D10 | 21 μM | 17 μM | 16 μM | 14 μM |
| D50 | 129 μM | 123 μM | 107 μM | 107 μM |
| D90 | 468 μM | 335 μM | 320 μM | 327 μM |

In some embodiments, the anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) has a particle size D10 of about 8 μM to about 35 μM. In some embodiments, the anhydrous crystalline form (Compound 1, free base) has a particle size D10 of about 10 μM to about 30 μM. In some embodiments, the anhydrous crystalline form (Compound 1, free base) has a particle size D10 of about 10 μM to about 27 μM. In some embodiments, the anhydrous crystalline form (Compound 1, free base) has a particle size D10 of about 12 μM to about 25 μM. In some embodiments, the anhydrous crystalline form (Compound 1, free base) has a particle size D10 of about 12 μM to about 23 μM.

In some embodiments, the anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) has a particle size D50 of about 80 μM to about 150 μM. In some embodiments, the anhydrous crystalline form (Compound 1, free base) has a particle size D50 of about 90 μM to about 145 μM. In some embodiments, the anhydrous crystalline form (Compound 1, free base) has a particle size D50 of about 100 μM to about 140 μM. In some embodiments, the anhydrous crystalline form (Compound 1, free base) has a particle size D50 of about 100 μM to about 135 μM. In some embodiments, the anhydrous crystalline form (Compound 1, free base) has a particle size D50 of about 105 μM to about 130 μM.

In some embodiments, the anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) has a particle size D90 of about 280 μM to about 490 μM. In some embodiments, the anhydrous crystalline form (Compound 1, free base) has a particle size D90 of about 290 μM to about 485 μM. In some embodiments, the anhydrous crystalline form (Compound 1, free base) has a particle size D90 of about 300 μM to about 480 μM. In some embodiments, the anhydrous crystalline form (Compound 1, free base) has a particle size D90 of about 305 μM to about 475 μM. In some embodiments, the anhydrous crystalline form (Compound 1, free base) has a particle size D90 of about 310 μM to about 470 PM.

B. (S)-4-(2-Chloro-4-methoxy-5-methylphenyl)-N-(2-cyclopropyl-1-(3-fluoro-4-methylphenyl)ethyl)-5-methylthiazol-2-amine (Compound 9A, Anhydrous Crystalline Form)

One aspect of the present invention relates to a novel anhydrous crystalline form of (S)-4-(2-chloro-4-methoxy-5-methylphenyl)-N-(2-cyclopropyl-11-(3-fluoro-4-methylphenyl)ethyl)-5-methylthiazol-2-amine (Compound 9A) and processes related thereto.

A summary of representative physical properties for the anhydrous crystalline form are below in Table 5 and Table 6.

TABLE 5

Figure 9:
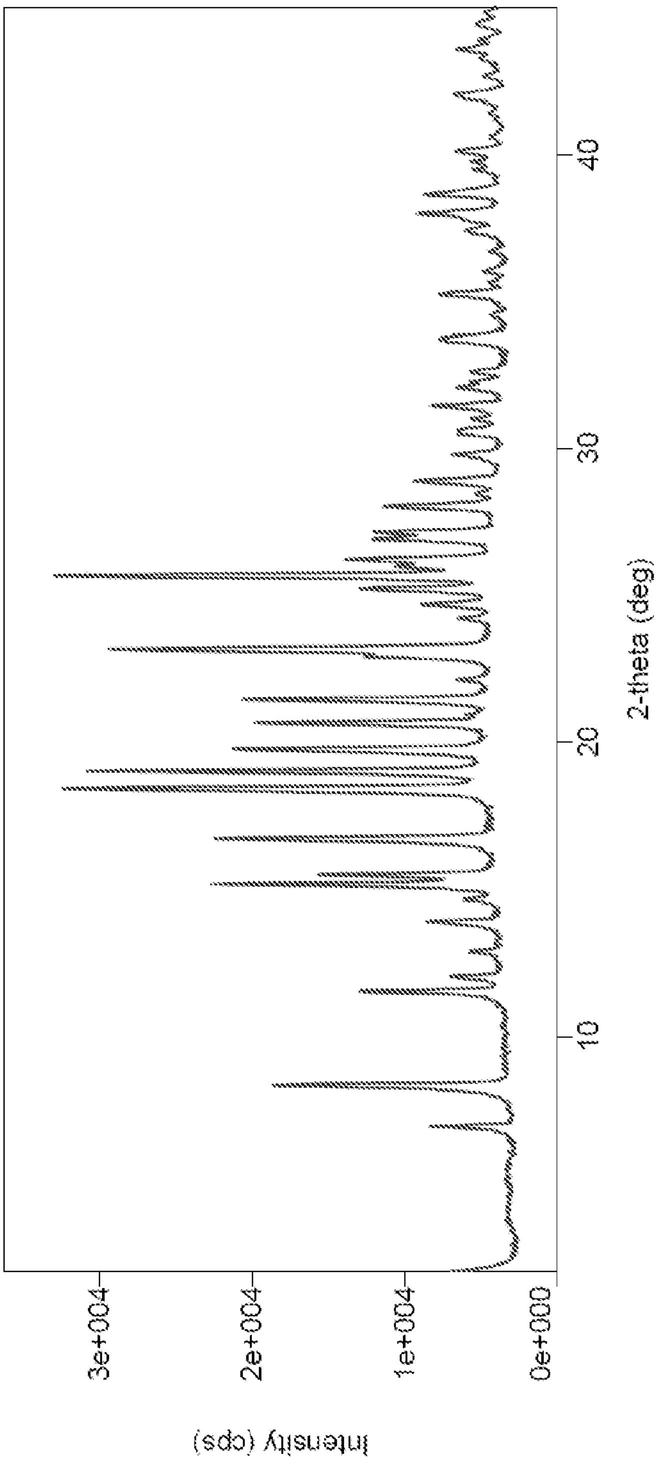
FIG. 9 shows an exemplary X-ray powder diffraction (XRPD) pattern for a sample of crystalline (S)-4-(2-chloro-4-methoxy-5-methylphenyl)-N-(2-cyclopropyl-1-(3-fluoro-4-methylphenyl)ethyl)-5-methylthiazol-2-amine (Compound 9A).

| | Compound 9A (Anhydrous Form) |
|---|---|
| PXRD | FIG. 9: Peaks at 8.3, 15.2, 16.7, 18.4, 19.0, 19.8, 20.7, 21.5, 23.1, and 25.7°2θ |
| TGA | FIG. 10: Decrease in weight of about 0.2% out to about 125° C. |
| DSC | FIG. 10: Endotherm extrapolated onset temperature: about 132.5° C. |

Certain other XRPD peaks for the crystalline form of (S')-4-(2-chloro-4-methoxy-5-methylphenyl)-N-(2-cyclopropyl-11-(3-fluoro-4-methylphenyl)ethyl)-5-methylthiazol-2-amine (Compound 9A) are shown in Table 6 below.

TABLE 6

| 2-Theta | Height (cps) |
|---|---|
| 6.9 | 3643 |
| 8.3 | 10896 |
| 11.5 | 6618 |
| 12 | 2294 |
| 12.9 | 1433 |
| 13.9 | 3413 |
| 14.7 | 1158 |
| 15.2 | 13136 |
| 15.5 | 8199 |
| 16.7 | 12477 |
| 18.4 | 19226 |
| 19 | 18818 |
| 19.8 | 11522 |
| 20.7 | 10872 |
| 21.5 | 10898 |
| 22.1 | 1251 |
| 22.9 | 5163 |
| 23.1 | 17329 |
| 24.7 | 2987 |
| 25.2 | 5834 |
| 25.7 | 20895 |
| 26 | 3751 |
| 26.2 | 6435 |
| 26.9 | 5510 |
| 27.1 | 5737 |
| 28 | 5154 |
| 28.4 | 744 |
| 28.9 | 3802 |
| 29.8 | 1824 |
| 30.5 | 2030 |
| 31 | 1030 |
| 31.4 | 2970 |
| 32.1 | 1687 |
| 32.6 | 1628 |
| 33.7 | 2844 |
| 34.5 | 497 |
| 35.6 | 646 |
| 36 | 975 |
| 36.7 | 694 |
| 37.4 | 1490 |
| 37.8 | 1794 |
| 38 | 3987 |
| 38.6 | 4047 |
| 39.5 | 1217 |
| 39.7 | 1138 |
| 40.1 | 2059 |
| 40.6 | 377 |
| 41.7 | 532 |
| 42 | 2005 |
| 42.7 | 589 |
| 43.3 | 794 |
| 43.6 | 1946 |
| 43.9 | 733 |

One aspect of the present invention relates to a crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A). In some embodiments, the crystal form is an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A). An anhydrous crystalline form refers to a crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has an X-ray powder diffraction pattern comprising at least three peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.20°±0.2°, 26.9°±0.2°, 27.1°±0.2°, and 28.0°±0.2°. In some embodiments, the anhydrous crystalline form has an X-ray powder diffraction pattern comprising at least four peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least five peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least six peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least seven peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least eight peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least nine peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.50°±0.2°, 23.1°±0.2°, 25.2°±0.2°, 25.7°±0.2°, 26.2°±0.2°, 26.9°±0.2°, 27.1°±0.2°, and 28.0°±0.2°. In some embodiments, the anhydrous crystalline form has an X-ray powder diffraction pattern comprising at least ten peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°.

One aspect of the present invention relates to an anhydrous crystalline form of (S)-4-(2-chloro-4-methoxy-5- methylphenyl)-N-(2-cyclopropyl-1-(3-fluoro-4-methylphenyl)ethyl)-5-methylthiazol-2-amine (Compound 9A), wherein the anhydrous crystalline form has an X-ray powder diffraction pattern comprising a peak, in terms of 2θ, at 25.7°±0.2°. In some embodiments, the anhydrous crystalline form has an X-ray powder diffraction pattern comprising a peak, in terms of 2θ, at 18.4°±0.2°. In some embodiments, the anhydrous crystalline form has an X-ray powder diffraction pattern comprising a peak, in terms of 2θ, at 19.0°±0.2°. In some embodiments, the anhydrous crystalline form has an X-ray powder diffraction pattern comprising peaks, in terms of 2θ, at 18.4°±0.2° and 19.0°±0.2°. In some embodiments, the anhydrous crystalline form has an X-ray powder diffraction pattern comprising peaks, in terms of 2θ, at 18.4°±0.2° and 25.7°±0.2°. In some embodiments, the anhydrous crystalline form has an X-ray powder diffraction pattern comprising peaks, in terms of 2θ, at 19.0°±0.2° and 25.7°±0.2°. In some embodiments, the anhydrous crystalline form has an X-ray powder diffraction pattern comprising peaks, in terms of 2θ, at 18.4°±0.2°, 19.0°±0.2°, and 25.7°±0.2°. In some embodiments, the anhydrous crystalline form has an X-ray powder diffraction pattern comprising peaks, in terms of 2θ, at 18.4°±0.2°, 19.0°±0.2°, 23.1°±0.2°, and 25.7°±0.2°. In some embodiments, the anhydrous crystalline form has an X-ray powder diffraction pattern comprising peaks, in terms of 2θ, at 15.2°±0.2°, 18.4°±0.2°, 19.0°±0.2°, 23.1°±0.2°, and 25.7°±0.2°. In some embodiments, the anhydrous crystalline form has an X-ray powder diffraction pattern comprising peaks, in terms of 2θ, at 15.2°±0.2°, 16.7°±0.2°, 18.4°±0.2°, 19.0°±0.2°, 19.8°±0.2°, 23.1°±0.2°, and 25.7°±0.2°. In some embodiments, the anhydrous crystalline form has an X-ray powder diffraction pattern comprising peaks, in terms of 2θ, at 15.2°±0.2°, 16.7°±0.2°, 18.4°±0.2°, 19.0°±0.2°, 19.8°±0.2°, 21.5°±0.2°, 23.1°±0.2°, and 25.7°±0.2°. In some embodiments, the anhydrous crystalline form has an X-ray powder diffraction pattern comprising peaks, in terms of 2θ, at 8.3°±0.2°, 15.2°±0.2°, 16.7°±0.2°, 18.4°±0.2°, 19.0°±0.2°, 19.8°±0.2°, 21.50°±0.2°, 23.1°±0.2°, and 25.7°±0.2°. In some embodiments, the anhydrous crystalline form has an X-ray powder diffraction pattern comprising peaks, in terms of 2θ, at 8.3°±0.2°, 15.2°±0.2°, 16.7°±0.2°, 18.4°±0.2°, 19.0°±0.2°, 19.8°±0.2°, 20.7°±0.2°, 21.5°±0.2°, 23.1°±0.2°, and 25.7°±0.2°. In some embodiments, the anhydrous crystalline form has an X-ray powder diffraction pattern comprising peaks, in terms of 2θ, at 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, and 25.7°±0.2°. In some embodiments, the anhydrous crystalline form has an X-ray powder diffraction pattern substantially as shown in FIG. 9, wherein by "substantially" is meant that the reported peaks can vary by about ±0.2°2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 10:
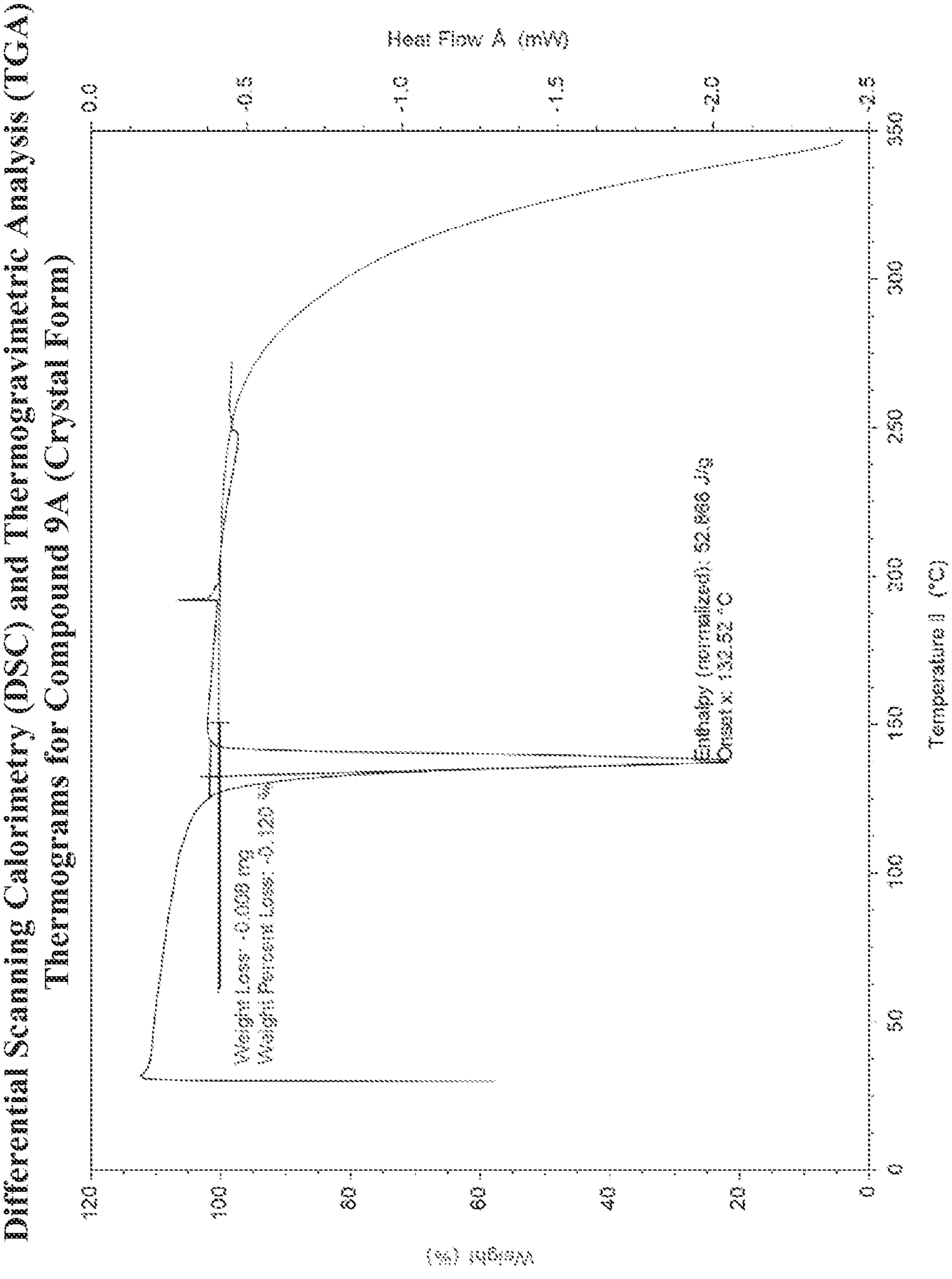
FIG. 10 shows an exemplary Differential Scanning Calorimetry (DSC) and Thermogravimetric Analysis (TGA) thermograms for a sample of crystalline (S)-4-(2-chloro-4-methoxy-5-methylphenyl)-N-(2-cyclopropyl-1-(3-fluoro-4-methylphenyl)ethyl)-5-methylthiazol-2-amine (Compound 9A).

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has a differential scanning calorimetry (DSC) thermogram comprising an endotherm with an extrapolated onset temperature of about 129° C. to about 136° C. In some embodiments, the anhydrous crystalline form has a differential scanning calorimetry thermogram comprising an endotherm with an extrapolated onset temperature of about 130.5° C. to about 135.5° C. In some embodiments, the anhydrous crystalline form has a differential scanning calorimetry thermogram comprising an endotherm with an extrapolated onset temperature of about 131° C. to about 134° C. In some embodiments, the anhydrous crystalline form has a differential scanning calorimetry thermogram comprising an endotherm with an extrapolated onset temperature of about 131.5° C. to about 133.5° C. In some embodiments, the anhydrous crystalline form has a differential scanning calorimetry thermogram comprising an endotherm with an extrapolated onset temperature of about 132° C. to about 133° C. In some embodiments, the anhydrous crystalline form has a differential scanning calorimetry thermogram substantially as shown in FIG. 10, wherein by "substantially" is meant that the reported DSC features can vary by about ±5° C. and the reported DSC features can vary by about ±20 joules per gram.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has a thermogravimetric analysis (TGA) profile showing about 1.0% or less weight loss out to about 125° C. In some embodiments, the anhydrous crystalline form has a thermogravimetric analysis profile showing about 0.7% or less weight loss out to about 125° C. In some embodiments, the anhydrous crystalline form has a thermogravimetric analysis profile showing about 0.4% or less weight loss out to about 125° C. In some embodiments, the anhydrous crystalline form has a thermogravimetric analysis profile showing about 0.2% or less weight loss out to about 125° C. In some embodiments, the anhydrous crystalline form has a thermogravimetric analysis profile showing about 0.15% or less weight loss out to about 125° C.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has a thermogravimetric analysis (TGA) profile showing about 0.05% to about 1.0% weight loss out to about 125° C. In some embodiments, the anhydrous crystalline form has a thermogravimetric analysis profile showing about 0.05% to about 0.7% weight loss out to about 125° C. In some embodiments, the anhydrous crystalline form has a thermogravimetric analysis profile showing about 0.05% to about 0.4% weight loss out to about 125° C. In some embodiments, the anhydrous crystalline form has a thermogravimetric analysis profile showing about 0.05% to about 0.2% weight loss out to about 125° C. In some embodiments, the anhydrous crystalline form has a thermogravimetric analysis profile showing about 0.05% to about 0.15% weight loss out to about 125° C. In some embodiments, the anhydrous crystalline form has a thermogravimetric analysis profile substantially as shown in FIG. 10, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has:

an X-ray powder diffraction pattern comprising at least three peaks, in terms of 2θ, selected from the group consisting of: 8.3°±0.2°, 11.5°±0.2°, 15.2°±0.2°, 15.5°±0.2°, 16.7°±0.2°, 18.4°±0.2°, 19.0°±0.2°, 19.8°±0.2°, 20.7°±0.2°, 21.5°±0.2°, 23.1°±0.2°, 25.2°±0.2°, 25.7°±0.2°, 26.2°±0.2°, 26.9°±0.2°, 27.1°±0.2°, and 28.0°±0.2°;

a differential scanning calorimetry thermogram comprising an endotherm with an extrapolated onset temperature of about 129° C. to about 136° C.; and/or a thermogravimetric analysis profile showing about 0.05% to about 1.0% weight loss out to about 125° C.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has:

an X-ray powder diffraction pattern comprising peaks, in terms of 2θ, at 18.4°±0.2°, 19.0°±0.2°, and 25.7°±0.2°;

a differential scanning calorimetry thermogram comprising an endotherm with an extrapolated onset temperature of about 131° C. to about 134° C.; and/or a thermogravimetric analysis profile showing about 0.7% or less weight loss out to about 125° C.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has:

an X-ray powder diffraction pattern comprising peaks, in terms of 2θ, at 8.3°±0.2°, 15.2°±0.2°, 16.7°±0.2°, 18.4°±0.2°, 19.0°±0.2°, 19.8°±0.2°, 21.5°±0.2°, 23.1°±0.2°, and 25.7°±0.2°;

a differential scanning calorimetry thermogram comprising an endotherm with an extrapolated onset temperature of about 132° C. to about 133° C.; and/or a thermogravimetric analysis profile showing about 0.4% or less weight loss out to about 125° C.

One aspect of the present invention relates to an anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A), wherein the anhydrous crystalline form has:

an X-ray powder diffraction pattern substantially as shown in FIG. 9;

a differential scanning calorimetry thermogram substantially as shown in FIG. 10; and/or a thermogravimetric analysis profile substantially as shown in FIG. 10.

In some embodiments, the anhydrous crystalline form of (S)-4-(2-chloro-4-methoxy-5-methylphenyl)-N-(2-cyclopropyl-1-(3-fluoro-4-methylphenyl)ethyl)-5-methylthiazol-2-amine (Compound 9A) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

C. 1-(2-Chloro-4-methoxy-5-methylphenyl)-2-thiocyanatopropan-1-one (Compound 8A, Crystalline Form)

One aspect of the present invention relates to a novel anhydrous crystalline form of 1-(2-chloro-4-methoxy-5-methylphenyl)-2-thiocyanatopropan-1-one (Compound 8A) and processes related thereto.

A summary of representative physical properties for the crystalline form are provided in Table 7 and Table 8.

TABLE 7

Figure 11:
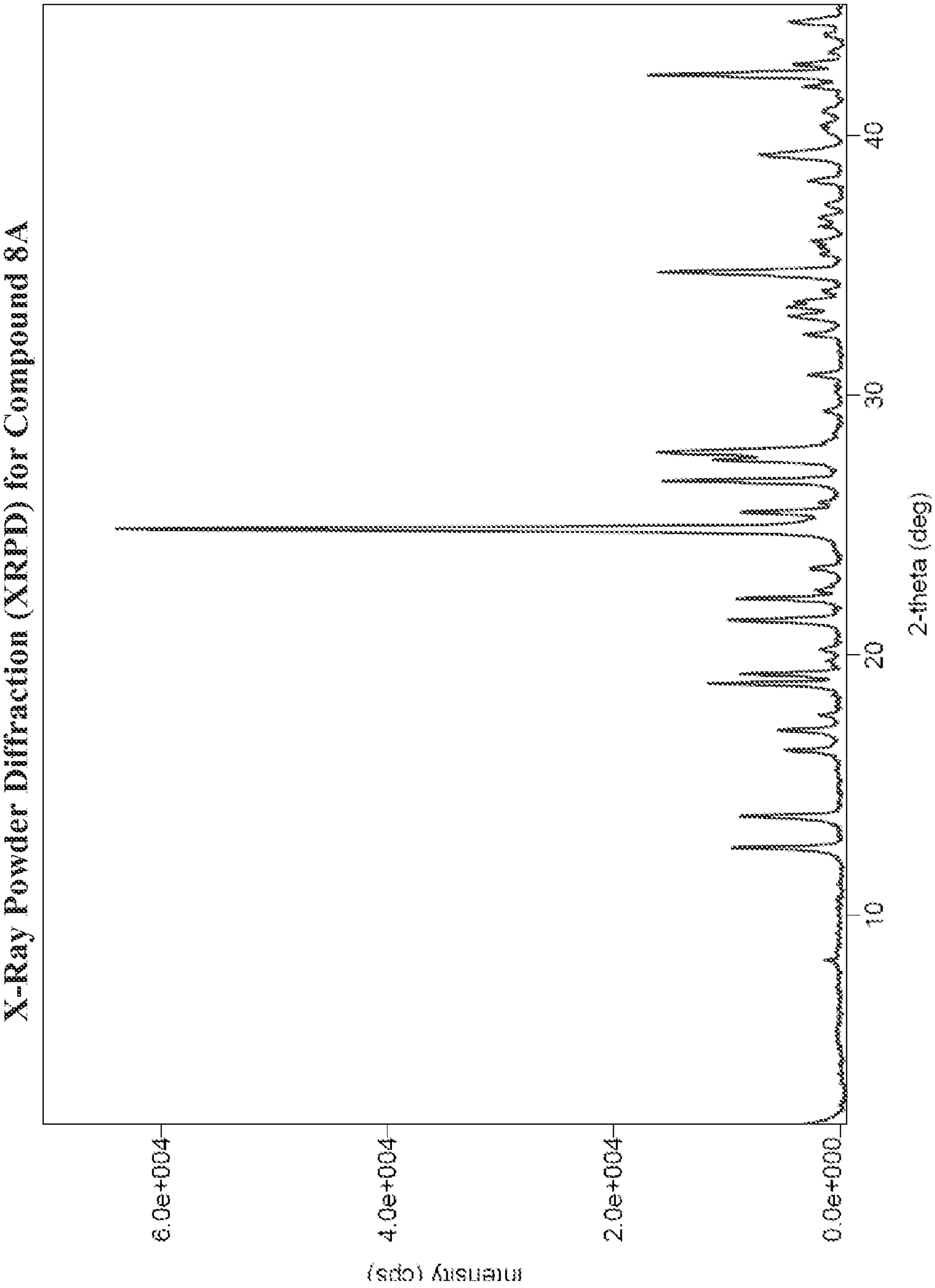
FIG. 11 shows an exemplary X-ray powder diffraction (XRPD) pattern for a sample of crystalline 1-(2-chloro-4-methoxy-5-methylphenyl)-2-thiocyanatopropan-1-one (Compound 8A).

| | Compound 8A (Anhydrous Form) |
|---|---|
| PXRD | FIG. 11: Peaks at 12.6, 18.9, 21.3, 22.2, 24.9, 26.7, 27.8, 34.8, and 42.3 °2θ |
| TGA | FIG. 12: Decrease in weight of about 0.3% out to about 125° C. |
| DSC | FIG. 12: Endotherm extrapolated onset temperature: about 73.1° C. |

Certain other XRPD peaks for the crystalline anhydrous form of 1-(2-chloro-4-methoxy-5-methylphenyl)-2-thiocyanatopropan-1-one (Compound 8A) are shown in Table 8 below.

TABLE 8

| 2-Theta | Height (cps) |
|---|---|
| 8.3 | 767 |
| 12.6 | 6589 |
| 13.8 | 6107 |
| 16.4 | 3455 |
| 17.1 | 3934 |
| 17.7 | 1196 |
| 18.9 | 8251 |
| 19.3 | 6016 |
| 19.8 | 546 |
| 20.2 | 1162 |
| 21.3 | 7007 |
| 22.2 | 6456 |
| 22.5 | 1290 |
| 22.7 | 352 |
| 23.3 | 1823 |
| 24.9 | 46622 |
| 25.5 | 6199 |
| 25.9 | 1137 |
| 26.7 | 11565 |
| 27.5 | 7283 |
| 27.8 | 11083 |
| 29.4 | 1033 |
| 30.8 | 2182 |
| 32.3 | 2349 |
| 33.0 | 3021 |
| 33.4 | 3388 |
| 33.6 | 2842 |
| 34.0 | 1033 |
| 34.8 | 11013 |
| 35.4 | 1250 |
| 35.7 | 1131 |
| 35.9 | 1679 |
| 36.5 | 1158 |
| 36.8 | 1086 |
| 37.3 | 874 |
| 38.2 | 2154 |
| 39.2 | 4626 |
| 40.2 | 878 |
| 40.9 | 1077 |
| 41.9 | 2734 |
| 42.3 | 13647 |
| 42.7 | 3438 |

TABLE 8-continued

| 2-Theta | Height (cps) |
|---|---|
| 43.2 | 819 |
| 43.8 | 1003 |
| 44.3 | 3522 |

One aspect of the present invention relates to a crystalline form of 1-(2-chloro-4-methoxy-5-methylphenyl)-2-thiocyanatopropan-1-one (Compound 8A). In some embodiments, the crystal form is an anhydrous crystalline form of 1-(2-chloro-4-methoxy-5-methylphenyl)-2-thiocyanatopropan-1-one (Compound 8A). An anhydrous crystalline form refers to a crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has an X-ray powder diffraction pattern comprising at least three peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least four peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°.

In some embodiments, the anhydrous crystalline form has an X-ray powder diffraction pattern comprising at least five peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least six peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least seven peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least eight peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least nine peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°. In some embodiments, the anhydrous crystalline form has an X-ray powder diffraction pattern comprising at least ten peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has an X-ray powder diffraction pattern comprising a peak, in terms of 2θ, at 24.9°±0.2°. In some embodiments, the anhydrous crystalline form has an X-ray powder diffraction pattern comprising peaks, in terms of 2θ, at 24.9°±0.2° and 26.7°±0.2°. In some embodiments, the anhydrous crystalline form has an X-ray powder diffraction pattern comprising peaks, in terms of 2θ, at 24.9°±0.2° and 27.8°±0.2°. In some embodiments, the anhydrous crystalline form has an X-ray powder diffraction pattern comprising peaks, in terms of 2θ, at 24.9°±0.2° and 34.8°±0.2°. In some embodiments, the anhydrous crystalline form has an X-ray powder diffraction pattern comprising peaks, in terms of 2θ, at 24.9°±0.2° and 42.3°±0.2°. In some embodiments, the anhydrous crystalline form has an X-ray powder diffraction pattern comprising peaks, in terms of 2θ, at 18.9°±0.2°, 24.9°±0.2°, and 26.7°±0.2°. In some embodiments, the anhydrous crystalline form has an X-ray powder diffraction pattern comprising peaks, in terms of 2θ, at 18.9°±0.2°, 24.9°±0.2°, and 27.8°±0.2°. In some embodiments, the anhydrous crystalline form has an X-ray powder diffraction pattern comprising peaks, in terms of 2θ, at 18.9°±0.2°, 24.9°±0.2°, and 34.8°±0.2°. In some embodiments, the anhydrous crystalline form has an X-ray powder diffraction pattern comprising peaks, in terms of 2θ, at 18.9°±0.2°, 24.9°±0.2°, and 42.3°±0.2°. In some embodiments, the anhydrous crystalline form has an X-ray powder diffraction pattern comprising peaks, in terms of 2θ, at 24.9°±0.2°, 26.7°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 18.9°±0.2°, 24.9°±0.2°, 26.7°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 18.9°±0.2°, 24.9°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 18.9°±0.2 , 21.3°±0.2°, 24.9°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 12.6°±0.2°, 18.9°±0.2°, 21.3°±0.2°, 24.9°±0.2°, 26.7°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 12.6°±0.2°, 18.9°±0.2°, 21.3°±0.2°, 24.9°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 12.6°±0.2°, 18.9°±0.2°, 21.3°±0.2°, 22.2°±0.2°, 24.9°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 12.6°±0.2°, 18.9°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern comprising peaks, in terms of 2θ, at 12.6°±0.2°, 13.8°±0.2°, 18.9°±0.2°, 21.3°±0.2°, 22.2°±±0.2°, 24.9°±0.2°, 25.5°±0.2°, 26.7°±0.2°, 27.5°±0.2°, 27.8°±0.2°, 34.8°±0.2°, and 42.3°±0.2°. In some embodiments, the anhydrous crystalline form has an X-ray powder diffraction pattern substantially as shown in FIG. 11, wherein by "substantially" is meant that the reported peaks can vary by about ±0.2° 2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 12:
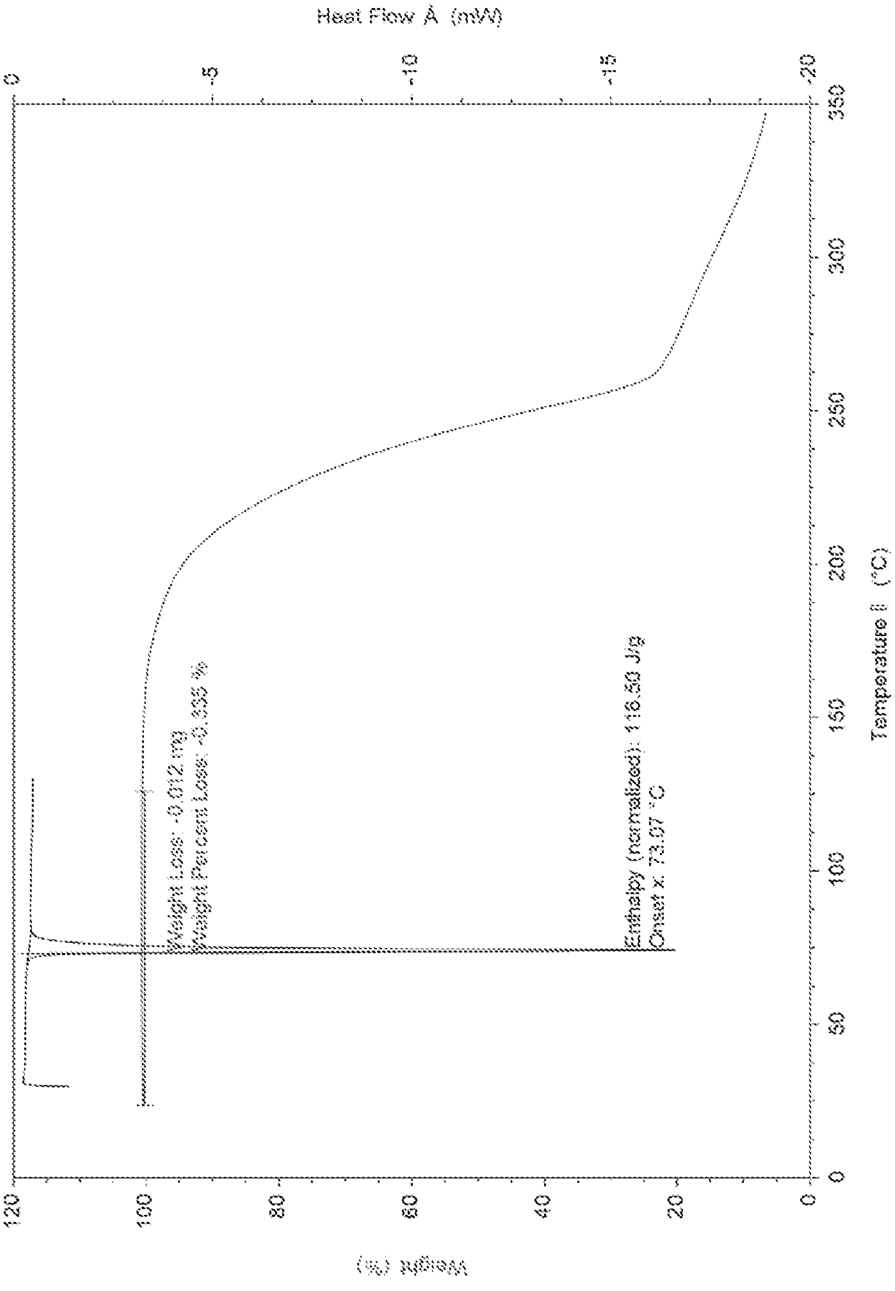
FIG. 12 shows an exemplary Differential Scanning Calorimetry (DSC) and Thermogravimetric Analysis (TGA) thermograms for a sample of crystalline 1-(2-chloro-4-methoxy-5-methylphenyl)-2-thiocyanatopropan-1-one (Compound 8A).

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has a differential scanning calorimetry (DSC) thermogram comprising an endotherm with an extrapolated onset temperature of about 70.5° C. to about 75.5° C. In some embodiments, the anhydrous crystalline form has a differential scanning calorimetry thermogram comprising an endotherm with an extrapolated onset temperature of about 71° C. to about 75° C. In some embodiments, the anhydrous crystalline form has a differential scanning calorimetry thermogram comprising an endotherm with an extrapolated onset temperature of about 71.5° C. to about 74.5° C. In some embodiments, the anhydrous crystalline form has a differential scanning calorimetry thermogram comprising an endotherm with an extrapolated onset temperature of about 72° C. to about 74° C. In some embodiments, the anhydrous crystalline form has a differential scanning calorimetry thermogram comprising an endotherm with an extrapolated onset temperature of about 72.5° C. to about 73.5° C. In some embodiments, the anhydrous crystalline form has a differential scanning calorimetry thermogram substantially as shown in FIG. 12, wherein by "substantially" is meant that the reported DSC features can vary by about ±5° C. and the reported DSC features can vary by about 20 joules per gram.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has a thermogravimetric analysis (TGA) profile showing about 1.0% or less weight loss out to about 125° C. In some embodiments, the anhydrous crystalline form has a thermogravimetric analysis profile showing about 0.8% or less weight loss out to about 125° C. In some embodiments, the anhydrous crystalline form has a thermogravimetric analysis profile showing about 0.5% or less weight loss out to about 125° C. In some embodiments, the anhydrous crystalline form has a thermogravimetric analysis profile showing about 0.4% or less weight loss out to about 125° C. In some embodiments, the anhydrous crystalline form has a thermogravimetric analysis profile showing about 0.35% or less weight loss out to about 125° C.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has a thermogravimetric analysis (TGA) profile showing about 0.10% to about 1.0% weight loss out to about 125° C. In some embodiments, the anhydrous crystalline form has a thermogravimetric analysis profile showing about 0.15% to about 0.8% weight loss out to about 125° C. In some embodiments, the anhydrous crystalline form has a thermogravimetric analysis profile showing about 0.2% to about 0.5% weight loss out to about 125° C. In some embodiments, the anhydrous crystalline form has a thermogravimetric analysis profile showing about 0.25% to about 0.4% weight loss out to about 125° C. In some embodiments, the anhydrous crystalline form has a thermogravimetric analysis profile showing about 0.3% to about 0.35% weight loss out to about 125° C. In some embodiments, the anhydrous crystalline form has a thermogravimetric analysis profile substantially as shown in FIG. 12, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has:

an X-ray powder diffraction pattern comprising at least three peaks, in terms of 2θ, selected from the group consisting of: 12.6°±0.2°, 13.8°±0.2°, 18.9°±0.2°, 19.3°±0.2°, 21.3°±0.2°, 22.2°±0.2°, 24.9°±0.2°, 25.5°±0.2°, 26.7°±0.2°, 27.5°±0.2°, 27.8°±0.2°, 34.8°±0.2°, 39.2°±0.2°, and 42.3°±0.2°;

a differential scanning calorimetry (DSC) thermogram comprising an endotherm with an extrapolated onset temperature of about 70.5° C. to about 75.5° C.; and/or a thermogravimetric analysis (TGA) profile showing about 0.1% to about 1.0% weight loss out to about 125° C.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has:

an X-ray powder diffraction pattern comprising peaks, in terms of 2θ, at 18.9°±0.2°, 24.9°±0.2°, 26.7°±0.2°, 27.8°±0.2°, 34.8°±0.2°, and 42.3°±0.2°;

a differential scanning calorimetry thermogram comprising an endotherm with an extrapolated onset temperature of about 71.5° C. to about 74.5° C.; and/or a thermogravimetric analysis profile showing about 1.0% or less weight loss out to about 125° C.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has:

an X-ray powder diffraction pattern comprising peaks, in terms of 2θ, at 12.6°±0.2°, 18.9°±0.2°, 21.3°±0.2°, 24.9°±0.2°, 26.7°±0.2°, 27.8°±0.2°, 34.8°±0.2°, and 42.3°±0.2°;

a differential scanning calorimetry thermogram comprising an endotherm with an extrapolated onset temperature of about 72.5° C. to about 73.5° C.; and/or a thermogravimetric analysis profile showing about 0.5% or less weight loss out to about 125° C.

One aspect of the present invention relates to an anhydrous crystalline form of 1-(2-chloro-4-methoxy-5-methylphenyl)-2-thiocyanatopropan-1-one (Compound 8A), wherein the anhydrous crystalline form has:

an X-ray powder diffraction pattern substantially as shown in FIG. 11;

a differential scanning calorimetry thermogram substantially as shown in FIG. 12; and/or a thermogravimetric analysis profile substantially as shown in FIG. 12.

In some embodiments, the anhydrous crystalline form of 1-(2-chloro-4-methoxy-5-methylphenyl)-2-thiocyanatopropan-1-one (Compound 8A) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

D. (S)-2-Cyclopropyl-1-(3-fluoro-4-methylphenyl) ethan-1-amine (Compound 6A, Hydrochloride Salt, Crystalline Form)

One aspect of the present invention relates to a novel anhydrous crystalline form of (S)-2-cyclopropyl-1-(3-fluoro-4-methylphenyl)ethan-1-amine (Compound 6A, HCl salt) and processes related thereto.

A summary of representative physical properties for the crystalline form are provided in Table 9 and Table 10.

TABLE 9

Figure 13:
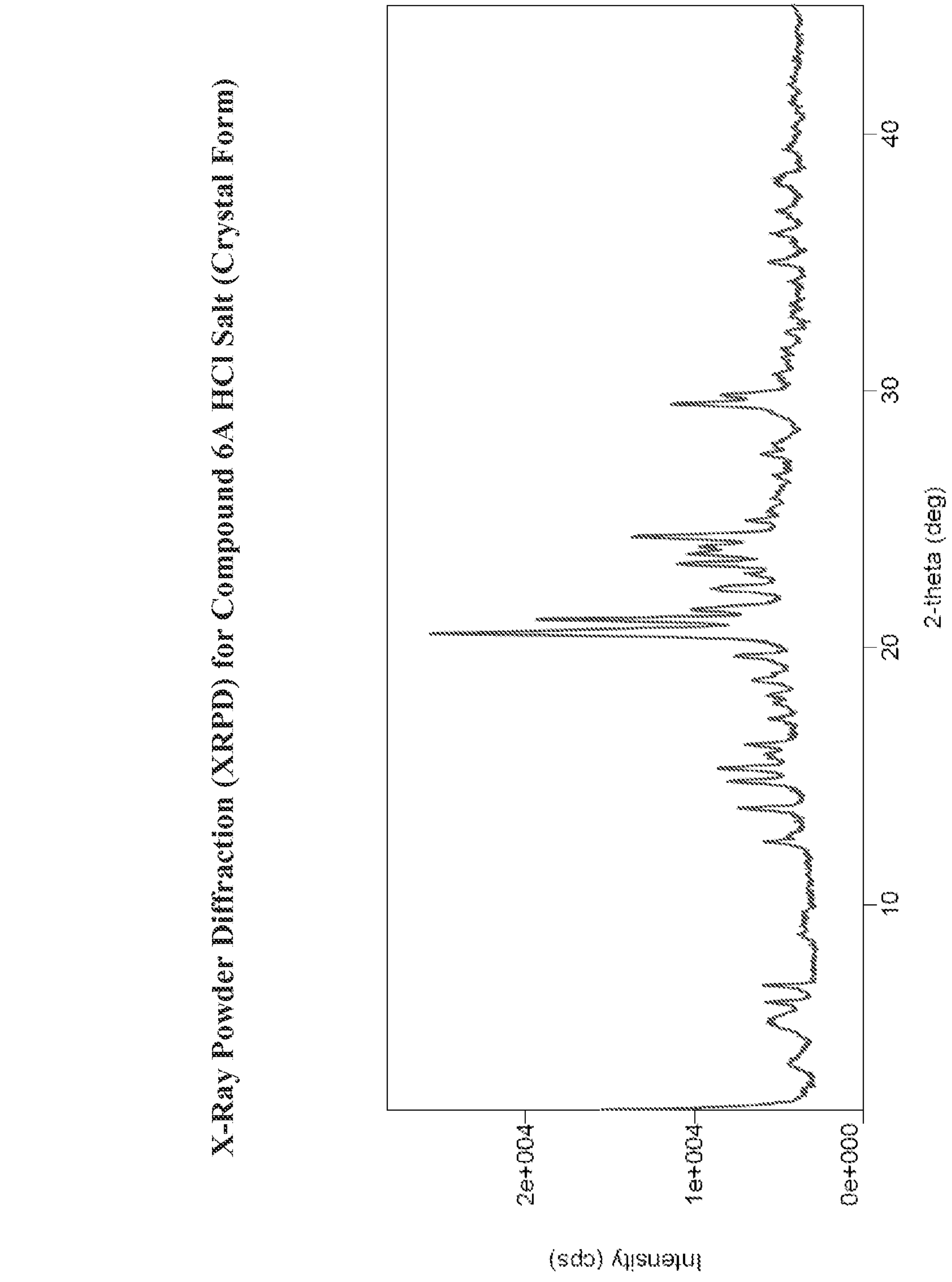
FIG. 13 shows an exemplary X-ray powder diffraction (XRPD) pattern for a sample of crystalline (S)-2-cyclopropyl-1-(3-fluoro-4-methylphenyl)ethan-1-amine (Compound 6A, HCl salt).

| | Compound 6A, HCl Salt |
|---|---|
| PXRD | FIG. 13: Peaks at 15.3, 20.5, 21.1, 21.5, 23.2, 23.6, 24.3, and 29.5°2θ |
| TGA | FIG. 14: Decrease in weight of about 0.3% out to about 125° C. |
| DSC | FIG. 14: Endotherm extrapolated onset temperature: about 159.5° C. |

Certain other XRPD peaks for the crystalline form of (S)-2-cyclopropyl-1-(3-fluoro-4-methylphenyl)ethan-1-amine (Compound 6A, HCl salt) are shown in Table 10 below.

TABLE 10

| 2-Theta | Height (cps) |
|---|---|
| 3.9 | 956 |
| 5.5 | 1646 |
| 6.2 | 1526 |
| 6.8 | 1657 |
| 9.1 | 303 |
| 12.4 | 1625 |
| 13.7 | 2538 |
| 14.8 | 2742 |
| 15.3 | 3077 |
| 16.2 | 1629 |
| 17.2 | 732 |
| 18.7 | 1236 |
| 19.0 | 364 |
| 19.7 | 1903 |
| 20.5 | 13009 |
| 21.1 | 9405 |
| 21.5 | 3420 |
| 22.3 | 2642 |
| 22.8 | 1094 |
| 23.2 | 4031 |
| 23.6 | 3439 |
| 23.9 | 2863 |
| 24.3 | 5761 |
| 24.9 | 1388 |
| 25.3 | 404 |
| 26.7 | 397 |
| 27.5 | 1009 |
| 27.9 | 480 |

TABLE 10-continued

| 2-Theta | Height (cps) |
|---|---|
| 29.2 | 805 |
| 29.5 | 4775 |
| 29.8 | 2679 |
| 30.6 | 547 |
| 32.2 | 577 |
| 34.2 | 444 |
| 35.0 | 1278 |
| 36.1 | 1130 |
| 37.0 | 839 |
| 38.1 | 897 |
| 39.4 | 517 |

One aspect of the present invention relates to a crystalline form of (S)-2-cyclopropyl-1-(3-fluoro-4-methylphenyl) ethan-1-amine (Compound 6A, HCl salt). In some embodiments, the crystal form is an anhydrous crystalline form of (S)-2-cyclopropyl-1-(3-fluoro-4-methylphenyl)ethan-1-amine (Compound 6A, HCl salt). An anhydrous crystalline form refers to a crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has an X-ray powder diffraction pattern comprising at least three peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least four peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least five peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least six peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least seven peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least eight peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least nine peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising at least ten peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has an X-ray powder diffraction pattern comprising a peak, in terms of 2θ, at 20.5°±0.2°. In some embodiments, the anhydrous crystalline form has an X-ray powder diffraction pattern comprising a peak, in terms of 2θ, at 21.1°±0.2°. In some embodiments, the anhydrous crystalline form has an X-ray powder diffraction pattern comprising a peak, in terms of 2θ, at 24.3°±0.2 . In some embodiments, the anhydrous crystalline form has an X-ray powder diffraction pattern comprising peaks, in terms of 2θ, at 20.5°±0.2° and 21.1°±0.2°. In some embodiments, the anhydrous crystalline form has an X-ray powder diffraction pattern comprising peaks, in terms of 2θ, at 20.5°±0.2° and 24.3°±0.2°. In some embodiments, the anhydrous crystalline form has an X-ray powder diffraction pattern comprising peaks, in terms of 2θ, at 21.1°±0.2° and 24.3°±0.2°. In some embodiments, the anhydrous crystalline form has an X-ray powder diffraction pattern comprising peaks, in terms of 2θ, at 20.5°±0.2°, 21.1°±0.2°, and 24.3°±0.2°. In some embodiments, the anhydrous crystalline form has an X-ray powder diffraction pattern comprising peaks, in terms of 2θ, at 20.5°±0.2°, 21.1°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 23.2°±0.2°, and 24.3°±0.2°. In some embodiments, the anhydrous crystalline form has an X-ray powder diffraction pattern comprising peaks, in terms of 2θ, at 20.5°±0.2°, 21.1°±0.2°, 23.2°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 23.2°±0.2°, 23.6°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 21.5°±0.2°, 23.2°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 21.5°±0.2°, 23.2°±0.2°, 23.6°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 24.3°±0.2°, 29.5°±0.2°, 23.2°±0.2°, 15.3°±0.2°, and 14.8°±0.2°. In some embodiments, the anhydrous crystalline form has an X-ray powder diffraction pattern comprising peaks, in terms of 2θ, at 15.3°±0.2°, 20.5°±0.2°, 21.1°±0.2°, 21.5°±0.2°, 23.2°±0.2°, 23.6°±0.2°, 24.3°±0.2°, and 29.5°±0.2°. In some embodiments, the anhydrous crystalline form has an X-ray powder diffraction pattern comprising peaks, in terms of 2θ, at 14.8°±0.2°, 20.5°±0.2°, 21.1°±0.2°, 21.5°±0.2°, 23.2°±0.2°, 23.6°±0.2°, 24.3°±0.2°, and 29.5°±0.2°. In some embodiments, the anhydrous crystalline form has an X-ray powder diffraction pattern comprising peaks, in terms of 2θ, at 20.5°±0.2°, 21.1°±0.2°, 21.5°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern comprising peaks, in terms of 2θ, at 14.8°±0.2°, 15.3°±0.2°, 20.5°±0.2°, 21.1°±0.2°, 21.5°±0.2°, 23.2°±0.2°, 23.6°±0.2°, 24.3°±0.2°, 29.5°±0.2°, and 29.8°±0.2°. In some embodiments, the anhydrous crystalline form has an X-ray powder diffraction pattern substantially as shown in FIG. 13, wherein by "substantially" is meant that the reported peaks can vary by about ±0.2° 2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 14:
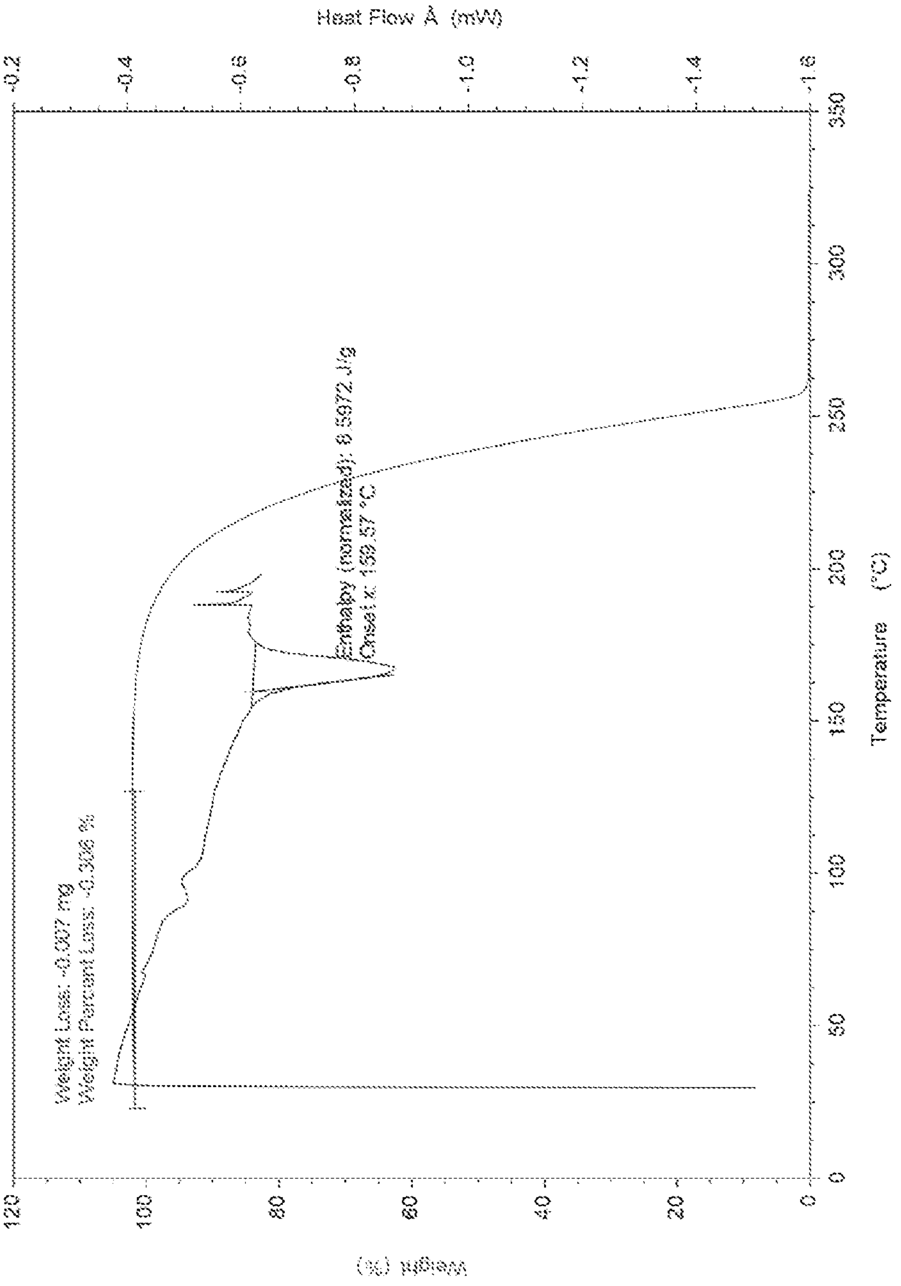
FIG. 14 shows an exemplary Differential Scanning Calorimetry (DSC) and Thermogravimetric Analysis (TGA) thermograms for a sample of crystalline (S)-2-cyclopropyl-1-(3-fluoro-4-methylphenyl)ethan-1-amine (Compound 6A, HCl salt).

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has a differential scanning calorimetry (DSC) thermogram comprising an endotherm with an extrapolated onset temperature of about 154° C. to about 164° C. In some embodiments, the anhydrous crystalline form has a differential scanning calorimetry thermogram comprising an endotherm with an extrapolated onset temperature of about 155° C. to about 163° C. In some embodiments, the anhydrous crystalline form has a differential scanning calorimetry thermogram comprising an endotherm with an extrapolated onset temperature of about 157° C. to about 162° C. In some embodiments, the anhydrous crystalline form has a differential scanning calorimetry thermogram comprising an endotherm with an extrapolated onset temperature of about 158.5° C. to about 160.5° C. In some embodiments, the anhydrous crystalline form has a differential scanning calorimetry thermogram comprising an endotherm with an extrapolated onset temperature of about 159° C. to about 160° C. In some embodiments, the anhydrous crystalline form has a differential scanning calorimetry thermogram substantially as shown in FIG. 14, wherein by "substantially" is meant that the reported DSC features can vary by about 5° C. and the reported DSC features can vary by about +20 joules per gram.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has a thermogravimetric analysis (TGA) profile showing about 1.0% or less weight loss out to about 125° C. In some embodiments, the anhydrous crystalline form has a thermogravimetric analysis profile showing about 0.8% or less weight loss out to about 125° C. In some embodiments, the anhydrous crystalline form has a thermogravimetric analysis profile showing about 0.6% or less weight loss out to about 125° C. In some embodiments, the anhydrous crystalline form has a thermogravimetric analysis profile showing about 0.4% or less weight loss out to about 125° C. In some embodiments, the anhydrous crystalline form has a thermogravimetric analysis profile showing about 0.35% or less weight loss out to about 125° C.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has a thermogravimetric analysis (TGA) profile showing about 0.05% to about 1.0% weight loss out to about 125° C. In some embodiments, the anhydrous crystalline form has a thermogravimetric analysis profile showing about 0.1% to about 0.8% weight loss out to about 125° C. In some embodiments, the anhydrous crystalline form has a thermogravimetric analysis profile showing about 0.15% to about 0.6% weight loss out to about 125° C. In some embodiments, the anhydrous crystalline form has a thermogravimetric analysis profile showing about 0.2% to about 0.4% weight loss out to about 125° C. In some embodiments, the anhydrous crystalline form has a thermogravimetric analysis profile showing about 0.25% to about 0.35% weight loss out to about 125° C. In some embodiments, the anhydrous crystalline form has a thermogravimetric analysis profile substantially as shown in FIG. 14, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has:

- an X-ray powder diffraction pattern comprising at least three peaks, in terms of 2θ, selected from the group consisting of: 13.7°±0.2°, 14.8°±0.2°, 15.3°±0.2°, 20.5°±0.2°, 21.1°±0.2°, 21.5°±0.2°, 22.3°±0.2°, 23.2°±0.2°, 23.6°±0.2°, 24.3°±0.2°, 29.5°±0.2°, and 29.8°±0.2°;
- a differential scanning calorimetry thermogram comprising an endotherm with an extrapolated onset temperature of about 154° C. to about 164° C.; and/or
- a thermogravimetric analysis profile showing about 0.05% to about 1.0% weight loss out to about 125° C.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has:

- an X-ray powder diffraction pattern comprising peaks, in terms of 2θ, at 20.5°±0.2°, 21.1°±0.2°, 24.3°±0.2°, and 29.5°±0.2°;
- a differential scanning calorimetry thermogram comprising an endotherm with an extrapolated onset temperature of about 157° C. to about 162° C.; and/or
- a thermogravimetric analysis profile showing about 1.0% or less weight loss out to about 125° C.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has:

- an X-ray powder diffraction pattern comprising peaks, in terms of 2θ, at 20.5°±0.2°, 21.1°±0.2°, 24.3°±0.2°, 29.5°±0.2°, 23.2°±0.2°, 15.3°±0.2°, and 14.8°±0.2°;
- a differential scanning calorimetry thermogram comprising an endotherm with an extrapolated onset temperature of about 159° C. to about 160° C.; and/or
- a thermogravimetric analysis profile showing about 0.4% or less weight loss out to about 125° C.

One aspect of the present invention relates to an anhydrous crystalline form of (S)-2-cyclopropyl-1-(3-fluoro-4-methylphenyl)ethan-1-amine (Compound 6A, HCl salt), wherein the anhydrous crystalline form has:

- an X-ray powder diffraction pattern substantially as shown in FIG. 13;
- a differential scanning calorimetry thermogram substantially as shown in FIG. 14; and/or
- a thermogravimetric analysis profile substantially as shown in FIG. 14.

In some embodiments, the anhydrous crystalline form of (S)-2-cyclopropyl-1-(3-fluoro-4-methylphenyl)ethan-1-amine (Compound 6A, HCl salt) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

E. 2-Cyclopropyl-1-(3-fluoro-4-methylphenyl)ethan-1-one (Compound 3A, Crystalline Form)

One aspect of the present invention relates to a novel anhydrous crystalline form of 2-cyclopropyl-1-(3-fluoro-4-methylphenyl)ethan-1-one (Compound 3A) and processes related thereto.

A summary of representative physical properties for the crystalline form are provided in Table 11 and Table 12.

TABLE 11

Figure 15:
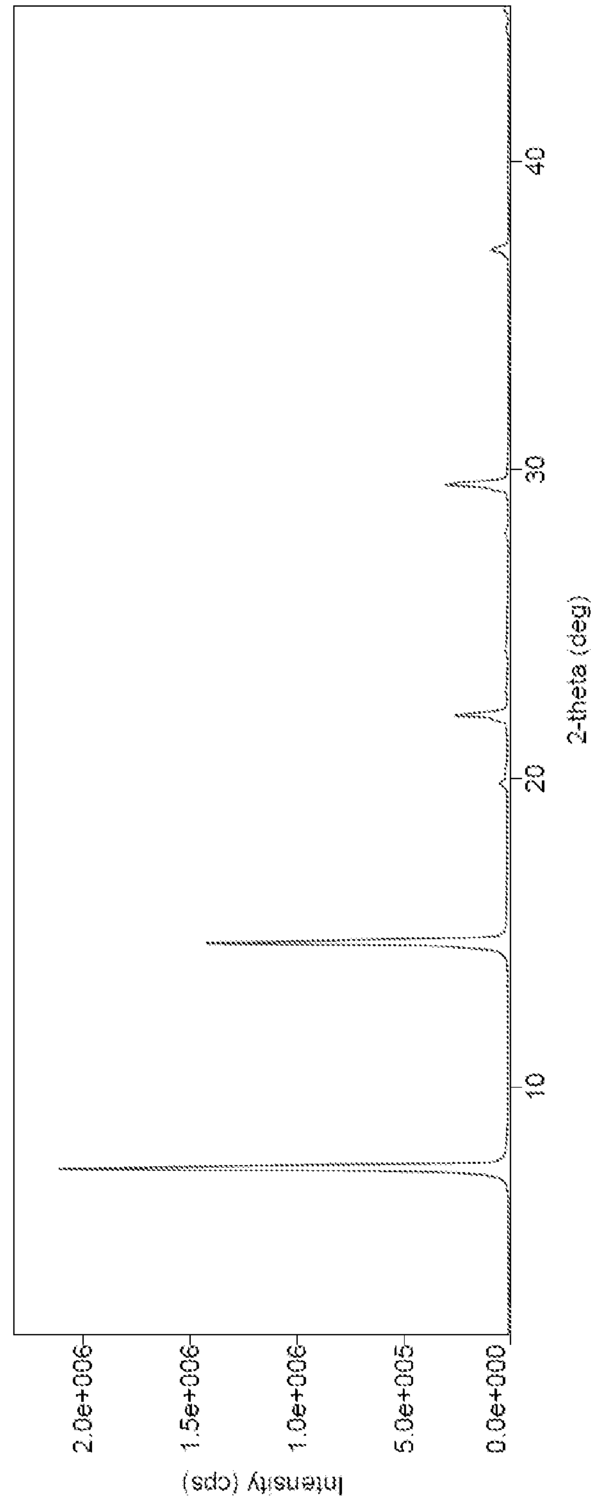
FIG. 15 shows an exemplary X-ray powder diffraction (XRPD) pattern for a sample of crystalline 2-cyclopropyl-1-(3-fluoro-4-methylphenyl)ethan-1-one (Compound 3A).

| | Compound 3A (Anhydrous) |
|---|---|
| PXRD | FIG. 15: Peaks at 7.4, 14.7, 22.0, and 29.5°2θ |
| TGA | FIG. 16: Decrease in weight of about 0.2% out to about 70° C. |
| DSC | FIG. 16: Endotherm extrapolated onset temperature: about 28° C. |

Certain other XRPD peaks for the crystalline form of 2-cyclopropyl-1-(3-fluoro-4-methylphenyl)ethan-1-one (Compound 3A) are shown in Table 12 below.

TABLE 12

| 2-Theta | Height (cps) |
|---|---|
| 7.4 | 1386059 |
| 7.5 | 604834 |
| 14.7 | 991447 |
| 14.8 | 388924 |
| 19.8 | 19675 |
| 20.2 | 7057 |
| 21.9 | 24114 |
| 22.0 | 176012 |
| 22.9 | 5778 |
| 23.3 | 1923 |
| 24.1 | 4228 |
| 24.3 | 3477 |
| 25.0 | 2327 |
| 27.0 | 1819 |
| 27.9 | 11066 |
| 28.7 | 2144 |
| 29.3 | 43357 |
| 29.5 | 222224 |
| 30.0 | 4106 |
| 30.5 | 1841 |
| 36.0 | 1032 |
| 36.9 | 16603 |
| 37.1 | 65489 |

One aspect of the present invention relates to a crystalline form of 2-cyclopropyl-1-(3-fluoro-4-methylphenyl)ethan-1-one (Compound 3A). In some embodiments, the crystal form is an anhydrous crystalline form of 2-cyclopropyl-1-(3-fluoro-4-methylphenyl)ethan-1-one (Compound 3A). An anhydrous crystalline form refers to a crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of 2-cyclopropyl-1-(3-fluoro-4-methylphenyl)ethan-1-one (Compound 3A), wherein the anhydrous crystalline form has an X-ray powder diffraction pattern comprising at least three peaks, in terms of 2θ, selected from the group consisting of: 7.4° 0.2°, 7.5° 0.2°, 14.7°±0.2°, 14.8°±0.2°, 22.0°±0.2°, 29.5°, and 37.1°±0.2°. In some embodiments, the anhydrous crystalline form has an X-ray powder diffraction pattern comprising at least four peaks, in terms of 2θ, selected from the group consisting of: 7.4°±0.2°, 7.5°±0.2°, 14.7°±0.2°, 14.8°±0.2°, 22.0°±0.2°, 29.5°, and 37.1°±0.2°. In some embodiments, the anhydrous crystalline form has an X-ray powder diffraction pattern comprising at least five peaks, in terms of 2θ, selected from the group consisting of: 7.4°±0.2°, 7.5°±0.2°, 14.7°±0.2°, 14.8°±0.2°, 22.0°±0.2°, 29.5°, and 37.1°±0.2°.

One aspect of the present invention relates to an anhydrous crystalline form of 2-cyclopropyl-1-(3-fluoro-4-methylphenyl)ethan-1-one (Compound 3A), wherein the anhydrous crystalline form has an X-ray powder diffraction pattern comprising a peak, in terms of 2θ, at 7.4°±0.2°. In some embodiments, the anhydrous crystalline form has an X-ray powder diffraction pattern comprising a peak, in terms of 2θ, at 7.5°±0.2°. In some embodiments, the anhydrous crystalline form has an X-ray powder diffraction pattern comprising a peak, in terms of 2θ, at 14.7°±0.2°. In some embodiments, the anhydrous crystalline form has an X-ray powder diffraction pattern comprising a peak, in terms of 2θ, at 14.8°±0.2°. In some embodiments, the anhydrous crystalline form has an X-ray powder diffraction pattern comprising peaks, in terms of 2θ, at 7.4° 0.2°, and 14.7°±0.2°. In some embodiments, the anhydrous crystalline form has an X-ray powder diffraction pattern comprising peaks, in terms of 2θ, at 7.4°±0.2°, and 14.8°±0.2°. In some embodiments, the anhydrous crystalline form has an X-ray powder diffraction pattern comprising peaks, in terms of 2θ, at 7.5°±0.2°, and 14.7°±0.2°. In some embodiments, the anhydrous crystalline form has an X-ray powder diffraction pattern comprising peaks, in terms of 2θ, at 7.5°±0.2°, and 14.8°±0.2°. In some embodiments, the anhydrous crystalline form has an X-ray powder diffraction pattern comprising peaks, in terms of 2θ, at 7.4°±0.2°, 14.7°±0.2°, and 22.0°±0.2°. In some embodiments, the anhydrous crystalline form has an X-ray powder diffraction pattern comprising peaks, in terms of 2θ, at 7.4°±0.2°, 14.8°±0.2°, and 22.0°±0.2°. In some embodiments, the anhydrous crystalline form has an X-ray powder diffraction pattern comprising peaks, in terms of 2θ, at 7.5°±0.2°, 14.7°±0.2°, and 22.0°±0.2°. In some embodiments, the anhydrous crystalline form has an X-ray powder diffraction pattern comprising peaks, in terms of 2θ, at 7.5°±0.2°, 14.8°±0.2°, and 22.0°±0.2°. In some embodiments, the anhydrous crystalline form has an X-ray powder diffraction pattern comprising peaks, in terms of 2θ, at 7.4°±0.2°, 14.7°±0.2°, and 29.5°±0.2°. In some embodiments, the anhydrous crystalline form has an X-ray powder diffraction pattern comprising peaks, in terms of 2θ, at 7.4°±0.2°, 14.8°±0.2°, and 29.5°±0.2°. In some embodiments, the anhydrous crystalline form has an X-ray powder diffraction pattern comprising peaks, in terms of 2θ, at 7.5°±0.2°, 14.7°±0.2°, and 29.5°±0.2°. In some embodiments, the anhydrous crystalline form has an X-ray powder diffraction pattern comprising peaks, in terms of 2θ, at 7.5°±0.2°, 14.8°±0.2°, and 29.5°±0.2°. In some embodiments, the anhydrous crystalline form has an X-ray powder diffraction pattern comprising peaks, in terms of 2θ, at 7.4°±0.2°, 14.7°±0.2°, 22.0°±0.2°, and 29.5°±0.2°. In some embodiments, the anhydrous crystalline form has an X-ray powder diffraction pattern comprising peaks, in terms of 2θ, at 7.4°±0.2°, 14.8°±0.2°, 22.0°±0.2°, and 29.5°±0.2°. In some embodiments, the anhydrous crystalline form has an X-ray powder diffraction pattern comprising peaks, in terms of 2θ, at 7.5°±0.2°, 14.7°±0.2°, 22.0°±0.2°, and 29.5°±0.2°. In some embodiments, the anhydrous crystalline form has an X-ray powder diffraction pattern comprising peaks, in terms of 2θ, at 7.5°±0.2°, 14.8°±0.2°, 22.0°±0.2°, and 29.5°±0.2°. In some embodiments, the anhydrous crystalline form has an X-ray powder diffraction pattern comprising peaks, in terms of 2θ, at 7.4°±0.2°, 14.7°±0.2°, 22.0°±0.2°, 29.5°±0.2°, and 37.1°±0.2°. In some embodiments, the anhydrous crystalline form has an X-ray powder diffraction pattern comprising peaks, in terms of 2θ, at 7.4°±0.2°, 14.8°±0.2°, 22.0°±0.2°, 29.5°±0.2°, and 37.1°±0.2°. In some embodiments, the anhydrous crystalline form has an X-ray powder diffraction pattern comprising peaks, in terms of 2θ, at 7.5°±0.2°, 14.7°±0.2°, 22.0°±0.2°, 29.5°±0.2°, and 37.1°±0.2°. In some embodiments, the anhydrous crystalline form has an X-ray powder diffraction pattern comprising peaks, in terms of 2θ, at 7.5° 0.2°, 14.8°±0.2°, 22.0°±0.2°, 29.5°±0.2°, and 37.1°±0.2°. In some embodiments, the anhydrous crystalline form has an X-ray powder diffraction pattern comprising peaks, in terms of 2θ, at 7.4° 0.2°, 7.5° 0.2°, 14.7°±0.2°, 14.8°±0.2°, 22.0°±0.2°, 29.5°±0.2°, and 37.1°±0.2°. In some embodiments, the anhydrous crystalline form has an X-ray powder diffraction pattern substantially as shown in FIG. 15, wherein by "substantially" is meant that the reported peaks can vary by about ±0.2° 2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 16:
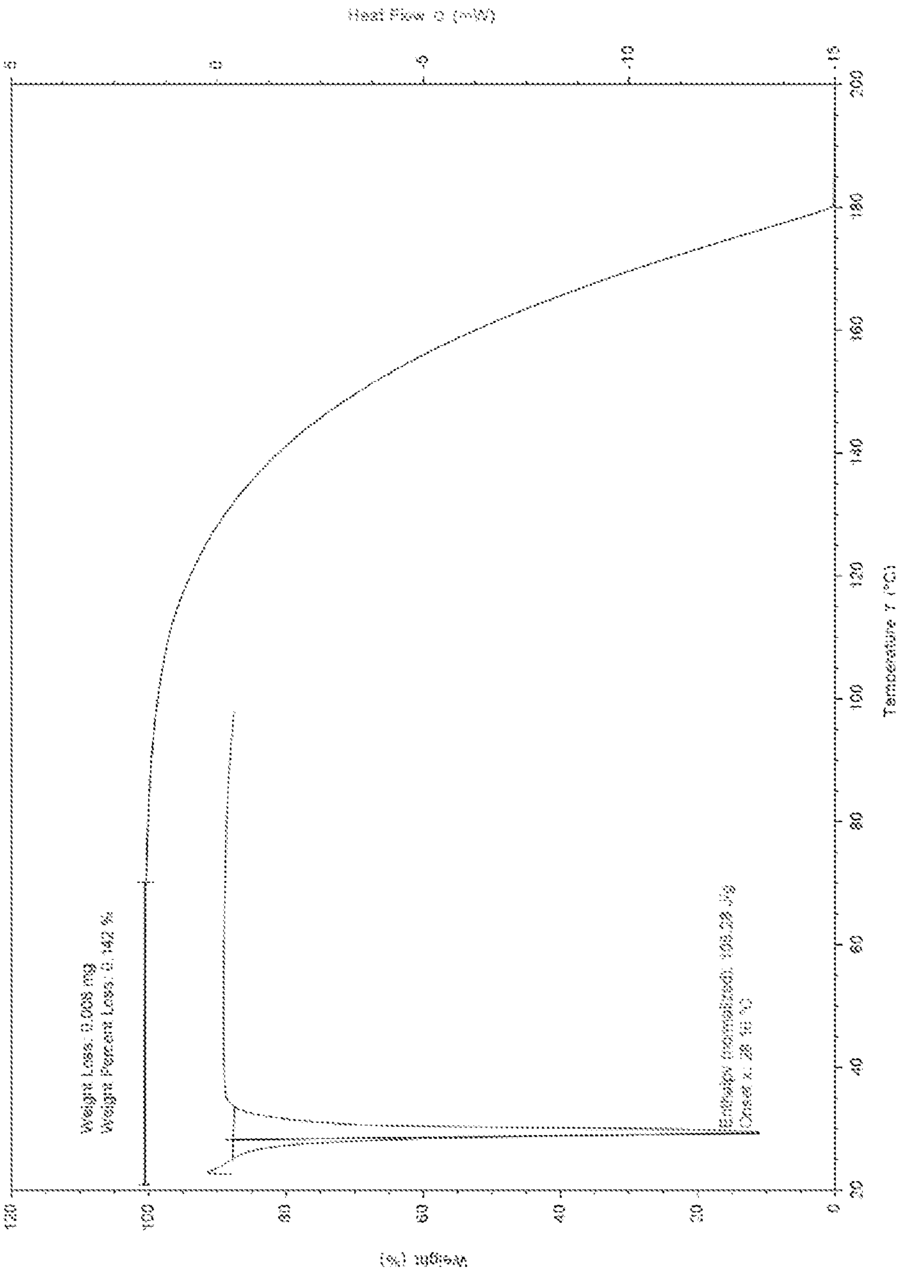
FIG. 16 shows an exemplary Differential Scanning Calorimetry (DSC) and Thermogravimetric Analysis (TGA) thermograms for a sample of crystalline 2-cyclopropyl-1-(3-fluoro-4-methylphenyl)ethan-1-one (Compound 3A).

One aspect of the present invention relates to an anhydrous crystalline form of 2-cyclopropyl-1-(3-fluoro-4-methylphenyl)ethan-1-one (Compound 3A), wherein the anhydrous crystalline form has a differential scanning calorimetry (DSC) thermogram comprising an endotherm with an extrapolated onset temperature of about 25° C. to about 31° C. In some embodiments, the anhydrous crystalline form has a differential scanning calorimetry thermogram comprising an endotherm with an extrapolated onset temperature of about 26.5° C. to about 30° C. In some embodiments, the anhydrous crystalline form has a differential scanning calorimetry thermogram comprising an endotherm with an extrapolated onset temperature of about 26.5° C. to about 29.5° C. In some embodiments, the anhydrous crystalline form has a differential scanning calorimetry thermogram comprising an endotherm with an extrapolated onset temperature of about 27° C. to about 29° C. In some embodiments, the anhydrous crystalline form has a differential scanning calorimetry thermogram comprising an endotherm with an extrapolated onset temperature of about 27.5° C. to about 28.5° C. In some embodiments, the anhydrous crystalline form has a differential scanning calorimetry thermogram substantially as shown in FIG. 16, wherein by "substantially" is meant that the reported DSC features can vary by about ±5° C. and the reported DSC features can vary by about ±20 joules per gram.

One aspect of the present invention relates to an anhydrous crystalline form of 2-cyclopropyl-1-(3-fluoro-4-methylphenyl)ethan-1-one (Compound 3A), wherein the anhydrous crystalline form has a thermogravimetric analysis (TGA) profile showing about 1.0% or less weight loss out to about 70° C. In some embodiments, the anhydrous crystalline form has a thermogravimetric analysis profile showing about 0.7% or less weight loss out to about 70° C. In some embodiments, the anhydrous crystalline form has a thermogravimetric analysis profile showing about 0.6% or less weight loss out to about 70° C. In some embodiments, the anhydrous crystalline form has a thermogravimetric analysis profile showing about 0.4% or less weight loss out to about 70° C. In some embodiments, the anhydrous crystalline form has a thermogravimetric analysis profile showing about 0.2% or less weight loss out to about 70° C.

One aspect of the present invention relates to an anhydrous crystalline form of 2-cyclopropyl-1-(3-fluoro-4-methylphenyl)ethan-1-one (Compound 3A), wherein the anhydrous crystalline form has a thermogravimetric analysis (TGA) profile showing about 0.02% to about 1.0% weight loss out to about 70° C. In some embodiments, the anhydrous crystalline form has a thermogravimetric analysis profile showing about 0.03% to about 0.7% weight loss out to about 70° C. In some embodiments, the anhydrous crystalline form has a thermogravimetric analysis profile showing about 0.04% to about 0.6% weight loss out to about 70° C. In some embodiments, the anhydrous crystalline form has a thermogravimetric analysis profile showing about 0.05% to about 0.4% weight loss out to about 70° C. In some embodiments, the anhydrous crystalline form has a thermogravimetric analysis profile showing about 0.1% to about 0.2% weight loss out to about 70° C. In some embodiments, the anhydrous crystalline form has a thermogravimetric analysis profile substantially as shown in FIG. 16, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of 2-cyclopropyl-1-(3-fluoro-4-methylphenyl)ethan-1-one (Compound 3A), wherein the anhydrous crystalline form has:

- an X-ray powder diffraction pattern comprising at least three peaks, in terms of 2θ, selected from the group consisting of: 7.4°±0.2°, 7.5°±0.2°, 14.7°±0.2°, 14.8°±0.2°, 22.0°±0.2°, 29.5°, and 37.1°±0.2°;
- a differential scanning calorimetry (DSC) thermogram comprising an endotherm with an extrapolated onset temperature of about 25° C. to about 31° C.; and/or
- a thermogravimetric analysis profile showing about 1.0% or less weight loss out to about 70° C.

One aspect of the present invention relates to an anhydrous crystalline form of 2-cyclopropyl-1-(3-fluoro-4-methylphenyl)ethan-1-one (Compound 3A), wherein the anhydrous crystalline form has:

- an X-ray powder diffraction pattern comprising at least four peaks, in terms of 2θ, selected from the group consisting of: 7.4°±0.2°, 7.5°±0.2°, 14.7°±0.2°, 14.8°±0.2°, 22.0°±0.2°, 29.5°, and 37.1°±0.2°;
- a differential scanning calorimetry thermogram comprising an endotherm with an extrapolated onset temperature of about 26.5° C. to about 29.5° C.; and/or
- a thermogravimetric analysis profile showing about 0.02% to about 1.0% weight loss out to about 70° C.

One aspect of the present invention relates to an anhydrous crystalline form of 2-cyclopropyl-1-(3-fluoro-4-methylphenyl)ethan-1-one (Compound 3A), wherein the anhydrous crystalline form has:

- an X-ray powder diffraction pattern comprising peaks, in terms of 2θ, at 7.4°±0.2°, 7.5°±0.2°, 14.7°±0.2°, 14.8°±0.2°, 22.0°±0.2°, 29.5°±0.2°, and 37.1°±0.2°;
- a differential scanning calorimetry thermogram comprising an endotherm with an extrapolated onset temperature of about 27.5° C. to about 28.5° C.; and/or
- a thermogravimetric analysis profile showing about 0.05% to about 0.4% weight loss out to about 70° C.

One aspect of the present invention relates to an anhydrous crystalline form of 2-cyclopropyl-1-(3-fluoro-4-methylphenyl)ethan-1-one (Compound 3A), wherein the anhydrous crystalline form has:

- an X-ray powder diffraction pattern substantially as shown in FIG. 15;
- a differential scanning calorimetry thermogram substantially as shown in FIG. 16; and/or
- a thermogravimetric analysis profile substantially as shown in FIG. 16.

In some embodiments, the anhydrous crystalline form of 2-cyclopropyl-1-(3-fluoro-4-methylphenyl)ethan-1-one (Compound 3A) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

F. Crystalline (S)-2-cyclopropyl-1-(3-fluoro-4-methylphenyl)-N—((S)-1-phenylethyl)ethan-1-amine (Compound 5A, HCl salt)

One aspect of the present invention relates to a novel anhydrous crystalline form of(S)-2-cyclopropyl-1-(3-fluoro-4-methylphenyl)-N—((S')-1-phenylethyl)ethan-1-amine (Compound 5A, HCl salt) and processes related thereto.

A summary of representative physical properties for crystalline Compound 5A (HCl salt) are provided in Table 13 and Table 14.

TABLE 13

Figure 17:
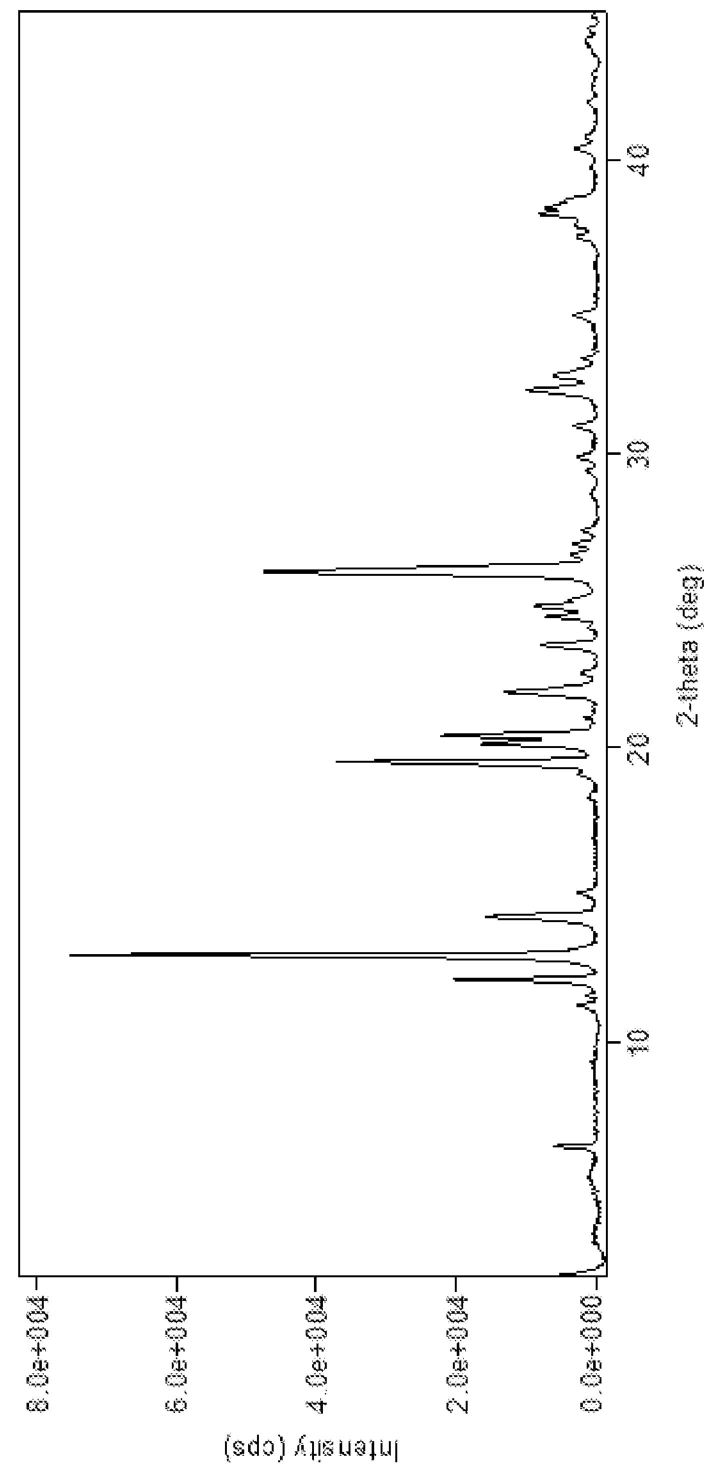
FIG. 17 shows an exemplary X-ray powder diffraction (XRPD) pattern for a sample of (S)-2-cyclopropyl-1-(3-fluoro-4-methylphenyl)-N—((S)-1-phenylethyl)ethan-1-amine (Compound 5A, HCl salt).

| | Compound 5A |
|---|---|
| PXRD | FIG. 17: Peaks at 12.1, 13.0, 14.2, 19.5, 20.4, 25.9°2θ |
| TGA | FIG. 18: Decrease in weight of about 0.1% out to about 125° C. |
| DSC | FIG. 18: Endotherm extrapolated onset temperature: about 215.7° C. |

Certain other XRPD peaks for the anhydrous crystalline form of (S)-2-cyclopropyl-1-(3-fluoro-4-methylphenyl)-N—((S')-1-phenylethyl)ethan-1-amine (Compound 5A, HCl salt) are shown in Table 14 below.

TABLE 14

| 2-Theta | Height (cps) |
|---|---|
| 5.6 | 635 |
| 6.5 | 4164 |
| 11.2 | 1737 |

TABLE 14-continued

| 2-Theta | Height (cps) |
|---|---|
| 11.6 | 840 |
| 12.1 | 14378 |
| 13.0 | 51387 |
| 14.2 | 10968 |
| 15.1 | 1951 |
| 18.3 | 570 |
| 19.1 | 857 |
| 19.5 | 28622 |
| 20.1 | 10642 |
| 20.4 | 16183 |
| 21.0 | 1222 |
| 21.9 | 8494 |
| 22.5 | 1443 |
| 23.5 | 5206 |
| 24.1 | 819 |
| 24.5 | 4905 |
| 24.8 | 6021 |
| 25.0 | 2188 |
| 25.9 | 33361 |
| 26.5 | 2447 |
| 26.9 | 2322 |
| 27.3 | 1464 |
| 28.6 | 488 |
| 29.4 | 1081 |
| 29.9 | 2004 |
| 30.9 | 2169 |
| 32.1 | 6743 |
| 32.6 | 4016 |
| 33.2 | 1404 |
| 34.7 | 2218 |
| 37.1 | 460 |
| 37.3 | 2290 |
| 37.8 | 2072 |
| 38.1 | 5892 |
| 38.4 | 5410 |
| 38.6 | 3220 |
| 39.7 | 573 |
| 40.4 | 2308 |
| 40.8 | 1119 |
| 41.9 | 765 |
| 42.4 | 404 |
| 42.9 | 549 |
| 43.6 | 450 |
| 44.0 | 1094 |
| 44.4 | 1022 |

One aspect of the present invention relates to a crystalline form of (S)-2-cyclopropyl-1-(3-fluoro-4-methylphenyl)-N—((S)-1-phenylethyl)ethan-1-amine (Compound 5A, HCl salt). In some embodiments, the crystal form is an anhydrous crystalline form of (S)-2-cyclopropyl-1-(3-fluoro-4-methylphenyl)-N—((S)-1-phenylethyl)ethan-1-amine (Compound 5A, HCl salt). An anhydrous crystalline form refers to a crystalline form that contains 2% or less of water. In some embodiments, the anhydrous crystalline form contains 1% or less water. In some embodiments, the water content is determined by Karl Fischer (KF) analysis.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has an X-ray powder diffraction pattern comprising at least three peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least four peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least five peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least six peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least seven peaks, in terms of 2θ, selected from the group consisting of: 6.50°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least eight peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least nine peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°. In some embodiments, the anhydrous crystalline form has an X-ray powder diffraction pattern comprising at least ten peaks, in terms of 2θ, selected from the group consisting of: 6.5°±0.2°, 12.1°±0.2°, 13.0°±0.2°, 14.2°±0.2°, 19.5°±0.2°, 20.1°±0.2°, 20.4°±0.2°, 21.9°±0.2°, 23.5°±0.2°, 24.5°±0.2°, 24.8°±0.2°, 25.9°±0.2°, and 32.1°±0.2°.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has an X-ray powder diffraction pattern comprising a peak, in terms of 2θ, at 13.0°±0.2°. In some embodiments, the anhydrous crystalline form has an X-ray powder diffraction pattern comprising a peak, in terms of 2θ, at 19.5°±0.2°. In some embodiments, the anhydrous crystalline form has an X-ray powder diffraction pattern comprising a peak, in terms of 2θ, at 25.9°±0.2°. In some embodiments, the anhydrous crystalline form has an X-ray powder diffraction pattern comprising peaks, in terms of 2θ, at 13.0°±0.2° and 19.5°±0.2°. In some embodiments, the anhydrous crystalline form has an X-ray powder diffraction pattern comprising peaks, in terms of 2θ, at 13.0°±0.2° and 25.9°±0.2°. In some embodiments, the anhydrous crystalline form has an X-ray powder diffraction pattern comprising peaks, in terms of 2θ, at 19.5°±0.2° and 25.9°±0.2°. In some embodiments, the anhydrous crystalline form has an X-ray powder diffraction pattern comprising peaks, in terms of 2θ, at 13.0°±0.2°, 19.5°±0.2°, and 25.9°±0.2°. In some embodiments, the anhydrous crystalline form has an X-ray powder diffraction pattern comprising peaks, in terms of 2θ, at 13.0°±0.2°, 19.5°±0.2°, 20.4°±0.2°, and 25.9°±0.2°. In some embodiments, the anhydrous crystalline form has an X-ray powder diffraction pattern comprising peaks, in terms of 2θ, at 12.1°±0.2°, 13.0°±0.2°, 19.5°±0.2°, 20.4°±0.2°, and 25.9°±0.2°. In some embodiments, the anhydrous crystalline form has an X-ray powder diffraction pattern comprising peaks, in terms of 2θ, at 12.1°±0.2°, 13.0°±0.2°, 14.2°±0.2°, 19.5°±0.2°, 20.4°±0.2°, and 25.9°±0.2°. In some embodiments, the anhydrous crystalline form has an X-ray powder diffraction pattern comprising peaks, in terms of 2θ, at 12.1°±0.2°, 13.0°±0.2°, 14.2°±0.2°, 19.5°±0.2°, 20.1°±0.2°, 20.4°±0.2°, 21.9°±0.2°, and 25.9°±0.2°. In some embodiments, the anhydrous crystalline form has an X-ray powder diffraction pattern substantially as shown in FIG. 17, wherein by "substantially" is meant that the reported peaks can vary by about ±0.2° 2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 18:
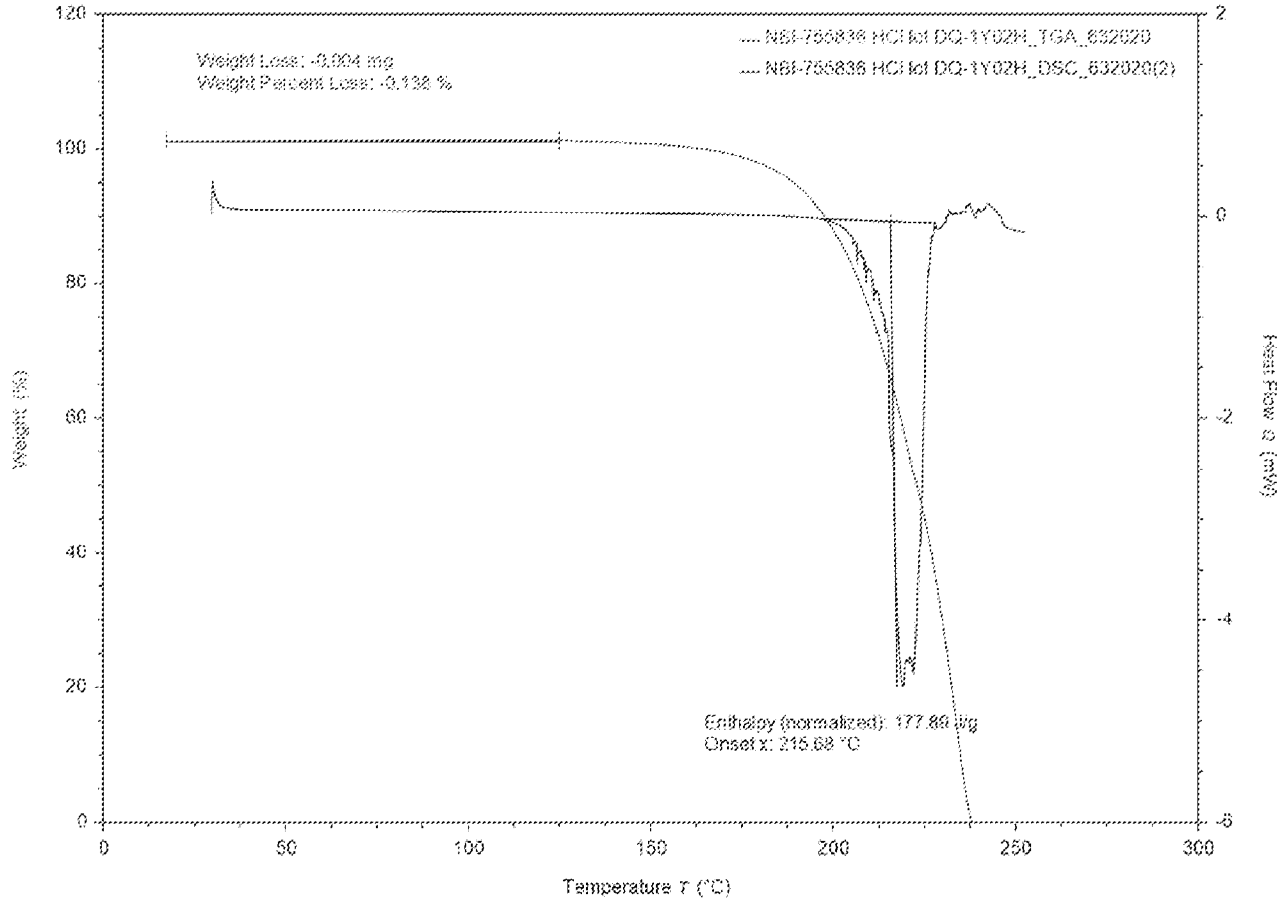
FIG. 18 shows an exemplary Differential Scanning Calorimetry (DSC) and Thermogravimetric Analysis (TGA) thermograms for a sample of (S)-2-cyclopropyl-1-(3-fluoro-4-methylphenyl)-N—((S)-1-phenylethyl)ethan-1-amine (Compound 5A, HCl salt).

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has a differential scanning calorimetry (DSC) thermogram comprising an endotherm with an extrapolated onset temperature of about 212° C. to about 218.5° C. In some embodiments, the anhydrous crystalline form has a differential scanning calorimetry thermogram comprising an endotherm with an extrapolated onset temperature of about 213° C. to about 218° C. In some embodiments, the anhydrous crystalline form has a differential scanning calorimetry thermogram comprising an endotherm with an extrapolated onset temperature of about 214° C. to about 217.5° C. In some embodiments, the anhydrous crystalline form has a differential scanning calorimetry thermogram comprising an endotherm with an extrapolated onset temperature of about 214.5° C. to about 217° C. In some embodiments, the anhydrous crystalline form has a differential scanning calorimetry thermogram comprising an endotherm with an extrapolated onset temperature of about 215° C. to about 216.5° C. In some embodiments, the anhydrous crystalline form has a differential scanning calorimetry thermogram substantially as shown in FIG. 18, wherein by "substantially" is meant that the reported DSC features can vary by about ±5° C. and the reported DSC features can vary by about ±20 joules per gram.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has a thermogravimetric analysis (TGA) profile showing about 1.0% or less weight loss out to about 125° C. In some embodiments, the anhydrous crystalline form has a thermogravimetric analysis profile showing about 0.8% or less weight loss out to about 125° C. In some embodiments, the anhydrous crystalline form has a thermogravimetric analysis profile showing about 0.6% or less weight loss out to about 125° C. In some embodiments, the anhydrous crystalline form has a thermogravimetric analysis profile showing about 0.4% or less weight loss out to about 125° C. In some embodiments, the anhydrous crystalline form has a thermogravimetric analysis profile showing about 0.2% or less weight loss out to about 125° C.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has a thermogravimetric analysis (TGA) profile showing about 0.01% to about 1.0% weight loss out to about 125° C. In some embodiments, the anhydrous crystalline form has a thermogravimetric analysis profile showing about 0.02% to about 0.8% weight loss out to about 125° C. In some embodiments, the anhydrous crystalline form has a thermogravimetric analysis profile showing about 0.03% to about 0.6% weight loss out to about 125° C. In some embodiments, the anhydrous crystalline form has a thermogravimetric analysis profile showing about 0.04% to about 0.4% weight loss out to about 125° C. In some embodiments, the anhydrous crystalline form has a thermogravimetric analysis profile showing about 0.05% to about 0.2% weight loss out to about 125° C. In some embodiments, the anhydrous crystalline form has a thermogravimetric analysis profile substantially as shown in FIG. 18, wherein by "substantially" is meant that the reported TGA features can vary by about ±5° C., and the reported TGA features can vary by about ±2% weight change (i.e., ±about 2% weight change).

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has:

- an X-ray powder diffraction pattern comprising at least three peaks, in terms of 2θ, selected from the group consisting of: 6.5°±0.2°, 12.1°±0.2°, 13.0°±0.2°, 14.2°±0.2°, 19.5°±0.2°, 20.1 0.2°, 20.4°±0.2°, 21.9°±0.2°, 23.5°±0.2°, 24.5°±0.2°, 24.8°±0.2°, 25.9°±0.2°, and 32.1°±0.2°;
- a differential scanning calorimetry (DSC) thermogram comprising an endotherm with an extrapolated onset temperature of about 212° C. to about 218.5° C.; and/or
- a thermogravimetric analysis profile showing about 1.0% or less weight loss out to about 125° C.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has:

- an X-ray powder diffraction pattern comprising peaks, in terms of 2θ, selected from the group consisting of: 13.0°±0.2°, 19.5°±0.2°, and 25.9°±0.2°;
- a differential scanning calorimetry thermogram comprising an endotherm with an extrapolated onset temperature of about 214° C. to about 217.5° C.; and/or
- a thermogravimetric analysis profile showing about 0.02% to about 0.8% weight loss out to about 125° C.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has:

- an X-ray powder diffraction pattern comprising peaks, in terms of 2θ, at 12.1°±0.2°, 13.0°±0.2°, 14.2°±0.2°, 19.5°±0.2°, 20.4°±0.2°, and 25.9°±0.2°;
- a differential scanning calorimetry thermogram comprising an endotherm with an extrapolated onset temperature of about 214.5° C. to about 217° C.; and/or a thermogravimetric analysis profile showing about 0.04% to about 0.4% weight loss out to about 125° C.

One aspect of the present invention relates to an anhydrous crystalline form of (S)-2-cyclopropyl-1-(3-fluoro-4-methylphenyl)-N—((S)-1-phenylethyl)ethan-1-amine (Compound 5A, HCl salt), wherein the anhydrous crystalline form has:

an X-ray powder diffraction pattern substantially as shown in FIG. 17;

a differential scanning calorimetry thermogram substantially as shown in FIG. 18; and/or a thermogravimetric analysis profile substantially as shown in FIG. 18.

In some embodiments, the anhydrous crystalline form of (S)-2-cyclopropyl-1-(3-fluoro-4-methylphenyl)-N—((S)-1-phenylethyl)ethan-1-amine (Compound 5A, HCl salt) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

G. Crystalline 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, Tosylate Salt, Form I)

One aspect of the present invention relates to a novel crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) and processes related thereto.

A summary of representative physical properties for crystalline Compound 1 (tosylate salt) are provided in Table 15 and Table 16.

TABLE 15

Figure 24:
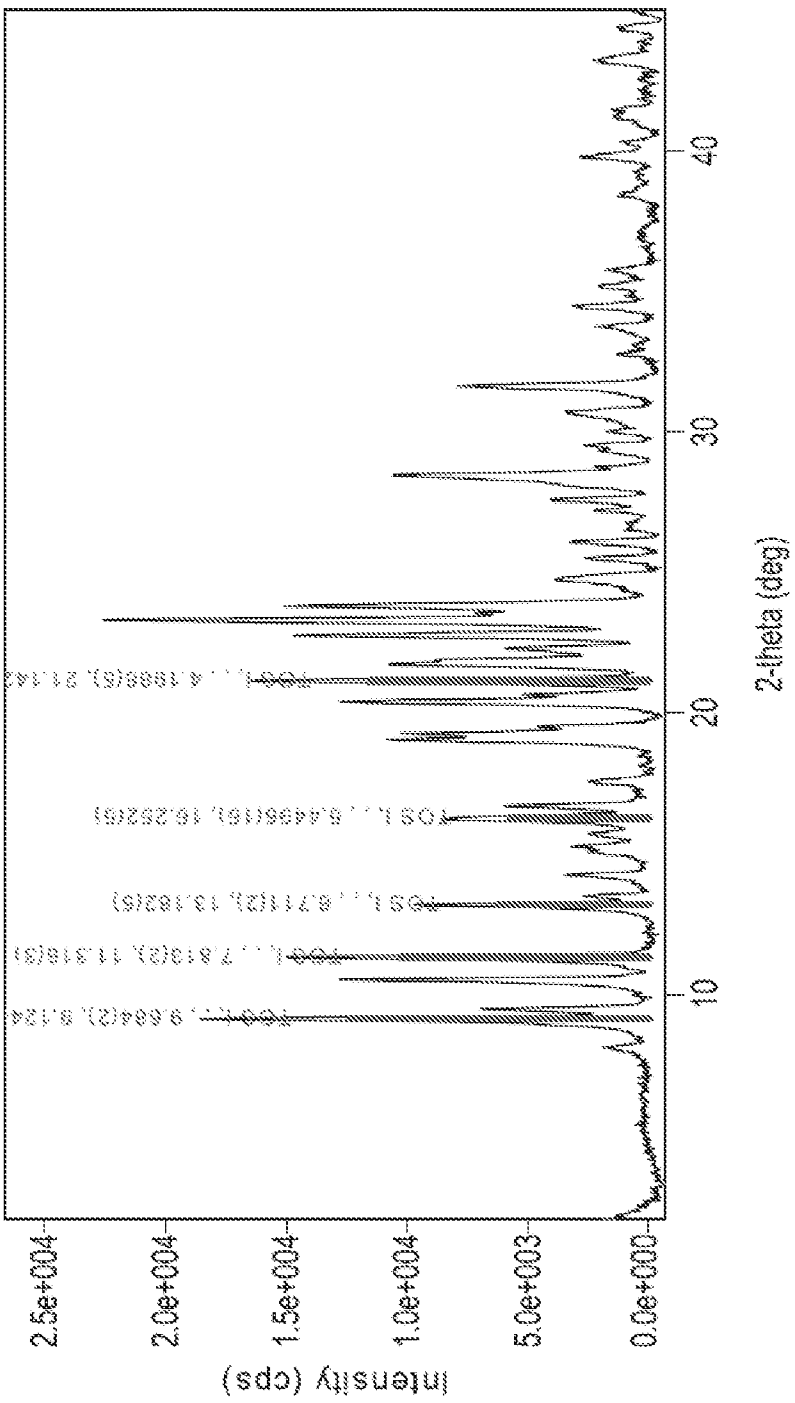
FIG. 24 shows an exemplary X-ray powder diffraction (XRPD) pattern for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt).

| Crystalline Compound 1 (Tosylate salt, Form I) | |
|---|---|
| PXRD | FIG. 24: Peaks at 9.1, 10.5, 11.3, 20.4, 21.1, 22.8, 23.3, and 23.8°2θ |
| TGA | FIG. 25: Decrease in weight of about 0.5% out to about 125° C. |
| DSC | FIG. 25: Endotherm extrapolated onset temperature: about 155.7° C. |

Certain other XRPD peaks for crystalline 4-(2-chloro-4-methoxy-5-methylphenyl)-N-[(1S)-2-cyclopropyl-11-(3-fluoro-4-methylphenyl)ethyl]-5-methyl-N-prop-2-ynyl-1,3-thiazol-2-amine (Compound 1, tosylate salt) are shown in Table 16 below.

TABLE 16

Selected X-Ray Powder Diffraction (XRPD) Peaks for Compound 1 (tosylate salt, Form I)

| 2-Theta | Height (cps) |
|---|---|
| 8.1 | 957 |
| 9.1 | 12296 |
| 9.5 | 4519 |
| 10.5 | 8507 |
| 11.3 | 10211 |
| 13.2 | 6158 |
| 13.5 | 1598 |
| 14.2 | 2197 |
| 15.2 | 1746 |
| 15.7 | 1437 |
| 16.3 | 5723 |
| 16.7 | 3848 |
| 17.5 | 1578 |
| 19.0 | 6774 |
| 19.3 | 6491 |
| 19.5 | 3152 |
| 20.4 | 8581 |
| 20.7 | 3040 |
| 21.1 | 11498 |
| 21.7 | 4979 |
| 21.9 | 5331 |
| 22.3 | 3701 |
| 22.8 | 10159 |
| 23.3 | 14954 |
| 23.5 | 3597 |
| 23.8 | 9590 |
| 24.7 | 2325 |
| 25.5 | 1704 |
| 26.1 | 2413 |
| 26.7 | 422 |
| 27.2 | 1648 |
| 27.6 | 2825 |
| 28.5 | 6417 |
| 29.5 | 1423 |
| 30.0 | 849 |
| 30.6 | 1262 |
| 30.8 | 1121 |
| 31.6 | 5563 |
| 32.7 | 874 |
| 33.7 | 1111 |
| 34.4 | 2054 |
| 34.8 | 706 |
| 35.1 | 1320 |
| 35.7 | 1028 |
| 38.4 | 751 |
| 39.7 | 1790 |
| 40.2 | 762 |
| 41.2 | 925 |
| 43.2 | 1540 |
| 44.3 | 1142 |

One aspect of the present invention relates to an crystalline form of 4-(2-chloro-4-methoxy-5-methylphenyl)-N-[(1S)-2-cyclopropyl-11-(3-fluoro-4-methylphenyl)ethyl]-5-methyl-N-prop-2-ynyl-1,3-thiazol-2-amine (Compound 1, tosylate salt, Form I).

One aspect of the present invention relates to an crystalline form of 4-(2-chloro-4-methoxy-5-methylphenyl)-N-[(1S)-2-cyclopropyl-11-(3-fluoro-4-methylphenyl)ethyl]-5-methyl-N-prop-2-ynyl-1,3-thiazol-2-amine (Compound 1, tosylate salt, Form I), wherein the crystalline form has an X-ray powder diffraction pattern comprising at least three peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least four peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least five peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least six peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.30° 0.2°, 23.8°±0.2°, and 28.5°±0.2°. In some embodiments, the crystalline form (Compound 1, tosylate salt) has an X-ray powder diffraction pattern comprising at least seven peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least eight peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least nine peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°. In some embodiments, the crystalline form (Compound 1, tosylate salt) has an X-ray powder diffraction pattern comprising at least ten peaks, in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°.

One aspect of the present invention relates to a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the crystalline form has an X-ray powder diffraction pattern comprising a peak, in terms of 2θ, at 9.1°±0.2°. In some embodiments, the crystalline form (Compound 1, tosylate salt) has an X-ray powder diffraction pattern comprising a peak, in terms of 2θ, at 21.10°±0.2°. In some embodiments, the crystalline form (Compound 1, tosylate salt) has an X-ray powder diffraction pattern comprising a peak, in terms of 2θ, at 23.3°±0.2°. In some embodiments, the crystalline form (Compound 1, tosylate salt) has an X-ray powder diffraction pattern comprising peaks, in terms of 2θ, at 9.1°±0.2° and 21.1°±0.2°. In some embodiments, the crystalline form (Compound 1, tosylate salt) has an X-ray powder diffraction pattern comprising peaks, in terms of 2θ, at 9.1°±0.2° and 23.3°±0.2°. In some embodiments, the crystalline form (Compound 1, tosylate salt) has an X-ray powder diffraction pattern comprising peaks, in terms of 2θ, at 21.1°±0.2° and 23.3°±0.2°. In some embodiments, the crystalline form (Compound 1, tosylate salt) has an X-ray powder diffraction pattern comprising peaks, in terms of 2θ, at 9.1°±0.2°, 21.1°±0.2°, and 23.3°±0.2°. In some embodiments, the crystalline form (Compound 1, tosylate salt) has an X-ray powder diffraction pattern comprising peaks, in terms of 2θ, at 9.1°±0.2°, 11.3°±0.2°, 21.1°±0.2°, and 23.3°±0.2°. In some embodiments, the crystalline form (Compound 1, tosylate salt) has an X-ray powder diffraction pattern comprising peaks, in terms of 2θ, at 9.1°±0.2°, 11.3°±0.2°, 21.1°±0.2°, 22.8°±0.2°, and 23.3°±0.2°. In some embodiments, the crystalline form (Compound 1, tosylate salt) has an X-ray powder diffraction pattern comprising peaks, in terms of 2θ, at 9.1°±0.2°, 11.3°±0.2°, 13.2°±0.2°, 16.3°±0.2°, and 21.1°±0.2°. In some embodiments, the crystalline form (Compound 1, tosylate salt) has an X-ray powder diffraction pattern comprising peaks, in terms of 2θ, at 9.1°±0.2°, 11.3°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 11.3°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 19.0°±0.2°, 20.4°±±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 19.3°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 20.4°±0.2°, 21.1°±0.2°, 23.3°±0.2°, 23.8°±0.2°, and 28.5°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 13.2°±0.2°, 19.0°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 13.2°±0.2°, 19.3°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 13.2°±0.2°, 20.4°±0.2°, 21.1°±0.2°, 23.3°±0.2°, 23.8°±0.2°, and 28.5°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 16.3°±0.2°, 19.0°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 16.3°±0.2°, 19.3°±0.2°, 20.4°±0.2°, 21.1°±0.2°, 23.3°±0.2°, and 23.8°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 16.3°±0.2°, 20.4°±0.2°, 21.1°±0.2°, 23.3°±0.2°, 23.8°±0.2°, and 28.5°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 19.0°±0.2°, 19.3°±0.2°, 20.4°±0.2°, 21.1°±0.2°, 23.3°±0.2°, 23.8°±0.2°, and 28.5°±0.2°. In some embodiments, the crystalline form (Compound 1, tosylate salt) has an X-ray powder diffraction pattern comprising peaks, in terms of 2θ, at 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 23.3°±0.2°, 23.8°±0.2°, and 28.5°±0.2°. In some embodiments, the crystalline form (Compound 1, tosylate salt) has an X-ray powder diffraction pattern substantially as shown in FIG. 24, wherein by "substantially" is meant that the reported peaks can vary by about ±0.2° 2θ.

It is understood that peak intensities can vary from one diffractogram to another for the same crystalline form based on any number of factors that are known to those skilled in the art, such as, preferred orientation effects, preparation technique, the sample mounting procedure, the instrument employed, etc. In some instances, peak intensities can be rather dramatical. Accordingly, the diffraction peak intensities shown herein are illustrative and identical diffraction peak intensities are not necessarily required. One skilled in the art would readily be capable of comparing the diffractogram provided herein with a diffractogram generated for an unknown crystal form and confirm whether the diffractogram is characterizing the same crystal form as provided herein or a different form.

Figure 25:
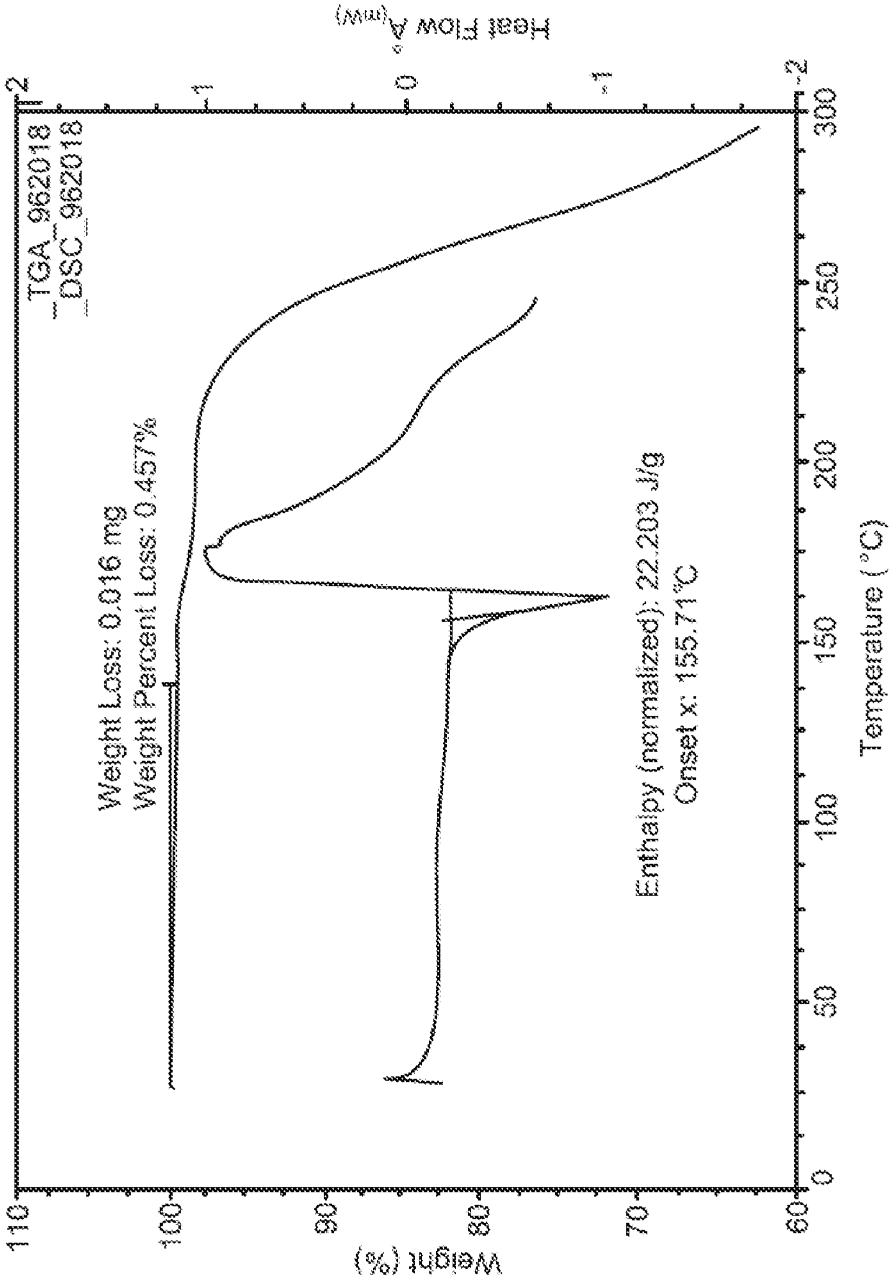
FIG. 25 shows an exemplary Differential Scanning Calorimetry (DSC) and Thermogravimetric Analysis (TGA) thermograms for a sample of crystalline Form I of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt).

One aspect of the present invention relates to a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the crystalline form has a differential scanning calorimetry (DSC) thermogram comprising an endotherm with an extrapolated onset temperature of about 154° C. to about 159° C. In some embodiments, the crystalline form (Compound 1, tosylate salt) has a differential scanning calorimetry thermogram comprising an endotherm with an extrapolated onset temperature of about 154.5° C. to about 158.5° C. In some embodiments, the crystalline form (Compound 1, tosylate salt) has a differential scanning calorimetry thermogram comprising an endotherm with an extrapolated onset temperature of about 155° C. to about 158° C. In some embodiments, the crystalline form (Compound 1, tosylate salt) has a differential scanning calorimetry thermogram comprising an endotherm with an extrapolated onset temperature of about 155.5° C. to about 157.5° C. In some embodiments, the crystalline form (Compound 1, tosylate salt) has a differential scanning calorimetry thermogram comprising an endotherm with an extrapolated onset temperature of about 156° C. to about 157° C. In some embodiments, the crystalline form (Compound 1, tosylate salt) has a differential scanning calorimetry thermogram substantially as shown in FIG. 25, wherein by "substantially" is meant that the reported DSC features can vary by about ±5° C. and the reported DSC features can vary by about ±20 joules per gram.

One aspect of the present invention relates to a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the crystalline form has a thermogravimetric analysis (TGA) profile showing about 1.0% or less weight loss out to about 125° C. In some embodiments, the crystalline form (Compound 1, tosylate salt) has a thermogravimetric analysis (TGA) profile showing about 0.9% or less weight loss out to about 125° C. In some embodiments, the crystalline form (Compound 1, tosylate salt) has a thermogravimetric analysis (TGA) profile showing about 0.7% or less weight loss out to about 125° C. In some embodiments, the crystalline form (Compound 1, tosylate salt) has a thermogravimetric analysis (TGA) profile showing about 0.6% or less weight loss out to about 125° C. In some embodiments, the crystalline form (Compound 1, tosylate salt) has a thermogravimetric analysis (TGA) profile showing about 0.5% or less weight loss out to about 125° C.

One aspect of the present invention relates to a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the crystalline form has a thermogravimetric analysis (TGA) profile showing about 0.05% to about 1.0% weight loss out to about 125° C. In some embodiments, the crystalline form (Compound 1, tosylate salt) has a thermogravimetric analysis (TGA) profile showing about 0.1% to about 0.9% weight loss out to about 125° C. In some embodiments, the crystalline form (Compound 1, tosylate salt) has a thermogravimetric analysis (TGA) profile showing about 0.2% to about 0.7% weight loss out to about 125° C. In some embodiments, the crystalline form (Compound 1, tosylate salt) has a thermogravimetric analysis (TGA) profile showing about 0.3% to about 0.6% weight loss out to about 125° C. In some embodiments, the crystalline form (Compound 1, tosylate salt) has a thermogravimetric analysis (TGA) profile showing about 0.4% to about 0.5% weight loss out to about 125° C. In some embodiments, the crystalline form (Compound 1, tosylate salt) has a thermogravimetric analysis profile substantially as shown in FIG. 25, wherein by "substantially" is meant that the reported TGA features can vary by about ±5° C., and the reported TGA features can vary by about ±2% weight change (i.e., ±about 2% weight change).

One aspect of the present invention relates to an crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the crystalline form has:

an X-ray powder diffraction pattern comprising at least three peaks, in terms of 2θ, selected from the group consisting of: 9.1°±0.2°, 10.5°±0.2°, 11.3°±0.2°, 13.2°±0.2°, 16.3°±0.2°, 19.0° 0.2°, 19.3°±0.2°, 20.4°±0.2°, 21.1°±0.2°, 22.8°±0.2°, 23.3°±0.2°, 23.8°±0.2°, and 28.5°±0.2°;

a differential scanning calorimetry thermogram comprising an endotherm with an extrapolated onset temperature of about 154° C. to about 159° C.; and/or a thermogravimetric analysis profile showing about 0.05% to about 1.0% weight loss out to about 125° C.

One aspect of the present invention relates to an crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the anhydrous crystalline form has:

an X-ray powder diffraction pattern comprising peaks, in terms of 2θ, at 9.1°±0.2°, 11.3°±0.2°, 21.1°±0.2°, 22.8°±0.2°, and 23.3°±0.2°;

a differential scanning calorimetry thermogram comprising an endotherm with an extrapolated onset temperature of about 155° C. to about 158° C.; and/or a thermogravimetric analysis profile showing about 0.9% or less weight loss out to about 125° C.

One aspect of the present invention relates to an anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the anhydrous crystalline form has:

an X-ray powder diffraction pattern comprising peaks, in terms of 2θ, at 9.1°±0.2°, 11.3°±0.2°, 13.2°±0.2°, 16.3°±0.2°, and 21.1°±0.2°;

a differential scanning calorimetry thermogram comprising an endotherm with an extrapolated onset temperature of about 155.5° C. to about 157.5° C.; and/or a thermogravimetric analysis profile showing about 0.6% or less weight loss out to about 125° C.

One aspect of the present invention relates to a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt), wherein the anhydrous crystalline form has:

- an X-ray powder diffraction pattern substantially as shown in FIG. 24;
- a differential scanning calorimetry thermogram substantially as shown in FIG. 25; and/or
- a thermogravimetric analysis profile substantially as shown in FIG. 25.

In some embodiments, the anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) can be isolated as the crystalline form described herein, with a crystalline purity of at least about 75% by weight. In some embodiments, about 80% by weight. In some embodiments, about 85% by weight. In some embodiments, about 90% by weight. In some embodiments, about 95% by weight. In some embodiments, about 96% by weight. In some embodiments, about 97% by weight. In some embodiments, about 98% by weight. In some embodiments, about 99% by weight.

Isotopically Labeled Compounds of the Invention

The compounds disclosed and described herein allow atoms at each position of the compound independently to have an isotopic distribution for a chemical element in proportional amounts to those usually found in nature or an isotopic distribution in proportional amounts different to those usually found in nature unless the context clearly dictates otherwise. Accordingly, one aspect of the present invention relates to Compounds of Formula (Ia):

(Ia)

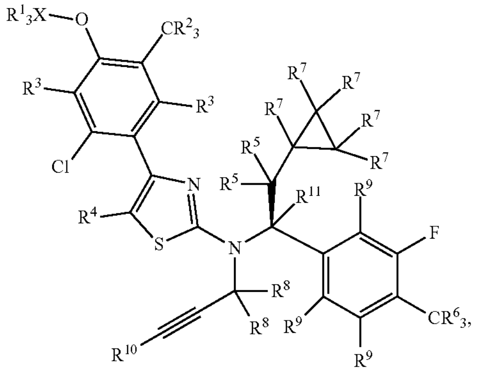

wherein:

- $R^1$, $R^2$, $R^3$, $R^4$, $R^5$, $R^6$, $R^7$, $R^8$, $R^9$, $R^{10}$, and $R^{11}$ are each independently selected from the group consisting of hydrogen and deuterium; and
- X is selected from the group consisting of carbon-12 ($^{12}C$) and carbon-13 ($^{13}C$); provided that at least one $R^1$, $R^2$, $R^3$, $R^4$, $R^5$, $R^6$, $R^7$, $R^8$, $R^9$, $R^{10}$, and $R^{11}$ is deuterium.

In some embodiments, each $R^1$ is independently deuterium. In some embodiments, each $R^2$ is independently deuterium. In some embodiments, each $R^3$ is independently deuterium. In some embodiments, $R^4$ is deuterium. In some embodiments, each $R^5$ is independently deuterium. In some embodiments, each $R^6$ is independently deuterium. In some embodiments, each $R^7$ is independently deuterium. In some embodiments, each $R^8$ is independently deuterium. In some embodiments, each $R^9$ is independently deuterium. In some embodiments, $R^{10}$ is deuterium. In some embodiments, $R^{11}$ is deuterium.

In some embodiments, X is carbon-12 ($^{12}C$). In some embodiments, X is carbon-13 ($^{13}C$).

In some embodiments, each $R^1$ is independently deuterium and X is carbon-13 ($^{13}C$).

Compounds of Formula (Ia) can be prepared using processes described herein by introducing one or more isotopes into any of the intermediates using methods known in the art, such as, the representative process shown in Example 6.

A chemical element has an atomic number defined by the number of protons within the atom's nucleus. Each atomic number identifies a specific element, but not the isotope; an atom of a given element can have a wide range in its number of neutrons. The number of both protons and neutrons in the nucleus is the atom's mass number, and each isotope of a given element has a different mass number. A compound wherein one or more atoms have an isotopic distribution for a chemical element in proportional amounts different to those usually found in nature is commonly referred to as being an isotopically labeled compound. Each chemical element as represented in a compound structure can include any isotopic distribution of said element. For example, in a compound structure a hydrogen atom can be explicitly disclosed or understood to be present in the compound. At any position of the compound that a hydrogen atom can be present, the hydrogen atom can be an isotopic distribution of hydrogen, including but not limited to protium ($^1H$) and deuterium ($^2H$) in proportional amounts to those usually found in nature and in proportional amounts different to those usually found in nature.

Thus, reference herein to a compound encompasses all potential isotopic distributions for each atom unless the context clearly dictates otherwise. Examples of isotopes include isotopes of hydrogen, carbon, nitrogen, oxygen, phosphorous, sulfur, fluorine, chlorine, bromine and iodine. As one of skill in the art would appreciate, any of the compounds as disclosed and described herein can include radioactive isotopes. Accordingly, also contemplated is use of compounds as disclosed and described herein, wherein one or more atoms have an isotopic distribution different to those usually found in nature, such as having $^2H$ or $^3H$ in greater proportion, or $^{11}C$, $^{13}C$, or $^{14}C$ in greater proportion than found in nature. By way of general example, and without limitation, isotopes of hydrogen include protium ($^1H$), deuterium ($^2H$) and tritium ($^3H$). Isotopes of carbon include carbon-11 ($^{11}C$), carbon-12 ($^{12}C$), carbon-13 ($^{13}C$), and carbon-14 ($^{14}C$). Isotopes of nitrogen include nitrogen-13 ($^{13}N$), nitrogen-14 ($^{14}N$) and nitrogen-15 ($^{15}N$). Isotopes of oxygen include oxygen-14 ($^{14}O$), oxygen-15 ($^{15}O$), oxygen-16 ($^{16}O$), oxygen-17 ($^{17}O$), and oxygen-18 ($^{18}O$). Isotope of fluorine include fluorine-17 ($^{17}F$), fluorine-18 ($^{18}F$) and fluorine-19 ($^{19}F$). Isotopes of phosphorous include phosphorus-31 ($^{31}P$), phosphorus-32 ($^{32}P$), phosphorus-33 ($^{33}P$), phosphorus-34 ($^{34}P$), phosphorus-35 ($^{35}P$) and phosphorus-36 ($^{36}P$) Isotopes of sulfur include sulfur-32 ($^{32}S$), sulfur-33 ($^{33}S$), sulfur-34 ($^{34}S$), sulfur-35 ($^{35}S$), sulfur-36 ($^{36}S$) and sulfur-38 ($^{38}S$). Isotopes of chlorine include chlorine-35 ($^{35}Cl$), chlorine-36 ($^{36}Cl$) and chlorine-37 ($^{37}Cl$). Isotopes of bromine include bromine-75 ($^{7}Br$), bromine-76 ($^{76}Br$), bromine-77 ($^{77}Br$), bromine-79 ($^{79}Br$), bromine-81 ($^{81}Br$) and bromine-82 ($^{82}Br$). Isotopes of iodine include iodine-123 ($^{123}I$), iodine-124 ($^{124}I$), iodine-125 ($^{125}I$), iodine-131 ($^{131}I$) and iodine-135 ($^{135}I$). In some embodiments, atoms at every position of the compound have an isotopic distribution for each chemical element in proportional amounts to those usually found in nature. In some embodiments, atoms at least one position of the compound has an isotopic distribution for a chemical element in proportional amounts different to those usually found in nature (remainder atoms having an isotopic distribution for a chemical element in proportional amounts to those usually found in nature). In some embodiments, atoms at least two positions of the compound independently have an isotopic distribution for a chemical element in proportional amounts different to those usually found in nature (remainder atoms having an isotopic distribution for a chemical element in proportional amounts to those usually found in nature). In some embodiments, atoms at least three positions of the compound independently have an isotopic distribution for a chemical element in proportional amounts different to those usually found in nature (remainder atoms having an isotopic distribution for a chemical element in proportional amounts to those usually found in nature). In some embodiments, atoms at least four positions of the compound independently have an isotopic distribution for a chemical element in proportional amounts different to those usually found in nature (remainder atoms having an isotopic distribution for a chemical element in proportional amounts to those usually found in nature). In some embodiments, atoms at least five positions of the compound independently have an isotopic distribution for a chemical element in proportional amounts different to those usually found in nature (remainder atoms having an isotopic distribution for a chemical element in proportional amounts to those usually found in nature). In some embodiments, atoms at least six positions of the compound independently have an isotopic distribution for a chemical element in proportional amounts different to those usually found in nature (remainder atoms having an isotopic distribution for a chemical element in proportional amounts to those usually found in nature).

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

Certain Processes of the Invention

The present invention is directed, inter alia, to processes useful in the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) and crystalline forms thereof.

Any of the processes either, collectively as one or more steps together, or individual steps as described herein, infra and supra, can be conducted under an inert atmosphere. Accordingly, in some embodiments, the process step as described herein is conducted under a substantially inert atmosphere.

In some embodiments, the process step as described herein is conducted under a substantially inert atmosphere comprising argon or nitrogen. In some embodiments, the process step as described herein is conducted under a substantially inert atmosphere comprising nitrogen.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the reaction step, suitable solvents for a particular reaction step can be selected. In some embodiments, reactions can be carried out in the absence of solvent, such as when at least one of the intermediates or reagents is a liquid.

Suitable solvents can include halogenated solvents such as: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 1,2-dichloroethane, 2-chloropropane, hexafluorobenzene, 1,2,4-trichlorobenzene, 1,2-dichlorobenzene, 1,3-dichlorobenzene, 1,4-dichlorobenzene, chlorobenzene, fluorobenzene, fluorotrichloromethane, chlorotrifluoromethane, bromotrifluoromethane, carbon tetrafluoride, dichlorofluoromethane, chlorodifluoromethane, trifluoromethane, 1,2-dichlorotetrafluorethane, hexafluoroethane, and mixtures thereof.

Suitable solvents can include ether solvents, such as: 1,2-dimethoxyethane (DME), tetrahydrofuran (THF), cyclopentyl methyl ether (CPME), 2-methyltetrahydrofuran (2-MeTHF), 1,3-dioxane, 1,4-dioxane, diethyl ether, ethylene glycol dimethyl ether, ethylene glycol diethyl ether, diethylene glycol dimethyl ether, diethylene glycol diethyl ether, triethylene glycol dimethyl ether, 5-methyl-2-hexanone (MIAK), 4-methyl-2-pentanone (MIBK), tert-amyl methyl ether (TAME, also referred to as 2-methoxy-2-methylbutane), methyl tert-butyl ether (MTBE), mixtures thereof.

Suitable solvents can include alcohol or protic solvents, such as: methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, isobutyl alcohol, t-butyl alcohol, 2-ethoxyethanol, diethylene glycol, 1-pentanol, 2-pentanol, 3-pentanol, neo-pentyl alcohol, t-pentyl alcohol, diethylene glycol monomethyl ether, diethylene glycol monoethyl ether, cyclohexanol, benzyl alcohol, glycerol, and mixtures thereof.

Suitable solvents can include aprotic solvents, such as: benzene, chlorobenzene, cyclohexane, pentane, hexane, toluene, cycloheptane, methylcyclohexane, heptanes, n-heptane, ethylbenzene, o-xylene, m-xylene, p-xylene, mixtures of xylenes, octane, indane, nonane, naphthalene, tetrahydrofuran, acetonitrile, dimethyl sulfoxide, propionitrile, ethyl formate, methyl acetate, hexachloroacetone, acetone, ethyl methyl ketone, ethyl acetate, isopropyl acetate, sulfolane, 1,3-dimethyl-3,4,5,6-tetrahydro-2(1H)-pyrimidinone, 1,3-dimethyl-2-imidazolidinone, N-methylpyrrolidinone, tetramethylurea, nitromethane, and nitrobenzene, and amides, including but not limited to, N,N-dimethylformamide, N,N-dimethylacetamide, formamide, N-methylacetamide, N-methylformamide, N,N-dimethylpropionamide, hexamethylphosphoramide, and mixtures thereof.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, naphthalene, and mixtures thereof.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, gas chromatography (GC), or by chromatography, such as, high performance liquid chromatography (HPLC) or thin layer chromatography.

Upon carrying out preparation of compounds according to the processes described herein, the usual isolation and purification operations such as concentration, filtration, extraction, solid-phase extraction, recrystallization, enantiomeric-enrichment via recrystallization, chromatography, and the like, may be used to isolate the desired product.

Example processes and certain intermediates of the present invention are shown in Scheme I to Scheme VII below.

A representative Coupling-Step of 2-cyclopropylacetic acid (Compound 1A) with N,O-dimethylhydroxylamine or a salt thereof in the presence of a coupling-step reagent (e.g., 1,1'-carbonyldiimidazole), a coupling-step base (e.g., triethylamine), and a coupling-step solvent (e.g., dichloromethane) to prepare 2-cyclopropyl-N-methoxy-N-methylacetamide (Compound 2A) is provided below in Scheme I.

Scheme I

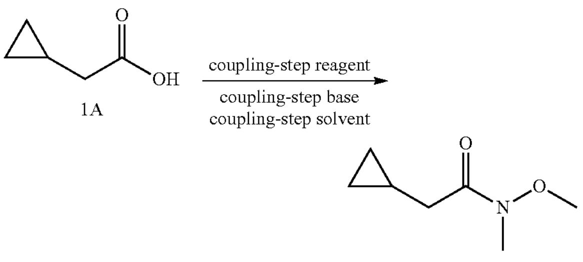

1A

2A

A representative Reacting-Step between 2-cyclopropyl-N-methoxy-N-methylacetamide (Compound 2A) with an organomagnesium reagent of 4-bromo-2-fluoro-1-methylbenzene in the presence of a reacting-step solvent (e.g., tetrahydrofuran (THF)) to prepare 2-cyclopropyl-1-(3-fluoro-4-methylphenyl)ethan-1-one (Compound 3A) is provided below in Scheme II.

Scheme II

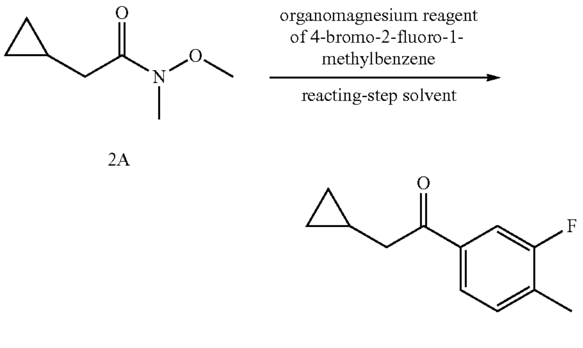

2A

3A

A representative Condensing-Step of 2-cyclopropyl-1-(3-fluoro-4-methylphenyl)ethan-1-one (Compound 3A) with a Compound of Formula (Ic) or a salt thereof, in the presence of a condensing-step acid (e.g., p-toluenesulfonic acid) and a condensing-step solvent (e.g., toluene) to prepare a Compound of Formula (Ie) is provided below in Scheme III.

Scheme III

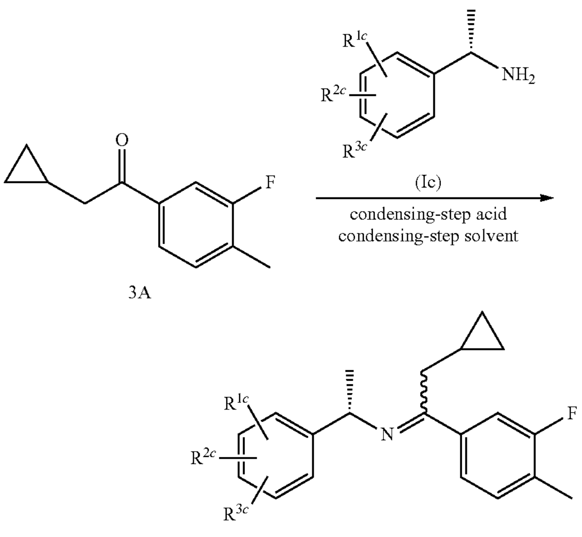

(Ic)

3A (Ie)

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

A representative Reducing-Step of a Compound of Formula (Ie) in the presence of a reducing-catalyst (e.g., sponge nickel and Pd/Cu—C), hydrogen, and a reducing-step solvent (e.g., ethanol) to prepare a Compound of Formula (Ig) is provided below in Scheme IV.

Scheme IV

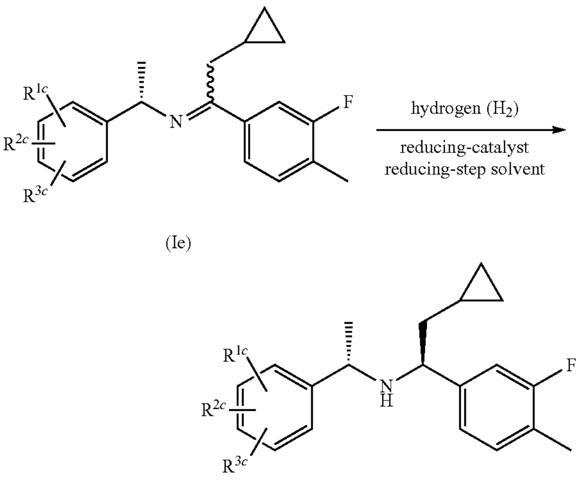

(Ie)

(Ig)

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

A representative Deprotecting-Step of a Compound of Formula (Ig), or a salt thereof, in the presence of a deprotecting-catalyst t (e.g., Pd), hydrogen, and a deprotecting-step solvent (e.g., ethanol) to prepare (S)-2-cyclopropyl-1-(3-fluoro-4-methylphenyl)ethan-1-amine (Compound 6A) or a salt thereof is provided below in Scheme V.

Scheme V

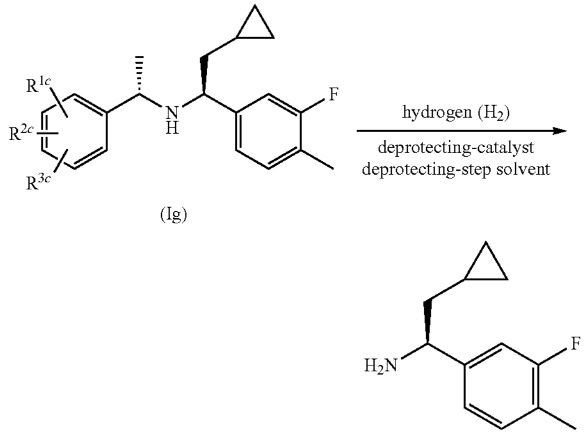

(Ig)

6A wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

A representative Cyclizing-Step of (S)-2-cyclopropyl-1-(3-fluoro-4-methylphenyl)ethan-1-amine (Compound 6A) or a salt thereof, with 1-(2-chloro-4-methoxy-5-methylphenyl)-2-thiocyanatopropan-1-one (Compound 8A) or a tautomeric form thereof, in the presence of a cyclizing-step solvent (e.g., n-heptane) to prepare (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof is provided below in Scheme VI.

Scheme VI

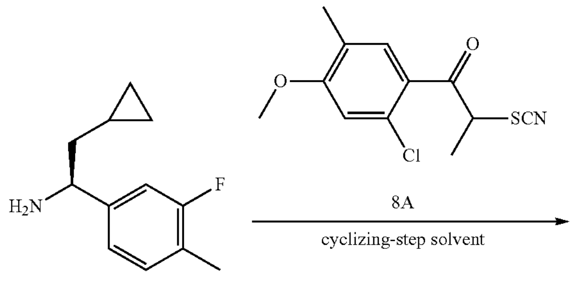

8A

6A

-continued

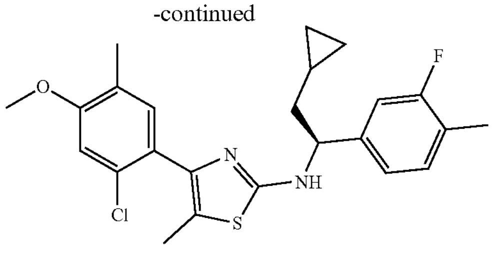

9A

A representative Alkylating-Step of (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof, with a Compound of Formula (Ii), wherein LG is suitable leaving group (e.g., Br), in the presence of an alkylating-step solvent (e.g., methyl tert-butyl ether (MTBE), toluene, and mixtures thereof), a phase-transfer catalyst (e.g., tetra-n-butylammonium bromide (TBAB)), an alkylating-step base (e.g., potassium hydroxide), and water to prepare 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof is provided below in Scheme VII.

Scheme VII

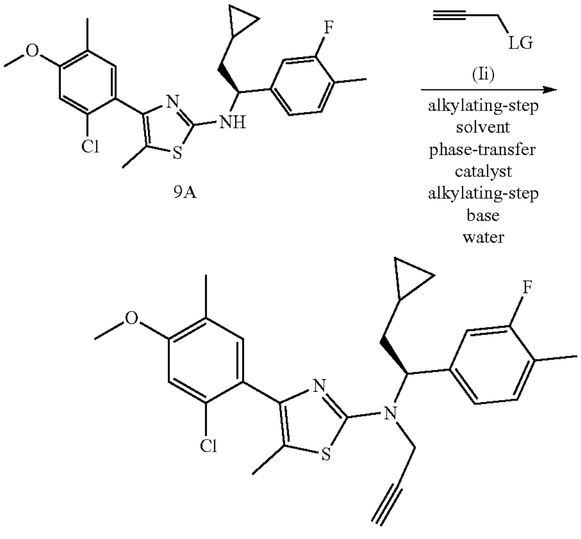

9A

Compound 1

One aspect of the present invention includes every combination of one or more process steps and intermediates related thereto used in the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), and/or pharmaceutically acceptable salts, and crystalline forms thereof, such as those processes exemplified by Schemes I, II, III, IV, V, VI, VII, and VII (supra) and Compounds contained therein.

One aspect of the present invention pertains to one or more of the intermediates, such as, Compounds (2A), (3A), (4A), (5A), (6A), (7A), (8A), and (9A); and compounds of Formulae (Ia), (Ic), (Ie), (Ig), and (Ii), and those compounds prepared by the processes exemplified in Schemes I, II, III, IV, V, VI, VII, and VII (supra), that are useful in the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), and/or pharmaceutically acceptable salts, and crystalline forms thereof.

Certain synthetic processes for the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) have been described in PCT application PCT/FR00/01995, filed 11 Jul. 2000 (International Publication Number WO2001/05776). Several improvements have been discovered and are described herein.

One such improvement is the use of PTC conditions as shown in Scheme VII which eliminated the need for moisture sensitive bases, such as sodium hydride, and dimethylformamide as described in WO2001/05776 (see Example 25).

Other improvements include the steps as shown in Scheme III to IV which converted ketone (Compound 3A) to the chiral amine (Compound 6A) in high yield and high enantiomeric excess.

Compounds of the invention also include all isotopes of atoms occurring in the intermediates and/or final compounds. Isotopes include those atoms having the same atomic number but different mass numbers, for example, isotopes of hydrogen include deuterium and tritium.

I. Processes useful for the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutical salt thereof (Alkylating-Step)

One aspect of the present invention relates to processes for preparing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof:

Compound 1

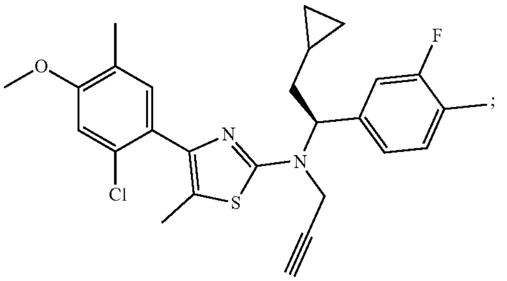

comprising:

alkylating (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

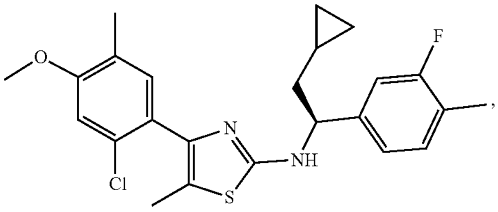

with a Compound of Formula (Ii):

(Ii)

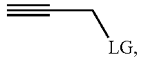

wherein: LG is a leaving group;

in the presence of an alkylating-step solvent, a phase-transfer catalyst, an alkylating-step base, and water to form 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof.

In some embodiments, LG is selected from the group: $C_1$-$C_4$ alkylsulphonyloxy, $C_6$-$C_{10}$ arylsulfonyloxy, halogen, and hydroxy; wherein $C_1$-$C_4$ alkylsulphonyloxy and $C_6$-$C_{10}$ arylsulfonyloxy are each optionally substituted with one or more groups selected from the group: $C_1$-$C_4$ alkyl, $C_1$-$C_4$ alkoxy, halogen, $C_1$-$C_4$ haloalkyl, $C_1$-$C_4$ haloalkoxy, and nitro.

In some embodiments, the Compound of Formula (Ii) is a compound of the following Formula:

(Ii-A)

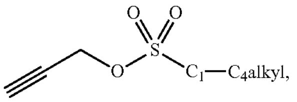

wherein the alkyl group is optionally substituted with one or more groups selected from the group: $C_1$-$C_4$ alkoxy, halogen, $C_1$-$C_4$ haloalkyl, $C_1$-$C_4$ haloalkoxy, and nitro. In some embodiments, the phrase "one or more groups" is one, two, or three groups. In some embodiments, the alkyl group is optionally substituted with one or more halogen groups. In some embodiments, the alkyl group is optionally substituted with one or more fluoro groups.

In some embodiments, the Compound of Formula (Ii) is a compound of the following Formula:

(Ii-B)

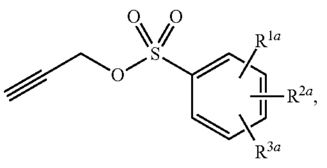

wherein: $R^{1a}$, $R^{2a}$ and $R^{3a}$ are each selected independently from the group consisting of: H, $C_1$-$C_4$ alkyl, $C_1$-$C_4$ alkoxy, halogen, $C_1$-$C_4$ haloalkyl, $C_1$-$C_4$ haloalkoxy, and nitro. In some embodiments, $R^{1a}$, $R^{2a}$, and $R^{3a}$ are each selected independently from the group consisting of: H, methyl, methoxy, fluoro, chloro, bromo, iodo, trifluoromethyl, trifluoromethoxy, and nitro. In some embodiments, $R^{1a}$, $R^{2a}$, and $R^{3a}$ are each selected independently from the group consisting of: H, methyl, methoxy, fluoro, chloro, bromo, trifluoromethyl, trifluoromethoxy, and nitro. In some embodiments, $R^{1a}$, $R^{2a}$, and $R^{3a}$ are each selected independently from the group consisting of: H, methyl, fluoro, trifluoromethyl, trifluoromethoxy, and nitro. In some embodiments, $R^{1a}$, $R^{2a}$, and $R^{3a}$ are each selected independently from the group consisting of: H and methyl.

In some embodiments, LG is halogen.

In some embodiments, LG is Cl, Br, or I.

In some embodiments, LG is Br.

In some embodiments, the Compound of Formula (Ii) is selected from the group consisting of: propargyl bromide, propargyl chloride, propargyl alcohol, propargyl methanesulfonate, propargyl trifluoromethanesulfonate, propargyl benzenesulfonate, and propargyl p-toluenesulfonate. In some embodiments, the Compound of Formula (Ii) is selected from the group consisting of: propargyl bromide, propargyl methanesulfonate, propargyl trifluoromethanesulfonate, propargyl benzenesulfonate, and propargyl p-toluenesulfonate.

In some embodiments, the Compound of Formula (Ii) is propargyl bromide.

In some embodiments, the Compound of Formula (Ii) and Compound 9A are present in substantially equal molar quantities. In some embodiments, the Compound of Formula (Ii) is present in a molar excess compared to Compound 9A. In some embodiments, the Compound of Formula (Ii) is present in about 30% molar excess compared to Compound 9A. In some embodiments, the Compound of Formula (Ii) is present in about 25% molar excess compared to Compound 9A. In some embodiments, the Compound of Formula (Ii) is present in about 20% molar excess compared to Compound 9A.

In some embodiments, Compound 9A and the phase-transfer catalyst are present in substantially equal molar quantities. In some embodiments, the molar ratio between Compound 9A and the phase-transfer catalyst is about 1:0.05 to about 1:0.9. In some embodiments, the molar ratio between Compound 9A and the phase-transfer catalyst is about 1:0.05 to about 1:0.8. In some embodiments, the molar ratio between Compound 9A and the phase-transfer catalyst is about 1:0.05 to about 1:0.7. In some embodiments, the molar ratio between Compound 9A and the phase-transfer catalyst is about 1:0.05 to about 1:0.6. In some embodiments, the molar ratio between Compound 9A and the phase-transfer catalyst is about 1:0.05 to about 1:0.5.

In some embodiments, the molar ratio between Compound 9A and the phase-transfer catalyst is about 1:0.05 to about 1:0.4. In some embodiments, the molar ratio between Compound 9A and the phase-transfer catalyst is about 1:0.1 to about 1.3:0.2. In some embodiments, the molar ratio between Compound 9A and the phase-transfer catalyst is about 1:0.15.

In some embodiments, the molar ratio between Compound 9A, the phase-transfer catalyst, and the alkylating-step base is about 1:0.05:5 to about 1:0.4:25. In some embodiments, the molar ratio between Compound 9A, the phase-transfer catalyst, and the alkylating-step base is about 1:0.1:10 to about 1:0.2:20. In some embodiments, the molar ratio between Compound 9A, the phase-transfer catalyst, and the alkylating-step base is about 1:0.15:16.

In some embodiments, the alkylating-step solvent is any suitable solvent, such as, a solvent as described herein, or mixtures thereof.

In some embodiments, the alkylating-step solvent is selected from a halogenated solvent, an ether solvent, an aprotic solvent, and mixtures thereof. In some embodiments, the alkylating-step solvent is selected from: dichloromethane, tetrachloroethylene, 1,1-dichloroethane, 1,2-dichloroethane, 1,2-dichlorobenzene, chlorobenzene, 1,2-dimethoxyethane (DME), cyclopentyl methyl ether (CPME), 2-methyltetrahydrofuran (2-MeTHF), 1,4-dioxane, ethylene glycol diethyl ether, tert-amyl methyl ether (TAME, also referred to as 2-methoxy-2-methylbutane), methyl tert-butyl ether (MTBE), benzene, cyclohexane, hexane, toluene, cycloheptane, methylcyclohexane, heptanes, n-heptane, ethylbenzene, o-xylene, m-xylene, p-xylene, mixtures of xylenes, octane, and mixtures thereof. In some embodiments, the alkylating-step solvent is selected from: 1,2-dimethoxyethane (DME), cyclopentyl methyl ether (CPME), 2-methyltetrahydrofuran (2-MeTHF), 1,4-dioxane, ethylene glycol diethyl ether, tert-amyl methyl ether (TAME, also referred to as 2-methoxy-2-methylbutane), methyl tert-butyl ether (MTBE), benzene, toluene, and mixtures thereof. In some embodiments, the alkylating-step solvent is selected from: methyl tert-butyl ether (MTBE), toluene, and mixtures thereof.

In some embodiments, the phase-transfer catalyst is a quaternary ammonium salt. In some embodiments, the phase-transfer catalyst is a quaternary ammonium salt selected from: tricaprylyl methyl ammonium chloride (Aliquat 336), tetra-n-butylammonium bromide (TBAB), benzyltriethylammonium chloride (BTEAC), cetyltrimethylammonium bromide (CTAB), tetra-n-butylammonium chloride (TBAC), tetra-n-butylammonium hydroxide, tetra-n-butylammonium iodide, tetraethylammonium chloride (TEAC), benzyltributylammonium chloride (BTBAC), cetyltrimethylammonium chloride (CTAC), tetramethylammonium chloride, cetyltrimethylammonium chloride (CTAC), octyltrimethylammonium chloride, and combinations thereof. In some embodiments, the phase-transfer catalyst is tetra-n-butylammonium bromide (TBAB).

In some embodiments, the alkylating-step base is any suitable base, such as, a base as described herein, or mixtures thereof.

In some embodiments, the alkylating-step base an "inorganic base" as described herein.

In some embodiments, the alkylating-step base is an alkali metal hydroxide. In some embodiments, the alkylating-step base is an alkali metal hydroxide selected from: lithium hydroxide, sodium hydroxide, potassium hydroxide, and cesium hydroxide. In some embodiments, the alkylating-step base is an alkali metal hydroxide selected from: sodium hydroxide and potassium hydroxide. In some embodiments, the alkylating-step base is potassium hydroxide.

In some embodiments, the alkylating step further comprises the steps of:

forming a first-alkylating mixture comprising the alkylating-step solvent, the alkylating-catalyst, and Compound 9A at a first-alkylating temperature; and adding the alkylating-step base and the Compound of Formula (Ii) to the first-alkylating mixture at the first-alkylating temperature to form an alkylating-biphasic mixture at a second-alkylating temperature.

In some embodiments, the alkylating step further comprises heating the first-alkylating mixture comprising the alkylating-step solvent, the alkylating-catalyst, and Compound 9A to a temperature of about 40° C. to about 75° C. and subsequently cooling to the first-alkylating temperature. In some embodiments, the alkylating step further comprises heating first-alkylating mixture comprising the alkylating-step solvent, the alkylating-catalyst, and Compound 9A to a temperature of about 55° C. to about 65° C. and subsequently cooling to the first-alkylating temperature. In some embodiments, the alkylating step further comprises heating first-alkylating mixture comprising the alkylating-step solvent, the alkylating-catalyst, and Compound 9A to a temperature of about 60° C. and subsequently cooling to the first-alkylating temperature.

In some embodiments, adding the alkylating-step base to the first-alkylating mixture is conducted as a solution of the alkylating-step base in water.

In some embodiments, adding the alkylating-step base to the first-alkylating mixture is conducted as a solution of the alkylating-step base in water and the concentration in terms of percent weight/weight (% w/w) of the alkylating-step base and water is about 40 to about 60. In some embodiments, adding the alkylating-step base to the first-alkylating mixture is conducted as a solution of the alkylating-step base in water and the concentration in terms of percent weight/weight (% w/w) of the alkylating-step base and water is about 45 to about 55. In some embodiments, adding the alkylating-step base to the first-alkylating mixture is conducted as a solution of the alkylating-step base in water and the concentration in terms of percent weight/weight (% w/w) of the alkylating-step base and water is about 52 to about 53. In some embodiments, adding the alkylating-step base to the first-alkylating mixture is conducted as a solution of the alkylating-step base in water and the concentration in terms of percent weight/weight (% w/w) of the alkylating-step base and water is about 52.4.

In some embodiments, adding the Compound of Formula (Ii) to the first-alkylating mixture is conducted as a solution of the Compound of Formula (Ii) in the alkylating-step solvent. In some embodiments, adding the Compound of Formula (Ii) to the first-alkylating mixture is conducted as a solution of the Compound of Formula (Ii) in the alkylating-step solvent and the concentration in terms of percent weight/weight (% w/w) of the Compound of Formula (Ii) in the alkylating-step solvent is about 65 to about 90. In some embodiments, adding the Compound of Formula (Ii) to the first-alkylating mixture is conducted as a solution of the Compound of Formula (Ii) in the alkylating-step solvent and the concentration in terms of percent weight/weight (% w/w) of the Compound of Formula (Ii) in the alkylating-step solvent is about 75 to about 85. In some embodiments, adding the Compound of Formula (Ii) to the first-alkylating mixture is conducted as a solution of the Compound of Formula (Ii) in the alkylating-step solvent and the concentration in terms of percent weight/weight (% w/w) of the Compound of Formula (Ii) in the alkylating-step solvent is about 80.

In some embodiments, adding the alkylating-step base and the Compound of Formula (Ii) to the first-alkylating mixture is conducted concurrently at a rate to maintain the first-alkylating temperature.

In some embodiments, adding the alkylating-step base and the Compound of Formula (Ii) to the first-alkylating mixture is conducted serially at a rate to maintain the first-alkylating temperature.

In some embodiments, serially is conducted by adding the alkylating-step base followed by adding the Compound of Formula (Ii) to the first-alkylating mixture at a rate to maintain the first-alkylating temperature during each addition.

In some embodiments, the first-alkylating temperature is about −15° C. to about 15° C. In some embodiments, the first-alkylating temperature is about −10° C. to about 10° C. In some embodiments, the first-alkylating temperature is about −5° C. to about 7° C. In some embodiments, the first-alkylating temperature is about 0° C. to about 5° C.

In some embodiments, the second-alkylating temperature is about −10° C. to about 20° C. In some embodiments, the second-alkylating temperature is about −5° C. to about 15° C. In some embodiments, the second-alkylating temperature is about 0° C. to about 10° C. In some embodiments, the second-alkylating temperature is about 4° C. to about 6° C.

In some embodiments, alkylating is conducted with stirring. In some embodiments, alkylating is conducted with vigorous stirring. In some embodiments, alkylating is conducted with vigorous stirring at a rate to increase the water and organic interface.

In some embodiments, the alkylating step further comprises preparing (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof, by the step of:

cyclizing (S)-2-cyclopropyl-1-(3-fluoro-4-methylphenyl)ethan-1-amine (Compound 6A) or a salt thereof:

6A

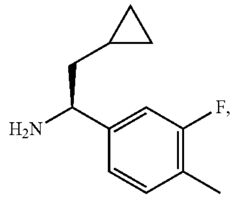

with 1-(2-chloro-4-methoxy-5-methylphenyl)-2-thiocyanatopropan-1-one (Compound 8A) or a tautomeric form thereof:

8A

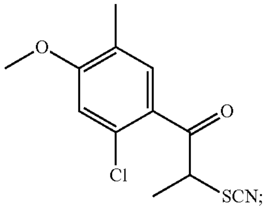

in the presence of a cyclizing-step solvent to form (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof.

In some embodiments, the alkylating step further comprises preparing (S)-2-cyclopropyl-1-(3-fluoro-4-methylphenyl)ethan-1-amine (Compound 6A) or a salt thereof, by the step of:

deprotecting a Compound of Formula (Ig), or a salt thereof, (Ig)

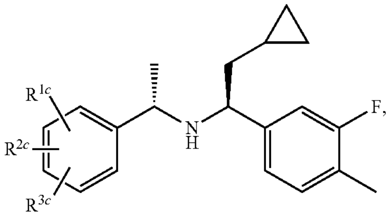

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a deprotecting-catalyst, hydrogen, and a deprotecting-step solvent to form (S)-2-cyclopropyl-1-(3-fluoro-4-methylphenyl)ethan-1-amine (Compound 6A) or a salt thereof.

In some embodiments, the alkylating step further comprises preparing a Compound of Formula (Ig), or a salt thereof, (Ig)

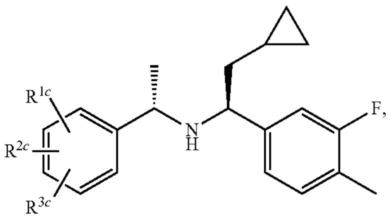

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen; comprising:

reducing a Compound of Formula (Ie):

(Ie)

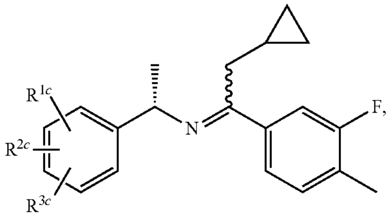

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a reducing-catalyst, hydrogen, and a reducing-step solvent to form the Compound of Formula (Ig), or a salt thereof.

In some embodiments, the alkylating step further comprises preparing a Compound of Formula (Ie):

(Ie)

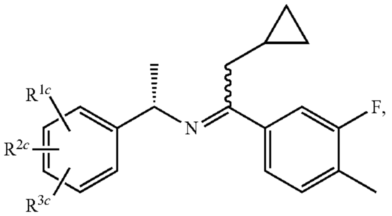

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

condensing 2-cyclopropyl-1-(3-fluoro-4-methylphenyl)ethan-1-one (Compound 3A):

3A

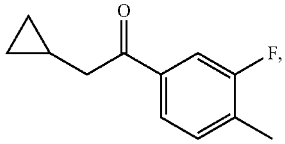

with a Compound of Formula (Ic), or a salt thereof (Ic)

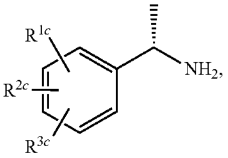

in the presence of a condensing-step acid and a condensing-step solvent to form the Compound of Formula (Ie).

In some embodiments, the alkylating step further comprising preparing 2-cyclopropyl-1-(3-fluoro-4-methylphenyl)ethan-1-one (Compound 3A), by the step of:

reacting 2-cyclopropyl-N-methoxy-N-methylacetamide_ (Compound 2A):

2A

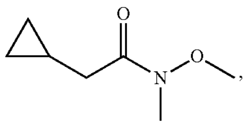

with an organomagnesium reagent of 4-bromo-2-fluoro-1-methylbenzene in the presence of a reacting-step solvent to form 2-cyclopropyl-1-(3-fluoro-4-methylphenyl)ethan-1-one (Compound 3A).

In some embodiments, the alkylating step further comprising the step of isolating 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof.

In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is the free base. In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is crystalline. In some embodiments, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is crystalline Form I.

In some embodiments, the alkylating step further comprising the step of formulating 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine to form a pharmaceutical composition. In some embodiments, the step of formulating comprises admixing 4-(2-chloro-4-methoxy-5-methylphenyl)-N—[(1S)-2-cyclopropyl-1-(3-fluoro-4-methylphenyl)ethyl]-5-methyl-N-prop-2-ynyl-1,3-thiazol-2-amine with a pharmaceutical excipient.

In some embodiments, the alkylating step further comprises the step of isolating 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof.

In some embodiments, the alkylating step comprises the step of formulating 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, to form a pharmaceutical composition. In some embodiments, the step of formulating comprises admixing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, with a pharmaceutical excipient. In some embodiments, the step of formulating comprising preparing a spray-dried dispersion as described in the examples.

In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is the free base. In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is crystalline. In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine is crystalline Form I.

II. Processes useful for the preparation of (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof (Cyclizing-Step)

One aspect of the present invention relates to processes for preparing (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

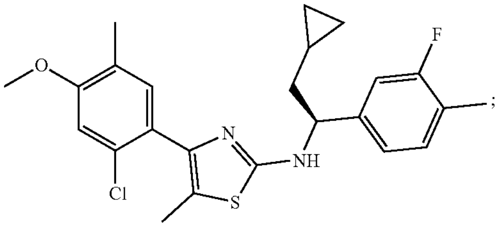

comprising:

cyclizing (S)-2-cyclopropyl-1-(3-fluoro-4-methylphenyl)ethan-1-amine (Compound 6A) or a salt thereof:

6A

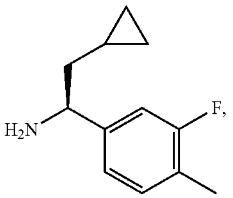

with 1-(2-chloro-4-methoxy-5-methylphenyl)-2-thiocyanatopropan-1-one (Compound 8A) or a tautomeric form thereof:

8A

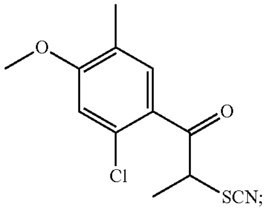

in the presence of a cyclizing-step solvent to form (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof.

In some embodiments, the tautomeric form of Compound 8A has the following chemical structure:

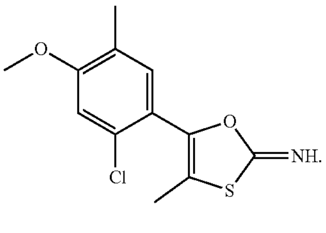 [SMILES: COc1cc(Cl)c(-c2oc(=N)sc2C)cc1C]

In some embodiments, the cyclizing-step solvent is any suitable solvent, such as, a solvent as described herein, or mixtures thereof.

In some embodiments, the cyclizing-step solvent is an aprotic solvent. In some embodiments, the cyclizing-step solvent is an aprotic solvent selected from: benzene, cyclohexane, pentane, hexane, acetonitrile, toluene, o-xylene, m-xylene, p-xylene, a mixture of xylenes, heptanes, n-heptane, octanes, n-octanes, ethylbenzene, and mixtures thereof. In some embodiments, the cyclizing-step solvent is an aprotic solvent selected from: benzene, cyclohexane, hexane, toluene, cycloheptane, o-xylene, m-xylene, p-xylene, a mixture of xylenes, heptanes, n-heptane, octanes, n-octane, ethylbenzene, and mixtures thereof. In some embodiments, the cyclizing-step solvent comprises a mixture of heptanes. In some embodiments, the cyclizing-step solvent is n-heptane.

In some embodiments, Compound 6A and Compound 8A are present in substantially equal molar quantities. In some embodiments, Compound 6A is present in a molar excess compared to Compound 8A. In some embodiments, Compound 6A is present in about 5% molar excess compared to Compound 8A. In some embodiments, Compound 6A is present in about 2% molar excess compared to Compound 8A. In some embodiments, Compound 6A is present in about 1% molar excess compared to Compound 8A.

In some embodiments, the cyclizing step further comprises the step of adding Compound 6A to a first-cyclizing mixture comprising Compound 8A and the cyclizing-step solvent at a first-cyclizing temperature.

In some embodiments, the first-cyclizing temperature is about 50° C. to about 110° C. In some embodiments, the first-cyclizing temperature is about 60° C. to about 95° C. In some embodiments, the first-cyclizing temperature is about 70° C. to about 90° C. In some embodiments, the first-cyclizing temperature is about 80° C. to about 87° C. In some embodiments, the first-cyclizing temperature is about 85° C.

In some embodiments, cyclizing is conducted with stirring.

III. Processes Useful for The Preparation (S)-2-cyclopropyl-1-(3-fluoro-4-methylphenyl)ethan-1-amine (Compound 6A) or a Salt Thereof (Deprotecting-Step)

One aspect of the present invention relates to processes for preparing (S)-2-cyclopropyl-1-(3-fluoro-4-methylphenyl)ethan-1-amine (Compound 6A) or a salt thereof:

6A

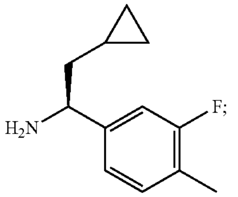

comprising:

deprotecting a Compound of Formula (Ig), or a salt thereof, (Ig)

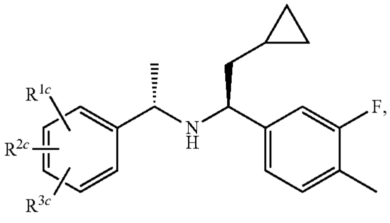

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a deprotecting-catalyst, hydrogen, and a deprotecting-step solvent to form (S)-2-cyclopropyl-1-(3-fluoro-4-methylphenyl)ethan-1-amine (Compound 6A) or a salt thereof.

In some embodiments, the deprotecting-catalyst comprises palladium. In some embodiments, the deprotecting-catalyst comprises palladium on carbon. In some embodiments, the deprotecting-catalyst comprises about 2% palladium on carbon to about 20% palladium on carbon. In some embodiments, the deprotecting-catalyst comprises about 5% palladium on carbon to about 15% palladium on carbon. In some embodiments, the deprotecting-catalyst comprises about 10% palladium on carbon.

In some embodiments, the weight ratio between the Compound of Formula (Ig) and the deprotecting-catalyst is about 1:0.01 to about 1:0.15. In some embodiments, the weight ratio between the Compound of Formula (Ig) and the deprotecting-catalyst is about 1:0.02 to about 1:0.1. In some embodiments, the weight ratio between the Compound of Formula (Ig) and the deprotecting-catalyst is about 1:0.03 to about 1:0.07. In some embodiments, the weight ratio between the Compound of Formula (Ig) and the deprotecting-catalyst is about 1:0.05.

In some embodiments, the deprotecting-step solvent is any suitable solvent, such as, a solvent as described herein, or mixtures thereof.

In some embodiments, the deprotecting-step solvent comprises an alcohol solvent. In some embodiments, the deprotecting-step solvent comprises an alcohol solvent selected from: methanol, ethanol, ethylene glycol, 1-propanol, 2-propanol, 2-methoxyethanol, 1-butanol, 2-butanol, isobutyl alcohol, 2-ethoxyethanol, 1-pentanol, 2-pentanol, 3-pentanol, diethylene glycol monomethyl ether, diethylene glycol monoethyl ether, and mixtures thereof. In some embodiments, the deprotecting-step solvent comprises an alcohol solvent selected from: methanol, ethanol, 1-propanol, 2-propanol, and mixtures thereof. In some embodiments, the deprotecting-step solvent comprises an alcohol solvent selected from: methanol, ethanol, and mixtures thereof. In some embodiments, the deprotecting-step solvent is methanol.

In some embodiments, the deprotecting step further comprises the steps of:

forming a first-deprotecting mixture comprising the Compound of Formula (Ig), the deprotecting-catalyst, and the deprotecting-step solvent;

pressurizing the first-deprotecting mixture with hydrogen to form a second-deprotecting mixture; and heating the second-deprotecting mixture to a first-deprotecting temperature.

In some embodiments, pressurizing the first-deprotecting mixture with hydrogen is conducted at about 5 to about 12 bar. In some embodiments, pressurizing the first-deprotecting mixture with hydrogen is conducted at about 9 to about 11 bar. In some embodiments, pressurizing the first-deprotecting mixture with hydrogen is conducted at about 9.8 to about 10.2 bar.

In some embodiments, the first-deprotecting temperature is about 40° C. to about 80° C. In some embodiments, the first-deprotecting temperature is about 50° C. to about 70° C. In some embodiments, the first-deprotecting temperature is about 58° C. to about 62° C.

Some embodiments relate to compounds of Formula (Ig), wherein $R^{1c}$, $R^{2c}$, and $R^{3c}$ are each independently selected from: H, methoxy, methyl, trifluoromethyl, fluoro, chloro, and bromo. Some embodiments relate to compounds of Formula (Ig), wherein $R^{1c}$, $R^{2c}$, and $R^{3c}$ are each H (i.e., (S)-2-cyclopropyl-1-(3-fluoro-4-methylphenyl)-N—((S)-1-phenylethyl)ethan-1-amine (Compound 5A)).

In some embodiments, deprotecting is conducted with stirring.

IV. Processes Useful for the Preparation of Compounds of Formula (Ig) or Salts Thereof (Reducing-Step)

One aspect of the present invention relates to processes for preparing a Compound of Formula (Ig), or a salt thereof:

(Ig)

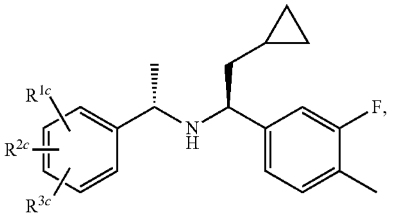

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

reducing a Compound of Formula (Ie):

(Ie)

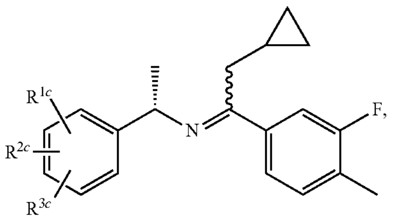

in the presence of a reducing-catalyst, hydrogen, and a reducing-step solvent to form the Compound of Formula (Ig), or a salt thereof.

In some embodiments, the reducing-catalyst is sponge nickel or Pd/Cu—C.

In some embodiments, the reducing-catalyst is sponge nickel. In some embodiments, the weight ratio between the Compound of Formula (Ie) and the reducing-catalyst is about 1:0.5 to about 1:0.9. In some embodiments, the weight ratio between the Compound of Formula (Ie) and the reducing-catalyst is about 1:0.6 to about 1:0.8. In some embodiments, the weight ratio between the Compound of Formula (Ie) and the reducing-catalyst is about 1:0.65 to about 1:0.75. In some embodiments, the weight ratio between the Compound of Formula (Ie) and the reducing-catalyst is about 1:0.7.

In some embodiments, the reducing-catalyst is Pd/Cu—C. In some embodiments, the Pd/Cu—C catalyst comprises about 1% to about 10% Pd and about 0.2% to about 4% Cu. In some embodiments, the Pd/Cu—C catalyst comprises about 2% to about 6% Pd and about 0.5% to about 2% Cu. In some embodiments, the Pd/Cu—C catalyst comprises about 4% Pd and 1% Cu. In some embodiments, the weight ratio between the Compound of Formula (Ie) and the reducing-catalyst is about 1:0.01 to about 1:0.3. In some embodiments, the weight ratio between the Compound of Formula (Ie) and the reducing-catalyst is about 1:0.015 to about 1:0.1. In some embodiments, the weight ratio between the Compound of Formula (Ie) and the reducing-catalyst is about 1:0.02 to about 1:0.05. In some embodiments, the weight ratio between the Compound of Formula (Ie) and the reducing-catalyst is about 1:0.03.

In some embodiments, the reducing-step solvent is any suitable solvent, such as, a solvent as described herein, or mixtures thereof.

In some embodiments, the reducing-step solvent comprises an alcohol solvent. In some embodiments, the reducing-step solvent comprises an alcohol solvent selected from: methanol, ethanol, ethylene glycol, 1-propanol, 2-propanol, 2-methoxyethanol, 1-butanol, 2-butanol, isobutyl alcohol, 2-ethoxyethanol, 1-pentanol, 2-pentanol, 3-pentanol, diethylene glycol monomethyl ether, diethylene glycol monoethyl ether, and mixtures thereof. In some embodiments, the reducing-step solvent comprises an alcohol solvent selected from: methanol, ethanol, 1-propanol, 2-propanol, and mixtures thereof. In some embodiments, the deprotecting-step solvent comprises an alcohol solvent selected from: methanol, ethanol, and mixtures thereof. In some embodiments, the reducing-step solvent comprises ethanol.

In some embodiments, the reducing step further comprises the steps of:

forming a first-reducing mixture comprising the reducing-catalyst and the reducing-step solvent;

adding the Compound of Formula (Ie) to the first-reducing mixture to form a second-reducing mixture;

pressurizing the second-reducing mixture with hydrogen to form a third-reducing mixture; and heating the third-reducing mixture to a first-reducing temperature.

In some embodiments, adding the Compound of Formula (Ie) to the first-reducing mixture is conducted as a solution of the Compound of Formula (Ie) in toluene. In some embodiments, adding the Compound of Formula (Ie) to the first-reducing mixture is conducted as a solution of about 40% to about 80% of the Compound of Formula (Ie) in toluene. In some embodiments, adding the Compound of Formula (Ie) to the first-reducing mixture is conducted as a solution of about 50% to about 70% of the Compound of Formula (Ie) in toluene. In some embodiments, adding the Compound of Formula (Ie) to the first-reducing mixture is conducted as a solution of about 60% to about 65% of the Compound of Formula (Ie) in toluene.

In some embodiments, pressurizing the second-reducing mixture with hydrogen is conducted at about 5 to about 12 bar. In some embodiments, pressurizing the second-reducing mixture with hydrogen is conducted at about 9 to about 11 bar. In some embodiments, pressurizing the second-reducing mixture with hydrogen is conducted at about 9.8 to about 10.2 bar.

In some embodiments, the first-reducing temperature is about 25° C. to about 55° C. In some embodiments, the first-reducing temperature is about 30° C. to about 45° C. In some embodiments, the first-reducing temperature is about 33° C. to about 37° C.

Some embodiments relate to compounds of Formula (Ie), wherein $R^{1c}$, $R^{2c}$, and $R^{3c}$ are each independently selected from: H, methoxy, methyl, trifluoromethyl, fluoro, chloro, and bromo. Some embodiments relate to compounds of Formula (Ie), wherein $R^{1c}$, $R^{2c}$, and $R^{3c}$ are each H (i.e., (S)-2-cyclopropyl-1-(3-fluoro-4-methylphenyl)-N-(1-phenylethyl)ethan-1-imine (Compound 4A)).

In some embodiments, reducing is conducted with stirring.

V. Processes Useful for the Preparation of Compounds of Formula (Ie) (Condensing-Step)

One aspect of the present invention relates to processes for preparing a Compound of Formula (Ie):

(Ie)

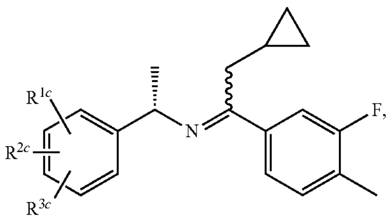

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

condensing 2-cyclopropyl-1-(3-fluoro-4-methylphenyl)ethan-1-one (Compound 3A):

3A

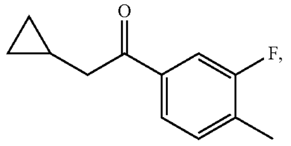

with a Compound of Formula (Ic), or a salt thereof:

(Ic)

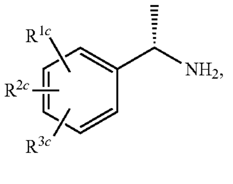

in the presence of a condensing-step acid and a condensing-step solvent to form the Compound of Formula (Ie).

In some embodiments, the Compound of Formula (Ic) and Compound 3A are present in substantially equal molar quantities. In some embodiments, the Compound of Formula (Ic) is present in a molar excess compared to Compound 3A. In some embodiments, the molar ratio between Compound 3A and the Compound of Formula (Ic) is about 1:1 to about 1:1.5. In some embodiments, the molar ratio between Compound 3A and the Compound of Formula (Ic) is about 1:1.1 to about 1:1.3. In some embodiments, the molar ratio between Compound 3A and the Compound of Formula (Ic) is about 1:1.2.

In some embodiments, the molar ratio between Compound 3A, the Compound of Formula (Ic), and the condensing-step acid is about 1:1:0.01 to about 1:1.5:0.2. In some embodiments, the molar ratio between Compound 3A, the Compound of Formula (Ic), and the condensing-step acid is about 1:1.1:0.03 to about 1:1.3:0.1. In some embodiments, the molar ratio between Compound 3A, the Compound of Formula (Ic), and the condensing-step acid is about 1:1.2:0.05.

In some embodiments, the condensing-step acid comprises a Brønsted acid. In some embodiments, the condensing-step acid comprises a Brønsted acid selected from: acetic acid, trifluoroacetic acid (TFA), p-toluenesulfonic acid (pTSA), $H_3PO_4$, $H_2SO_4$, methanesulfonic acid (MSA), formic acid, and HCl. In some embodiments, the condensing-step acid is p-toluenesulfonic acid (pTSA).

In some embodiments, the condensing-step solvent is any suitable solvent, such as, a solvent as described herein, or mixtures thereof.

In some embodiments, the condensing-step solvent is an aprotic solvent. In some embodiments, the condensing-step solvent is an aprotic solvent selected from: benzene, cyclohexane, pentane, hexane, acetonitrile, toluene, cycloheptane, o-xylene, m-xylene, p-xylene, a mixture of xylenes, heptanes, n-heptane, octanes, n-octanes, ethylbenzene, and mixtures thereof. In some embodiments, the condensing-step solvent is acetonitrile or toluene. In some embodiments, the condensing-step solvent is acetonitrile. In some embodiments, the condensing-step solvent is toluene.

In some embodiments, condensing is conducted at the boiling point of the condensing-step solvent.

In some embodiments, condensing further comprises the removal of water. In some embodiments, condensing further comprises the removal of water using a Dean-Stark process, a desiccant, or a combination thereof. In some embodiments, condensing further comprises the removal of water using a desiccant. In some embodiments, condensing further comprises the removal of water using a Dean-Stark process.

In some embodiments, condensing further comprises the step of isolating the Compound of Formula (Ie) from a condensing-step mixture comprising the Compound of Formula (Ie) and the Compound of Formula (Ic). In some embodiments, isolating comprises substantially removing the Compound of Formula (Ic) from the condensing-step mixture using an isolating-step acid. In some embodiments, the isolating-step acid is a water-soluble acid. In some embodiments, the isolating-step acid is an ammonium halide. In some embodiments, the isolating-step acid is ammonium chloride (i.e., $NH_4Cl$).

Some embodiments relate to compounds of Formula (Ic), wherein $R^{1c}$, $R^{2c}$, and $R^{3c}$ are each independently selected from: H, methoxy, methyl, trifluoromethyl, fluoro, chloro, and bromo. Some embodiments relate to compounds of Formula (Ic), wherein $R^{1c}$, $R^{2c}$, and $R^{3c}$ are each H (i.e., (S)-(−)-1-phenylethylamine). In some embodiments, the compound of Formula (Ic) is (S)-(−)-1-phenylethylamine.

In some embodiments, condensing is conducted with stirring.

VI. Processes Useful for the Preparation of 2-cyclopropyl-1-(3-fluoro-4-methylphenyl)ethan-1-one (Compound 3A) (Reacting-Step)

One aspect of the present invention relates to processes for preparing 2-cyclopropyl-1-(3-fluoro-4-methylphenyl)ethan-1-one (Compound 3A),

3A

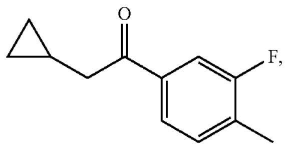

comprising:

reacting 2-cyclopropyl-N-methoxy-N-methylacetamide (Compound 2A):

2A

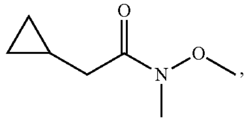

with an organomagnesium reagent of 4-bromo-2-fluoro-1-methylbenzene in the presence of a reacting-step solvent to form 2-cyclopropyl-1-(3-fluoro-4-methylphenyl)ethan-1-one (Compound 3A).

In some embodiments, the organomagnesium reagent of 4-bromo-2-fluoro-1-methylbenzene is prepared by the process comprising the steps of:

forming a first-reacting mixture comprising magnesium and the reacting-step solvent;

adding a magnesium activator to the first-reacting mixture at a first-reacting temperature to form a second-reacting mixture; and adding 4-bromo-2-fluoro-1-methylbenzene to the second-reacting mixture at a second-reacting temperature to form the organomagnesium reagent of 4-bromo-2-fluoro-1-methylbenzene.

In some embodiments, the first-reacting temperature is about 15° C. to about 45° C. In some embodiments, the first-reacting temperature is about 25° C. to about 40° C. In some embodiments, the first-reacting temperature is about 25° C. to about 35° C.

In some embodiments, the second-reacting temperature is about 20° C. to about 65° C. In some embodiments, the second-reacting temperature is about 25° C. to about 60° C. In some embodiments, the second-reacting temperature is about 30° C. to about 50° C.

In some embodiments, the reacting-step solvent is any suitable solvent, such as, a solvent as described herein or mixtures thereof.

In some embodiments, the reacting-step solvent is an ether solvent. In some embodiments, the reacting-step solvent is selected from: diethyl ether, 1,2-dimethoxyethane (DME), tetrahydrofuran (THF), cyclopentyl methyl ether (CPME), and 2-methyltetrahydrofuran (2-MeTHF). In some embodiments, the reacting-step solvent is selected from: tetrahydrofuran (THF), cyclopentyl methyl ether (CPME), and 2-methyltetrahydrofuran (2-MeTHF). In some embodiments, the reacting-step solvent is tetrahydrofuran (THF).

In some embodiments, the magnesium activator is $I_2$, 1,2-dibromoethane, diisobutylaluminium hydride (DIBAL-H), $LiAlH_4$, $NaBH_4$, sodium bis(2-methoxyethoxy)aluminum hydride (Red-Al), and borane dimethyl sulfide complex ($BH_3$—$SMe_2$). In some embodiments, the magnesium activator is diisobutylaluminium hydride (DIBAL-H).

In some embodiments, the organomagnesium reagent of 4-bromo-2-fluoro-1-methylbenzene is:

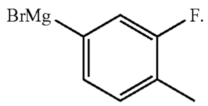

In some embodiments, reacting is conducted with stirring.

VII. Processes Useful for the Preparation 2-cyclopropyl-N-methoxy-N-methylacetamide (Compound 2A) (Coupling-Step)

One aspect of the present invention relates to processes for preparing 2-cyclopropyl-N-methoxy-N-methylacetamide (Compound 2A),

2A

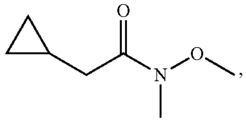

comprising:

coupling 2-cyclopropylacetic acid (Compound 1A) with N,O-dimethylhydroxylamine or a salt thereof in the presence of a coupling-step reagent, a coupling-step base, and a coupling-step solvent to form 2-cyclopropyl-N-methoxy-N-methylacetamide (Compound 2A)

In some embodiments, the coupling step further comprises mixing 2-cyclopropylacetic acid (Compound 1A), the coupling-step reagent, and the coupling-step solvent together to form a first-coupling mixture.

In some embodiments, the first-coupling mixture is at a suitable first temperature to form 2-cyclopropyl-N-methoxy-N-methylacetamide (Compound 2A).

In some embodiments, the first-coupling mixture is at a first-coupling temperature of about −15° C. to about 35° C. In some embodiments, the first-coupling mixture is at a first-coupling temperature of about −10° C. to about 30° C. In some embodiments, the first-coupling mixture is at a first-coupling temperature of about −10° C. to about 25° C. In some embodiments, the first-coupling mixture is at a first-coupling temperature of ≤25° C.

In some embodiments, coupling further comprising adding N,O-dimethylhydroxylamine or a salt thereof to the first-coupling mixture to form a second-coupling mixture at a second-coupling temperature.

In some embodiments, the second-coupling temperature is ≤30° C. In some embodiments, the second-coupling temperature is about −15° C. to about 30° C. In some embodiments, the second-coupling temperature is about −10° C. to about 25° C. In some embodiments, the second-coupling temperature is about 20° C. to about 25° C.

In some embodiments, N,O-dimethylhydroxylamine or a salt thereof is added to the first-coupling mixture at a rate to maintain the temperature at the second-coupling temperature.

In some embodiments, the coupling step further comprises adding the coupling-step base to the second-coupling mixture.

In some embodiments, the coupling step further comprises adding the coupling-step base to the second-coupling mixture and maintaining a third-coupling temperature at about −10° C. to about 25° C. In some embodiments, the coupling step further comprising adding the coupling-step base to the second-coupling mixture and maintaining a third-coupling temperature at about 20° C. to about 25° C.

In some embodiments, the coupling-step reagent is a tetramethyluronium-based coupling reagent. In some embodiments, the coupling-step reagent is a tetramethyluronium-based coupling agent selected from: 2-(1H-benzotriazole-1-yl)-1,1,3,3-tetramethyluronium hexafluorophosphate (HBTU), 2-(1H-benzotriazole-1-yl)-1,1,3,3-tetramethyluronium tetrafluoroborate (TBTU), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), and N,N,N,N-tetramethyl-O-(3,4-dihydro-4-oxo-1,2,3-benzotriazin-3-yl)uranium tetrafluoroborate (TDBTU). In some embodiments, the coupling-step reagent is 1,1'-carbonyldiimidazole (CDI).

In some embodiments, the coupling-step solvent is any suitable solvent, such as, a solvent as described herein or mixtures thereof.

In some embodiments, the coupling-step solvent is an aprotic solvent. In some embodiments, the coupling-step solvent is selected from a halogenated solvent, an ether solvent, and mixtures thereof. In some embodiments, the coupling-step solvent comprises dichloromethane (DCM).

In some embodiments, the coupling-step base is a tertiary amine. In some embodiments, the coupling-step base is selected from: N,N-diisopropylethylamine (DIEA), triethylamine (TEA), N-methylmorpholine (NMM), 4-dimethylaminopyridine (DMAP), 2,4,6-trimethylpyridine (collidine), 2,3,5,6-tetramethylpyridine (TEMP), and 2,6-di-tert-butyl-4-(dimethylamino)pyridine (DBDMAP). In some embodiments, the coupling-step base is triethylamine.

In some embodiments, coupling is conducted with stirring.

Intermediate Compounds

One aspect of the present invention includes every combination of one or more compounds as described herein, and salts, solvates, and hydrates thereof.

One aspect of the present invention pertains to certain compounds of Formula (Ic):

(Ic)

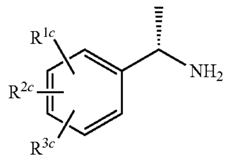

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

Some embodiments relate to compounds of Formula (Ic), wherein $R^{1c}$, $R^{2c}$, and $R^{3c}$ are each independently selected from: H, methoxy, methyl, trifluoromethyl, fluoro, chloro, and bromo.

Some embodiments relate to compounds of Formula (Ic), wherein $R^{1c}$, $R^{2c}$, and $R^{3c}$ are each H (i.e., (S)-(−)-1-phenylethylamine):

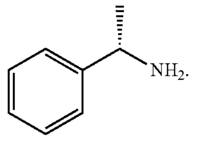

One aspect of the present invention pertains to certain compounds of Formula (Ie):

(Ie)

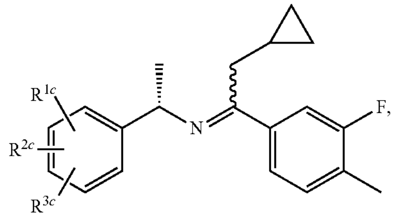

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

Some embodiments relate to compounds of Formula (Ie), wherein $R^{1c}$, $R^{2c}$, and $R^{3c}$ are each independently selected from: H, methoxy, methyl, trifluoromethyl, fluoro, chloro, and bromo.

Some embodiments relate to compounds of Formula (Ie), wherein $R^{1c}$, $R^{2c}$, and $R^{3c}$ are each H (i.e., (S)-2-cyclopropyl-1-(3-fluoro-4-methylphenyl)-N-(1-phenylethyl)ethan-1-imine (Compound 4A)):

4A

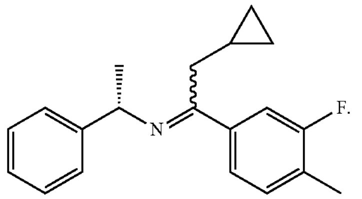

One aspect of the present invention pertains to certain compounds of Formula (Ig):

(Ig)

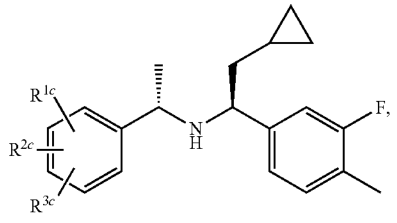

or a salt thereof:

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

Some embodiments relate to compounds of Formula (Ig), wherein $R^{1c}$, $R^{2c}$, and $R^{3c}$ are each independently selected from: H, methoxy, methyl, trifluoromethyl, fluoro, chloro, and bromo.

Some embodiments relate to compounds of Formula (Ig), wherein $R^{1c}$, $R^{2c}$, and $R^{3c}$ are each H (i.e., (S)-2-cyclopropyl-1-(3-fluoro-4-methylphenyl)-N—((S)-1-phenylethyl) ethan-1-amine (Compound 5A)):

5A

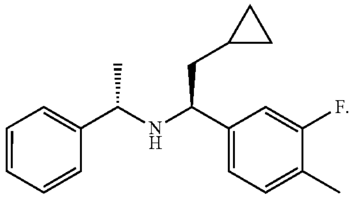

Some embodiments relate to compounds of Formula (Ig), wherein $R^{1c}$, $R^{2c}$, and $R^{3c}$ are each H as the HCl salt.

Some embodiments relate to compounds of Formula (Ig), wherein $R^{1c}$, $R^{2c}$, and $R^{3c}$ are each H and is an HCl salt. In some embodiments, the HCl salt is crystalline. In some embodiments, the crystalline form of the HCl salt is the crystalline (S)-2-cyclopropyl-1-(3-fluoro-4-methylphenyl)-N—((S)-1-phenylethyl)ethan-1-amine (Compound 5A, HCl salt) as described herein.

Disorders, Uses, and Methods of Treatment 4-(2-Chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is a Corticotropin Releasing Factor 1 ($CRF_1$) antagonist. Accordingly, Compound 1, as the free base, a pharmaceutically acceptable salt, such as the tosylate salt, and crystal forms thereof are useful in methods of antagonizing a Corticotropin Releasing Factor 1 by contacting the receptor. In some embodiments, the contacting is conducted in vivo. In some embodiments, the contacting is conducted ex vivo. In some embodiments, Compound 1, as the free base, a pharmaceutically acceptable salt, and a crystal form thereof, can be used in methods of antagonizing Corticotropin Releasing Factor 1 in a patient in need thereof by administering an effective amount of Compound 1, as the free base, a pharmaceutically acceptable salt, or a crystal form thereof.

Methods are provided herein for treating or preventing (i.e., reducing the likelihood of occurrence) a Corticotropin Releasing Factor 1 disorder.

In some embodiments, Compound 1, pharmaceutical salts, and crystal forms thereof, are useful for the treatment or prevention of a disorder. In some embodiments, Compound 1, pharmaceutical salts, and crystal forms thereof, are useful for the treatment or prevention of a subtype of a disorder. In some embodiments, Compound 1, pharmaceutical salts, and crystal forms thereof, are useful for the treatment or prevention of a symptom of a disorder. In some embodiments, Compound 1 is a free base. In some embodiments, Compound 1 (free base) is anhydrous crystalline Form I as described herein. In some embodiments, Compound 1 is as a pharmaceutical salt, wherein the salt is a tosylate salt. In some embodiments, the Compound 1 tosylate salt is crystal Form I as described herein.

One aspect of the present invention relates to methods of treating a disorder in a subject in need thereof, comprising administering to the subject a therapeutically effective amount of an anhydrous crystalline form (Compound 1, free base) as described herein, a crystalline form (Compound 1, tosylate base) as described herein, a pharmaceutical composition as described herein, a pharmaceutical product as described herein, or a composition as described herein, wherein the subject has abnormal levels of $CRF_1$.

One aspect of the present invention relates to methods of treating a Corticotropin Releasing Factor 1 ($CRF_1$) disorder in a subject in need thereof, comprising administering to the subject a therapeutically effective amount of an anhydrous crystalline form (Compound 1, free base) as described herein, a crystalline form (Compound 1, tosylate base) as described herein, a pharmaceutical composition as described herein, a pharmaceutical product as described herein, or a composition as described herein.

One aspect of the present invention relates to methods of treating congenital adrenal hyperplasia (CAH), in a subject in need thereof, comprising administering to the subject a therapeutically effective amount of an anhydrous crystalline form (Compound 1, free base) as described herein, a crystalline form (Compound 1, tosylate base) as described herein, a pharmaceutical composition as described herein, a pharmaceutical product as described herein, or a composition as described herein.

One aspect of the present invention relates to uses of an anhydrous crystalline form (Compound 1, free base) as described herein, or the crystalline form (Compound 1, tosylate base) as described herein, for the manufacture of a medicament for the treatment of a subject wherein the subject has abnormal levels of $CRF_1$.

One aspect of the present invention relates to uses of an anhydrous crystalline form (Compound 1, free base) as described herein, or the crystalline form (Compound 1, tosylate base) as described herein, for the manufacture of a medicament for the treatment of a Corticotropin Releasing Factor 1 ($CRF_1$) disorder.

One aspect of the present invention relates to uses of an anhydrous crystalline form (Compound 1, free base) as described herein, or the crystalline form (Compound 1, tosylate base) as described herein, for the manufacture of a medicament for the treatment of congenital adrenal hyperplasia (CAH).

One aspect of the present invention relates to an anhydrous crystalline form (Compound 1, free base) as described herein; a crystalline form (Compound 1, tosylate base) as described herein; a pharmaceutical composition as described herein, a pharmaceutical product as described herein, or a composition as described herein; for use in a method of treatment of the human or animal body by therapy.

One aspect of the present invention relates to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treatment of a disorder in a subject wherein the subject has abnormal levels of $CRF_1$.

One aspect of the present invention relates to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treatment of a Corticotropin Releasing Factor 1 ($CRF_1$) disorder.

One aspect of the present invention relates to an anhydrous crystalline form (Compound 1, free base) as described herein; a crystalline form (Compound 1, tosylate base) as described herein; a pharmaceutical composition as described herein; a pharmaceutical product as described herein; or a composition as described herein; for use in a method of treating congenital adrenal hyperplasia (CAH).

Pharmaceutical Compositions, Compositions, Formulation, and Dosage Forms

The present disclosure further provides for compositions comprising the crystalline forms of Compound 1, e.g., the free base and tosylate salt of Compound 1 as described herein, and an excipient such as a pharmaceutically acceptable excipient for use in the methods for treating Corticotropin Releasing Factor 1 ($CRF_1$) diseases or disorders, such as congenital adrenal hyperplasia. A pharmaceutically acceptable excipient is a physiologically and pharmaceutically suitable non-toxic and inactive material or ingredient that does not interfere with the activity of the drug substance; an excipient also may be called a carrier. The formulation methods and excipients described herein are exemplary and are in no way limiting. Pharmaceutically acceptable excipients are well known in the pharmaceutical art and described, for example, in Rowe et al., *Handbook of Pharmaceutical Excipients: A Comprehensive Guide to Uses, Properties, and Safety,* 5th Ed., 2006, and in *Remington: The Science and Practice of Pharmacy* (Gennaro, 21st Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, diluents, dispersing and surface active agents, binders, and lubricants. One skilled in this art may further formulate the active pharmaceutical ingredient (e.g., the free base and tosylate salt of Compound 1 as described herein) in an appropriate manner, and in accordance with accepted practices, such as those disclosed in Remington, supra.

Methods of administration include systemic administration of the active pharmaceutical ingredient (e.g., the free base and tosylate salt of Compound 1 as described herein), preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the active pharmaceutical ingredient (e.g., the free base and tosylate salt of Compound 1 as described herein) can be prepared in aqueous injection solutions which may contain buffers, antioxidants, bacteriostats, and other additives commonly employed in such solutions.

Pharmaceutical preparations for oral administration can be obtained by any suitable method, typically by uniformly mixing the active pharmaceutical ingredient (e.g., the free base and tosylate salt of Compound 1 as described herein) with liquids or finely divided solid carriers, or both, in the required proportions and then, if necessary, processing the mixture, after adding suitable auxiliaries, if desired, forming the resulting mixture into a desired shape to obtain tablets or dragee cores.

Conventional excipients, such as binding agents, fillers, adjuvant, carrier, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before lyophilization, or simply filling and sealing an appropriate vial or ampule.

As used herein, an "excipient" refers to a substance that is added to a composition to provide, without limitation, bulk, consistency, stability, binding ability, lubrication, disintegrating ability, etc., to the composition. A "diluent" is a type of excipient and refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion, or inhalation. A pharmaceutically acceptable excipient is a physiologically and pharmaceutically suitable non-toxic and inactive material or ingredient that does not interfere with the activity of the drug substance. Pharmaceutically acceptable excipients are well known in the pharmaceutical art and described, for example, in Rowe et al., *Handbook of Pharmaceutical Excipients: A Comprehensive Guide to Uses, Properties, and Safety,* 5th Ed., 2006, and in *Remington: The Science and Practice of Pharmacy* (Gennaro, 21st Ed. Mack Pub. Co., Easton, PA (2005)). Preservatives, stabilizers, dyes, buffers, and the like may be provided in the pharmaceutical composition. In addition, antioxidants and suspending agents may also be used. For compositions formulated as liquid solutions, acceptable carriers and/or diluents include saline and sterile water, and may optionally include antioxidants, buffers, bacteriostats and other common additives. In some embodiments, the diluents may be a buffered aqueous solution such as, without limitation, phosphate buffered saline. The compositions can also be formulated as capsules, granules, or tablets which contain, in addition to a compound as disclosed and described herein, diluents, dispersing and surface-active agents, binders, and lubricants. One skilled in this art may further formulate a compound as disclosed and described herein in an appropriate manner, and in accordance with accepted practices, such as those disclosed in Remington, supra.

One aspect of the present invention relates to processes for preparing a pharmaceutical composition comprising admixing a crystalline form (Compound 1, free base) as described herein, a crystalline form (Compound 1, tosylate base) as described herein; or a composition as described herein, and a pharmaceutically acceptable carrier.

In making pharmaceutical compositions, the active pharmaceutical ingredient (e.g., the free base and tosylate salt of Compound 1 as described herein) is typically mixed (i.e., admixed) with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier, or medium for the drug substance. Thus, the compositions can be in the form of tablets, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

For preparing solid form pharmaceutical compositions such as powders, tablets, capsules, cachets, suppositories and dispersible granules an excipient can be one or more substances which may also act as diluents, flavoring agents, solubilizers, lubricants, suspending agents, binders, preservatives, tablet disintegrating agents, or an encapsulating material. Also included are solid form preparations which are intended to be converted, shortly before use, to liquid form preparations for oral administration. Such liquid forms include solutions, suspensions and emulsions. These preparations may contain, in addition to the drug substance, colorants, flavors, stabilizers, buffers, artificial and natural sweeteners, dispersants, thickeners, solubilizing agents and the like.

For preparing suppositories, a low melting wax, such as an admixture of fatty acid glycerides or cocoa butter, is first melted and the drug substance is dispersed homogeneously therein, as by stirring. The molten homogenous mixture is then poured into convenient sized molds, allowed to cool and thereby to solidify.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may take such forms as suspensions, solutions, or emulsions in oily or aqueous vehicles and may contain formulatory agents such as suspending, stabilizing and/or dispersing agents. Alternatively, the pharmaceutical compositions may be in powder form, obtained by aseptic isolation of sterile solid or by lyophilization from solution, for constitution with a suitable vehicle, e.g., sterile, pyrogen-free water, before use.

The pharmaceutical compositions may be formulated as an aqueous solution, an aqua-alcoholic solution, a solid suspension, an emulsion, a liposomal suspension, or a freeze-dried powder for reconstitution. Such pharmaceutical compositions may be administered directly or as an admixture for further dilution/reconstitution. Route of administration includes intravenous bolus, intravenous infusion, irrigation, and instillation. Suitable solvents include water, alcohols, PEG, propylene glycol, and lipids; pH adjustments using an acid, e.g., HCl or citric acid, can be used to increase solubility and resulting compositions subjected to suitable sterilization procedures know in the art, such as, aseptic filtration. In some embodiments, the pH of the aqueous solution is about 2.0 to about 4.0. In some embodiments, the pH of the aqueous solution is about 2.5 to about 3.5.

Aqueous formulations suitable for oral use can be prepared by dissolving or suspending the drug substance in water and adding suitable colorants, flavors, stabilizing and thickening agents, as desired.

Aqueous suspensions suitable for oral use can be made by dispersing the finely divided drug substance in water with viscous material, such as natural or synthetic gums, resins, methylcellulose, sodium carboxymethylcellulose, or other well-known suspending agents.

For topical administration to the epidermis the active pharmaceutical ingredient (e.g., the free base and tosylate salt of Compound 1 as described herein) may be formulated as gels, ointments, creams or lotions, or as a transdermal patch. Also, formulations suitable for topical administration in the mouth include lozenges comprising drug substance in a flavored base, usually sucrose and acacia or tragacanth; pastilles comprising the active pharmaceutical ingredient (e.g., the free base and tosylate salt of Compound 1 as described herein) in an inert base such as gelatin and glycerin or sucrose and acacia; and mouthwashes comprising the active pharmaceutical ingredient (e.g., the free base and tosylate salt of Compound 1 as described herein) in a suitable liquid carrier. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. In some embodiments, topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

Solutions or suspensions may be applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation provided in a pressurized pack with a suitable propellant. If administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the active pharmaceutical ingredient (e.g., the free base and tosylate salt of Compound 1 as described herein) as an aerosol can be prepared by processes well known to the person skilled in the art. For their preparation, for example, solutions or dispersions of active pharmaceutical ingredient (e.g., the free base and tosylate salt of Compound 1 as described herein) in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

Alternatively, the pharmaceutical composition may be provided in the form of a dry powder, for example, a powder mix of the compound in a suitable, powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The active pharmaceutical ingredient (e.g., the free base and tosylate salt of Compound 1 as described herein) may also be administered via a rapid dissolving or a slow release composition, wherein the composition includes a biodegradable rapid dissolving or slow release carrier (such as a polymer carrier and the like). Rapid dissolving or slow release carriers are well known in the art and are used to form complexes that capture therein compounds of the present invention, or pharmaceutically acceptable salts thereof and either rapidly or slowly degrade/dissolve in a suitable environment (e.g., aqueous, acidic, basic, etc.).

The pharmaceutical preparations are preferably in unit dosage forms. In such form, the preparation is subdivided into unit doses containing appropriate quantities. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compositions can be formulated in a unit dosage form, each dosage containing the drug substance or equivalent mass of the drug substance. The term "unit dosage forms" refers to physically discrete units of a formulation suitable as unitary dosages for human subjects and other mammals, each unit containing a predetermined quantity of drug substance calculated to produce the desired therapeutic effect, in association with a suitable excipient, as described herein.

The compositions described herein can be formulated to provide immediate and/or timed release (also called extended release, sustained release, controlled release, or slow release) of the active pharmaceutical ingredient (e.g., the free base and tosylate salt of Compound 1 as described herein) after administration to a subject by employing procedures known in the art. For example, the tablets can be coated or otherwise compounded to provide a dosage form affording the advantage of prolonged action. The tablet can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms can be incorporated for administration orally or by injection include aqueous solutions, suitably flavored syrups, aqueous or oil suspensions, and flavored emulsions with edible oils such as cottonseed oil, sesame oil, coconut oil, or peanut oil, and similar excipients.

The pharmaceutical compositions described herein can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations is typically between 3 and 11, more preferably from 5 to 9 and most preferably from 7 to 8. It will be understood that use of certain of the foregoing excipients may result in the formation of pharmaceutically acceptable salts.

Compositions for inhalation or insufflation include solutions and suspensions in pharmaceutically acceptable, aqueous or organic solvents, or mixtures thereof, and powders. The liquid or solid compositions may contain suitable excipients as described herein. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions may, if desired, be presented in a pack or dispenser device which may contain one or more-unit dosage forms containing the drug substance. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

As used herein, a "dose" or "dosage" refers to the measured quantity of drug substance to be taken at one time by a patient. In certain embodiments, wherein the drug substance is not a free base or free acid, the quantity is the molar equivalent to the corresponding amount of free base or free acid.

For preparing solid compositions such as tablets, the active pharmaceutical ingredient (e.g., the free base and tosylate salt of Compound 1 as described herein) may be mixed with an excipient to form a solid preformulation composition containing a homogeneous mixture of components. When referring to these preformulation compositions as homogeneous, the drug substance is typically dispersed evenly throughout the composition so that the composition can be readily subdivided into equally effective unit dosage forms such as tablets and capsules.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Compounds, crystal forms, and compositions of the present invention may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The amount of compound or composition administered to a subject will also vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptomology and/or pathology of the disease and its complications. Therapeutically effective doses will depend on the disease condition being treated as well as by the judgment of the attending clinician depending upon factors such as the severity of the disease, the age, weight and general condition of the subject, and the like.

The desired dose may conveniently be presented in a single dose or presented as divided doses administered at appropriate intervals, for example, as two, three, four, or more sub-doses per day. The sub-dose itself may be further divided, e.g., into a number of discrete loosely spaced administrations.

The daily dose can be divided, especially when relatively large amounts are administered as deemed appropriate, into several, for example two, three, or four-part administrations. If appropriate, depending on individual behavior, it may be necessary to deviate upward or downward from the daily dose indicated.

Pharmaceutical Compositions and Pharmaceutical Products, Comprising Crystalline Compound 1, Free Base.

One aspect of the present invention relates to pharmaceutical compositions comprising a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) as described herein, and a pharmaceutically acceptable carrier. In some embodiments, the pharmaceutical composition is adapted for oral administration. In some embodiments, the pharmaceutical composition is in the form of a tablet or capsule. In some embodiments, the pharmaceutical composition is in the form of a tablet. In some embodiments, the pharmaceutical composition is in the form of a capsule.

One aspect of the present invention relates to pharmaceutical products selected from: a pharmaceutical composition, a formulation, a unit dosage form, and a kit; each comprising a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base) as described herein.

One aspect of the present invention relates to processes for preparing pharmaceutical compositions comprising admixing a crystalline form of 4-(2-chloro-4-methoxy-5-methylphenyl)-N—[(1S)-2-cyclopropyl-1-(3-fluoro-4-methylphenyl)ethyl]-5-methyl-N-prop-2-ynyl-1,3-thiazol-2-amine (Compound 1, free base) as described herein, and a pharmaceutically acceptable carrier.

Pharmaceutical Compositions and Pharmaceutical Products, Comprising Crystalline Compound 1, Tosylate Salt.

One aspect of the present invention relates to pharmaceutical compositions comprising a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) as described herein, and a pharmaceutically acceptable carrier. In some embodiments, the pharmaceutical composition is adapted for oral administration. In some embodiments, the pharmaceutical composition is in the form of a tablet or capsule. In some embodiments, the pharmaceutical composition is in the form of a tablet. In some embodiments, the pharmaceutical composition is in the form of a capsule.

One aspect of the present invention relates to pharmaceutical products selected from: a pharmaceutical composition, a formulation, a unit dosage form, and a kit; each comprising a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) as described herein.

One aspect of the present invention relates to processes for preparing pharmaceutical compositions comprising admixing a crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) as described herein, and a pharmaceutically acceptable carrier.

Pharmaceutical Compositions and Pharmaceutical Products, Comprising a Compound 1 Composition.

One aspect of the present invention relates to pharmaceutical compositions comprising a 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) composition as described herein, and a pharmaceutically acceptable carrier. In some embodiments, the pharmaceutical composition is adapted for oral administration. In some embodiments, the pharmaceutical composition is in the form of a tablet or capsule. In some embodiments, the pharmaceutical composition is in the form of a tablet. In some embodiments, the pharmaceutical composition is in the form of a capsule.

One aspect of the present invention relates to pharmaceutical products selected from: a pharmaceutical composition, a formulation, a unit dosage form, and a kit; each comprising a 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) composition as described herein.

One aspect of the present invention relates to processes for preparing a pharmaceutical compositions comprising admixing a 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) composition as described herein, and a pharmaceutically acceptable carrier.

One aspect of the present invention relates to processes for preparing pharmaceutical compositions comprising admixing the anhydrous crystal form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) with a pharmaceutically acceptable carrier, wherein the anhydrous crystalline form is prepared by any of the processes described herein.

Compound 1 Compositions.

One aspect of the present invention relates to compositions comprising:

a. 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof; and b. at least one compound selected from:

(S)-4-(2-Chloro-4-methoxy-5-methylphenyl)-N-(2-cyclopropyl-1-(3-fluoro-4-methylphenyl)ethyl)-5-methylthiazol-2-amine (Compound 9A);

(S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa);

(S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb);

4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc);

ethanol; and propargyl bromide.

In some embodiments, the composition comprising Compound 1, or a pharmaceutically acceptable salt thereof, has at least two compounds selected from: (S)-4-(2-Chloro-4-methoxy-5-methylphenyl)-N-(2-cyclopropyl-1-(3-fluoro-4-methylphenyl)ethyl)-5-methylthiazol-2-amine (Compound 9A); (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa); (S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb); 4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc); ethanol; and propargyl bromide. In some embodiments, the composition comprising Compound 1, or a pharmaceutically acceptable salt thereof, has at least three compounds. In some embodiments, the composition comprising Compound 1, or a pharmaceutically acceptable salt thereof, has at least four compounds. In some embodiments, the composition comprising Compound 1, or a pharmaceutically acceptable salt thereof, has at least five compounds.

In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is the free base.

In some embodiments, the composition contains at least 97% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) as determined by HPLC. In some embodiments, the composition contains at least 98% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) as determined by HPLC. In some embodiments, the composition contains at least 99% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) as determined by HPLC.

In some embodiments, the composition contains no more than 0.3% of (S)-4-(2-Chloro-4-methoxy-5-methylphenyl)-N-(2-cyclopropyl-1-(3-fluoro-4-methylphenyl)ethyl)-5-methylthiazol-2-amine (Compound 9A) as determined by HPLC. In some embodiments, the composition contains no more than 0.2% of (S)-4-(2-Chloro-4-methoxy-5-methylphenyl)-N-(2-cyclopropyl-1-(3-fluoro-4-methylphenyl)ethyl)-5-methylthiazol-2-amine (Compound 9A) as determined by HPLC. In some embodiments, the composition contains no more than 0.1% of (S)-4-(2-Chloro-4-methoxy-5-methylphenyl)-N-(2-cyclopropyl-1-(3-fluoro-4-methylphenyl)ethyl)-5-methylthiazol-2-amine (Compound 9A) as determined by HPLC.

In some embodiments, the composition contains no more than 0.8% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa) as determined by HPLC. In some embodiments, the composition contains no more than 0.7% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa) as determined by HPLC. In some embodiments, the composition contains no more than 0.6% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa) as determined by HPLC.

In some embodiments, the composition contains no more than 0.15% of (S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb) as determined by HPLC. In some embodiments, the composition contains no more than 0.1% of (S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb) as determined by HPLC. In some embodiments, the composition contains no more than 0.05% of (S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb) as determined by HPLC.

In some embodiments, the composition contains no more than 0.3% of 4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc) as determined by chiral HPLC. In some embodiments, the composition contains no more than 0.2% of 4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc) as determined by chiral HPLC. In some embodiments, the composition contains no more than 0.1% of 4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc) as determined by chiral HPLC.

In some embodiments, the composition contains no more than 5000 ppm of ethanol as determined by gas chromatography. In some embodiments, the composition contains no more than 3000 ppm of ethanol as determined by gas chromatography. In some embodiments, the composition contains no more than 1000 ppm of ethanol as determined by gas chromatography.

In some embodiments, the composition contains no more than 200 ppm of propargyl bromide as determined by gas chromatography. In some embodiments, the composition contains no more than 100 ppm of propargyl bromide as determined by gas chromatography. In some embodiments, the composition contains no more than 30 ppm of propargyl bromide as determined by gas chromatography.

In some embodiments, 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is an anhydrous crystalline Form I as described herein.

EXAMPLES

Detailed compound synthesis methods are described in the Examples provided herein. The compounds described herein, supra and infra, are named according to MarvinSketch 18.24.0 or ChemDraw Professional 18.2.0.48. In certain instances, when common names are used, it is understood that these common names would be recognized by those skilled in the art.

The following examples are included to demonstrate embodiments of the disclosure. However, those of skill in the art should, in light of the present disclosure, appreciate that many changes can be made in the specific embodiments which are disclosed and still obtain a like or similar result without departing from the spirit and scope of the disclosure.

Analytical HPLC analyses were performed on an LC-MS system with a UV Detector (Dionex™ UVD 170u UV/VIS Detector), Corona array detector (Thermo™ Veo™ RS), and mass spectrometer (Dionex MSQ Plus™). Reverse-phase preparative HPLC purifications were performed on an LCMS system C18 Kinetix 5μ 100 A 150×21.2 mm column by Phenomenex using ACN/water gradient containing 0.05% TFA. All final compounds were analyzed by analytical HPLC and peaks were monitored at 210, 254 and 280 nM for purity. $^{1}H$ was recorded in an appropriate NMR solvent, such as, DMSO-$d_6$, on a Bruker 400 MHz spectrometer equipped with a Broad Band NMR probe. The H chemical signals are given in parts per million (ppm) with the residual solvent signal used as reference. The chemical shifts are expressed in ppm (δ) and coupling constants (J) are reported in hertz (Hz). Reactions were performed under an atmosphere of dry nitrogen unless otherwise stated.

Compound 8A was previously described in International Publication Number WO2010/125414 by Sanofi-Aventis.

Figure 5:
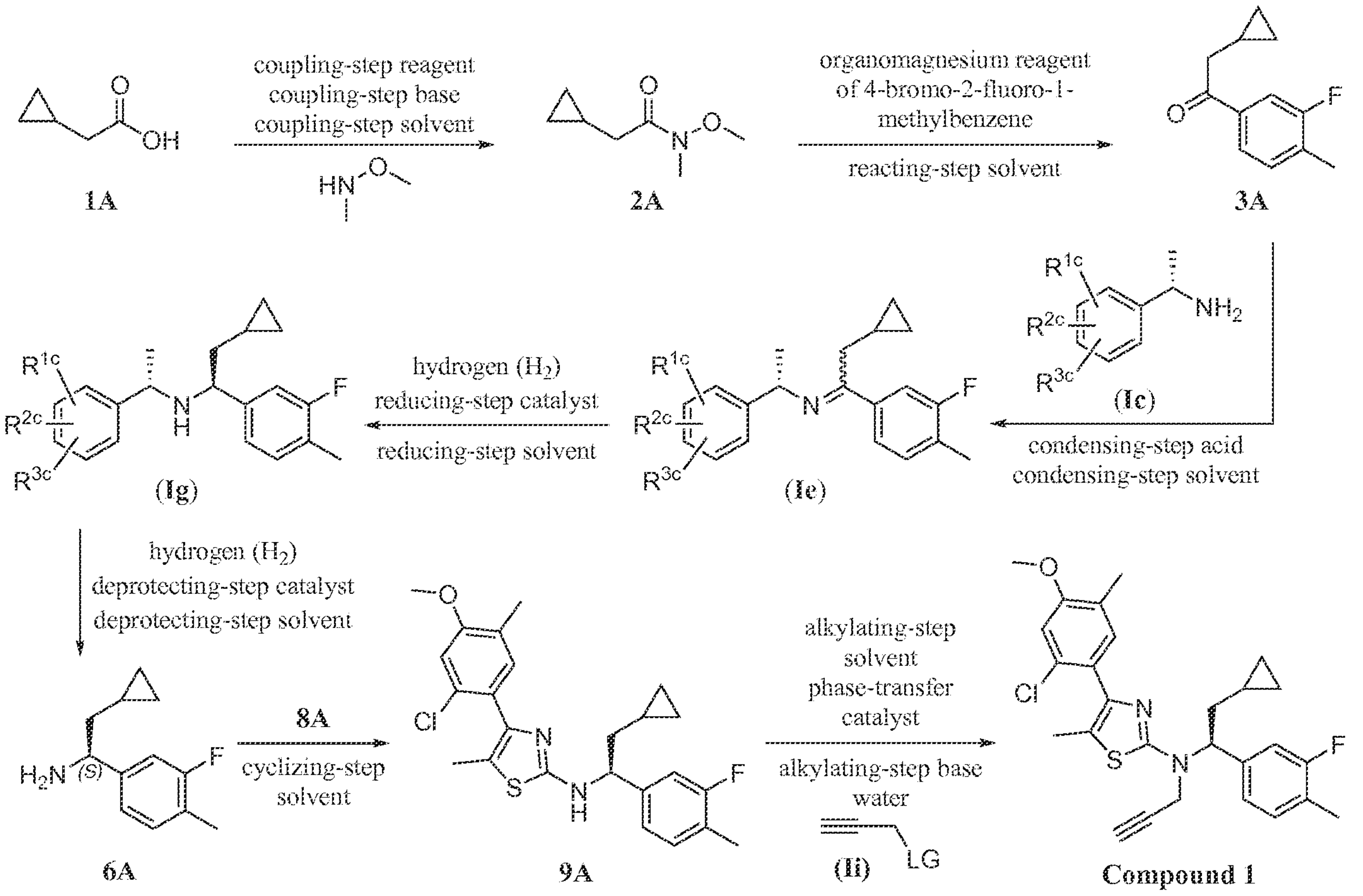
FIG. 5 shows a general scheme for the preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

Example 1: Preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), See FIG. 5 for a general synthetic scheme

Step 1A: Preparation of 2-Cyclopropyl-N-methoxy-N-methylacetamide (Compound 2A)

2A

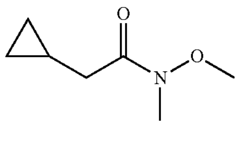

A suspension of 1,1'-carbonyldiimidazole (CDI, 152.6 kg, 1.01 eq.) in DCM (682 kg, 513 L, 7.3 w/w relative to 2-cyclopropylacetic acid) was treated with a solution of 2-cyclopropylacetic acid (Compound 1A, 93.6 kg, 1 eq.) in DCM (248 kg, 186 L, 2.65 w/w) over at least 1 h, keeping the temperature ≤25° C. and compensating for significant effervescence. The resulting mixture was stirred for 15 min at 22° C. and then N,O-dimethylhydroxylamine-HCl (93.6 kg, 1.03 eq.) was added in portions, keeping the temperature ≤30° C. Subsequently, triethylamine (46.4 kg, 0.49 eq.) was added to the stirring mixture at 20-25° C. The resulting mixture was stirred at 22° C. at least 1 h. The mixture was washed once with $KHSO_4$ solution (0.24 M, 357.1 kg, 0.09 eq.), once with $KHSO_4$ solution (0.40 M, 365.4 kg, 0.15 eq.), once with $KHSO_4$ solution (0.80 M, 384.5 kg, 0.30 eq.), and once with $NaHCO_3$ solution (0.60 M, 393.1 kg, 0.24 eq.). Residual DCM was removed by two put-and-takes of THF (166.6 kg, 1.78 w/w) and vacuum distillation (50-60° C., to minimum volume/until distillation stops) to provide Compound 2A. THF (333.2 kg. 3.56 w/w) was added and the yield was determined by correcting for the LOD and GC-FID purity of the sample (131.5 kg, 98.2% corrected). $^{1}H$-NMR (400 MHz, DMSO-$d_6$) δ (ppm) −0.01-0.03 (m, 2H), 0.32-0.36 (m, 2H), 0.81-0.90 (br m, 1H), 2.18 (d, J=6.80 Hz, 2H), 2.97 (s, 3H), 3.53 (s, 3H). ESI-MS: 144.0 $[M+H]^+$.

Step 1B: Preparation of 2-Cyclopropyl-1-(3-fluoro-4-methylphenyl)ethan-1-one (Compound 3A)

3A

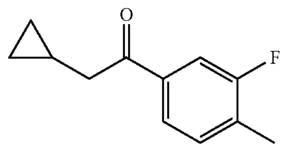

Mg (turnings, 28.6 kg, 1.37 eq.) were suspended in THF (244.7 kg, 2.0 w/w) and DIBAL-H (1 M in n-heptane, 18.9 kg, 0.03 eq.) was added dropwise at 30° C. The resulting mixture was stirred at 30° C. for at least 10 min and then 4-bromo-2-fluoro-1-methylbenzene (neat, 21.1 kg, 0.13 eq.) was added over at least 30 min at 30-50° C. Subsequently, the mixture was treated with a solution of 4-bromo-2-fluoro-1-methylbenzene (191.6 kg, 1.18 eq.) in THF (414.5 kg, 3.37 w/w) at 30-50° C. over 3 h or less. The mixture was stirred at 30° C. for at least 1 h. The mixture was cooled to 12-18° C. and subsequently treated with 2-cyclopropyl-N-methoxy-N-methylacetamide (Compound 2A, 123.0 kg, 1 eq., 25.9% w/w solution in THF) over at least 1 h at 15-25° C. The resulting mixture was stirred at 20-25° C. for at least 1 h. The stirring mixture was then treated with aqueous HCl (3 M, 10.3% w/w, 668.9 kg, 2.24 eq.) at 10-25° C. and the resulting mixture was stirred at least 2 h until no Mg turnings were observed (check pH 3.0-3.5). The layers were separated, and the aqueous layer discarded. The organic layer was distilled at 55-65° C. and 400 mbar until distillation halts. Heptane (290.3 kg, 2.36 w/w) was added. The layers were separated, and the organic layer was washed once with $NaHCO_3$ solution (0.63 M, 211.6 kg, 0.15 eq.) and once with NaCl solution (2.57 M, 213.0 kg, 0.55 eq.). The residual solvents were removed by vacuum distillation at 58-62° C. until distillation stops and then one put-and-take of toluene (275.5 kg, 2.24 w/w) at 107-117° C. until distillation stops. Toluene (275.5 kg, 2.24 w/w) was added and the yield was determined by correcting for the LOD and GC-FID purity of the sample (150.7 kg, 91.3% corrected). $^{1}H$ NMR (400 MHz, DMSO-$d_6$) δ (ppm) 0.07-0.21 (m, 2H), 0.40-0.54 (m, 2H), 1.02 (ttt, J=8.16, 8.16, 6.68, 6.68, 4.86, 4.86 Hz, 1H), 2.30 (d, J=1.77 Hz, 3H), 2.91 (d, J=6.57 Hz, 2H), 7.44 (t, J=7.83 Hz, 1H), 7.57-7.78 (m, 2H). ESI-MS: 193.1 $[M+H]^+$.

Step 1C: Preparation of (S)-2-cyclopropyl-1-(3-fluoro-4-methylphenyl)-N-(1-phenylethyl)ethan-1-imine (Compound 4A)

4A

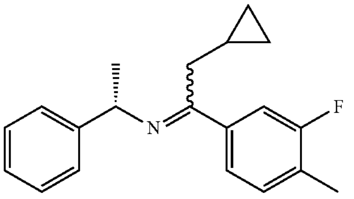

A mixture of 2-cyclopropyl-1-(3-fluoro-4-methylphenyl) ethan-1-one (Compound 3A, 150.7 kg, 1 eq., as a 27.6% w/w solution in toluene), (S)-(−)-1-phenylethylamine (112.9 kg, 1.19 eq.), and p-toluenesulfonic acid (7.4 kg, 0.05 eq.) was heated to reflux at 110-120° C. for 23-25 h in a reactor set up in a Dean-Stark configuration. The solvent was then removed at 125-135° C. under atmospheric pressure until distillation halts and a portion of toluene (275 kg, 2.24 w/w) was added to afford a suspension. The suspension was heated to reflux at 110-120° C. for 23-25 h. The mixture was cooled to 22° C. and washed twice with aqueous $NH_4Cl$ (10%, 301.2 kg, 0.72 eq.) and once with aqueous $NaHCO_3$ (5%, 301.2 kg, 0.23 eq., check pH 8-9). The solvent was removed at 125-135° C. and atmospheric pressure to a target volume of 256 L, the mixture was filtered over CELITE®, and the cake was washed with toluene (25 kg). The resulting mixture containing Compound 4A was used directly in the next step without further isolation. The yield was determined by correcting for the LOD and GC-FID purity of the sample (208.4 kg, 90.0% corrected). EI-MS: 294.1 $[M-H]^+$, 190.1 $[M-C_6H_5CH(CH_3)]^+$, 105.1 $[C_6H_5CH(CH_3)]^+$.

Step 1D: Preparation of (S)-2-Cyclopropyl-1-(3-fluoro-4-methylphenyl)-N—((S)-1-phenylethyl) ethan-1-amine (Compound 5A) as the Hydrochloride Salt

5A

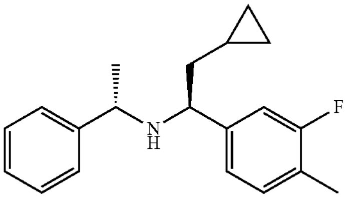

Sponge nickel catalyst (144 kg, 0.70 w/w, shipped as a 50% w/w suspension in water) was added to a hydrogenation reactor, equipped with a dip tube capable of removing material from the top of the mass inside, minimizing the amount of water introduced. The supernatant was discarded, ethanol (329.3 kg, 1.58 w/w, anhydrous) was added, the suspension was stirred and then allowed to settle. This process was repeated four more times and the supernatant is checked; ≤1% $H_2O$ w/w (Karl Fisher (KF)). Compound 4A (208.4 kg, 1 eq., as a 62.6% solution in toluene) was added to the mixture in the hydrogenation reactor. Ethanol (389.4 kg, 1.86 w/w) was used to rinse the addition flask into the hydrogenation reactor. The hydrogenation reactor was pressurized/depressurized twice with nitrogen (2 bar), twice with hydrogen (5 bar), and then pressurized with hydrogen (9.8-10.2 bar). The resulting mixture was heated to 33-37° C. and stirred for 17-19 h. The system was depressurized/pressurized three times with nitrogen (1 bar). The suspension was filtered and washed three times with ethanol (total amount, 493.8 kg, 2.37 w/w). The filtrate was combined with HCl (concentrated, 83.4 kg, 1.07 eq.) and the resulting mixture stirred 25-35 min at 20-24° C. The mixture was concentrated by distillation at 78-80° C. and atmospheric pressure to remove water with a distillate target volume of 1167 L (5.6 L/kg based on imine Compound 4A) and the KF of the solution checked (≤1.5% $H_2O$ w/w). The mixture was stirred at 48-52° C. for 55-65 min, then 68-72° C. for 55-65 min, then cooled to 20-24° C. at a rate of 12° C./h and stirred for 25-35 min, then cooled to 0-4° C. at a rate of 10° C./h and stirred for 55-65 min. The suspension was filtered, the cake was washed twice with precooled ethanol (total amount, 329.2 kg, 1.58 w/w, 0° C.), and the collected solid was dried at 40° C. to afford Compound 5A as the HCl salt (156.5 kg, 66.4% uncorrected). $^1H$ NMR (400 MHz, DMSO-$d_6$) δ (ppm) −0.33-−0.06 (m, 2H), 0.11-0.31 (m, 3H), 1.57 (d, J=6.57 Hz, 3H), 1.95 (br t, J=7.07 Hz, 2H), 2.26 (d, J=1.26 Hz, 3H), 3.68 (br d, J=7.83 Hz, 1H), 3.92 (br t, J=6.44 Hz, 1H), 6.98 (dd, J=7.71, 1.14 Hz, 1H), 7.28-7.36 (m, 2H), 7.37-7.50 (m, 5H). ESI-MS: 298.2 m/z $[M+H]^+$.

Step 1E: Preparation of (S)-2-Cyclopropyl-1-(3-fluoro-4-methylphenyl)ethan-1-amine (Compound 6A) as the Hydrochloride Salt

6A

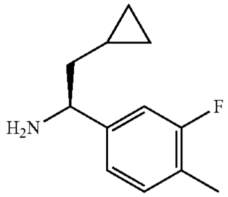

Compound 5A (HCl salt, 156.5 kg, 1.00 eq.) and Pd/C (7.8 kg, 10% Pd basis) were added to an inerted hydrogenation reactor. The reactor was then pressurized/depressurized twice with nitrogen (2 bar) and then methanol (494.5 kg, 3.16 w/w) was added. The reactor was depressurized/pressurized three times with nitrogen (2 bar) then three times with hydrogen (5 bar), pressurized with hydrogen (9.8-10.2 bar), heated to 58-62° C. and stirred for 7-9 h. The reaction mixture was cooled to 20-24° C. The reactor was depressurized/pressurized three times with nitrogen (1 bar) and the suspension was filtered and washed three times with methanol (total amount, 492.9 kg, 3.15 w/w). The solution was concentrated at 63-67° C. and atmospheric pressure to a distillate target volume of 1408 L (9.0 L/kg Compound 6A). n-Heptane (1173.8 kg, 7.5 w/w) was added and the resulting mixture was heated to reflux at 65-80° C. and atmospheric pressure in Dean-Stark configuration to remove methanol. The suspension was cooled to 31-35° C. and filtered, the cake washed with n-heptane (147.1 kg, 0.94 w/w), and the solid dried at 40° C. to provide Compound 6A as the HCl salt (101.0 kg, 93.8% uncorrected, 99.6% ee). $^1H$ NMR (400 MHz, DMSO-$d_6$) δ (ppm) −0.12-0.14 (m, 2H), 0.26-0.42 (m, 2H), 0.44-0.55 (m, 1H), 1.70-1.83 (m, 2H), 2.23 (d, J=1.52 Hz, 3H), 4.24 (t, J=7.33 Hz, 1H), 7.22-7.29 (m, 1H), 7.29-7.36 (m, 1H), 7.40 (dd, J=10.99, 1.39 Hz, 1H). ESI-MS: 194.2 $[M+H]^+$, 177.0 $[M-NH_2]^+$.

Step 1F: Preparation of (S)-4-(2-Chloro-4-methoxy-5-methylphenyl)-N-(2-cyclopropyl-1-(3-fluoro-4-methylphenyl)ethyl)-5-methylthiazol-2-amine (Compound 9A)

9A

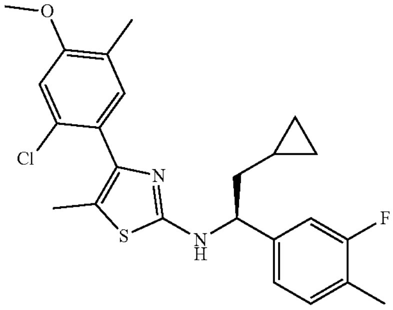

A mixture of n-heptane (146 kg), water (142 kg), Compound 6A (HCl salt, 57.4 kg), and aqueous sodium hydroxide (30% w/w, 41.0 kg) was stirred together. The layers were partitioned, and the aqueous layer removed. The organic layer was washed with water (170 kg) and the layers partitioned. The organic layer was set aside. n-Heptane (145 kg) and 1-(2-chloro-4-methoxy-5-methylphenyl)-2-thiocyanatopropan-1-one (Compound 8A, 66.1 kg, the preparation of Compound 8A has been previously described in International Publication Number WO2010/125414) were added to the reactor and heated to 85° C. The previously set aside organic layer containing the free base of Compound 6A was added at 84-85° C. to the reactor and rinsed with n-heptane (20 kg). The resulting mixture was stirred for 2 h at 83° C. Subsequently, the solvent was switched to methanol by four put-and-take additions/vacuum distillations of methanol (180 kg) at 55° C. with the target volume being 287 L remaining in the reactor. The suspension was cooled to 5° C. and water (570 kg) was added over 4 h at 5-10° C., with the first 60 kg added very slowly. The suspension was aged 2 h at 5° C. and then isolated by filtration, washed with a mixture of methanol/water (91/115 kg) and then a mixture of methanol/water (134/57 kg). The yellow solid was dried at 25° C. and 1 mbar for 17 h then 40° C. and 1 mbar for 22 h to afford Compound 9A (97.4 kg, 87.5% yield). $^1H$ NMR (400 MHz, DMSO-$d_6$) δ ppm −0.01-0.14 (m, 2H), 0.29-0.42 (m, 2H), 0.61-0.73 (m, 1H), 1.47 (dt, J=13.83, 6.85 Hz, 1H), 1.76 (dt, J=13.89, 7.20 Hz, 1H), 2.00 (s, 3H), 2.11 (s, 3H), 2.19 (d, J=1.01 Hz, 3H), 3.82 (s, 3H), 4.54 (q, J=7.58 Hz, 1H), 7.00 (s, 1H), 7.06 (d, J=0.76 Hz, 1H), 7.08-7.14 (m, 2H), 7.18-7.23 (m, 1H), 7.89 (d, J=8.08 Hz, 1H). ESI-MS: 445.3 m/z $[M+H]^+$.

Step 1G: Preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1)

Compound 1

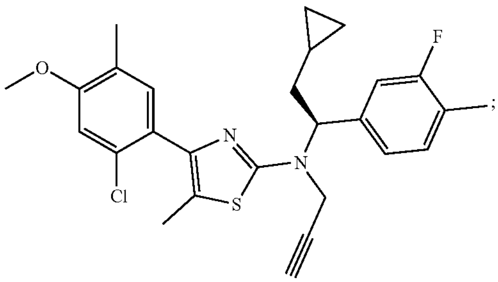

;

A mixture of MTBE (279 kg), tetra-n-butylammonium bromide (10.5 kg), and Compound 9A (95.4 kg) were heated at 60° C. external temperature for 30 min and then cooled to 0° C. Aqueous potassium hydroxide (52.4% w/w, 364 kg) and propargyl bromide (39.4 kg as an 80% w/w solution in toluene, 1.19 eq.) were added at 0-5° C. The propargyl bromide additional funnel was washed with MTBE (25 kg) and the biphasic mixture was aged 14.5 h at 4-6° C. with vigorous stirring. Subsequently, water (191 kg) was added and the aqueous layer was discharged at 20° C. The organic layer was washed twice with water (382 kg) and once with aqueous acetic acid (5.26% w/w, 190 kg) at 20° C. The mixture is polish filtered, rinsed with ethanol (11 kg) and then the solvent switched to ethanol by 3 put-and-take additions/vacuum distillations of ethanol (300 kg) at 25-30° C. for the first cycle and then 35-40° C. with the target volume of each cycle being 250 L remaining in the reactor. Ethanol (164 kg) was added and the mixture heated at 60° C. external for 0.5 h before it was cooled to 25° C. in 1 h and seeded with authentic Form I (free base) of Compound 1 (0.340 kg) which can be prepared as described below in Example 2 and Example 3. The suspension was aged for 5 h, cooled to 0° C. in 2 h, aged 12 h, filtered, and washed twice with ethanol (24 kg each) pre-cooled to 0° C. The white solid was dried at 40° C. and 1 mbar for 19 h to yield 80.15 kg of Compound 1 (77.2% yield). $^1H$ NMR (400 MHz, DMSO-$d_6$) δ (ppm) 0.14 (qt, J=8.59, 4.42 Hz, 2H), 0.29-0.48 (m, 2H), 0.61-0.82 (m, 1H), 1.89 (dt, J=14.08, 6.98 Hz, 1H), 2.07 (br d, J=7.83 Hz, 1H), 2.10 (s, 3H), 2.14 (s, 3 H), 2.20 (d, J=1.01 Hz, 3H), 3.11 (t, J=2.27 Hz, 1H), 3.83 (s, 3H), 3.94-4.22 (m, 2H), 5.26 (t, J=7.58 Hz, 1H), 7.05 (s, 1H), 7.10-7.36 (m, 4H). ESI-MS: 483.2 m/z $[M+H]^+$.

Example 2: Preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1)

A mixture of MTBE (2 mL), tetra-n-butylammonium bromide (110 mg), and Compound 9A (1.003 g) at 0° C. was treated with aqueous potassium hydroxide (52.4% w/w, 1.80 mL, 2.73 g) and propargyl bromide (405 mg as an 80% w/w solution in toluene) maintaining the temperature at 0-5° C. The resulting biphasic mixture was aged 23 h at 4-6° C. Subsequently, water (2 mL) and MTBE (2 mL) were added and the aqueous layer was discharged. The organic layer was washed twice with water (4 mL) and once with aqueous acetic acid (5% w/w, 2 mL) at 20° C. Ethanol (4 mL) was added and then the solvent was switched to ethanol by 3 put-and-take additions/vacuum distillations of ethanol (6 mL) at 35-40° C. with the target volume of each cycle being 2 mL remaining in the vessel, except for the third cycle where the mixture was concentrated to dryness. Ethanol (4 mL) was added to the vessel and the mixture heated at 60° C. (external) for 0.5 h before it was cooled to 20° C. in 1 h and aged 18 h. The resulting suspension was cooled to 0° C., aged 6 h, filtered, and washed twice with ethanol (2 mL each) pre-cooled to 0° C. to afford a solid. The solid was dried at 40° C. under vacuum to afford Compound 1 (506 mg, 46% yield) as Form I. The $^1$H NMR and ESI-MS data matches that as described above in Example 1, Step 1G.

Example 3: Preparation of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1)

A mixture of MTBE (40 mL), tetra-n-butylammonium bromide (1.1 g), and Compound 9A (10.0 g) was heated to 45° C., aged for 10 min, then cooled to 0° C. The solution was treated with aqueous potassium hydroxide (52.4% w/w, 38.2 g) and propargyl bromide (3.36 g as an 80% w/w solution in toluene) maintaining the temperature at 0-5° C. The resulting biphasic mixture stirred vigorously for 16 h at 4-6° C. Subsequently, water (20 mL) was added and the aqueous layer was discharged. The organic layer was washed twice with water (40 mL) and once with aqueous acetic acid (5.2% w/w, 20 mL) at 20° C. The solvent was switched to ethanol by 4 put-and-take additions/vacuum distillations of ethanol (15 mL) at 35-40° C. with the target volume of each cycle being 15 mL remaining in the vessel. The solution was weighed to approximate the amount of ethanol remaining, and ethanol (26 mL) was added to the vessel to bring the total amount of ethanol to 40 mL. The solution was cooled to 4° C. and stirred for 45 min to afford a suspension. The suspension was heated to 38° C. in 15 min, aged 10 min, then cooled to 20° C. over 14 h. The suspension was cooled to 0° C., aged 1.5 h, filtered, and the solids washed twice with ethanol (7.5 mL each) pre-cooled to 0° C. The solid was dried at 40° C. under vacuum to afford Compound 1 (8.27 g, 76% yield) as Form I. The $^1$H NMR and ESI-MS data matches that as described above in Example 1, Step 1G.

The crystalline free base Compound 1, Form I was characterized by X-ray powder diffraction (XRPD) (FIG. 1, Table 2) and DSC (FIG. 2). The DSC indicated the crystalline Compound 1, Form I has an onset of melt (temperature) at about 83.7° C. (76.6 J/g). The Thermogravimetric Analysis (TGA) (FIG. 2) of the crystalline free base exhibited substantially no weight loss (about 0.2%) from room temperature to ~125° C. indicating Form I for the free base of Compound 1 is anhydrous.

The XRPD analysis was performed on a Rigaku Powder X-Ray Diffractometer Miniflex 600 Serial Number BD66000190-01 using Cu-Kα radiation and a D/teX Ultra Detector. For analysis, approximately 0.5-1 mg of Compound 1 was added to a PXRD zero-background sample holder. The powder was pressed down gently with a piece of weighing paper, and the sample holder was placed in the sample changer. Run Parameters: Miniflex Counter Detector, Kb Filter (×2), Scan Axis Theta/2-Theta, Mode Continuous, Start (deg) 2.0, Stop (deg) 45.0, Step (deg) 0.020, Speed (deg/min) 10.0, Spin-yes, Voltage (kV) 40, Current (mA) 15.

The DSC and TGA analysis were performed on TA Instruments Discovery 2500 calorimeter with serial number: 2500-00547 (DSC) and Discovery 5500 with serial number: 5500-0126 (TGA).

For TGA analysis, a standard aluminum sample pan was placed into the platinum TGA pan and the blank was tared with the instrument. Approximately 1-5 mg of Compound 1 was added to the standard aluminum pan and analyzed at 10° C./min up to 450° C.

For the DSC analysis, obtained and recorded the weight of a Tzero pan and a Tzero lid. ~1-3 mg of Compound 1 was weighed into the Tzero Pan and the Tzero lid was pressed on. The pan was transferred to the DSC autosampler for analysis. The method for analysis was a ramp at 10° C./min to 222° C. The reference pan was prepared with the same procedures, absent material.

Example 4: Gravimetric Vapor Sorption Profile for 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, Form I)

The hygroscopicity analysis for a representative sample of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, Form I) was performed on a TA Instruments Q5000 sorption analyzer with serial number 5000-5273. Approximately 3-10 mg of material was placed into a quartz crucible. The crucible was then transferred to the sorption analyzer for analysis at 25° C., with 10% RH steps not exceeding 300 minutes and with stabilization criteria of 0.10%, from 10% RH up to the maximum RH needed, then back down to 10% RH.

The Gravimetric Vapor Sorption (GVS) profile for Form I of Compound 1 as the free base is shown in FIG. 3 with corresponding data shown in Table 3.

Example 5: Preparation of (S)-2-Cyclopropyl-1-(3-fluoro-4-methylphenyl)-N—((S)-1-phenylethyl)ethan-1-amine (Compound 5A) as the Hydrochloride Salt

5A

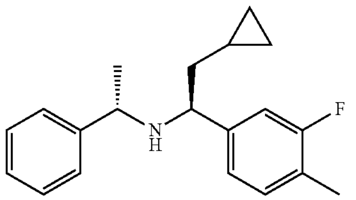

Pd/Cu—C catalyst (1.22 g, 0.0033 eq., 4% Pd basis, 1% Cu basis) was added to an inerted reactor. Compound 4A (40.7 g, 1 eq., as an ~60% solution in toluene) was added and ethanol (84 mL, 106 g, 2.6 w/w) was used to rinse. The reactor was pressurized/depressurized twice with nitrogen and twice with hydrogen then pressurized with hydrogen (2 bar) and heated to 25° C. and stirred for 10.5 h. The system was depressurized/pressurized three times with nitrogen (1 bar) and the suspension was filtered and washed three times with ethanol (96 g, 2.4 w/w). The filtrate was combined with HCl (concentrated, 14.2 g, 1.07 eq.) and the resulting mixture stirred 25-35 min at 20-24° C. The mixture was concentrated by distillation at 78-80° C. and atmospheric pressure to remove water with a distillate target volume of 230 mL (5.6 mL/g based on imine Compound 4A) and the KF of the solution is checked (≤1.5% $H_2O$ w/w). The mixture was stirred at 48-52° C. for 55-65 min, then 68-72° C. for 55-65 min, then cooled to 20-24° C. at a rate of 12° C./h and stirred for 25-35 min, then cooled to 0-4° C. at a rate of 10° C./h and stirred for 55-65 min. The suspension was filtered, the cake was washed twice with precooled ethanol (64.3 g, 1.58 w/w, 0° C.), and the solid was dried at 40° C. (26.7 g, 55.8% uncorrected) to provide Compound 5A as the HCl salt. The characterization data matches Compound 5A (HCl salt) as described above in Example 1, Step 1D.

Figure 4:
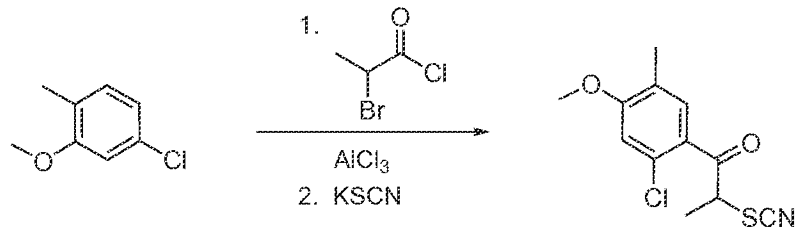
FIG. 4 shows general synthetic schemes for the preparation of 1-(2-chloro-4-methoxy-5-methylphenyl)-2-thiocyanatopropan-1-one (Compound 8A), 4-Chloro-2-(methoxy-$^{13}$C-$d_3$)-1-methylbenzene (Compound 7A'), and 1-(2-Chloro-4-(methoxy-$^{13}$C-$d_3$)-5-methylphenyl)-2-thiocyanatopropan-1-one (Compound 8A'). The synthesis of 1-(2-chloro-4-methoxy-5-methylphenyl)-2-thiocyanatopropan-1-one (Compound 8A) has previously been described in International Publication Number WO2010/125414 by Sanofi-Aventis.
Figure 4:
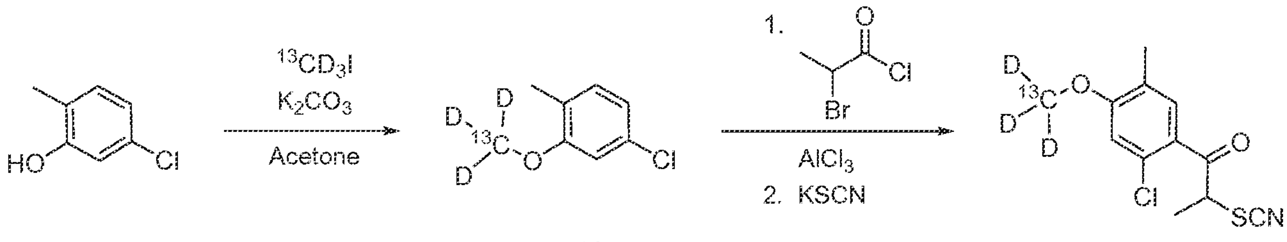
Figure 6:
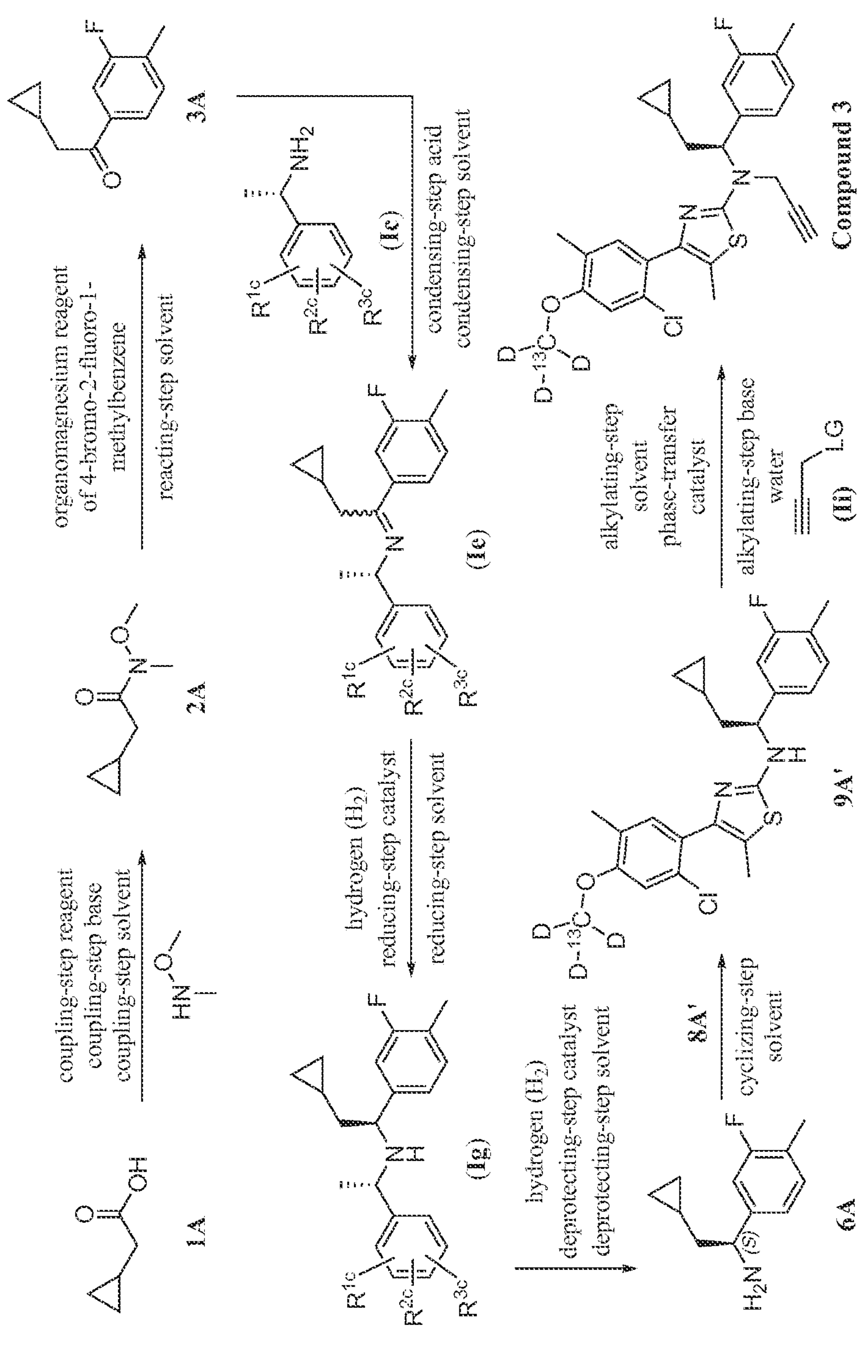
FIG. 6 shows a general scheme for the preparation of (S)-4-(2-chloro-4-(methoxy-$^{13}$C-$d_3$)-5-methylphenyl)-N-(2-cyclopropyl-1-(3-fluoro-4-methylphenyl)ethyl)-5-methyl-N-(prop-2-yn-1-yl)thiazol-2-amine (Compound 3).

Example 6: Preparation of (S)-4-(2-Chloro-4-(methoxy-$^{13}$C-$d_3$)-5-methylphenyl)-N-(2-cyclopropyl-1-(3-fluoro-4-methylphenyl)ethyl)-5-methyl-N-(prop-2-yn-1-yl)thiazol-2-amine (Compound 3), See FIG. 4 and FIG. 6

Step 6A: Preparation of 4-Chloro-2-(methoxy-$^{13}$C-d)-1-methylbenzene (Compound 7A')

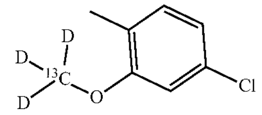

A mixture of 5-chloro-2-methylphenol (9 g, 0.063 mol., 1 equiv.) and potassium carbonate (13.21 g, 0.069 mol., 1.1 equiv.) was stirred for 15 min. at 20° C. in acetone (90 mL). A solution of iodomethane-$^{13}$C-$d_3$ in acetone (30 mL) was added over 30 minutes to the stirring mixture. The mixture was stirred at rt for 24 h and then diluted with DMF (30 mL) and stirred at rt for an additional 15 h. The acetone was removed at atmospheric pressure until all acetone is distilled off (80° C.). The remainder was combined with water (250 mL) and the resultant extracted with pentane (3×50 mL). The combined organic fractions were dried over $Na_2SO_4$, filtered to remove the solid, and concentrated under reduced pressure to afford Compound 7A' (10.6 g, assumed quant.) as a yellow oil.

Step 6B: Preparation of 1-(2-Chloro-4-(methoxy-$^{13}$C-$d_3$)-5-methylphenyl)-2-thiocyanato-propan-1-one (Compound 8A')

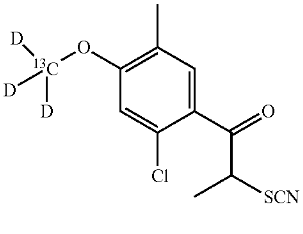

Aluminum trichloride is charged in a 500 mL-jacketed glass reactor, then DCM is added, and the resulting mixture stirred at rt. Compound 7A' is added to the stirring mixture over 10 minutes at rt. The resulting mixture is heated at 30° C. and stirred for 10 min. Subsequently, the mixture is cooled to 0° C. and treated with neat 2-bromopropanoyl chloride over 30 minutes. The resulting mixture is stirred at 0° C. for 20 h. Subsequently, the mixture is cooled to −5° C. and treated with water over 15 min. The resulting mixture is maintained at 0° C. and stirred for 30 min. The mixture is then combined with c-hexane and stirred overnight. The layers are then partitioned, and the organic layer is washed with water and a 1:1 mixture of 13% aq. NaCl+5% aq. $NaHCO_3$. The organic layer is dried over $Na_2SO_4$, filtered and concentrated under reduced pressure to provide bromo intermediate. The bromo intermediate is suspended in c-hexane and filtered. The solution is concentrated and diluted with DCM. In a round bottom flask, KSCN and TBAB are dissolved in water. The aqueous mixture is heated to 55° C. and then treated over 1 h with a solution containing the bromo intermediate. The resulting mixture is stirred for 3.5 h and then water is added. The resulting mixture is stirred for 10 min. and the layers partitioned at 50° C. The organic layer is concentrated under reduced pressure and the remainder combined with methanol. The mixture is stirred at rt for 30 min. and then at 0° C. for 1 h. Solid is collected by filtration and washed with cold methanol to afford Compound 8A'.

Step 6C: Preparation of (S)-4-(2-chloro-4-(methoxy-13C-d3)-5-methylphenyl)-N-(2-cyclopropyl-1-(3-fluoro-4-methylphenyl)ethyl)-5-methylthiazol-2-amine (Compound 9A')

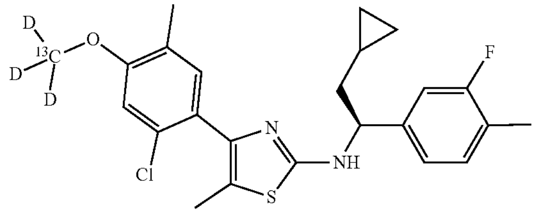 [SMILES: [2H][13C]([2H])([2H])Oc1cc(Cl)c(-c2nc(N[C@@H](CC3CC3)c3ccc(C)c(F)c3)sc2C)cc1C]

A mixture of Compound 8A' in heptane is heated to 90° C. and then treated with Compound 6A in heptane over 20 min. The resulting mixture is stirred at 85° C. for 5 h and then cooled to rt. The solvent is removed under reduced pressure to provide crude product. The crude product is purified by flash chromatography. The solvent is removed under reduced pressure to give Compound 9A'.

Step 6D: Preparation of (S)-4-(2-chloro-4-(methoxy-13C-$d_3$)-5-methylphenyl)-N-(2-cyclopropyl-1-(3-fluoro-4-methylphenyl)ethyl)-5-methyl-N-(prop-2-yn-1-yl)thiazol-2-amine (Compound 3)

A mixture of Compound 9A' and TBAB in methyl tert-butyl ether at −10° C. is treated with aq. KOH (64%) over 15 min. The resulting mixture is maintained at 0° C. and treated with propargyl bromide in toluene (80%) over 10 min. The resulting mixture is stirred at 5° C. overnight and then at rt for 1 h. The mixture is combined with methyl tert-butyl ether and water. The layers are allowed to partition, and the aqueous layer is extracted with methyl tert-butyl ether. The combined organic layers are dried over Na2SO4, filtered and concentrated under reduced pressure to give an intermediate product. The intermediate product is dissolved in acetone and 37% aqueous HCl is added. The resulting mixture is stirred at 55° C. for 1 h. The mixture is cooled to rt and combined with satd. Na2CO3 followed by water. The volatiles are removed under reduced pressure and the aqueous mixture combined with methyl tert-butyl ether. The organic layer is collected, and the aqueous phase is extracted with methyl tert-butyl ether. The combined organic layers are dried over $Na_2SO_4$, filtered to removed solids and concentrated under reduced pressure to afford a first isolate. The first isolate is purified by column chromatography (n-hexane/MTBE 100:0 to 60:40) to afford a second isolate. The second isolate is purified by column chromatography (DCM/MTBE 100:0 to 95:5) to afford Compound 3.

Example 7: Analytical Characterization of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1)

Four separate batches of Compound 1 were manufactured in a similar manner as described herein (i.e., Example 1) in compliance with applicable cGMPs for GLP and/or R&D use. Certain data are shown below in Table 17 for a representative batch.

TABLE 17

| Tests | Batch 1 Results | Batch 2 Results | Batch 3 Results | Batch 4 Results |
|---|---|---|---|---|
| Assay by HPLC (on dry basis), Compound 1 | 99.9% | 97.6% | 97.8% | 98.4% |
| Assay by HPLC, Compound 9A | <0.05% | 0.06% | n.d. | n.d. |
| Assay by HPLC, Compound IIa | 0.58% | 0.58% | 0.52% | 0.49% |
| Assay by HPLC, Compound IIb | <0.05% | n.d. | n.d. | n.d. |
| Chiral purity based on Compound IIc | <0.05% | n.d. | n.d. | n.d. |
| Methanol (residual solvent) | n.d. | n.d. | n.d. | n.d. |
| Heptane (residual solvent) | n.d. | n.d. | n.d. | n.d. |
| Toluene (residual solvent) | n.d. | n.d. | n.d. | n.d. |
| Methyl tert-butyl ether (MTBE) (residual solvent) | n.d. | n.d. | n.d. | n.d. |
| Ethanol (residual solvent) | 428 ppm | 392 ppm | 474 ppm | 545 ppm |
| Propargyl bromide, content | ≤30 ppm | <1 ppm | <1 ppm | <1 ppm |
| Propargyl alcohol, content | n.d. | n.d. | n.d. | n.d. |
| Particle size distribution, D10 | 21 μM | 17 μM | 16 μM | 14 μM |
| Particle size distribution, D50 | 129 μM | 123 μM | 107 μM | 107 μM |
| Particle size distribution, D90 | 468 μM | 335 μM | 320 μM | 327 μM |
| Water content | 0.03% | 0.03% | 0.03% | 0.01% |

n.d. = Not Detected, below limit of quantitation (LOQ).

9A

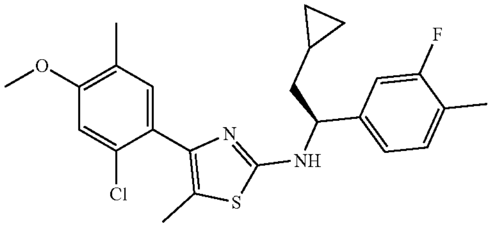

Compound IIa

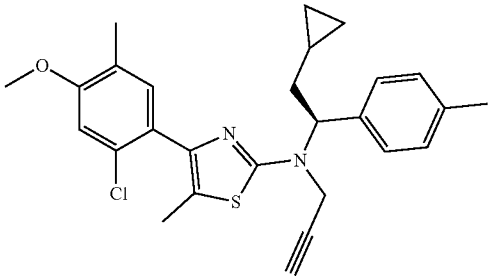

Compound IIb

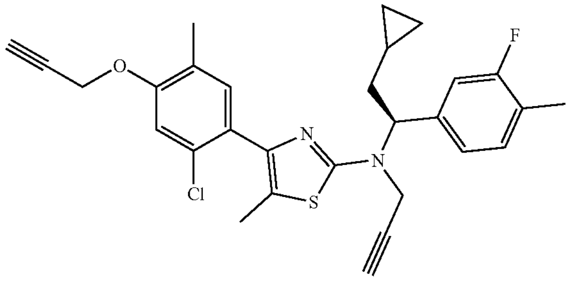

Compound IIc

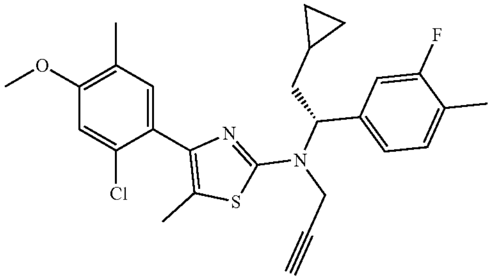

A representative list of for specification for each of the tests used to analyze the four batches are provided below in Table 18.

TABLE 18

| Tests | Specifications |
|---|---|
| Assay by HPLC (on dry basis), Compound 1 | 97.0%-103.0% |
| Assay by HPLC, Compound 9A (04-RORI) | Max 0.% |
| Assay by HPLC, Compound IIa (06-RORI.i2) | Max 0.8% |
| Assay by HPLC, Compound IIb (06-RORI.i3) | Max 0.15% |
| Chiral purity based on Compound IIc (06-RORI.i1) | Max 0.3% |
| Methanol (residual solvent) | Max 3000 ppm |
| Heptane (residual solvent) | Max 5000 ppm |
| Toluene (residual solvent) | Max 890 ppm |
| Methyl tert-butyl ether (MTBE) (residual solvent) | Max 5000 ppm |
| Ethanol (residual solvent) | Max 5000 ppm |
| Water content | Max 0.5% |

Example 8: Representative High-Performance Liquid Chromatography/High-Pressure Liquid Chromatography (HPLC) Methods for In-Process Control (IPC) and/or Assessing Purity for:

4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1);

(S)-4-(2-Chloro-4-methoxy-5-methylphenyl)-N-(2-cyclopropyl-1-(3-fluoro-4-methylphenyl)ethyl)-5-methylthiazol-2-amine (Compound 9A);

(S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa); and (S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb).

The sample solution in acetonitrile was injected into an Agilent 1100 HPLC System, or equivalent, with a Phenomenex, Kinetex C18 100×4.6 mm, 2.6 μm (P.N.: 00D-44-62-E0) and monitored by UV detection at 240 nm (BW 8, reference: off). The working concentration for the sample was about 0.25 mg/mL in acetonitrile. The positive identification for a component is established by comparing the retention time of the sample peak against the retention time for the authentic reference standard. The method conditions are presented below in Table 19:

TABLE 19

| Method Conditions | | Gradient Elution | | |
|---|---|---|---|---|
| Column | Phenomenex, Kinetex C18 100 × 4.6 mm, 2.6 μm (P.N.: 00D-44-62-E0) | Time | % A | % B |
| Mobile Phase A | TFA 0.1% in Purified Water | 0 | 80 | 20 |
| Mobile Phase B | TFA 0.1% in Acetonitrile | 1 | 80 | 20 |
| Solvent | Acetonitrile (CAN) | 6 | 60 | 40 |
| Flow Rate | 1.2 mL/min | 31 | 30 | 70 |
| Column Temperature | 30° C. | 34 | 15 | 85 |
| Auto-Sampler Temperature | Ambient | 37.9 | 15 | 85 |
| Detector Wavelength | 240 nm | 38 | 80 | 20 |
| Sample Injection Volume | 12 μL | 42 | 80 | 20 |
| Duration | 42 min | | | |

The representative retention times ($t_r$, minutes) for a certain compound/intermediates were determined using the method described above and are shown in the following Table 20.

TABLE 20

| Compound | Representative Retention Time ($t_r$) | RRT |
|---|---|---|
| Compound 9A (04-RORI) | 19.6 minutes | 0.75 |
| Compound IIa (06-RORI.i2) | 23.9 minutes | 0.91 |
| Compound 1 (06-RORI) | 26.3 minutes | 1.00 |
| Compound IIb (06-RORI.i3) | 27.0 minutes | 1.03 |

RRT refers to the Relative Retention Time and is the ratio of the retention time of an analyte peak (i.e., Compound 9A, Compound IIa, and Compound IIb) relative to the retention time of Compound 1 obtained under identical conditions.

Example 9: Representative Chiral High-Performance Liquid Chromatography/High-Pressure Liquid Chromatography (HPLC) Methods for In-Process Control (IPC) and/or Assessing Purity for 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1)

Compound 1

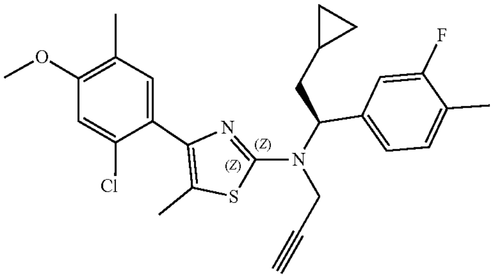

S-enamtiomer

Compound IIc

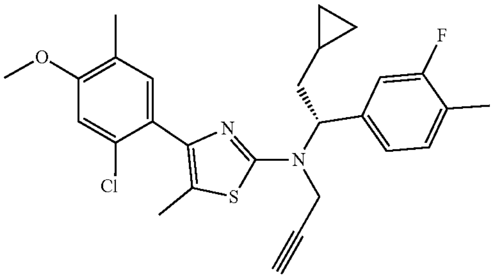

R-enamtiomer

The sample solution in acetonitrile was injected into an Agilent 1100 HPLC System, or equivalent, with a Daicel, Chiralcel OZ—H 250×4.6 mm, 5 μm (P.N.: 42325), or equivalent, and monitored by UV detection at 240 nm (BW 8, reference: off). The positive identification for a component is established by comparing the retention time of the sample peak against the retention time for the authentic reference standard. 9.1 The method conditions are presented below in Table 21:

TABLE 21

| Method Conditions | |
|---|---|
| Column | Daicel, Chiralcel OZ-H 250 × 4.6 mm, 5 μm (P.N.: 42325) |
| Mobile Phase A | Hexane/Isopropanol (98/2, V/V) |
| Gradient | Isocratic elution |
| Flow Rate | 0.9 mL/min |
| Column Temperature | 25° C. |
| Auto-Sampler Temperature | Ambient |
| Detector Wavelength | 240 nm |
| Sample Injection Volume | 5 μL |
| Duration | 10 min |

9.2 Preparation of "Mobile Phase A Solvent":

Hexane/Isopropanol, 98/2 (v/v), was prepared by mixing 980 mL of hexane and 20 mL of isopropanol.

9.3 Preparation of Stock Solution of Compound Ie (1 mg/mL).

The Stock Solution of Compound Ie was prepared by carefully weighing out approximately 10 mg of standard Compound Ie in a 10 mL amber flask and dissolved with approximately 5 mL of Mobile Phase A Solvent (9.2) by sonicating for 5 minutes. The resulting solution was cooled to room temperature, filled to volume with Mobile Phase A Solvent (9.2), and stir.

9.4 Preparation of Intermediate Solution of Compound IIc (0.03 mg/mL).

The intermediate solution of Compound IIc was prepared by transferring 3 mL of Stock Solution of Compound IIc (9.3) into a 100 mL amber flask, filled to volume with Mobile Phase A Solvent (9.2), and stirred.

9.5 Preparation of Resolution Solution (Compound 1: 1 mg/mL, Compound IIc: 0.003 mg/mL).

The resolution solution containing Compound 1 and Compound IIc was prepared by carefully weighing out approximately 10 mg of standard Compound 1 in a 10 mL amber flask and dissolved with approximately 5 mL of Mobile Phase A Solvent (9.2) by sonicating for 5 minutes. The resulting solution was cooled to room temperature, 1 mL of Intermediate Solution of Compound IIc (9.4) was transferred to the flask, filled to volume with Mobile Phase A Solvent (9.2), and stirred.

9.6 Preparation of Sensitivity Stock Solution of Compound 1 (1 mg/mL).

A stock solution of Compound 1 was prepared by carefully weighing out approximately 10 mg of standard Compound 1 in a 10 mL amber flask and dissolved with approximately 5 mL of Mobile Phase A Solvent (9.2) by sonicating for 5 minutes. The resulting solution was cooled to room temperature, filled to volume with Mobile Phase A Solvent (9.2), and stirred.

9.7 Preparation of Sensitivity Intermediate Solution of Compound 1 (0.01 mg/mL).

The intermediate sensitivity solution was prepared by transferring 1 mL of the Sensitivity Stock Solution of Compound 1 (9.6) to a 100 mL amber flask, filled to volume with Mobile Phase A Solvent (9.2), and stirred.

9.8 Preparation of Sensitivity Solution of Compound 1 (0.0005 mg/mL).

The "Sensitivity solution" containing was prepared by transferring 1 mL of the Sensitivity Stock Solution of Compound 1 (9.7) to a 100 mL amber flask, filled to volume with Mobile Phase A Solvent (9.2), and stirred.

9.9 Preparation of Sample for Analysis containing Compound 1 (1 mg/mL).

The sample solution for analysis was prepared by carefully weighing out approximately 10 mg of sample containing Compound 1 in a 10 mL amber flask and dissolved with approximately 5 mL of Mobile Phase A Solvent (9.2) by sonicating for 5 minutes. The resulting solution was cooled to room temperature, filled to volume with Mobile Phase A Solvent (9.2), and stirred.

The injection sequence for the chiral analysis of Compound 1 was performed in the following consecutive order:

1. Mobile Phase A Solvent (9.2) at least 1 time
2. Sensitivity Solution of Compound 1 (9.8), 1 time
3. Resolution Solution (Compound 1 and Compound IIc) (9.5), 6 times
4. First Sample containing Compound 1 (9.9), 1 time
5. Second Sample containing Compound 1 (9.9), 1 time The chiral purity for a Compound 1 sample, based on the Area % of Compound IIc present, was calculated using the area of the peaks for Compound 1 and Compound IIc and the following formula:

$$\text{Compound } IIc(A\%) = \frac{Acp}{\sum A} \times 100$$

Acp: Area of the Compound IIc peak in the Sample containing Compound 1 (9.9).

ΣA: Is the sum of the areas of the Compound 1 peak and the Compound IIc peak in the Sample containing Compound 1 (9.9).

100: Conversion factor %.

The representative retention times ($t_r$, minutes) for a certain compound/intermediates were determined using the method described above and are shown in the following Table 22.

TABLE 22

| Compound | Representative Retention Time ($t_r$) | RRT |
|---|---|---|
| Compound 1 | 5.8 minutes | 1.00 |
| Compound IIc | 5.3 minutes | 0.91 |

RRT refers to the Relative Retention Time and is the ratio of the retention time of an analyte peak (i.e., Compound IIc) relative to the retention time of Compound 1 obtained under identical conditions.

Example 10: Headspace Gas Chromatography Method for Residual Solvents Presence in Intermediates and Compound 1

Headspace gas chromatography (HSGC) was conducted using an Agilent GC 6890 gas chromatograph equipped with Head Space injector; or equivalent, and a flame-ionization detector (FID) using an Agilent DB-624, 25 m×0.20 mm×1.12 μm (P.N.: 128-1324); or equivalent.

Reagents used: dimethyl sulfoxide (DMSO) for Head Space; methanol standard; ethanol standard; methyl tert-butyl ether (MTBE) standard; heptane standard; and toluene standard.

Gas Chromatography Conditions (Table 23)

TABLE 23

| Parameter | Conditions | | |
|---|---|---|---|
| Column | DB-624, 25 m × 0.20 mm × 1.12 μm (P.N.: 128-1324); or equivalent | | |
| Initial temperature | 40° C. for 3 min. | | |
| Temperature program | Ramp | Final Temperature | Waiting time |
| | 20° C./min. | 80° C. | 1 min. |
| | 35° C./min. | 220° C. | 4 min. |
| Total time | | 14 min. | |
| Split Ratio | | 40:1 | |
| Inlet temperature | | 200° C. | |
| FID Temperature | | 280° C. | |
| Transport gas | | Nitrogen | |
| Flow | | 1.5 mL/min, constant flow | |
| Gas Detector Flows | | Air: 400 mL/min.<br>Hydrogen: 40 mL/min.<br>Makeup: 30 mL/min. | |

Headspace Conditions (Table 24)

TABLE 24

| Parameter | Conditions | Parameter | Conditions |
|---|---|---|---|
| Sample Shaker | High | Vial pressure | 15 psi |
| Oven Temperature | 100° C. | Loop Fill Time | 1 min. |
| Loop Temperature | 110° C. | Loop Equilibration Time | 0.05 min. |
| Transfer Line Temperature | 120° C. | GC Cycle Time | at least 28 min. |
| Inject Time | 1 min. | Multi-Extraction | Off |
| Vial Equilibration Time | 10 min. | Vial Size | 10 mL |
| Vial Pressurization Time | 0.2 min. | | |

The GC cycle time in Table 24 is a recommendation. This can vary from instrument to instrument. The GC cycle time should be about equal to the GC run time for the GC to equilibrate to initial conditions.

Preparation of the "Standard Solution"

"Standard Stock Solutions" were prepared for the following solvents at the following concentrations in DMSO: methanol (1.5 mg/mL), ethanol (2.5 mg/mL), MTBE (2.5 mg/mL), heptane (2.5 mg/mL), and toluene (0.45 mg/mL).

The "Standard Solution" was prepared from the above standard stock solutions by transferring 1 mL of each solvent to a 10 mL flask, mixing, and filling to volume with DMSO to obtain the "Standard Solution" containing the following solvents and concentrations: methanol: 3000 ppm, ethanol: 5000 ppm, MTBE: 5000 ppm, heptane: 5000 ppm, and Toluene: 900 ppm. To a 10 mL headspace vial was transferred 0.5 mL of the resulting solution.

Compound 1 Sample Preparation

Samples of Compound 1 were prepared using 25 mg in 0.50 mL of DMSO and used as the basis for all ppm concentrations in 10 mL headspace vials. A representative headspace GC method has been published, (e.g., Dai L, et. al. (2010) *LCGC North America,* 28 (1), 73-84).

The injection sequence for the analysis was performed in the following consecutive order:

the blank (DMSO), at least 1 time;

the "Standard Solution", 6 times;

the first Sample of Compound 1, 1 time;

the second Sample of Compound 1, 1 time; and the "Standard Solution", 1 time (bracketing).

The content of each solvent is calculated using the following formula:

$$\text{Solvent content (ppm)} = \frac{A(c)}{A(std)} \times \frac{C(std)}{P(c)} \times 0.5 \times 1000000$$

A(c)=area of the solvent of interest in the Sample

A(std)=average area of the solvent of interest for all Standard injections

C(std)=concentration of the Standard (mg/mL)

P(c)=sample weight (mg)

1000000 is the conversion factor for the unitary ratio to ppm

The retention times ($t_r$, minutes) for a certain list of solvents were determined and are shown Table 25 with the limit of quantitation (LOQ) for each.

TABLE 25

| Analyte | $t_r$ (min) | LOQ (ppm) |
|---|---|---|
| Methanol | 1.7 | 97 |
| Ethanol | 2.3 | 100 |
| MTBE | 3.5 | 101 |
| Heptane | 5.5 | 101 |
| Toluene | 7.1 | 101 |

Example 11: Gas Chromatography Method for Determining Propargyl Bromide in a Sample of Compound 1

Gas chromatography (GC) was conducted using an Agilent GC 6890 gas chromatograph, or equivalent, and a flame-ionization detector (FID) using an Agilent DB-624, 25 m×0.20 mm×1.12 μm (P.N.: 128-1324); or equivalent.

Reagents used: dichloromethane (DCM) for HPLC, GC and residue analysis, ≥99.9%, stabilized with 50-150 ppm amylene; or equivalent; and propargyl bromide standard solution ~80% in Toluene Gas Chromatography Conditions (Table 26)

TABLE 26

| Parameter | Conditions | | |
|---|---|---|---|
| Column | DB-624, 25 m × 0.20 mm × 1.12 μm (P.N.: 128-1324); or equivalent | | |
| Initial temperature | 40° C. for 3 min. | | |
| Temperature program | Ramp | Final Temperature | Waiting time |
| | 20° C./min. | 80° C. | 1 min. |
| | 35° C./min. | 220° C. | 10 min. |
| Total time | 20 min. | | |
| Injection Volume | 2 μL | | |
| Liner | Inert liner with glass wool, ID 4 mm (P.N. 5183-4674); or equivalent (new liner was installed prior to each analysis). | | |
| Split Ratio | 5:1 | | |
| Inlet temperature | 250° C. | | |
| FID Temperature | 300° C. | | |
| Transport gas | Nitrogen | | |
| Flow | 0.8 mL/min, constant flow | | |
| Gas Detector Flows | Air: 400 mL/min. Hydrogen: 40 mL/min. Makeup: 30 mL/min. | | |
| Approximate retention time | Propargyl bromide 6.5 min. | | |

Preparation of Standard Solution

A "Standard Stock Solution" of propargyl alcohol at a concentration of 1.5 mg/mL was prepared by weighing out the equivalent of 150 mg from the propargyl bromide toluene solution (taking the titer into account) into a 100 mL flask containing an aliquot of DCM, the mixture was shaken, and filled to volume with DCM.

An "Intermediate Standard Solution" of propargyl bromide at a concentration of 0.015 mg/mL was prepared by transferring 1 mL of the above Standard Stock Solution into a 100 mL flask containing an aliquot of DCM, the mixture was shaken, and filled to volume with DCM.

A "Standard Solution" of propargyl bromide at a concentration of 0.0015 mg/mL (30 ppm) was prepared by transferring 1 mL of the above Standard Stock Solution into a 10 mL flask containing an aliquot of DCM, the mixture was shaken, and filled to volume with DCM.

A "Sensitivity Standard Solution" of propargyl bromide at a concentration of 0.050 μg/mL (1 ppm) was prepared by transferring 333 μL of the above "Standard Solution" into a 10 mL flask containing an aliquot of DCM, the mixture was shaken, and filled to volume with DCM.

Sample Preparation

A 250 mg sample of Compound 1 was carefully weighed out into a 5 mL flask, DCM was added to dissolve the sample, and filled to volume with DCM.

The injection sequence for the analysis was performed in the following consecutive order:

the blank (DCM), at least 2 time;

the "Sensitivity Standard", 1 time;

the "Standard Solution" of propargyl bromide, 3 times; and the Sample of Compound 1, 1 time.

After the injection, the reporting is as follows:

if no peak corresponding to propargyl bromide peak in the sample of Compound 1 was detected then the concentration of propargyl bromide in the sample was reported as n.d. (not detected);

if the propargyl bromide area in the sample of Compound 1 was less the area of the "Sensitivity Standard" of propargyl bromide then the concentration of propargyl alcohol in the sample was reported as <1 ppm;

if the propargyl bromide area in the sample of Compound 1 was less than or equal to the average area of the three runs of the "Standard Solution" of propargyl bromide then the concentration of propargyl bromide in the sample was reported as ≤30 ppm; or if the propargyl bromide area in the sample of Compound 1 was greater than the average area of the three runs of the "Standard Solution" of propargyl bromide then the concentration of propargyl bromide in the sample was reported as >30 ppm.

Example 12: Gas Chromatography Method for Determining Propargyl Alcohol in a Sample of Compound 1

Gas chromatography (GC) was conducted using an Agilent GC 6890 gas chromatograph, or equivalent, and a flame-ionization detector (FID) using an Agilent DB-624, 25 m×0.20 mm×1.12 μm (P.N.: 128-1324); or equivalent.

Reagents used: dichloromethane (DCM) for HPLC, GC and residue analysis, ≥99.9%, stabilized with 50-150 ppm amylene; or equivalent; and propargyl alcohol standard.

Gas Chromatography Conditions (Table 27)

TABLE 27

| Parameter | Conditions | | |
|---|---|---|---|
| Column | DB-624, 25 m × 0.20 mm × 1.12 μm (P.N.: 128-1324); or equivalent | | |
| Initial temperature | 40° C. for 3 min. | | |
| Temperature program | Ramp | Final Temperature | Waiting time |
| | 20° C./min. | 80° C. | 1 min. |
| | 35° C./min. | 220° C. | 10 min. |
| Total time | 20 min. | | |
| Injection Volume | 2 μL | | |
| Liner | Inert liner with glass wool, ID 4 mm (P.N. 5183-4674); or equivalent (new liner was installed prior to each analysis). | | |
| Split Ratio | 10:1 | | |
| Inlet temperature | 250° C. | | |
| FID Temperature | 300° C. | | |
| Transport gas | Nitrogen | | |
| Flow | 0.5 mL/min, constant flow | | |
| Gas Detector Flows | Air: 400 mL/min. Hydrogen: 40 mL/min. Makeup: 30 mL/min. | | |
| Approximate retention time | Propargyl alcohol 6.1 min. | | |

Preparation of Standard Solution

A "Standard Stock Solution" of propargyl alcohol at a concentration of 0.5 mg/mL was prepared by weighing out the equivalent of 50 mg from the propargyl alcohol into a 100 mL flask containing an aliquot of DCM, the mixture was shaken, and filled to volume with DCM.

The "Standard Solution" of propargyl alcohol at a concentration of 0.05 mg/mL (1000 ppm) was prepared by transferring 1 mL of the above Standard Stock Solution into a 10 mL flask containing an aliquot of DCM, the mixture was shaken, and filled to volume with DCM.

Sample Preparation

A 250 mg sample of Compound 1 was carefully weighed out into a 5 mL flask, DCM was added to dissolve the sample, and filled to volume with DCM.

The injection sequence for the analysis was performed in the following consecutive order:

the blank (DCM), at least 2 time;

the "Standard Solution" of propargyl alcohol, 3 times; and the Sample of Compound 1, 1 time.

After the injection, the reporting is as follows:

if no peak corresponding to propargyl alcohol peak in the sample of Compound 1 is detected then the concentration of propargyl alcohol in the sample was reported as n.d. (not detected);

if the propargyl alcohol area in the sample of Compound 1 was less than or equal to the average area of the three runs of the "Standard Solution" of propargyl alcohol then the concentration of propargyl alcohol in the sample was reported as ≤1000 ppm; or if the propargyl alcohol area in the sample of Compound 1 was greater than the average area of the three runs of the "Standard Solution" of propargyl alcohol then the concentration of propargyl alcohol in the sample was reported as >1000 ppm.

Example 13: Spray-dried Dispersion Formulations Containing Compound 1, or Pharmaceutically Salts and/or Crystalline Forms thereof, and Various Polymers Spray-Dried Dispersion Formulations A series of spray-dried dispersion (SDD) formulations containing Compound 1 and a polymer were prepared. The SDD formulations included: (1) 10% Compound 1/90% hydroxypropylmethylcellulose acetate succinate-L (HPMCAS-L); (2) 25% Compound 1/75% HPMCAS-L; (3) 40% Compound 1/60% HPMCAS-L; (4) 25% Compound 1/75% polyvinyl pyrrolidone vinyl acetate 64 (PVP/VA 64); (5) 25% Compound 1/60% Cabosil (fumed silica)/15% HPMCAS-L; (6) 25% Compound 1/75% HPMCAS-M; and (7) 25% Compound 1/75% methyl methacrylate copolymer (1:1) (Eudragit® L100).

The PVP/VA polymer was a copolymer of 1-vinyl-2-pyrrolidone and vinyl acetate with a ratio of 60:40 by weight 1-vinyl-2-pyrrolidone:vinyl acetate with an average molecular weight of 45,000-70,000 (copovidone, sold as Kollidon® VA 64, BASF, Florham Park, NJ). The HPMCAS was a mixture of acetic acid and monosuccinic acid esters of hydroxypropylmethyl cellulose that was either grade L (HPMCAS-L), with an acetyl content of 5-9%, a succinoyl content of 14-18%, a methoxyl content of 20-24%, and a hydroxypropoxy content of 5-9% (sold by Shin-Etsu, Japan); or grade M (HPMCAS-M), with an acetyl content of 7-11%, a succinoyl content of 10-14%, a methoxyl content of 21-25%, and a hydroxypropoxy content of 5-9% (sold by Shin-Etsu, Japan).

Dissolution Performance.

Figure 19:
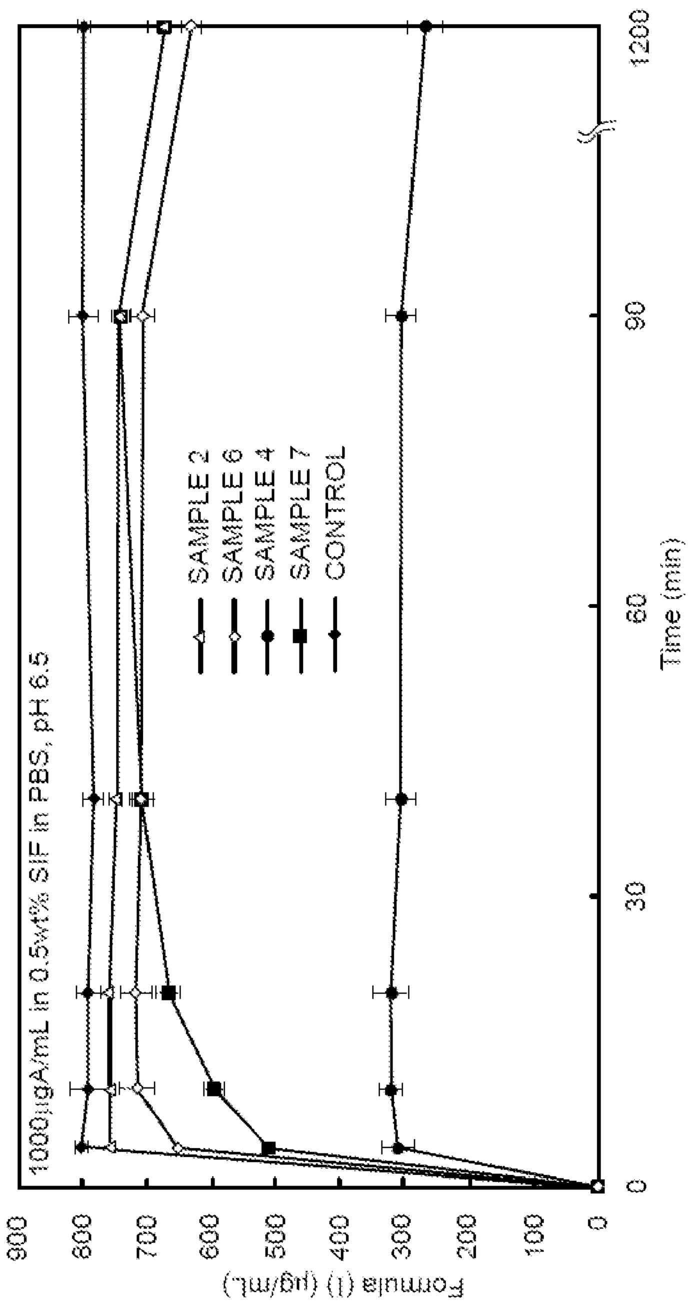
FIG. 19 shows the dissolution performance of several spray-dried dispersion formulations in 0.5 wt % simulated intestinal fluid (SIF) in phosphate buffered saline (PBS), pH 6.5.

Dissolution performance of several of the SDD formulations described above was tested (see FIG. 19). 1000 μgA/mL of each SDD was tested in 0.5 wt % simulated intestinal fluid (SIF) in PBS, pH 6.5. Samples were tested at 5, 10, 20, 45, 90, and 1200 minutes. A lipid formulation containing 10% of Compound 1 was used as a control. The results are shown in Table 28, below.

TABLE 28

Dissolution data of various SDDS

| Sample | $C_{max}90$ (μg/mL) | $AUC_{90}$ (min*μg/mL) | $Cmax_{90}$ (μg/mL) | $Ultra_{90}$ (μg/mL) | $C_{1200}$ (μg/mL) | $Ultra_{1200}$ (μg/mL) |
|---|---|---|---|---|---|---|
| 2 | 762 | 66,080 | 743 | 210 | 671 | 166 |
| 4 | 322 | 27,330 | 306 | 109* | 268 | 199 |
| 6 | 718 | 62,240 | 708 | 202 | 632 | 217 |
| 7 | 742 | 60,600 | 742 | 113* | 674 | 194 |
| Control | 802 | 69,580 | 800 | 253 | 799 | 270 |

*Large variability between replicates, high value discarded

Non-Sink Dissolution.

A membrane flux assay was performed (see, e.g., Stewart et al., Mol. Pharm. (2017) 14:2032-2046) and non-sink dissolution data was collected for several of the SDD formulations described above and compared to Compound 1 and several reference formulations, including a semi-solid lipidic formulation (Reference Formulation 1) and two self-emulsifying drug delivery system (SEDDS) formulations (Reference Formulations 2 and 3). The components of the Reference Formulations are shown in Table 29, below, and include, in addition to Compound 1, caprylic/capric triglyceride (Labrafac® Lipophile, Gattefossé, France); propylene glycol dicrapolate/dicaprate (Labrafac® PG, Gattefossé, France); oleoyl polyoxyl-6 glycerides (Labrafil® M 1944 CS, Gattefossé, France); polysorbate 20; polyoxyl castor oil (Kolliphor® RH 40, BASF, Germany); polyoxyl 15 hydroxystearate (Kolliphor® HS 15, BASF, Germany); lauroyl polyoxyl-32 glycerides (Gelucire® 44/14, Gattefossé, France); d-α-tocopheryl polyethylene glycol 1000 succinate (TPGS); and diethylene glycol monoethyl ether (Transcutol®, Gattefossé, France).

TABLE 29

Reference formulations (capsules)

| Formulation (mg/caps) | Reference Formulation 1 | Reference Formulation 2 | Reference Formulation 3 |
|---|---|---|---|
| Cmpd 1 | 50 | 50 | 50 |
| Labrafac ® Lipophile | 196 | 100 | 100 |
| Labrafac ® PG | 102 | — | — |
| Labrafil ® M 1944 CS | — | 135 | 46 |
| Polysorbate 20 | — | — | 89.9 |
| Kolliphor ® RH 40 | — | — | 100 |
| Kolliphor ® HS 15 | — | 165 | — |
| Gelucire ® 44/14 | 95 | — | — |
| TPGS | 57 | — | 65 |
| Transcutol ® | — | 50 | 50 |
| Total | 500 | 500 | 500 |

Figure 20:
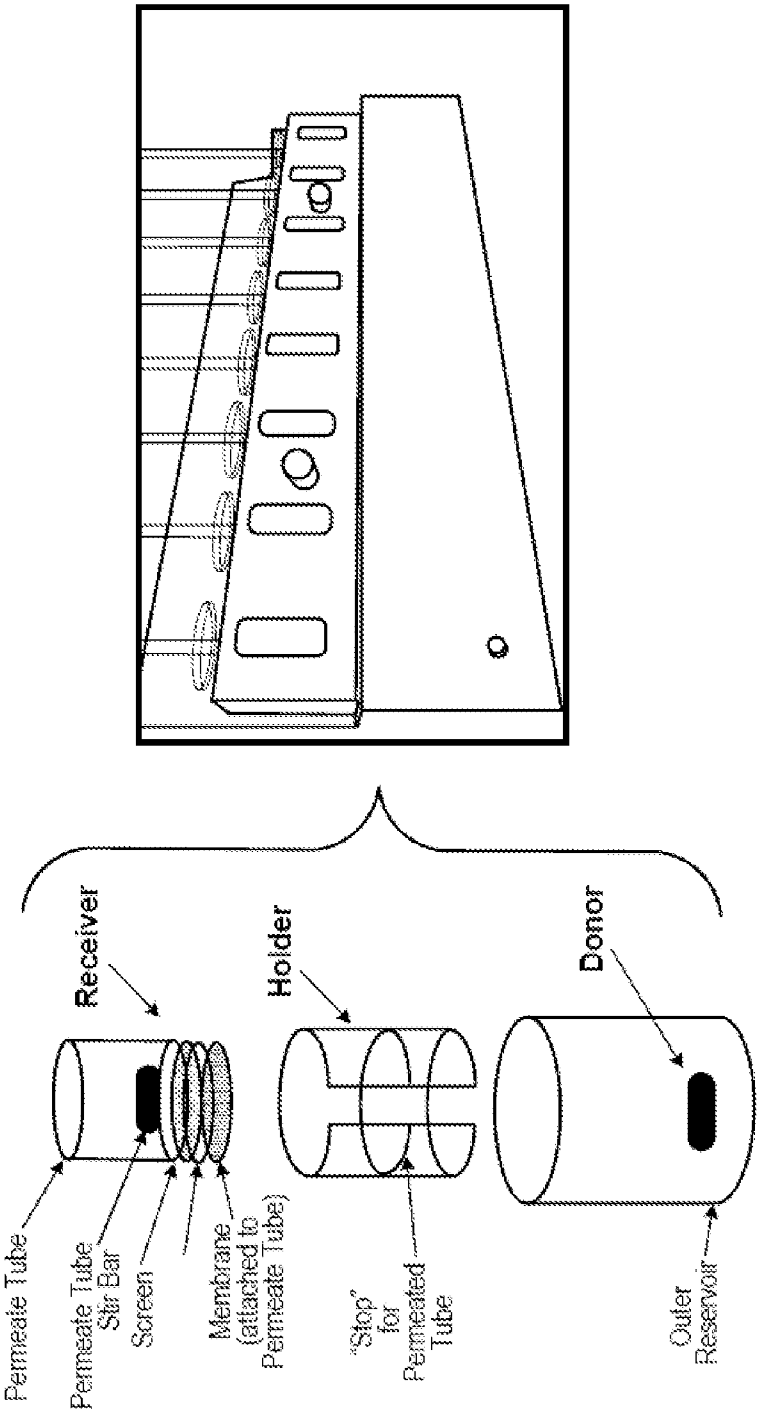
FIG. 20 shows the vertical membrane flux cell integrated in the μDiss Profiler™ used for the membrane flux assay.
Figure 21:
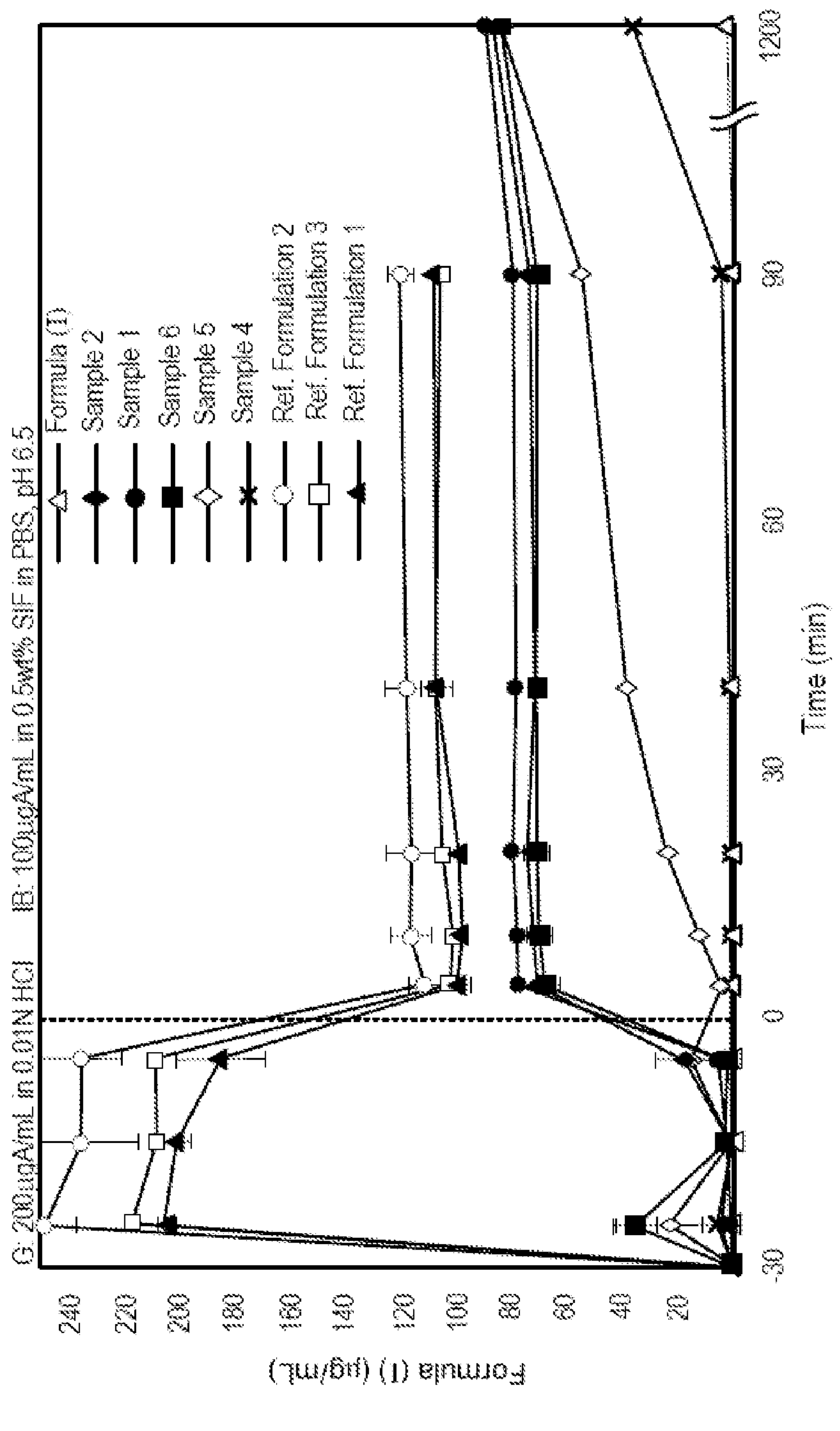
FIG. 21 shows non-sink dissolution data for several spray-dried dispersion formulations and the compound of Formula (I) in 0.5 wt % SIF in PBS, pH 6.5.

The assay measured the flux across simulated gastric and intestinal walls via UV spectroscopy (μDiss Profiler™, Pion Inc., Billerica, MA). Briefly, the assay was performed as follows. A vertical membrane flux cell consisting of a donor compartment and a receiver compartment, and separated by an Accurel PP 1E (55% porous, 100 μm thickness) polypropylene membrane (3 M, Maplewood, MN) (FIG. 20), was impregnated with 50 μL of Pion GIT-0 lipid solution consisting of 20% w/w phospholipid dissolved into dodecane (Pion Inc., Billerica, MA) and attached to the receiver vessel. Both the donor and receiver compartments were agitated by magnetic stirring. The receiver compartment contained a plastic spacer and grating to elevate the stir bar above the membrane. Samples were introduced to the donor vessel by pre-weighing directly into the donor vessel and subsequently adding dissolution medium. Once the dissolution medium was added to the donor vessel, the receiver vessel was inserted into the donor vessel and suspended vertically 5 mm above the donor compartment by a plastic sleeve. For this assay, the simulated gastric (feed) media was 0.1 N HCl, pH 2 and included 200 μgA/mL of each SDD, and the simulated intestinal (receiver) media was 0.5 wt % SIF in PBS, pH 6.5 and included 100 μgA/mL of each SDD. The temperature for the assay was maintained at 44.5° C. UV probes (10 mm path length) connected to a Rainbow UV spectrometer (Pion Inc.) system were used to determine the apparent drug concentration in the receiver vessels. Samples of the donor compartment were removed with a disposable pipet for centrifugation followed by HPLC and DLS analysis of the supernatant. The results are shown in FIG. 21 and Table 30, below.

TABLE 30

Non-sink dissolution data

| Sample | $C_{maxGB}$ (μg/mL) | $C_{max90\ IB}$ (μg/mL) | $AUC_{4\text{-}90IB}$ (min*μg/mL) | $C_{90}$ (μg/mL) | $Ultra_{90}$ (μg/mL) | $C_{1200}$ (μg/mL) |
|---|---|---|---|---|---|---|
| Cmpd 1 | 0 | 1 | 10 | 0 | 0 | 3 |
| 1 | 6 | 80 | 6,800 | 80 | 79 | 90 |
| 2 | 17 | 74 | 6,240 | 73 | 73 | 86 |
| 4 | 6 | 4 | 200 | 4 | 5 | 36 |
| 5 | 23 | 55 | 3,180 | 55 | 54 | 83 |
| 6 | 35 | 71 | 6,070 | 71 | 77 | 83 |
| Reference Formulation 1 | 205 | 109 | 9,050 | 109 | — | — |
| Reference Formulation 2 | 249 | 120 | 10,160 | 120 | — | — |
| Reference Formulation 3 | 218 | 107 | 9,100 | 107 | — | — |

Figure 22:
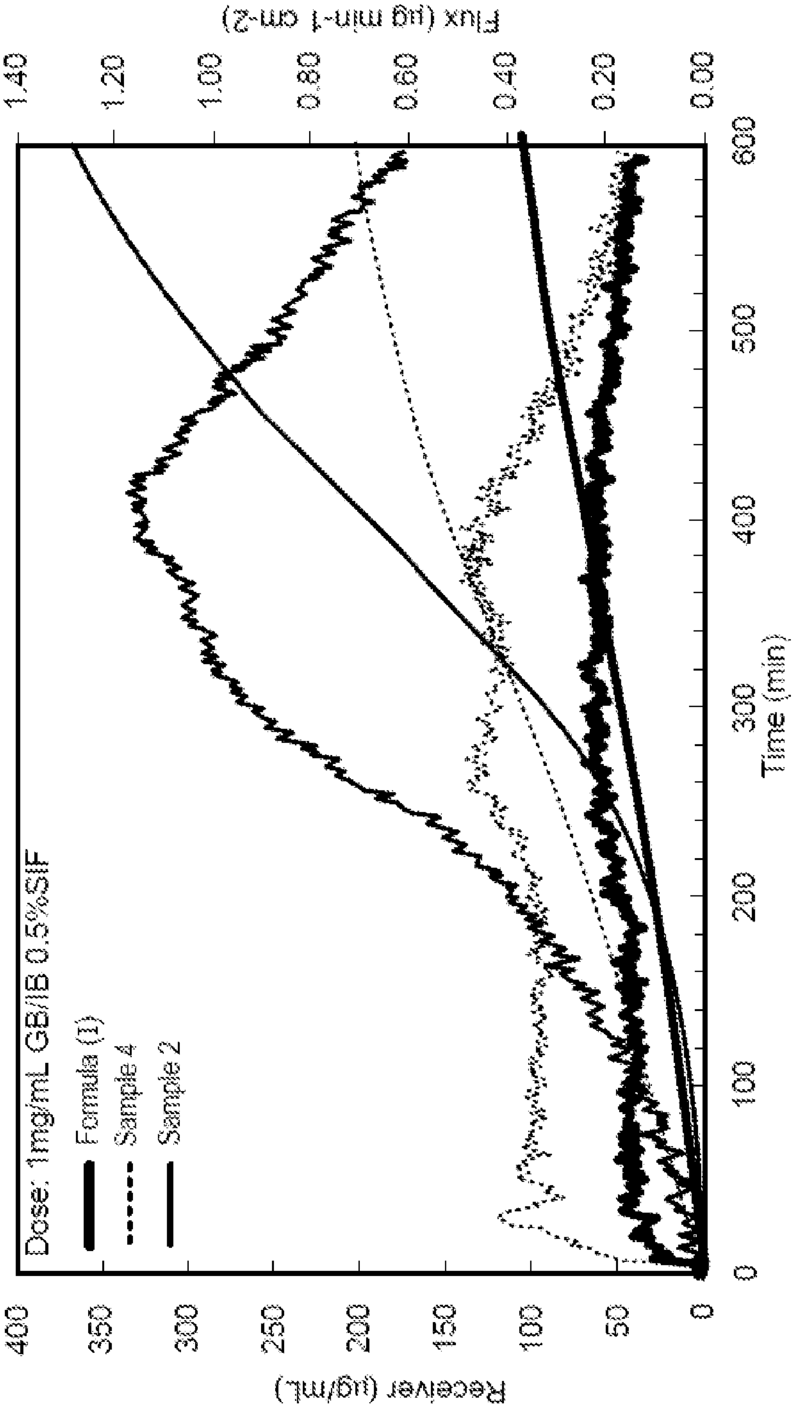
FIG. 22 is a graph showing membrane flux of 1 mg/mL GB/IB 0.5 wt % SIF doses of Compound 1 and various spray-dried dispersion formulations over time. The solid lines indicate flux (μg min-1 cm-2) and the broken lines indicate concentration (μg/mL) in 0.5% SIF.

The membrane flux of 1 mg/mL gastric barrier/intestinal barrier (GB/IB) 0.5 wt % SIF doses of Compound 1 and spray-dried dispersions (2) 25% Compound 1/75% HPMCAS-L and (4) 25% Compound 1/75% PVP/VA 64 were also determined. The results are shown in FIG. 22 as receiver concentration vs. time and flux vs. time (smoothed derivative of receiver concentration×volume/surface area).

Example 14: Characterization of a Spray-Dried Dispersion Containing 25% of Compound 1 and 75% of a Polyvinyl Pyrrolidone Vinyl Acetate (PVP/VA) Polymer SDD Stability Screening.

Several of the SDDs described in Example 13 were tested for chemical and physical stability. Wet SDD stability studies were performed, with samples stored at both 5° C. and 25° C. Measurements were taken after 1 week and 2 weeks of storage. The results are shown in Table 31 below. The column with a retention time of 32.36 min correlates with Compound 1.

TABLE 31

Wet SDD stability data

| | Storage Temp | Time Point | | | | | | Total Impurities |
|---|---|---|---|---|---|---|---|---|
| RT (min) | | | 11.04 | 16.79 | 17.26 | 30.94 | 32.26 | |
| RRT | | | 0.34 | 0.52 | 0.53 | 0.96 | 1 | |
| Ref. Std. | | | | | | 0.37 | 99.63 | 0.37 |
| Cmpd 1 | | | | | | 0.26 | 99.74 | 0.26 |
| Sample 1 | | initial | | 0.13 | 0.16 | 0.25 | 99.46 | 0.54 |
| | 5° C. | 1 week | | 0.03 | 0.03 | 0.26 | 99.69 | 0.31 |
| | | 2 weeks | | 0.12 | 0.16 | 0.28 | 99.45 | 0.55 |
| | 25° C. | 1 week | | 0.03 | 0.04 | 0.26 | 99.67 | 0.33 |
| | | 2 weeks | | 0.21 | 0.27 | 0.28 | 99.24 | 0.76 |
| Sample 2 | | initial | <LOQ | 0.07 | 0.08 | 0.26 | 99.59 | 0.41 |
| | 5° C. | 1 week | <LOQ | 0.02 | 0.03 | 0.26 | 99.7 | 0.3 |
| | | 2 weeks | <LOQ | 0.22 | 0.27 | 0.27 | 99.24 | 0.76 |
| | 25° C. | 1 week | <LOQ | 0.02 | 0.03 | 0.26 | 99.69 | 0.31 |
| | | 2 weeks | <LOQ | 0.23 | 0.28 | 0.26 | 99.23 | 0.77 |

RT = Retention Time
RRT = Relative Retention Time
LOQ = limit of quantification

Solution stability studies were also performed, with samples stored at both 5° C. and 25° C. Measurements were taken after 1 week and 2 weeks of storage. The results are shown in Table 32 below. The column with a retention time of 32.36 min correlates with Compound 1.

TABLE 32

SDD solution stability data

| | Storage Temp | Time Point | | | Total Impurities |
|---|---|---|---|---|---|
| RT (min) | | | 31.51 | 32.26 | |
| RRT | | | 0.97 | 1 | |
| Ref. Std. | | | 0.74 | 99.26 | 0.74 |
| Cmpd 1 | | | 0.26 | 99.74 | 0.26 |
| Sample 1 | | initial | 0.33 | 99.67 | 0.33 |
| | 5° C. | 2 weeks | 0.29 | 99.71 | 0.29 |
| | 25° C. | 2 weeks | 0.38 | 99.62 | 0.38 |
| Sample 2 | | initial | 0.25 | 99.75 | 0.25 |
| | 5° C. | 2 weeks | 0.26 | 99.74 | 0.26 |
| | 25° C. | 2 weeks | 0.33 | 99.67 | 0.33 |

RT = Retention Time
RRT = Relative Retention Time

Stability studies were also performed for the SDD containing 25% of Compound 1 and 75% PVP/VA 64, with samples stored at both 5° C. (closed with desiccant), 25° C. (60% RH, closed with desiccant), and 30° C. (65% RH, closed with desiccant). Measurements were taken after storage for 1 month, 2 months, 3 months, 6 months, and 12 months. No change in purity was observed after 12 months of storage. The results are shown in Table 33 below. The column with a retention time of 30.2 min correlates with Compound 1.

TABLE 33

SDD stability data

| | Storage Conditions | Time Point | | | Total Impurities | Potency (mgA/g) |
|---|---|---|---|---|---|---|
| RT (min) | | | 28.7 | 30.2 | | |
| RRT | | | 0.95 | 1.00 | | |
| Cmpd 1 (FB) Form I | | | 0.26 | 99.74 | 0.26 | 1001 |
| Sample 4 (25% Cmpd 1:75% PVP/VA 64) | | initial | 0.26 | 99.74 | 0.26 | 245 |
| | 5° C. (closed with desiccant) | 1 month | 0.25 | 99.75 | 0.25 | 247 |
| | | 2 months | 0.25 | 99.75 | 0.25 | 244 |
| | | 3 months | 0.26 | 99.74 | 0.26 | 246 |
| | | 6 months | 0.25 | 99.75 | 0.25 | 245 |
| | | 12 months | 0.25 | 99.75 | 0.25 | 248 |
| | 25° C./60% RH (closed with desiccant) | 1 month | 0.25 | 99.75 | 0.25 | 245 |
| | | 2 months | 0.25 | 99.75 | 0.25 | 247 |
| | | 3 months | 0.25 | 99.75 | 0.25 | 246 |
| | | 6 months | 0.25 | 99.75 | 0.25 | 242 |
| | | 12 months | 0.25 | 99.75 | 0.25 | 245 |
| | 30° C./65% RH (closed with desiccant) | 1 month | 0.25 | 99.75 | 0.25 | 249 |
| | | 2 months | 0.25 | 99.75 | 0.25 | 242 |
| | | 3 months | 0.25 | 99.75 | 0.25 | 246 |
| | | 6 months | 0.25 | 99.73 | 0.25 | 243 |
| | | 12 months | 0.25 | 99.75 | 0.25 | 242 |

RT = Retention Time
RRT = Relative Retention Time

While Samples 1 and 2 showed degradation after about 2 weeks of storage, the SDD containing 25%0 of Compound 1 and 7500 PVP/VA 64 (Sample 4) was found to be both chemically and physically stable and was further screened and characterized as described below.

25% Compound 1/75% PVPP/A 64 SDD process parameter screening manufacture Round 1.

The 25%0 Compound 1/75%0 PVP/VA 64 SDD was prepared on a Pharmaceutical Spray Dryer with 100 kg/hr drying gas capacity (PSD-1). The manufacturing summary is shown in Table 34, below.

TABLE 34

| Manufacturing summary of process parameters | |
|---|---|
| Formulation | 25% Compound 1:75% PVP/VA 64 |
| Solids Loading (wt %) | 10 |
| Batch Size (kg) | 1.5 |
| Solvent | Acetone |
| Atomizer (Pressure Swirl) | SK 80-16 |
| Solution Flow-rate (g/min) | 160 |
| Atomization Pressure (psig) | 480 |
| Inlet Temperature (° C.) | 94 |
| Outlet Temperature (° C.) | 40 |
| Calculated Outlet Acetone Saturation (% RS) | 6.2 |
| Dry Yield (%) | 73 |

Based on the 73%~yield observed in the first round of process screening, three sprays were performed to investigate the effect of reducing solution throughput and outlet temperature on product yield. All sprays were conducted at a reduced flow-rate of 110 g/min. The outlet temperature was varied at 40° C. (Lot A), 35° C. (Lot B), and 30° C. (Lot C). The outlet temperature was decreased while maintaining a low outlet acetone saturation to increase the difference between the chamber outlet temperature and the wet SDD Tg, thus improving product yields. The spray dryer chamber and outlet ductwork were cleaned between all manufactures. A manufacturing summary is shown in Table 35.

TABLE 35

Manufacturing summary for process parameters (1.5 kg batch size)

| Description | Low Flow-Rate | Low Flow-Rate/Low Outlet Temperature | Low Flow-Rate/Lower Outlet Temperature |
|---|---|---|---|
| Lot | A | B | C |
| Solids Loading (wt %) | 10 | 10 | 10 |
| Batch Size (kg) | 1.5 | 1.5 | 1.5 |
| Solvent | Acetone | Acetone | Acetone |
| Atomizer (Pressure Swirl) | Steinen A75 | Steinen A75 | Steinen A75 |
| Solution Flow-Rate (g/min) | 110 | 110 | 110 |
| Atomization Pressure (psig) | 275 | 285 | 285 |
| Inlet Temperature (° C.) | 79 | 72 | 63 |
| Outlet Temperature (° C.) | 40 | 35 | 30 |
| Calculated Outlet Acetone Saturation (% RS) | 4.3 | 5.2 | 6.4 |
| Calculated wet SDD Tg (° C.) | 72 | 71 | 69 |
| Dry Yield (%) | 55 | 80 | 43 |

The conditions used for Lot B were found to give the highest yield. One additional spray was then performed at the same processing conditions as Lot B while increasing the batch size from 1.5 kg to 3.5 kg to evaluate process consistency and to determine if product yield would continue to improve over time. The averaged process conditions for this lot are shown in Table 36.

TABLE 36

Manufacturing summary of process parameters (1.5 kg and 3.5 kg batch sizes)

| Description | Low Flow-Rate/Low Outlet Temperature | Low Flow-Rate/Lower Outlet Temperature |
|---|---|---|
| Lot | B | D |
| Solids Loading (wt %) | 10 | 10 |
| Batch Size (kg) | 1.5 | 3.5 |
| Solvent | Acetone | Acetone |
| Atomizer (Pressure Swirl) | Steinen A75 | Steinen A75 |
| Solution Flow-Rate (g/min) | 110 | 110 |
| Atomization Pressure (psig) | 285 | 285 |
| Inlet Temperature (° C.) | 72 | 72 |
| Outlet Temperature (° C.) | 35 | 35 |
| Calculated Outlet Acetone Saturation (% RS) | 5.2 | 5.2 |
| Calculated wet SDD Tg (° C.) | 71 | 71 |
| Dry Yield (%) | 80 | 84 |

The 1.5 kg batch size (Lot D) was sprayed with an 84% yield compared to the 80% yield of the 3.5 kg batch (Lot B).

25% Compound 1/75% PVP/VA 64 SDD Process Parameter Screening Characterization.

The 25% Compound 1/75% PVP/VA 64 SDDs manufactured to evaluate processing parameters were characterized for powder properties, performance, and physical and chemical properties. Testing included particle size distribution by Malvern, determination of bulk and tapped density, microcentrifuge dissolution, modulated differential scanning calorimetry (mDSC), powder x-ray diffraction (PXRD), scanning electron microscope (SEM), and assay and related substances. The results did not show any significant differences between the lots.

The particle size distribution (PSD) and tabulated powder properties data of the 25% Compound 1/75% PVP/VA 64 SDDs are shown in Table 37. All 25% Compound 1/75% PVP/VA 64 SDDs were observed to have a very similar PSD with a D50 of approximately 16 μm. All 25% Compound 1/75% PVP/VA 64 SDDs were observed to have low bulk and tapped densities.

TABLE 37

| Powder properties of process parameter screening PVP/VA-64 SDDS | | | | | | | | | | |
|---|---|---|---|---|---|---|---|---|---|---|
| Sample | Lot | D10 (μm) | D50 (μm) | D90 (μm) | D(3,2) (μm) | D(4,3) (μm) | Span | Bulk Density (g/mL) | Tapped Density (g/mL) |
| 40° C. Outlet | A | 5 | 15 | 34 | 8 | 17 | 1.93 | 0.12 | 0.25 |
| 35° C. Outlet | B | 5 | 16 | 36 | 9 | 19 | 1.97 | 0.11 | 0.23 |
| 30° C. Outlet | C | 5 | 15 | 32 | 7 | 17 | 1.86 | 0.12 | 0.27 |
| 35° C. Outlet, 3.5 kg batch | D | 5 | 16 | 38 | 9 | 19 | 1.98 | 0.12 | 0.24 |

The 3.5 kg batch size lot was analyzed and compared to process parameter Lot A. Dissolution performance was similar for each of these lots. Dissolution was rapid to Cmax and high free drug was sustained through 90 minutes. These data are shown in Table 38.

TABLE 38

| Dissolution performance of Lot A (1.5 kg batch size) vs. Lot D (3.5 kg batch size) | | | | |
|---|---|---|---|---|
| Sample | $C_{max90}$ (μg/mL) | $AUC_{90}$ (min*μg/mL) | $C_{90}$ (μg/mL) | $Ultra_{90}$ (μg/mL) |
| Lot A | 447 | 37,740 | 437 | 319 |
| Lot D | 437 | 37,120 | 433 | 301 |

The 25% Compound 1/75% PVP/VA 64 SDDs were also evaluated by DSC, PXRD, and SEM. The DSC thermograms showed a single Tg at 84° C., indicating homogeneous dispersions. PXRD diffractograms showed no evidence of crystals in the SDDs. SEM images showed inflated sphere morphology with some broken particles and some very small particles.

Additional testing on Lot B was carried out, which included assessing the chemical/physical stability of both spray solution and SDD prior to secondary drying (wet SDD) to establish maximum in-process hold times. Residual acetone concentration as a function of secondary drying time in a convection tray dryer was also evaluated to nominate tray drying conditions to ensure the SDD is dried below International Council for Harmonization of Technical Requirements for Pharmaceuticals for Human Use (ICH) guidelines for acetone.

Residual acetone content as a function of drying time was assessed by drying wet SDD in a tray dryer and collecting samples over a 24-hour period. Wet SDD was dried at 40° C./15% relative humidity (RH) and was observed to dry below ICH acetone guidelines (0.5 wt %, 5000 ppm) by four hours.

Spray solution hold time was determined by making up a representative solution that contained 2.5 wt % Compound 1, 7.5 wt % PVP/VA 64, and 90 wt % acetone. These solutions were analyzed initially for related substances. and then aged at 5° C. and 25° C. Aliquots were taken and analyzed for related substances periodically for 14 days. Results showed no change in impurity profile at either condition through 14 days.

Wet SDD was analyzed for impurities after storage at 5° C. and 25° C. for 1 and 2 weeks and compared to the impurity profiles of the ingoing Compound 1 and the SDD that was secondarily dried immediately after spray drying. The impurity profiles were similar to that of the initial dried sample and the ingoing Compound 1 through 2 weeks of storage.

The wet SDD stability samples were characterized for physical stability by DSC, PXRD, and SEM. DSC thermograms showed a single Tg at 81° C., indicative of a homogeneous dispersion with no phase separation. The PXRD diffractograms did not show any evidence of crystals after storage at either condition. SEM images showed a typical morphology of mostly inflated spheres with some broken particles.

Example 15: Preparation of a 1000 g Batch of a Spray-Dried Dispersion Containing 25% of Compound 1 and 75% PVP/VA 64

A 1000 g batch of the spray-dried dispersion containing 25% of Compound 1 and 75% PVP/VA 64 was prepared as described in Example 14 for the 1.5 kg and 3.5 kg batches. Briefly, acetone (90% (w/w) of the total mixture) was added to the mixing tank followed by the addition of 250.0 g of Compound 1 (2.5% (w/w) of the total mixture). The mixture was mixed for 30 minutes in the dark at a temperature range of 15° C. to 27° C. At the end of the mixing period, the solution was clear and free of undissolved solids. The PVP/VA 64 (750.0 g, 7.5% (w/w) of the total mixture) was then added and the mixture was stirred for an additional 30 minutes in the dark at a temperature range of 15° C. to 27° C. At the end of the mixing period, the solution was clear and free of undissolved solids.

Figure 23:
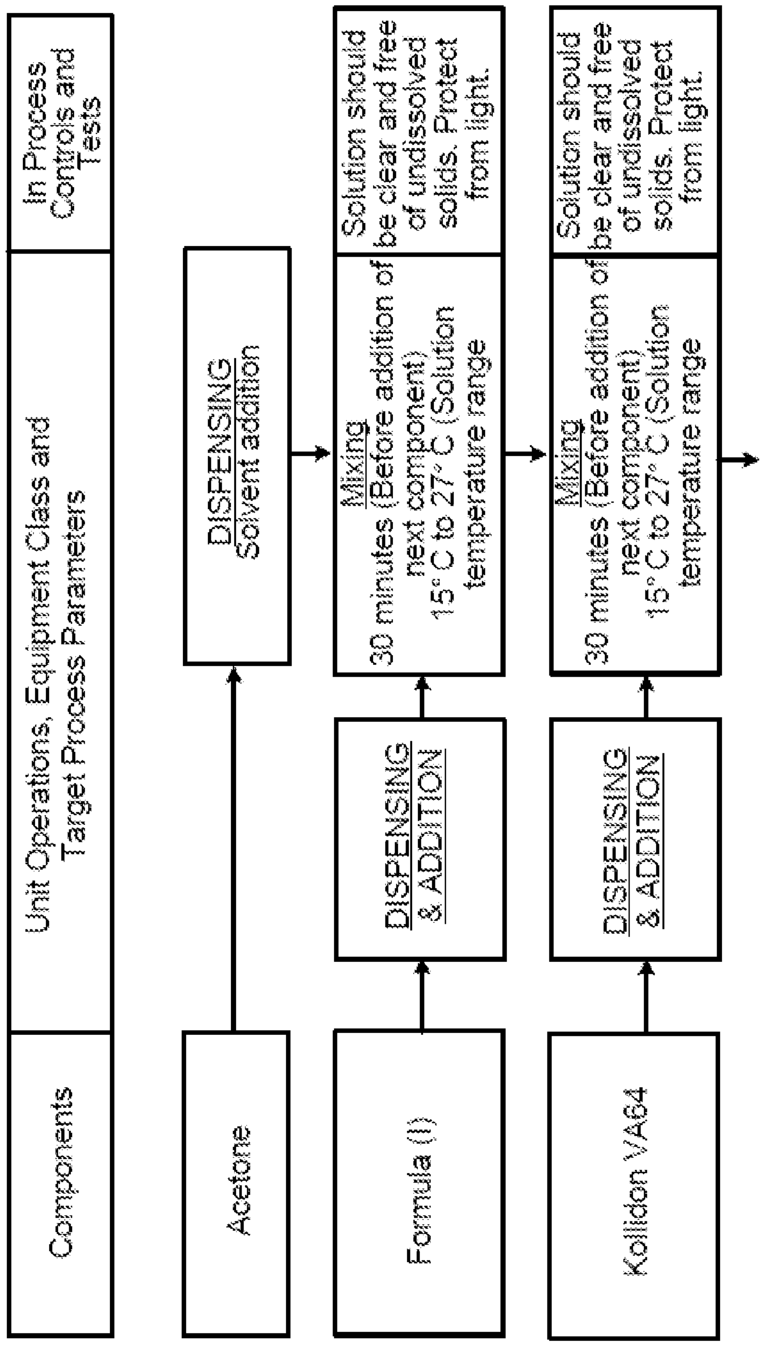
FIG. 23 is a flow diagram of the spray drying manufacturing process used to prepare a 1000 g batch of an SDD containing 25% of Compound 1 and 75% PVP/VA 64.

The solution was pumped and atomized in a drying chamber. The spray-dried dispersions were prepared in a Pharmaceutical Spray Dryer with 100 kg/hr drying gas capacity (PSD-1). The inlet temperature was set at 75° C. (varied between 60° C.-90° C.). The outlet temperature was set at 35° C. (varied between 32° C.-38° C.). The feed pressure was set at 280 psig (varied between 230-330 psig). The feed rate was set at 110 g/min (varied between 90-130 g/min). The spray dried powder was then dried in a convection tray dryer with a bed depth of ≤2.5 cm at 40° C. (±5° C.) and 15% relative humidity (±10%) for 24 hours under amber light. The residual acetone after drying was <0.5 wt % (5000 ppm). FIG. 23 is a flow diagram of the manufacturing process.

Example 16: Preparation of Spray-Dried Dispersion Formulations of Compound 1 for Clinical Use The spray-dried dispersion (SDD) containing 25% Compound 1 and 75% PVP/VA 64, prepared as described above, was formulated as a suspension or a capsule for clinical use.

Suspension Preparation.

A suspension that contained 50 mg of the SDD was prepared as follows. A 30 mL amber dosing bottle was tared on a balance. 200.0 mg SDD (50 mgA)±5% was then weighed into the dosing bottle. Using a 10-mL syringe, 5.0 mL of water (purified, USP) was added to the dosing bottle and the bottle was capped and shaken moderately for 30 seconds. The SDD suspension was stored in an amber vial at 2-8° C. prior to use, and dosed within 24 hours of preparation.

Capsule Preparation.

An empty hard gelatin capsule, size 0 (Capsugel, Morristown, NJ), was placed on a balance and the weight was recorded. 200.0 mg SDD (50 mgA)±5% was then weighed onto weigh paper or an equivalent. All contents were transferred to the capsule using a ProFunnel device for Size 0 capsules. The filled capsule was placed on the balance and the weight was recorded. The weight of the empty capsule was subtracted from the filled weight, ensuring that the weight of the SDD within the capsule was 200.0 mg SDD±5%, or from 190.0 mg to 210.0 mg. The capsule was securely closed with the head, assuring it clicked into place. The capsules were stored in an amber vial at 2-8° C. prior to use, and were dosed within 24 hours of preparation.

Example 17: Compound 1 Crystalline Tosylate Salt Form 1

Approximately 20 mg of Compound 1 was weighed into a vial. Using a positive displacement pipette, 250 μL of solvent (IPA) was added to the vial along with a stir bar. The vial was placed in an aluminum block on a Reacti-Therm mixer and heated to 60° C. for ~1 hour. A molar equivalent of para-toluenesulfonic acid was added to the vial (20 μL of a 2 M solution in water) and allowed to stir. The sample was slow cooled back to room temperature along with mild Nitrogen gas for evaporation. Precipitate was collected, left to dry overnight, and then analyzed by XRPD, DSC, and TGA.

The crystallinity of the tosylate Form 1 of Compound 1 was confirmed by XRPD (FIG. 24, Table 16) and further supported by DSC (FIG. 25), indicating the crystalline compound having an onset of melt at about 156° C. (22.2 J/g). TGA of the crystalline compound is provided in FIG. 28 and exhibited about 0.5% of weight loss due to solvent/$H_2O$.

Various modifications of the embodiments, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

The invention claimed is:

1. A process for preparing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof:

Compound 1

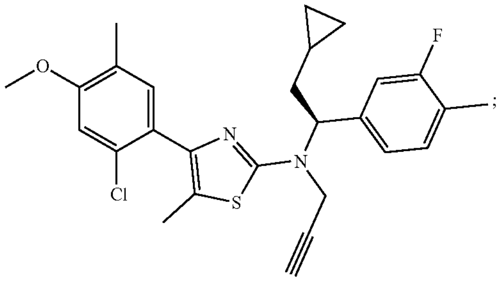

comprising:

alkylating (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

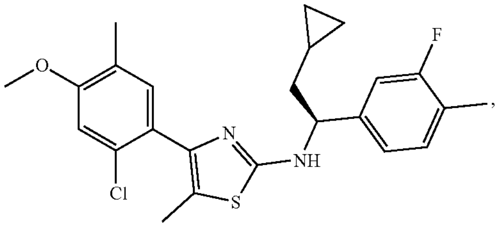

with a Compound of Formula (Ii):

(Ii)

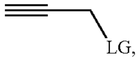

wherein: LG is a leaving group;

in the presence of an alkylating-step solvent, a phase-transfer catalyst, an alkylating-step base, and water to form 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) or a pharmaceutically acceptable salt thereof.

2. The process according to claim 1, wherein the Compound of Formula (Ii) is present in a molar excess compared to Compound 9A.

3. The process according to claim 1, wherein the Compound of Formula (Ii) is present in about 20% molar excess compared to Compound 9A.

4. The process according to claim 1, wherein the molar ratio between Compound 9A and the phase-transfer catalyst is about 1:0.05 to about 1:0.5.

5. The process according to claim 1, wherein the molar ratio between Compound 9A and the phase-transfer catalyst is about 1:0.1 to about 1.3:0.2.

6. The process according to claim 1, wherein the molar ratio between Compound 9A, the phase-transfer catalyst, and the alkylating-step base is about 1:0.05:5 to about 1:0.4:25.

7. The process according to claim 1, wherein the molar ratio between Compound 9A, the phase-transfer catalyst, and the alkylating-step base is about 1:0.1:10 to about 1:0.2:20.

8. The process according to claim 1, wherein the alkylating-step solvent is selected from a halogenated solvent, an ether solvent, an aprotic solvent, and mixtures thereof.

9. The process according to claim 1, wherein the alkylating-step solvent is selected from: dichloromethane, tetrachloroethylene, 1,1-dichloroethane, 1,2-dichloroethane, 1,2-dichlorobenzene, chlorobenzene, 1,2-dimethoxyethane (DME), cyclopentyl methyl ether (CPME), 2-methyltetrahydrofuran (2-MeTHF), 1,4-dioxane, ethylene glycol diethyl ether, tert-amyl methyl ether (TAME, also referred to as 2-methoxy-2-methylbutane), methyl tert-butyl ether (MTBE), benzene, cyclohexane, hexane, toluene, cycloheptane, methylcyclohexane, heptanes, n-heptane, ethylbenzene, o-xylene, m-xylene, p-xylene, mixtures of xylenes, octane, and mixtures thereof.

10. The process according to claim 1, wherein the alkylating-step solvent is selected from: methyl tert-butyl ether (MTBE), toluene, and mixtures thereof.

11. The process according to claim 1, wherein the phase-transfer catalyst is a quaternary ammonium salt.

12. The process according to claim 1, wherein the phase-transfer catalyst is a quaternary ammonium salt selected from: tricaprylyl methyl ammonium chloride (Aliquat 336), tetra-n-butylamnmonium bromide (TBAB), benzyltriethylammonium chloride (BTEAC), cetyltrimethylammonium bromide (CTAB), tetra-n-butylammonium chloride (TBAC), tetra-n-butylammonium hydroxide, tetra-n-butylammonium iodide, tetraethylammonium chloride (TEAC), benzyltributylammonium chloride (BTBAC), cetyltrimethylammonium chloride (CTAC), tetramethylammonium chloride, cetyltrimethylammonium chloride (CTAC), octyltrimethylammonium chloride, and combinations thereof.

13. The process according to claim 1, wherein the phase-transfer catalyst is tetra-n-butylammonium bromide (TBAB).

14. The process according to claim 1, wherein the alkylating-step base is an alkali metal hydroxide.

15. The process according to claim 1, wherein the alkylating-step base is potassium hydroxide.

16. The process according to claim 1, wherein alkylating further comprises the steps of:

forming a first-alkylating mixture comprising the alkylating-step solvent, the alkylating-catalyst, and Compound 9A at a first-alkylating temperature; and adding the alkylating-step base and the Compound of Formula (Ii) to the first-alkylating mixture at the first-alkylating temperature to form an alkylating-biphasic mixture at a second-alkylating temperature.

17. The process according to claim 16, further comprising heating first-alkylating mixture comprising the alkylating-step solvent, the alkylating-catalyst, and Compound 9A to a temperature of about 55° C. to about 65° C. and subsequently cooling to the first-alkylating temperature.

18. The process according to claim 16, wherein adding the alkylating-step base to the first-alkylating mixture is conducted as a solution of the alkylating-step base in water.

19. The process according to claim 16, wherein adding the alkylating-step base to the first-alkylating mixture is conducted as a solution of the alkylating-step base in water and the concentration in terms of percent weight/weight (% w/w) of the alkylating-step base and water is about 52 to about 53.

20. The process according to claim 16, wherein adding the Compound of Formula (Ii) to the first-alkylating mixture is conducted as a solution of the Compound of Formula (Ii) in the alkylating-step solvent.

21. The process according to claim 16, wherein adding the Compound of Formula (Ii) to the first-alkylating mixture is conducted as a solution of the Compound of Formula (Ii) in the alkylating-step solvent and the concentration in terms of percent weight/weight (% w/w) of the Compound of Formula (Ii) in the alkylating-step solvent is about 75 to about 85.

22. The process according to claim 16, wherein adding the alkylating-step base and the Compound of Formula (Ii) to the first-alkylating mixture is conducted concurrently at a rate to maintain the first-alkylating temperature.

23. The process according to claim 16, wherein adding the alkylating-step base and the Compound of Formula (Ii) to the first-alkylating mixture is conducted serially at a rate to maintain the first-alkylating temperature.

24. The process according to claim 16, wherein the first-alkylating temperature is about −5° C. to about 7° C.

25. The process according to claim 16, wherein the second-alkylating temperature is about 0° C. to about 10° C.

26. The process according to claim 1, wherein the LG is selected from the group: $C_1$-$C_4$ alkylsulphonyloxy, $C_6$-$C_{10}$ arylsulfonyloxy, halogen, and hydroxy; wherein $C_1$-$C_4$ alkylsulphonyloxy and $C_6$-$C_{10}$ arylsulfonyloxy are each optionally substituted with one or more groups selected from the group: $C_1$-$C_4$ alkyl, $C_1$-$C_4$ alkoxy, halogen, $C_1$-$C_4$ haloalkyl, $C_1$-$C_4$ haloalkoxy, and nitro.

27. The process according to claim 1, wherein LG is halogen.

28. The process according to claim 1, wherein the Compound of Formula (Ii) is selected from the group consisting of: propargyl bromide, propargyl methanesulfonate, propargyl trifluoromethanesulfonate, propargyl benzenesulfonate, and propargyl p-toluenesulfonate.

29. The process according to claim 1, wherein the Compound of Formula (Ii) is propargyl bromide.

30. The process according to claim 1, wherein alkylating is conducted with stirring.

31. The process according to claim 1, further comprising preparing (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof, by the step of:

cyclizing (S)-2-cyclopropyl-1-(3-fluoro-4-methylphenyl) ethan-1-amine (Compound 6A) or a salt thereof:

6A

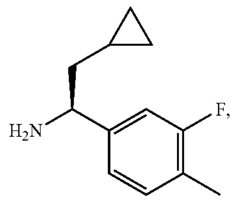

with 1-(2-chloro-4-methoxy-5-methylphenyl)-2-thiocyanatopropan-1-one (Compound 8A) or a tautomeric form thereof:

8A

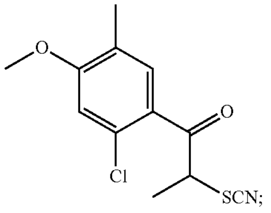

in the presence of a cyclizing-step solvent to form (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof.

32. The process according to claim 31, further comprising preparing (S)-2-cyclopropyl-1-(3-fluoro-4-methylphenyl) ethan-1-amine (Compound 6A) or a salt thereof, comprising:

deprotecting a Compound of Formula (Ig), or a salt thereof:

(Ig)

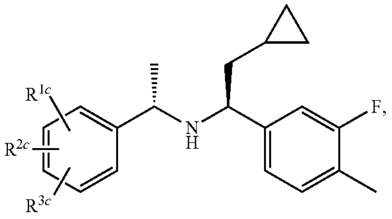

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a deprotecting-catalyst, hydrogen, and a deprotecting-step solvent to form (S)-2-cyclopropyl-1-(3-fluoro-4-methylphenyl)ethan-1-amine (Compound 6A) or a salt thereof.

33. The process according to claim 32, further comprising preparing a Compound of Formula (Ig), or a salt thereof, comprising:

reducing a Compound of Formula (Ie):

(Ie)

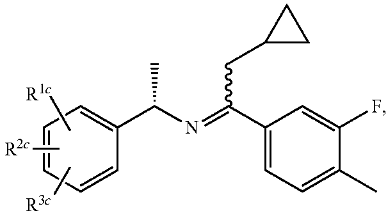

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a reducing-catalyst, hydrogen, and a reducing-step solvent to form the Compound of Formula (Ig), or a salt thereof.

34. The process according to claim 33, further comprising preparing a Compound of Formula (Ie), comprising:

condensing 2-cyclopropyl-1-(3-fluoro-4-methylphenyl) ethan-1-one (Compound 3A):

3A

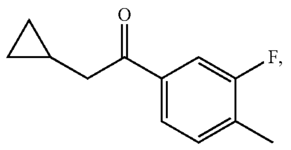

with a Compound of Formula (Ic), or salt thereof:

(Ic)

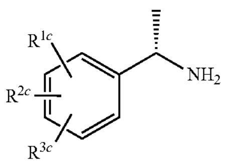

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

in the presence of a condensing-step acid and a condensing-step solvent to form the Compound of Formula (Ie).

35. The process according to claim 34, further comprising preparing 2-cyclopropyl-1-(3-fluoro-4-methylphenyl)ethan-1-one (Compound 3A), by the step of:

reacting 2-cyclopropyl-N-methoxy-N-methylacetamide (Compound 2A):

2A

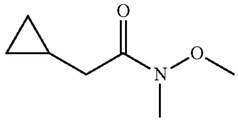

with an organomagnesium reagent of 4-bromo-2-fluoro-1-methylbenzene in the presence of a reacting-step solvent to form 2-cyclopropyl-1-(3-fluoro-4-methylphenyl)ethan-1-one (Compound 3A).

36. The process according to claim 1, further comprising the step of isolating 4-(2-chloro-4-methoxy-5-methylphenyl)-N-[(1S)-2-cyclopropyl-1-(3-fluoro-4-methylphenyl) ethyl]-5-methyl-N-prop-2-ynyl-1,3-thiazol-2-amine (Compound 1), or a pharmaceutically acceptable salt thereof.

37. The process according to claim 1, further comprising the step of formulating 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof, to form a pharmaceutical composition.

38. The process according to claim 37, wherein the step of formulating comprises admixing 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine, or a pharmaceutically acceptable salt thereof, with a pharmaceutical excipient.

39. The process according to claim 1, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is the free base.

40. The process according to claim 1, wherein 4-(2-chloro-4-methoxy-5-methylphenyl-N-[(1S)-2-cyclopropyl-1-(3-fluoro-4-methylphenyl)ethyl]-5-methyl-N-prop-2-ynyl-1,3-thiazol-2-amine (Compound 1) is crystalline.

41. The process according to claim 1, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is anhydrous crystalline Form I.

42. A process for preparing (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof:

9A

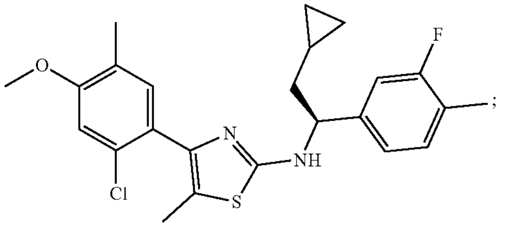

comprising:

cyclizing (S)-2-cyclopropyl-1-(3-fluoro-4-methylphenyl)ethan-1-amine (Compound 6A) or a salt thereof:

6A

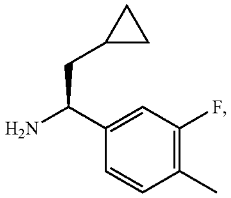

with 1-(2-chloro-4-methoxy-5-methylphenyl)-2-thiocyanatopropan-1-one (Compound 8A) or a tautomeric form thereof:

8A

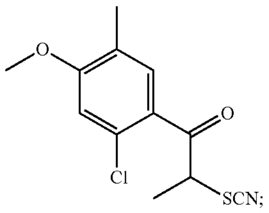

in the presence of a cyclizing-step solvent to form (S)-4-(2-chloro-4-methoxy-5-methylphenyl)-N-(2-cyclopropyl-1-(3-fluoro-4-methylphenyl)ethyl)-5-methylthiazol-2-amine (Compound 9A) or a salt thereof.

43. A process for preparing (S)-2-cyclopropyl-1-(3-fluoro-4-methylphenyl)ethan-1-amine (Compound 6A) or a salt thereof:

6A

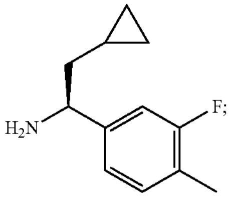

comprising:

deprotecting a Compound of Formula (Ig), or a salt thereof:

(Ig)

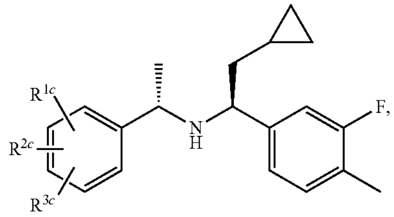

wherein $R^{1c}$, $R^{2c}$ and $R^{3c}$ are each independently selected from: H, $C_1$-$C_6$ alkoxy, $C_1$-$C_6$ alkyl, $C_1$-$C_6$ haloalkyl, and halogen;

in the presence of a deprotecting-catalyst, hydrogen, and a deprotecting-step solvent to form (S)-2-cyclopropyl-1-(3-fluoro-4-methylphenyl)ethan-1-amine (Compound 6A) or a salt thereof.

44. A process for preparing a Compound of Formula (Ig), or a salt thereof:

(Ig)

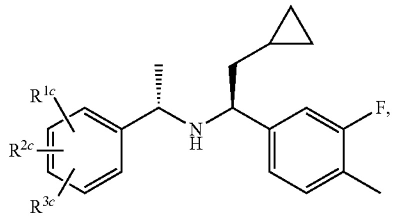

wherein $R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen;

comprising:

reducing a Compound of Formula (Ie):

(Ie)

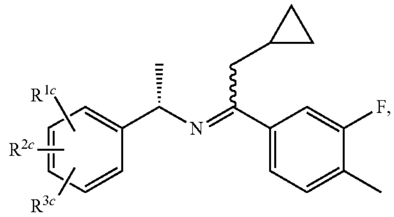

in the presence of a reducing-catalyst, hydrogen, and a reducing-step solvent to form the Compound of Formula (Ig), or a salt thereof.

45. A process for preparing a Compound of Formula (Ie):

(Ie)

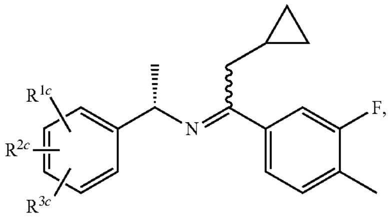

wherein:

$R^{1c}$, $R^{2c}$, and $R^{3c}$ are each independently selected from: H, $C_1$-$C_6$ alkoxy, $C_1$-$C_6$ alkyl, $C_{1-6}$ haloalkyl, and halogen;

comprising:

condensing 2-cyclopropyl-1-(3-fluoro-4-methylphenyl) ethan-1-one (Compound 3A):

3A

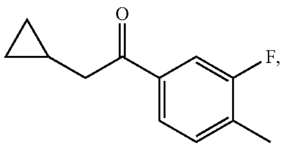

with a Compound of Formula (Ie), or a salt thereof:

(Ic)

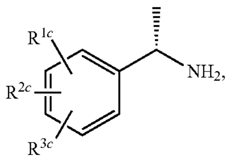

in the presence of a condensing-step acid and a condensing-step solvent to form the Compound of Formula (Ie).

46. An anhydrous crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, free base), wherein the anhydrous crystalline form has an X-ray powder diffraction (XRPD) pattern comprising at least three peaks, in terms of 2θ, selected from the group consisting of: 6.0°±0.2°, 11.9°±0.2°, 13.9°±0.2°, 14.3°±0.2°, 16.8°±0.2°, 17.9°±0.2°, 19.7°±0.2°, 20.2°±0.2°, 20.9°±0 2°, 21.8°±0.2°, 22.3°±0.2°, 23.2°±0.2°, 23.9°±0.2°, 24.2°±0.2°, 25.7°±0.2°, 26.8°±0.2°, 28.7°±0.2°, 29.6°±0.2°, 36.1°±0.2°, and 43.5°±0.2°.

47. A crystalline form of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1, tosylate salt) wherein the anhydrous crystalline form has an X-ray powder diffraction XRPD pattern comprising at least three peaks in terms of 2θ, selected from the group consisting of: 9.1°±0.2°, 10.5°±0.2°, 11.3°±0.2°, 13.2°±0.2°, 16.3°±0.2°, 19.0°±0.2°, 19.3°±0.2°, 20.4°±0.2°, 21.1°±0.2°, 22.8°±0.2°, 23.3°±0.2°, 23.8°±0.2°, and 28.5°±0.2°.

48. A pharmaceutical composition comprising a crystalline form (Compound 1, free base) according to claim 46, and a pharmaceutically acceptable carrier.

49. A pharmaceutical composition comprising a crystalline form (Compound 1, tosylate salt) according to claim 47, and a pharmaceutically acceptable carrier.

50. A composition comprising:

a. 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof; and b. at least one compound selected from:

(S)-4-(2-chloro-4-methoxy-5-methylphenyl)-N-(2-cyclopropyl-1-(p-tolyl)ethyl)-5-methyl-N-(prop-2-yn-1-yl) thiazol-2-amine (Compound IIa);

(S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb); and ethanol;

wherein the compound in the composition contains no more than:

0.8% of Compound IIa;

0.15% of Compound IIb; and 500 ppm of ethanol.

51. A Compound of Formula (Ie):

(Ie)

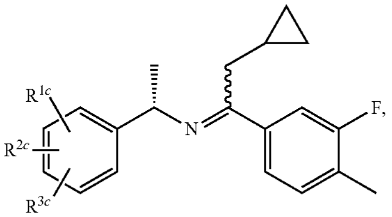

wherein:

$R^{1c}$, $R^{2c}$, and $R^{3c}$ are each independently selected from: H, $C_1$-$C_6$ alkoxy, $C_1$-$C_6$ alkyl, $C_1$-$C_6$ haloalkyl, and halogen.

52. A Compound of Formula (g) or a salt thereof:

(Ig)

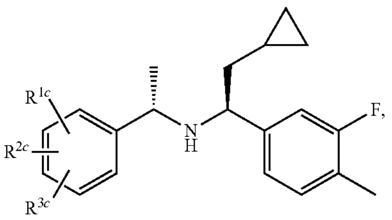

wherein:

$R^{1c}$, $R^{2c}$, and $R^{3c}$ are each independently selected from: H, $C_{1-6}$ alkoxy, $C_1$-$C_6$ alkyl, $C_1$-$C_6$ haloalkyl, and halogen.

53. A process for preparing a pharmaceutical composition comprising admixing a crystalline form (Compound 1, free base) according to claim 46; a crystalline form (Compound 1, tosylate base) according to claim 47; or a composition according to claim 50; and a pharmaceutically acceptable carrier.

54. The composition according to claim 50, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is a free base.

55. The composition according to claim 50, wherein the composition contains at least 97% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

56. The composition according to claim 50, wherein the composition contains at least 98% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

57. The composition according to claim 50, wherein the composition contains at least 99% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

58. The composition according to claim 50, wherein Compound IIa is present, and the composition contains no more than 0.7% of Compound IIa.

59. The composition according to claim 50, wherein Compound IIa is present, and the composition contains no more than 0.6% of Compound IIa.

60. The composition according to claim 50, wherein Compound IIb is present, and the composition contains no more than 0.1% of Compound IIb.

61. The composition according to claim 50, wherein Compound IIb is present, and the composition contains no more than 0.05% of Compound IIb.

62. The composition according to claim 50, wherein ethanol is present, and the composition contains no more than 3000 ppm of ethanol.

63. The composition according to claim 50, wherein ethanol is present, and the composition contains no more than 1000 ppm of ethanol.

64. The composition according to claim 50, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is an anhydrous crystalline form.

65. The composition according to claim 50, further comprising a pharmaceutically acceptable excipient.

66. The composition according to claim 54, further comprising a pharmaceutically acceptable excipient.

67. A composition comprising:

4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof; and (S)-4-(2-chloro-4-methoxy-5-methylphenyl)-N-(2-cyclopropyl-1-(p-tolyl)ethyl)-5-methyl-A-(prop-2-yn-1-yl)thiazol-2-amine (Compound IIa).

68. The composition according to claim 67, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-anine (Compound 1) is a free base.

69. The composition according to claim 67, wherein the composition contains at least 97% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

70. The composition according to claim 67, wherein the composition contains at least 98% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

71. The composition according to claim 67, wherein the composition contains at least 99% of 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1).

72. The composition according to claim 67, wherein the composition contains no more than 0.8% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa).

73. The composition according to claim 67, wherein the composition contains no more than 0.7% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa).

74. The composition according to claim 67, wherein the composition contains no more than 0.6% of (S)-4-(2-chloro-4-methoxy-5-methylphenyl)-N-(2-cyclopropyl-1-(p-tolyl)ethyl)-5-methyl-N-(prop-2-yn-1-yl)thiazol-2-amine (Compound IIa).

75. The composition according to claim 67, wherein the composition further comprises Compound 9A.

76. The composition according to claim 75, wherein the composition comprises no more than 0.3% of Compound 9A.

77. The composition according to claim 75, wherein the composition comprises no more than 0.2% of Compound 9A.

78. The composition according to claim 75, wherein the composition comprises no more than 0.1% of Compound 9A.

79. The composition according to claim 67, wherein the composition further comprises Compound IIb.

80. The composition according to claim 79, wherein the composition comprises no more than 0.15% of Compound IIb.

81. The composition according to claim 79, wherein the composition comprises no more than 0.1% of Compound IIb.

82. The composition according to claim 79, wherein the composition comprises no more than 0.05% of Compound IIb.

83. The composition according to claim 67, wherein the composition further comprises Compound IIc.

84. The composition according to claim 83, wherein the composition comprises no more than 0.3% of Compound IIc.

85. The composition according to claim 83, wherein the composition comprises no more than 0.2% of Compound IIc.

86. The composition according to claim 83, wherein the composition comprises no more than 0.1% of Compound IIc.

87. The composition according to claim 67, wherein the composition further comprises ethanol.

88. The composition according to claim 87, wherein the composition comprises no more than 5000 ppm of ethanol.

89. The composition according to claim 87, wherein the composition comprises no more than 3000 ppm of ethanol.

90. The composition according to claim 87, wherein the composition comprises no more than 1000 ppm of ethanol.

91. The composition according to claim 67, wherein the composition further comprises propargyl bromide.

92. The composition according to claim 91, wherein the composition comprises no more than 200 ppm of propargyl bromide.

93. The composition according to claim 91, wherein the composition comprises no more than 100 ppm of propargyl bromide.

94. The composition according to claim 91, wherein the composition comprises no more than 30 ppm of propargyl bromide.

95. The composition according to claim 67, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is an anhydrous crystalline form.

96. The composition according to claim 67, wherein the composition further comprises a pharmaceutically acceptable excipient.

97. The composition according to claim 68, wherein the composition further comprises a pharmaceutically acceptable excipient.

98. The composition according to claim 67, comprising:

a. 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1), or a pharmaceutically acceptable salt thereof; and (S)-4-(2-chloro-4-methoxy-5-methylphenyl)-N-(2-cyclopropyl-1-(p-tolyl)ethyl)-5-methyl-N-(prop-2-yn-1-yl) thiazol-2-amine (Compound IIa); and b. at least one compound selected from:

(S)-4-(2-Chloro-4-methoxy-5-methylphenyl)-N-(2-cyclopropyl-1-(3-fluoro-4-methylphenyl)ethyl)-5-methylthiazol-2-amine (Compound 9A);

(S)-4-(2-chloro-5-methyl-4-(prop-2-yn-1-yloxy)phenyl)-N-(2-cyclopropyl-1-(3-fluoro-4-methylphenyl)ethyl)-5-methyl-N-(prop-2-yn-1-yl)thiazol-2-amine (Compound IIb);

4-(2-chloro-4-methoxy-5-methylphenyl)-N-[(1R)-2-cyclopropyl-1-(3-fluoro-4-methylphenyl)ethyl]-5-methyl-N-(2-propyn-1-yl)-2-thiazolamine (Compound IIc);

ethanol; and propargyl bromide;

wherein the compound in the composition, when present, contains no more than:

0.8% of Compound IIa;

0.2% of Compound 9A;

0.15% of Compound IIb;

0.2% of Compound IIc;

5000 ppm of ethanol; and 30 ppm of propargyl bromide.

99. The composition according to claim 98, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is a free base.

100. The composition according to claim 98, wherein 4-(2-chloro-4-methoxy-5-methylphenyl)-N-[(1S)-2-cyclopropyl-1-(3-fluoro-4-methylphenyl)ethyl]-5-methyl-N-prop-2-ynyl-1,3-thiazol-2-amine (Compound 1) is an anhydrous crystalline form.

101. The composition according to claim 98, wherein the composition further comprises a pharmaceutically acceptable excipient.

* * * * *